US008257969B2

(12) United States Patent
Farrar et al.

(10) Patent No.: US 8,257,969 B2

(45) Date of Patent: Sep. 4, 2012

(54) GENETIC SUPPRESSION AND REPLACEMENT

(75) Inventors: Gwyneth Jane Farrar, Co Dublin (IE); Sophia Millington-Ward, Dublin 9 (IE); Naomi Chadderton, Dublin 4 (IE); Arpad Palfi, Co Wicklow (IE); Mary O'Reilly, Co Dublin (IE); Paul Kenna, Dublin 7 (IE); Peter Humphries, Co Dublin (IE)

(73) Assignee: The Provost Fellows and Scholars of the College of the Holy and Undivided Trinity of Queen Elizabeth, Dublin (IE)

( * ) Notice: Subject to any disclaimer, the term of this patent is extended or adjusted under 35 U.S.C. 154(b) by 0 days.

(21) Appl. No.: 12/595,080

(22) PCT Filed: Apr. 14, 2008

(86) PCT No.: PCT/GB2008/001310

§ 371 (c)(1), (2), (4) Date: Mar. 3, 2010

(87) PCT Pub. No.: WO2008/125846

PCT Pub. Date: Oct. 23, 2008

(65) Prior Publication Data

US 2010/0190841 A1 Jul. 29, 2010

Related U.S. Application Data

(60) Provisional application No. 60/923,067, filed on Apr. 12, 2007.

(51) Int. Cl.

*C12N 15/00* (2006.01)

*C12N 5/00* (2006.01)

(52) U.S. Cl. .................................... 435/320.1; 435/325

(58) Field of Classification Search ........................ None

See application file for complete search history.

(56) References Cited

U.S. PATENT DOCUMENTS

| | | | | |
|---|---|---|---|---|
| 4,748,119 | A * | 5/1988 | Rich et al. | 435/91.52 |
| 6,225,291 | B1 * | 5/2001 | Lewin et al. | 514/44 R |
| 7,090,864 | B2 * | 8/2006 | Pardridge | 424/450 |
| 2003/0097670 | A1 * | 5/2003 | Palczewski et al. | 800/18 |

FOREIGN PATENT DOCUMENTS

| | | | |
|---|---|---|---|
| WO | WO 00/24359 | * | 5/2002 |
| WO | 2004/020631 | A | 3/2004 |
| WO | 2004/022782 | A | 3/2004 |

OTHER PUBLICATIONS

Tan et al., 2001, Investigative Ophthalmology and Visual Science, 42: 589-600.*

Gorbatyuk et al., Vision Research, 47(9):1202-1208 (2007). "Suppression of mouse rhodopsin expression in vivo by AAV mediated siRNA delivery."

Kiang et al., Molecular Therapy, 12(3):555-561 (2005). "Toward a gene therapy for dominant disease: Validation of an RNA interference-based mutation-independent approach."

Nie et al., The Journal of Biological Chemistry, 271(5):2667-2675 (1996). "RER, an evolutionarily conserved sequence upstream of the rhodopsin gene, has enhance activity."

O'Reilly et al., American Journal of Human Genetics, 81(1):127-135 (2007). "RNA interference-mediated suppression and replacement of human rhodopsin in vivo."

Zhang et al., Gene, 313:189-200 (2003). "The regulation of retina specific expression of rhodopsin gene in vertebrates."

* cited by examiner

*Primary Examiner* — Joanne Hama

(74) *Attorney, Agent, or Firm* — Nixon Peabody LLP; David S. Resnick; Leena H. Karttunen Contarino

(57) ABSTRACT

The invention relates to gene suppression and replacement. In particular, the invention relates to enhanced expression of suppression agents for suppressing gene expression in a cell and in vivo and replacement nucleic acids that are not inhibited by the suppression agent. Regulatory elements are included in expression vectors to optimize expression of the suppression agent and/or replacement nucleic acid.

20 Claims, 28 Drawing Sheets

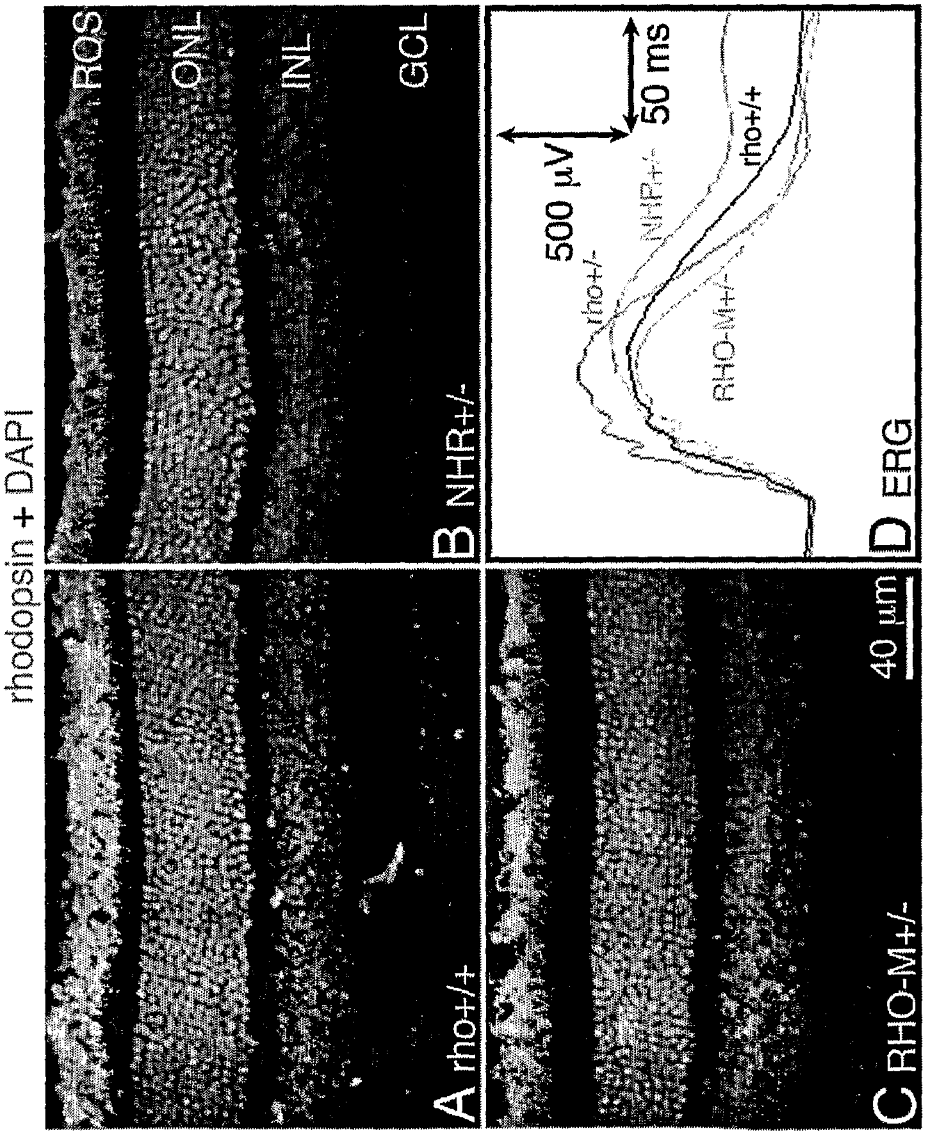
Figure 6 A-D

Figure 9 (Continued)
pAAV-shBB-EGFP
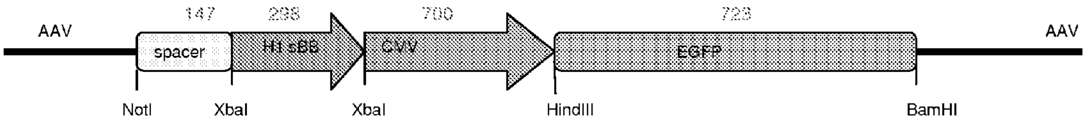
pAAV-shQ1-EGFP
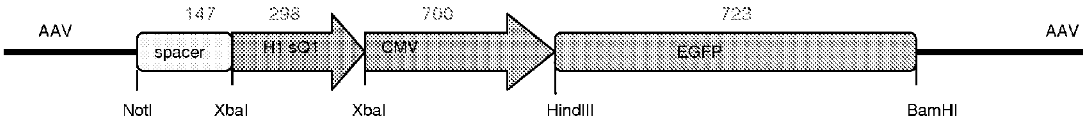
pAAV-shC-EGFP
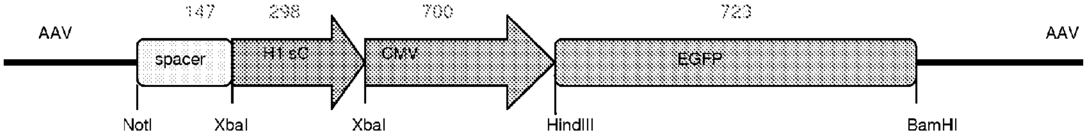
pAAV-shCC-EGFP
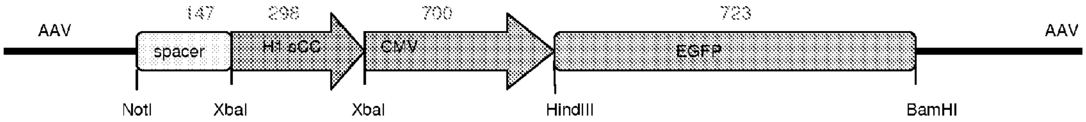
pAAV-shNT-EGFP
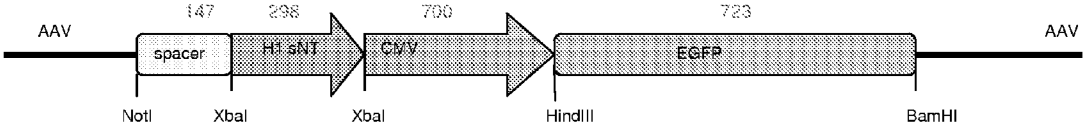

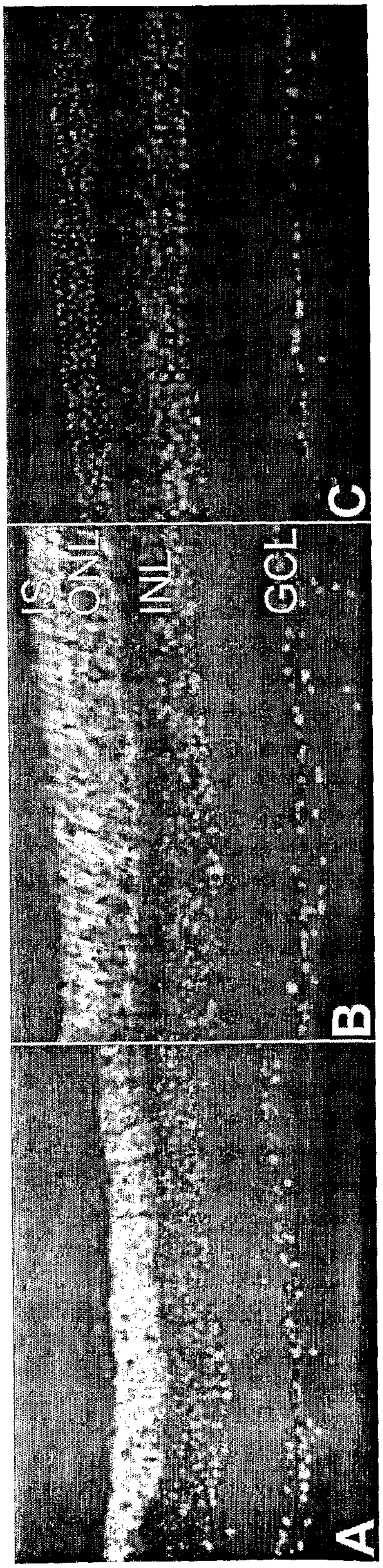
Figure 14A-C

Figure 16: Sequences of exemplary elements that can facilitate modulation of chromatin structures

```
UCOE 1.5 (SEQ ID NO: 422)

CCCCCGGCCC TCCGCGCCTA CAGCTCAAGC CACATCCGAA GGGGGAGGGA
GCCGGGAGCT GCGCGCGGGG CCGCCGGGGG GAGGGGTGGC ACCGCCCACG
CCGGGCGGCC ACGAAGGGCG GGGCAGCGGG CGCGCGCGCG GCGGGGGGAG
GGGCCGGCGC CGCGCCCGCT GGGAATTGGG GCCCTAGGGG GAGGGCGGAG
GCGCCGACGA CCGCGGCACT TACCGTTCGC GGCGTGGCGC CCGGTGGTCC
CCAAGGGGAG GGAAGGGGGA GGCGGGGCGA GGACAGTGAC CGGAGTCTCC
TCAGCGGTGG CTTTTCTGCT TGGCAGCCTC AGCGGCTGGC GCCAAAACCG
GACTCCGCCC ACTTCCTCGC CCGCCGGTGC GAGGGTGTGG AATCCTCCAG
ACGCTGGGGG AGGGGGAGTT GGGAGCTTAA AAACTAGTAC CCCTTTGGGA
CCACTTTCAG CAGCGAACTC TCCTGTACAC CAGGGGTCAG TTCCACAGAC
GCGGGCCAGG GGTGGGTCAT TGCGGCGTGA ACAATAATTT GACTAGAAGT
TGATTCGGGT GTTTCCGGAA GGGGCCGAGT CAATCCGCCG AGTTGGGGCA
CGGAAAACAA AAAGGGAAGG CTACTAAGAT TTTTCTGGCG GGGGTTATCA
TTGGCGTAAC TGCAGGGACC ACCTCCCGGG TTGAGGGGGC TGGATCTCCA
GGCTGCGGAT TAAGCCCCTC CCGTCGGCGT TAATTTCAAA CTGCGCGACG
TTTCTCACCT GCCTTCGCCA AGGCAGGGGC CGGGACCCTA TTCCAAGAGG
TAGTAACTAG CAGGACTCTA GCCTTCCGCA ATTCATTGAG CGCATTTACG
GAAGTAACGT CGGGTACTGT CTCTGGCCGC AAGGGTGGGA GGAGTACGCA
TTTGGCGTAA GGTGGGGCGT AGAGCCTTCC CGCCATTGGC GGCGGATAGG
GCGTTTACGC GACGGCCTGA CGTAGCGGAA GACGCGTTAG TGGGGGGGAA
GGTTCTAGAA AAGCGGCGGC AGCGGCTCTA GCGGCAGTAG CAGCAGCGCC
GGGTCCCGTG CGGAGGTGCT CCTCGCAGAG TTGTTTCTCG AGCAGCGGCA
GTTCTCACTA CAGCGCCAGG ACGAGTCCGG TTCGTGTTCG TCCGCGGAGA
TCTCTCTCAT CTCGCTCGGC TGCGGGAAAT CGGGCTGAAG CGACTGAGTC
CGCGATGGAG GTAACGGGTT TGAAATCAAT GAGTTATTGA AAAGGGCATG
GCGAGGCCGT TGGCGCCTCA GTGGAAGTCG GCCAGCCGCC TCCGTGGGAG
AGAGGCAGGA AATCGGACCA ATTCAGTAGC AGTGGGGCTT AAGGTTTATG
AACGGGGTCT TGAGCGGAGG CCTGAGCGTA CAAACAGCTT CCCCACCCTC
AGCCTCCCGG CGCCATTTCC CTTCACTGGG GGTGGGGGAT GGGGAGCTTT
CACATGGCGG ACGCTGCCCC GCTGGGGTGA AAGTGGGGCG CGGAGGCGGG
AATTCTTATT CCCTTTCTAA AGCACGCTGC TTCGGGGGCC ACGGCGTCTC
C
```

Figure 16 (cont.)

UCOE 2.2 (SEQ ID NO: 423)

AAAACAGCTT CACATGGCTT AAAATAGGGG ACCAATGTCT TTTCCAATCT
AAGTCCCATT TATAATAAAG TCCATGTTCC ATTTTTAAAG GACAATCCTT
TCGGTTTAAA ACCAGGCACG ATTACCCAAA CAACTCACAA CGGTAAAGCA
CTGTGAATCT TCTCTGTTCT GCAATCCCAA CTTGGTTTCT GCTCAGAAAC
CCTCCCTCTT TCCAATCGGT AATTAAATAA CAAAAGGAAA AAACTTAAGA
TGCTTCAACC TTCAACCCCG TTTCGTGACA CTTTGAAAAA AGAATCACCT
CTTGCAAACA CCCGCTCCCG ACCCCCGCCG CTGAAGCCCG GCGTCCAGAG
GCCTAAGCGC GGGTGCCCAC CCCCACCCGG GAGCGCGGGC CTCGTGGTCA
GCGCATCCGC GGGGAGAAAC AAAGGCCGCG GCACGGGGGC TCAAGGGCAC
TGCGCCACAC CGCACGCGCC TACCCCCGCG CGGCCACGTT AACTGGCGGT
CGCCGCAGCC TCGGGACAGC CGGCCGCGCG CCGCCAGGCT CGCGGACGCG
GGACCACGCG CCGCCCTCCG GGAGGCCCAA GTCTCGACCC AGCCCCGCGT
GGCGCTGGGG GAGGGGGCGC CTCCGCCGGA ACGCGGGTGG GGGAGGGGAG
GGGGAAATGC GCTTTGTCTC GAAATGGGGC AACCGTCGCC ACAGCTCCCT
ACCCCCTCGA GGGCAGAGCA GTCCCCCCAC TAACTACCGG GCTGGCCGCG
CGCCAGGCCA GCCGCGAGGC CACCGCCCGA CCCTCCACTC CTTCCCGCAG
CTCCCGGCGC GGGGTCCGGC GAGAAGGGGA GGGGAGGGGA GCGGAGAACC
GGGCCCCCGG GACGCGTGTG GCATCTGAAG CACCACCAGC GAGCGAGAGC
TAGAGAGAAG GAAAGCCACC GACTTCACCG CCTCCGAGCT GCTCCGGGTC
GCGGGTCTGC AGCGTCTCCG GCCCTCCGCG CCTACAGCTC AAGCCACATC
CGAAGGGGGA GGGAGCCGGG AGCTGCGCGC GGGGCCGCCG GGGGGAGGGG
TGGCACCGCC CACGCCGGGC GGCCACGAAG GGCGGGGCAG CGGGCGCGCG
CGCGGCGGGG GGAGGGGCCG GCGCCGCGCC CGCTGGGAAT TGGGGCCCTA
GGGGGAGGGC GGAGGCGCCG ACGACCGCGG CACTTACCGT TCGCGGCGTG
GCGCCCGGTG GTCCCCAAGG GGAGGGAAGG GGGAGGCGGG GCGAGGACAG
TGACCGGAGT CTCCTCAGCG GTGGCTTTTC TGCTTGGCAG CCTCAGCGGC
TGGCGCCAAA ACCGGACTCC GCCCACTTCC TCGCCCGCCG GTGCGAGGGT
GTGGAATCCT CCAGACGCTG GGGGAGGGGG AGTTGGGAGC TTAAAAACTA
GTACCCCTTT GGGACCACTT TCAGCAGCGA ACTCTCCTGT ACACCAGGGG
TCAGTTCCAC AGACGCGGGC CAGGGGTGGG TCATTGCGGC GTGAACAATA
ATTTGACTAG AAGTTGATTC GGGTGTTTCC GGAAGGGGCC GAGTCAATCC
GCCGAGTTGG GGCACGGAAA ACAAAAAGGG AAGGCTACTA AGATTTTTCT
GGCGGGGGTT ATCATTGGCG TAACTGCAGG GACCACCTCC CGGGTTGAGG
GGGCTGGATC TCCAGGCTGC GGATTAAGCC CCTCCCGTCG GCGTTAATTT
CAAACTGCGC GACGTTTCTC ACCTGCCTTC GCCAAGGCAG GGGCCGGGAC
CCTATTCCAA GAGGTAGTAA CTAGCAGGAC TCTAGCCTTC CGCAATTCAT
TGAGCGCATT TACGGAAGTA ACGTCGGGTA CTGTCTCTGG CCGCAAGGGT
GGGAGGAGTA CGCATTTGGC GTAAGGTGGG GCGTAGAGCC TTCCCGCCAT
TGGCGGCGGA TAGGGCGTTT ACGCGACGGC CTGACGTAGC GGAAGACGCG
TTAGTGGGGG GGAAGGTTCT AGAAAAGCGG CGGCAGCGGC TCTAGCGGCA
GTAGCAGCAG CGCCGGGTCC CGTGCGGAGG TGCTCCTCGC AGAGTTGTTT
CTCGAGCAGC GGCAGTTCTC ACTACAGCGC CAGGACGAGT CCGGTTCGTG
TTCGTCCGCG GAGATCTCTC TCATCTCGCT CGGCTGCGGG AAATCGGGCT
GAAGCGACTG ATCTGCAGTC GAGGTCGACG GTATCGAT

Figure 17

GDNF Homo sapiens

ATGAAGTTAT GGGATGTCGT GGCTGTCTGC CTGGTGCTGC TCCACACCGC GTCCGCCTTC
CCGCTGCCCG CCGCAAATAT GCCAGAGGAT TATCCTGATC AGTTCGATGA TGTCATGGAT
TTTATTCAAG CCACCATTAA AAGACTGAAA AGGTCACCAG ATAAACAAAT GGCAGTGCTT
CCTAGAAGAG AGCGGAATCG GCAGGCTGCA GCTGCCAACC CAGAGAATTC CAGAGGAAAA
GGTCGGAGAG GCCAGAGGGG CAAAAACCGG GGTTGTGTCT TAACTGCAAT ACATTTAAAT
GTCACTGACT TGGGTCTGGG CTATGAAACC AAGGAGGAAC TGATTTTTAG GTACTGCAGC
GGCTCTTGCG ATGCAGCTGA GACAACGTAC GACAAAATAT TGAAAAACTT ATCCAGAAAT
AGAAGGCTGG TGAGTGACAA AGTAGGGCAG GCATGTTGCA GACCCATCGC CTTTGATGAT
GACCTGTCGT TTTTAGATGA TAACCTGGTT TACCATATTC TAAGAAAGCA TTCCGCTAAA
AGGTGTGGAT GTATCTGA (SEQ ID NO:424)

Translation:

MKLWDVVAVC LVLLHTASAF PLPAANMPED YPDQFDDVMD FIQATIKRLK
RSPDKQMAVL PRRERNRQAA AANPENSRGK GRRGQRGKNR GCVLTAIHLN
VTDLGLGYET KEELIFRYCS GSCDAAETTY DKILKNLSRN RRLVSDKVGQ
ACCRPIAFDD DLSFLDDNLV YHILRKHSAK RCGCI (SEQ ID NO:425)

---

Homo sapiens ciliary neurotrophic factor (CNTF)
Nucleotide Sequence (603 nt):

ATGGCTTTCA CAGAGCATTC ACCGCTGACC CCTCACCGTC GGGACCTCTG
TAGCCGCTCT ATCTGGCTAG CAAGGAAGAT TCGTTCAGAC CTGACTGCTC
TTACGGAATC CTATGTGAAG CATCAGGGCC TGAACAAGAA CATCAACCTG
GACTCTGCGG ATGGGATGCC AGTGGCAAGC ACTGATCAGT GGAGTGAGCT
GACCGAGGCA GAGCGACTCC AAGAGAACCT TCAAGCTTAT CGTACCTTCC
ATGTTTTGTT GGCCAGGCTC TTAGAAGACC AGCAGGTGCA TTTTACCCCA
ACCGAAGGTG ACTTCCATCA AGCTATACAT ACCCTTCTTC TCCAAGTCGC
TGCCTTTGCA TACCAGATAG AGGAGTTAAT GATACTCCTG GAATACAAGA
TCCCCCGCAA TGAGGCTGAT GGGATGCCTA TTAATGTTGG AGATGGTGGT
CTCTTTGAGA AGAAGCTGTG GGGCCTAAAG GTGCTGCAGG AGCTTTCACA
GTGGACAGTA AGGTCCATCC ATGACCTTCG TTTCATTTCT TCTCATCAGA
CTGGGATCCC AGCACGTGGG AGCCATTATA TTGCTAACAA CAAGAAAATG
TAG (SEQ ID NO:426)

Translation:

MAFTEHSPLT PHRRDLCSRS IWLARKIRSD LTALTESYVK HQGLNKNINL
DSADGMPVAS TDQWSELTEA ERLQENLQAY RTFHVLLARL LEDQQVHFTP
TEGDFHQAIH TLLLQVAAFA YQIEELMILL EYKIPRNEAD GMPINVGDGG

Figure 17 (cont.)

LFEKKLWGLK VLQELSQWTV RSIHDLRFIS SHQTGIPARG SHYIANNKKM (SEQ ID NO:427)

---

NM_170735 744 bp mRNA linear PRI
Homo sapiens brain-derived neurotrophic factor (BDNF)

ATGACCATCC TTTTCCTTAC TATGGTTATT TCATACTTTG GTTGCATGAA
GGCTGCCCCC ATGAAAGAAG CAAACATCCG AGGACAAGGT GGCTTGGCCT
ACCCAGGTGT GCGGACCCAT GGGACTCTGG AGAGCGTGAA TGGGCCCAAG
GCAGGTTCAA GAGGCTTGAC ATCATTGGCT GACACTTTCG AACACGTGAT
AGAAGAGCTG TTGGATGAGG ACCAGAAAGT TCGGCCCAAT GAAGAAAACA
ATAAGGACGC AGACTTGTAC ACGTCCAGGG TGATGCTCAG TAGTCAAGTG
CCTTTGGAGC CTCCTCTTCT CTTTCTGCTG GAGGAATACA AAAATTACCT
AGATGCTGCA AACATGTCCA TGAGGGTCCG GCGCCACTCT GACCCTGCCC
GCCGAGGGGA GCTGAGCGTG TGTGACAGTA TTAGTGAGTG GGTAACGGCG
GCAGACAAAA AGACTGCAGT GGACATGTCG GGCGGGACGG TCACAGTCCT
TGAAAAGGTC CCTGTATCAA AAGGCCAACT GAAGCAATAC TTCTACGAGA
CCAAGTGCAA TCCCATGGGT TACACAAAAG AAGGCTGCAG GGGCATAGAC
AAAAGGCATT GGAACTCCCA GTGCCGAACT ACCCAGTCGT ACGTGCGGGC
CCTTACCATG GATAGCAAAA AGAGAATTGG CTGGCGATTC ATAAGGATAG
ACACTTCTTG TGTATGTACA TTGACCATTA AAAGGGGAAG ATAG (SEQ ID NO:428)

Translation:
MTILFLTMVI SYFGCMKAAP MKEANIRGQG GLAYPGVRTH GTLESVNGPK
AGSRGLTSLA DTFEHVIEEL LDEDQKVRPN EENNKDADLY TSRVMLSSQV
PLEPPLLFLL EEYKNYLDAA NMSMRVRRHS DPARRGELSV CDSISEWVTA
ADKKTAVDMS GGTVTVLEKV PVSKGQLKQY FYETKCNPMG YTKEGCRGID
KRHWNSQCRT TQSYVRALTM DSKKRIGWRF IRIDTSCVCT LTIKRGR (SEQ ID NO:429)

---

HSU78110
NM_004558 1159 bp mRNA linear PRI
Homo sapiens neurturin (NRTN),

ATGCAGCGCT GGAAGGCGGC GGCCTTGGCC TCAGTGCTCT GCAGCTCCGT
GCTGTCCATC TGGATGTGTC GAGAGGGCCT GCTTCTCAGC CACCGCCTCG
GACCTGCGCT GGTCCCCCTG CACCGCCTGC CTCGAACCCT GGACGCCCGG
ATTGCCCGCC TGGCCCAGTA CCGTGCACTC CTGCAGGGGG CCCCGGATGC
GATGGAGCTG CGCGAGCTGA CGCCCTGGGC TGGGCGGCCC CCAGGTCCGC

Figure 17 (cont.)

GCCGTCGGGC GGGGCCCCGG CGGCGGCGCG CGCGTGCGCG GTTGGGGGCG
CGGCCTTGCG GGCTGCGCGA GCTGGAGGTG CGCGTGAGCG AGCTGGGCCT
GGGCTACGCG TCCGACGAGA CGGTGCTGTT CCGCTACTGC GCAGGCGCCT
GCGAGGCTGC CGCGCGCGTC TACGACCTCG GGCTGCGACG ACTGCGCCAG
CGGCGGCGCC TGCGGCGGGA GCGGGTGCGC GCGCAGCCCT GCTGCCGCCC
GACGGCCTAC GAGGACGAGG TGTCCTTCCT GGACGCGCAC AGCCGCTACC
ACACGGTGCA CGAGCTGTCG GCGCGCGAGT GCGCCTGCGT GTGA (SEQ ID NO:430)

Translation:
MQRWKAAALA SVLCSSVLSI WMCREGLLLS HRLGPALVPL HRLPRTLDAR
IARLAQYRAL LQGAPDAMEL RELTPWAGRP PGPRRRAGPR RRRARARLGA
RPCGLRELEV RVSELGLGYA SDETVLFRYC AGACEAAARV YDLGLRRLRQ
RRRLRRERVR AQPCCRPTAY EDEVSFLDAH SRYHTVHELS ARECACV (SEQ ID NO:431)

GENETIC SUPPRESSION AND REPLACEMENT

CROSS REFERENCE TO RELATED APPLICATIONS

This application is a 371 National Phase Entry Application of International Application No. PCT/GB2008/001310 filed Apr. 14, 2008, which designated the U.S., and which claims the benefit of priority under 35 U.S.C. §119(e) of U.S. Provisional No. 60/923,067 filed Apr. 12, 2007, the contents of which are incorporated herein by reference.

FIELD OF THE INVENTION

The invention relates to mutation independent suppression and replacement of disease-causing mutant genes.

BACKGROUND OF THE INVENTION

Many mutation-based diseases are more genetically diverse than can be predicted from clinical presentation. Some mutation-based diseases are Mendelian and involve the inheritance of a single mutant gene, others are polygenic or multifactorial and involve multiple genetic insults. In the case of some Mendelian disorders, many different mutations within the same gene can give rise to, or can predispose an individual to, a disease. Similarly, for some multifactorial disorders, many different mutations within one or more genes can predispose an individual to a disease or can act in an additive manner with other genetic and environmental influences to give rise to a disease. This mutational heterogeneity underlying the molecular etiologies of many diseases represents a significant barrier to the development of therapies for such diseases. Moreover, genetic strategies for suppressing and replacing a mutant protein face many challenges with regard to the effectiveness of the machinery used to deliver and regulate the expression of the suppressor and replacement nucleic acids in vivo. Therefore, a need exists for effective mutation-independent therapeutics that achieve effective suppression and replacement.

SUMMARY OF THE INVENTION

The invention relates to gene suppression and replacement. In particular, the invention relates to enhanced expression of suppression agents for suppressing gene expression in a cell and in vivo and of replacement nucleic acids that are not inhibited and/or are partially inhibited by the suppression agent. Expression vectors used to express the suppression agent(s) and replacement nucleic acids comprise regulatory elements to optimize expression of the suppression agent(s) and or replacement nucleic acids.

The invention embodies use of replacement genes using sequences to enhance expression of replacement genes from viral and or non-viral vectors. In a further aspect the invection relates to enhanced expression of suppression agent(s) and or replacement genes from viral or and non-viral vectors. In a further embodiment the invention relates to enhanced expression of suppression agent(s) and or replacement genes and or genes encoding neurotrophic factors from viral and or non-viral vectors.

In one aspect the invention relates to use of conserved sequences from retinal genes to enhance expression of suppression agent(s) and or replacement genes and or genes encoding neurotrophic factors. The use of such conserved sequences has been found to result in surprisingly efficient expression. In a particular aspect the invention relates to use of conserved sequences from retinal genes to enhance expression of suppression agent(s) and or replacement genes and or genes encoding neurotrophic factors from adeno associated virus (AAV) vectors. In another aspect the invention provides vectors for expression of suppression agent(s) and or replacement gene(s) and or genes encoding neurotrophic factors using regulatory sequences from retinal gene(s) and or non-retinal gene(s) and or ubiquitously expressing genes to enhance expression from vectors.

In one aspect, the invention provides vectors for expressing a suppression agent for a disease causing gene and/or a replacement nucleic acid that is not recognized or is partially recognized by the suppression agent.

In an embodiment, the vector comprises an enhancer sequence, such as, for example, a sequence of SEQ ID NOs: 402-413 or functional variants or equivalents thereof. In another embodiment, the vector comprises at least one regulatory element selected from the group consisting of a promoter, a stuffer, an insulator, a silencer, an intron sequence, a post translational regulatory element, a polyadenylation site, and a transcription factor binding site.

In another embodiment, the vector comprises at least one of conserved regions A through I from the rhodopsin gene, as represented by SEQ ID NOs: 92-99, or functional variant or equivalent thereof. In another embodiment, the vector comprises at least one transcription factor binding site sequence selected from the group consisting of SEQ ID NOs: 100-401, or functional variant or equivalent thereof.

The suppression agent may be a nucleic acid, protein, amino acid(s), antibody, aptamer, or any such agent that can bind to and inhibit a DNA, RNA, or protein. In an embodiment, the suppression agent is a siRNA selected from the group consisting of SEQ ID NOs: 1, 3, 5, 7, 9, 11, 13, 15, 17, 19, 21, 23, 25, 27, 29, 31, 33, 35-67, 75, 77, 79, 81, 83, 85, and 414-421 or functional variant or equivalent thereof.

The replacement nucleic acid is not recognized or is recognized partially by the suppression effector, because its sequence has been altered such that it cannot bind or binds less efficiently to the suppression agent but still encodes a normal or enhanced gene product. In an embodiment, the replacement nucleic acid is a siRNA selected from the group consisting of SEQ ID NOs: 2, 4, 6, 8, 10, 12, 14, 16, 18, 20, 22, 24, 26, 28, 30, 32, 34, 68, 76, 78, 80, 82, 84, and 86, or functional variant or equivalent thereof.

In an embodiment, the invention provides vectors, such as viral vectors, that comprise a suppression agent and/or a replacement nucleic acid. For example, the vector comprises at least one suppression agent nucleotide sequence selected from the group consisting of SEQ ID NOs: 1, 3, 5, 7, 9, 11, 13, 15, 17, 19, 21, 23, 25, 27, 29, 31, 33, 35-67, 75, 77, 79, 81, 83, and 85, or functional variant or equivalent thereof, and at least one replacement nucleic acid nucleotide sequence selected from the group consisting of SEQ ID NOs: 2, 4, 6, 8, 10, 12, 14, 16, 18, 20, 22, 24, 26, 28, 30, 32, 34, 68, 76, 78, 80, 82, 84, and 86, or functional variant or equivalent thereof.

In another aspect, the invention provides therapeutic compositions comprising at least one vector comprising at least one suppression agent nucleotide sequence selected from the group consisting of SEQ ID NOs: 1, 3, 5, 7, 9, 11, 13, 15, 17, 19, 21, 23, 25, 27, 29, 31, 33, 35-67, 75, 77, 79, 81, 83, 85 and 414-421 or functional variant or equivalent thereof, and at least one replacement nucleic acid nucleotide sequence selected from the group consisting of SEQ ID NOs: 2, 4, 6, 8, 10, 12, 14, 16, 18, 20, 22, 24, 26, 28, 30, 32, 34, 68, 76, 78, 80, 82, 84, and 86, or functional variant or equivalent thereof. In an embodiment, the vector of the therapeutic composition further comprises a regulatory element selected from the group consisting of an enhancer, a promoter, a stuffer, an insulator, a silencer, an antirepressor, an intron sequence, a post translational regulatory element, a polyadenylation signal (e.g. minimal poly A), a conserved region A through I, and a transcription factor binding site.

In another aspect the invention provides suppression and replacement in conjunction with provision of a gene encoding a neurotrophic/neuroprotective factor(s).

In another aspect, the invention provides cells comprising the nucleic acids and vectors of the invention.

In another aspect, the invention provides transgenic animals comprising the nucleic acids and vectors of the invention.

In yet another aspect, the invention provides methods of suppressing the expression of a mutant gene and replacing expression of the mutant gene with a replacement nucleic acid, the method comprising administering to a mammal a therapeutic composition of the invention.

In yet another aspect, the invention provides methods of suppressing the expression of a mutant gene and replacing expression of the mutant gene with a replacement nucleic acid in conjunction with a gene encoding a neurotrophic/neuropeotective factor(s), the method comprising administering to a mammal a therapeutic composition of the invention.

BRIEF DESCRIPTION OF THE DRAWINGS

The foregoing and other objects, features and advantages of the present invention, as well as the invention itself, will be more fully understood from the following description of preferred embodiments when read together with the accompanying drawings, in which:

FIG. 1A is a diagrammatic representation of a RHO suppressor-EGFP construct shBB-EGFP (shQ1-EGFP and shNT-EGFP have the same format). shRNAs were expressed from the H1 promoter and EGFP from the CMV immediate early promoter. The SV40 polyadenylation signal was located at the 3' end of the EGFP gene. FIG. 1B illustrates a two component suppression and replacement construct shBB-rBB (shQ1-rQ1 and shNT-rBB have the same format). Suppressors were expressed from the H1 promoter and replacement RHO cDNAs from a 1.7 kb mouse rhodopsin promoter (rhoP). Polyadenylation signals of the RHO gene were included in the 1829 by fragment. HGH int: human growth hormone intron. For tissue culture and retinal explant experiments these constructs were maintained in pEGFP-1 (A) or a CMV-promoterless derivative of pcDNA-3.1-(B) and for in vivo experiments in the AAV vector. Restriction enzyme sites used for cloning are indicated. Promoters were separated by spacer DNA fragments. Numbers indicate molecular sizes (bp) and arrows indicate direction of transcription.

FIG. 4B shows a bar chart which indicates RHO mRNA levels in retinal explant cells expressing sNT-EGFP, sBB-EGFP and sQ1-EGFP, quantified by real time RT-PCR. Error bars represent SD values.

shQ1: 20.6% when compared to the non-targeting control shNT which was set at 100% expression.

Figure 6E:
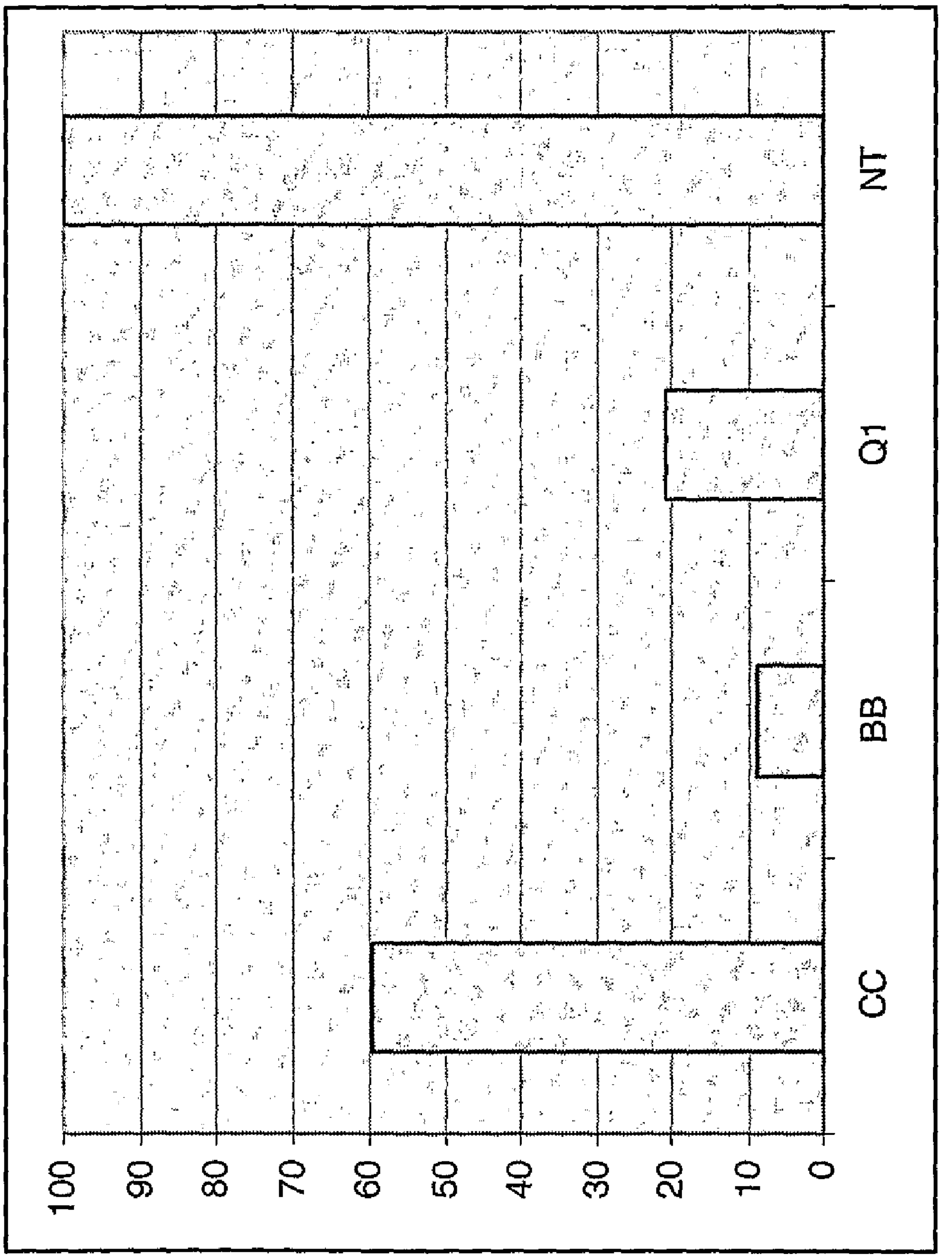
FIG. 6E illustrates RNAi-mediated suppression of human rhodopsin in RHO-M mice. RHO-M mice were subretinally injected with AAV2/5 vectors carrying an shRNA-based suppressor and an EGFP reporter gene. Mice were sacrificed 14 days post-injection, retinas taken and retinal cells dissociated as in Palfi et al. 2006. RNAi-mediated suppression was evaluated using real-time RT-PCR assays. Retinal cells transduced with AAV-shBB-EGFP, AAV-shCC-EGFP and AAV-shQ1-EGFP vs AAV-shNT-EGFP were FACS sorted from adult RhoM mouse retinas, 14 days post subretinal injection. Of note is that AAV-shCC-EGFP suppresses RHO less in RHO-M mice due to the presence of a 2 bp mismatch in the human rhodopsin transgenic in RHO-M animals. Levels of rhodopsin expression were shCC: 59.73%; shBB: 8.77%.
Figure 6F:
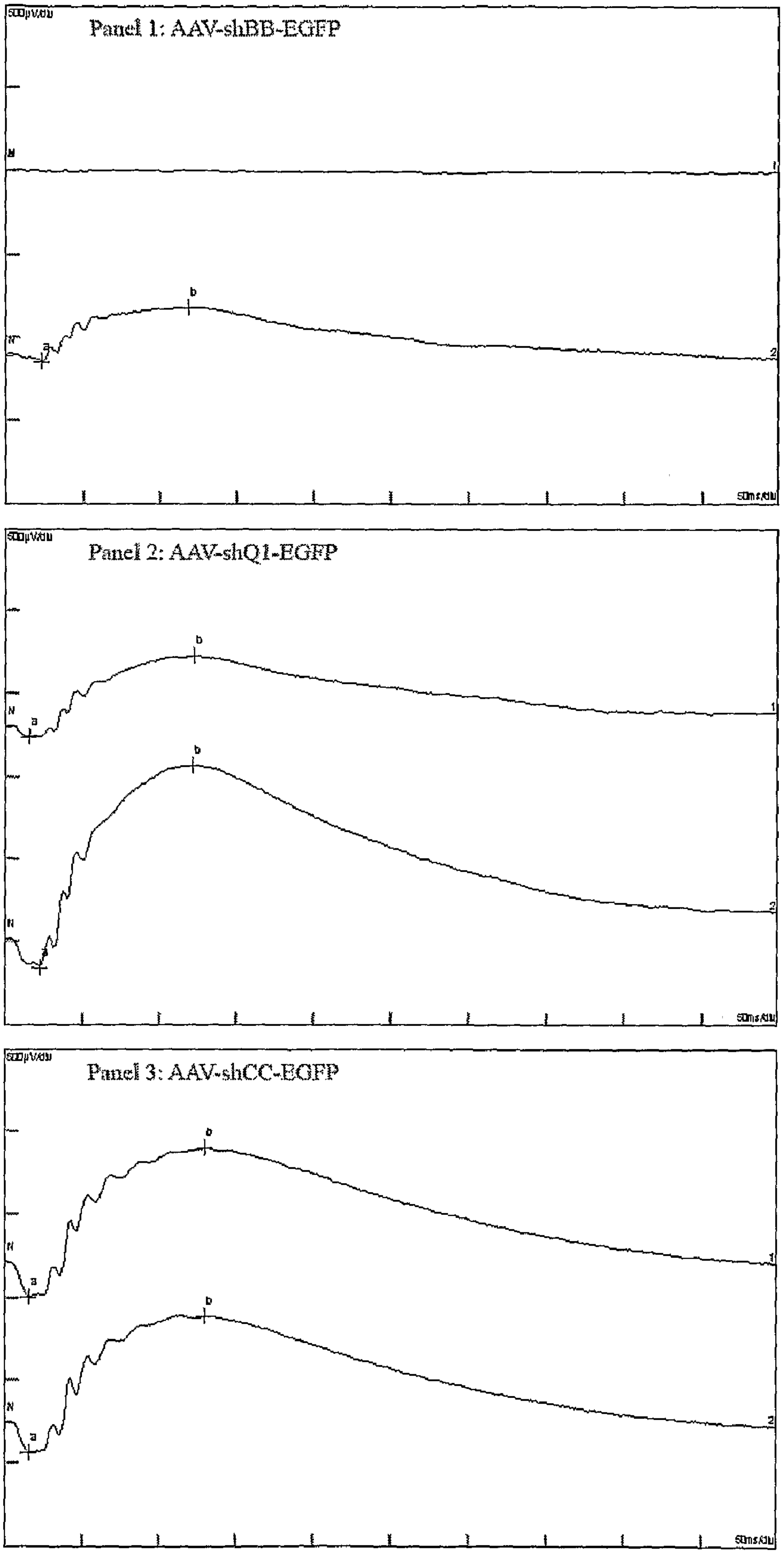
FIG. 6A-D illustrates retinal histology and ERG analysis of RHO-M mouse. Two month old rho+/+(wild type), rho+/−, NHR+/− rho−/− and RHO-M+/− rho−/− mice were analysed by retinal histology and ERG (n=8). A, B and C: rhodopsin immunocytochemistry (Cy3) showing similar rod outer segment (ROS) labelling in rho+/+, NHR+/− rho−/− and RHO-M+/− rho−/− retinas respectively. Nuclear layers were stained with DAPI. D: representative rod-isolated ERG responses. ONL: outer nuclear layer. INL: inner nuclear layer. GCL: ganglion cell layer.

FIG. 6F illustrates depression of the ERG response in RHO-M eyes that have received AAV-shBB-EGFP or AAV-shQ1-EGFP when compared to eyes subretinally injected with AAV-shNT-EGFP. The top tracing in each panel represents the right eye which received the targeting AAV-shRNA vector and the bottom tracing in each panel represents the left eye which received the control non-targeting AAV-shNT vector. In contrast no reduction/depression of the ERG was observed in RHO-M mice subretinally injected with AAV-shCC-EGFP vector.

Figure 7:
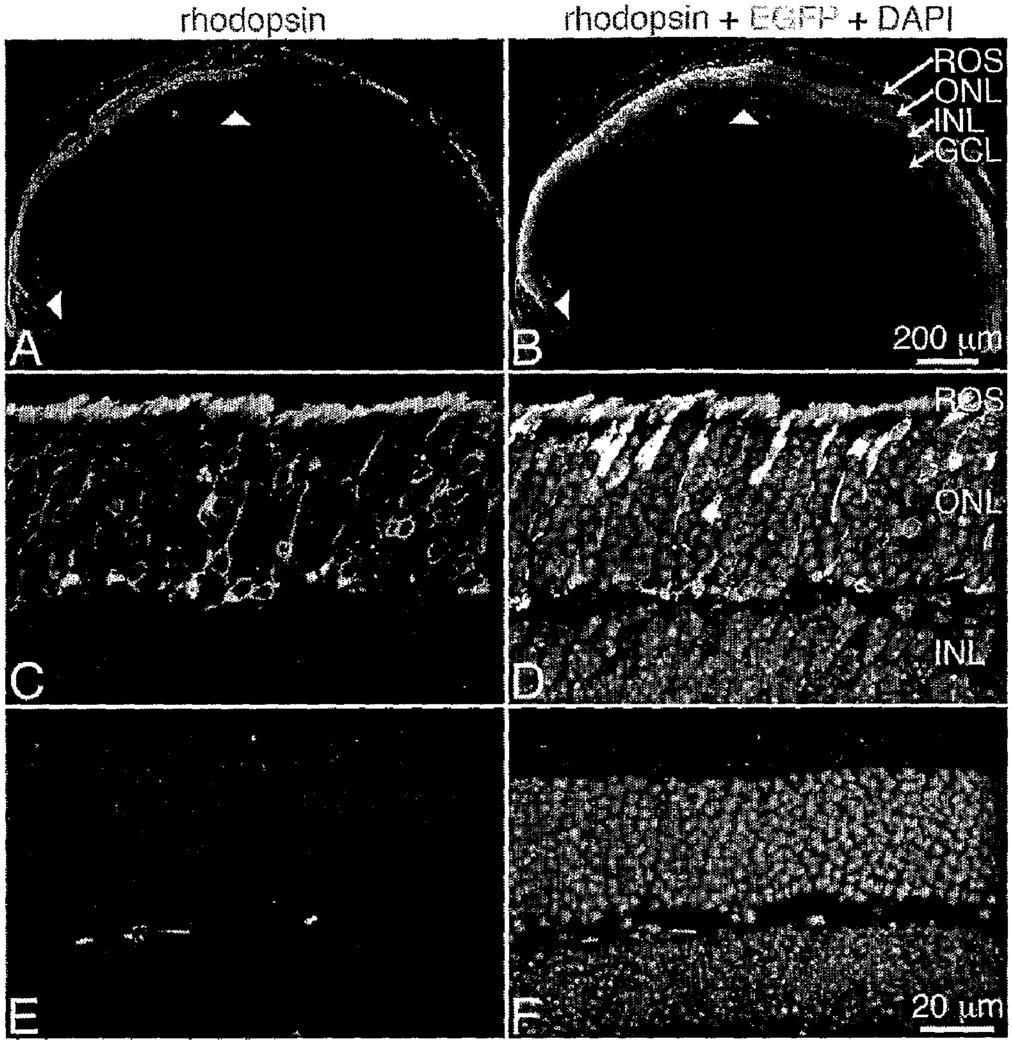

FIG. 7 illustrates the expression of replacement RHO in vivo. Ten day old rho−/− mice were subretinally injected with a 1:1 mixture of 2 μl $2\times10^{12}$ vp/ml of two AAV vectors, AAV-EGFP (also termed AAV-CMV-EGFP) and AAV-shBB-rBB (also termed AAV-BB8). Rhodopsin, EGFP protein and nuclei were detected by Cy3-labeled immunocytochemistry, native fluorescence and nuclear DAPI staining respectively. Low magnification images show a cross section of a whole injected eye with arrowheads indicating the transduced area (A and B). High magnification laser scanning micrographs show transduced (C and D) and non-transduced (E and F) areas. INL: inner nuclear layer. GCL: ganglion cell layer. ROS: rod outer segments. ONL: outer nuclear layer. FIG. 7 provides evidence of rhodopsin protein expression from replacement genes in retinal sections obtained from rho−/− mice subretinally injected with AAV2/5 suppression and replacement vectors.

Figure 8:
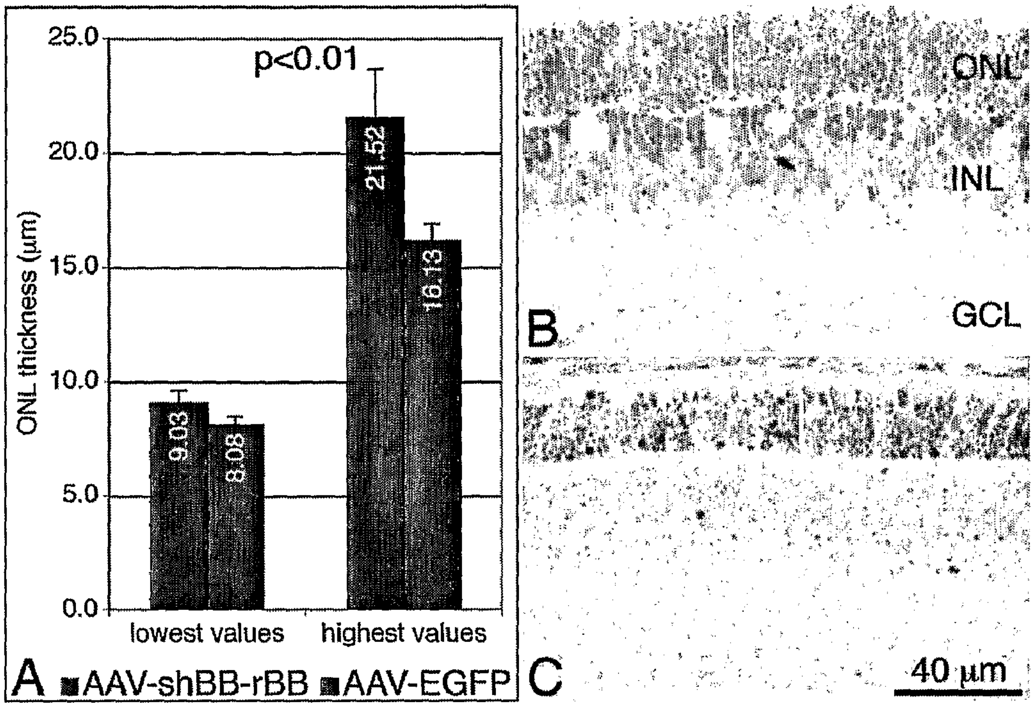

FIG. 8 illustrates the histology of AAV-transduced Pro23His retinas. Newborn Pro23His+/− rho+/− mice were subretinally injected with 1 μl $2\times10^{12}$ vp/ml AAV-shBB-rBB or AAV-EGFP (n=6). Ten days post-transduction eyes were processed for semi-thin sectioning and stained with toluidine blue. Approximately 40 measurements in three layers per eye of outer nuclear layer (ONL) thickness (μm) were taken. A: bars represent ONL thickness, of the central meridian of the eye, of the lowest and highest 15% values ($p<0.01$). B and C: representative images of AAV-shBB-rBB- and AAV-EGFP-(control) injected sections corresponding to highest ONL thickness values. Yellow arrows indicate ONL thickness. INL: inner nuclear layer. GCL: ganglion cell layer. Error bars represent SD values.

Figure 9:
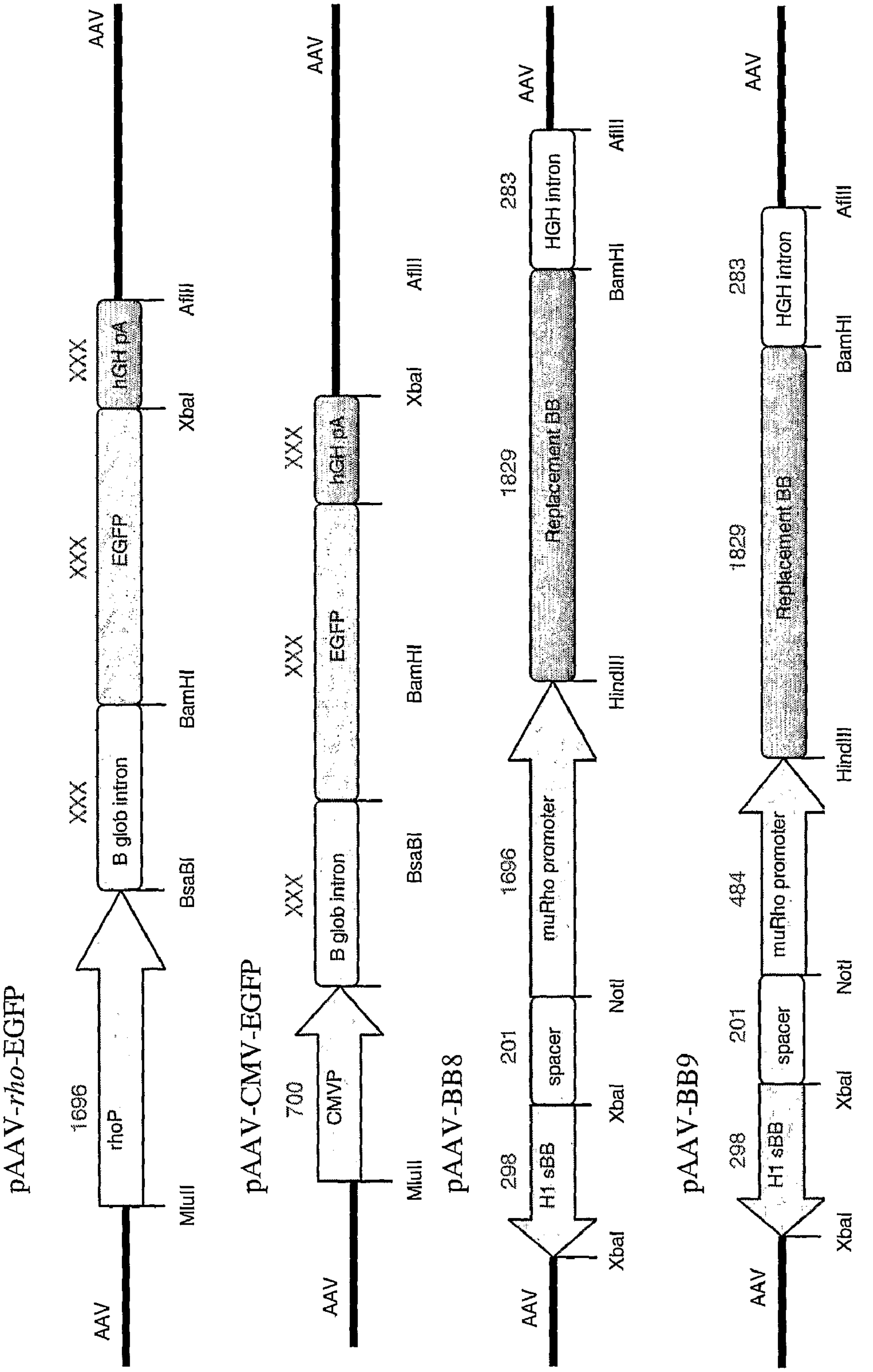
Figure 9:
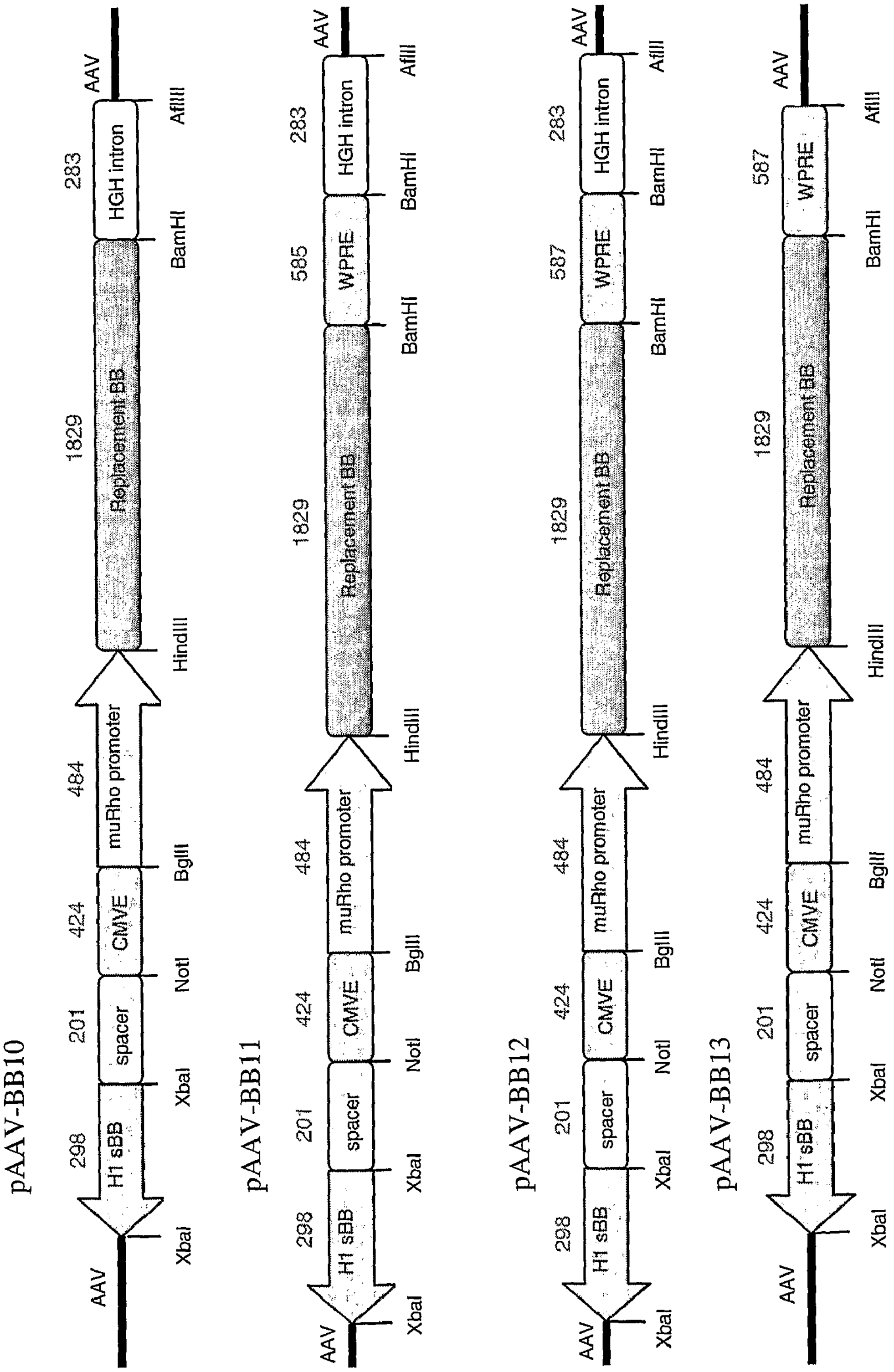
Figure 9:
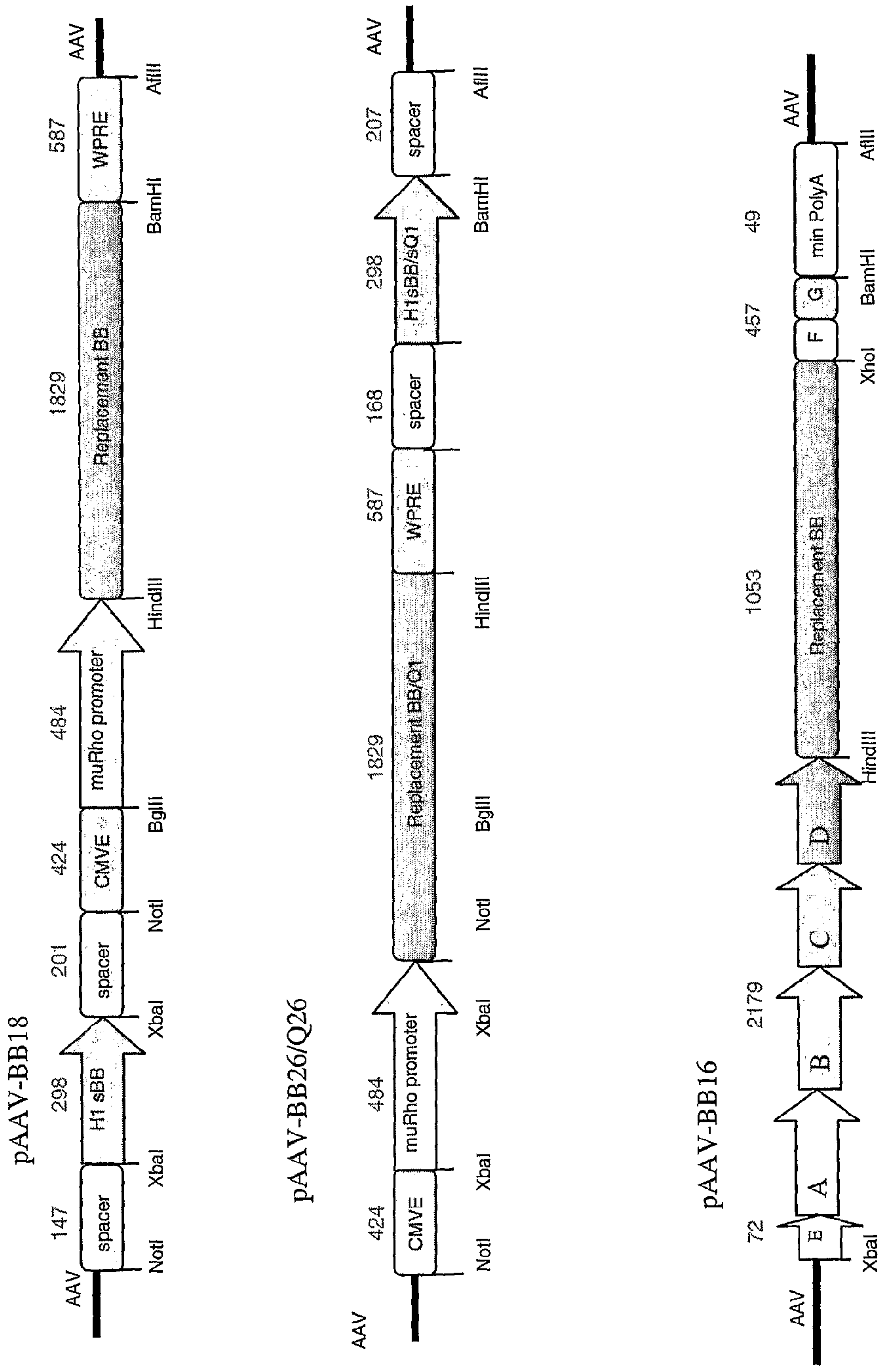
Figure 9:
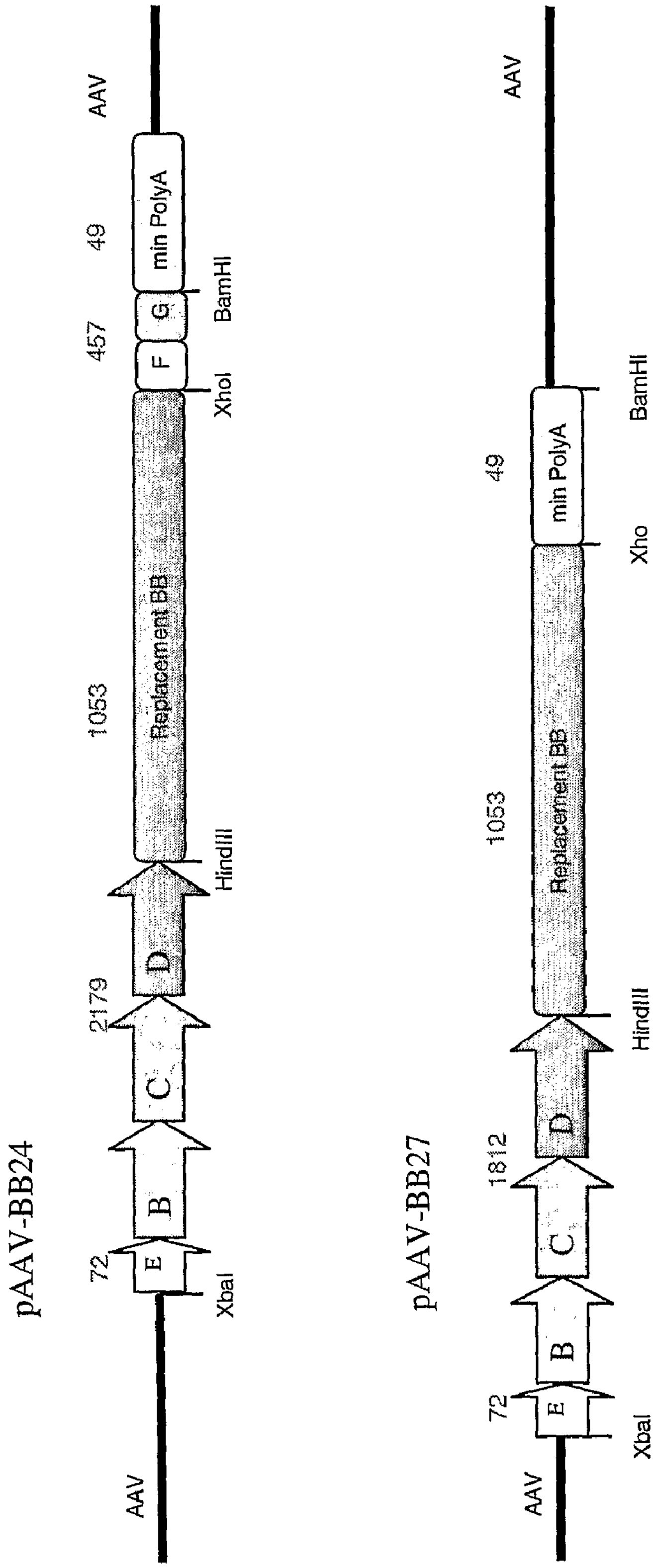

FIG. 9 illustrates suppression and/or replacement constructs used to generate recombinant AAV2/5 viruses using the procedures provided in Example 1. RHO suppression and or replacement constructs, pAAV-BB8, pAAV-BB9, pAAV-BB10, pAAV-BB11, pAAV-BB12, pAAV-BB13, pAAV-BB18, pAAV-BB26/Q26, pAAV-BB16, pAAV-BB24 and pAAV-BB27. Illustrations of some control constructs are also provided (pAAV-rho-EGFP and pAAV-CMV-EGFP). Suppression constructs with EGFP reporter genes are also provided (pAAV-shBB-EGFP, pAAV-shQ1-EGFP, pAAV-shCC-EGFP). Suppressors were expressed from the H1 promoter and replacement RHO cDNAs from differently sized mouse rhodopsin promoter sequences. HGH int: human growth hormone intron. CRX-NRL indicates enhancer element SEQ ID NO: 94. Restriction enzyme sites used for cloning are indicated. Promoters were separated by spacer DNA fragments. Numbers indicate molecular sizes (bp) and arrows indicate direction of transcription. Notably, any combination of the elements and conserved regions outlined and indeed other elements that can modulate gene expression could be used in the invention to exert control over expression of suppression and or replacement components.

Figure 10:
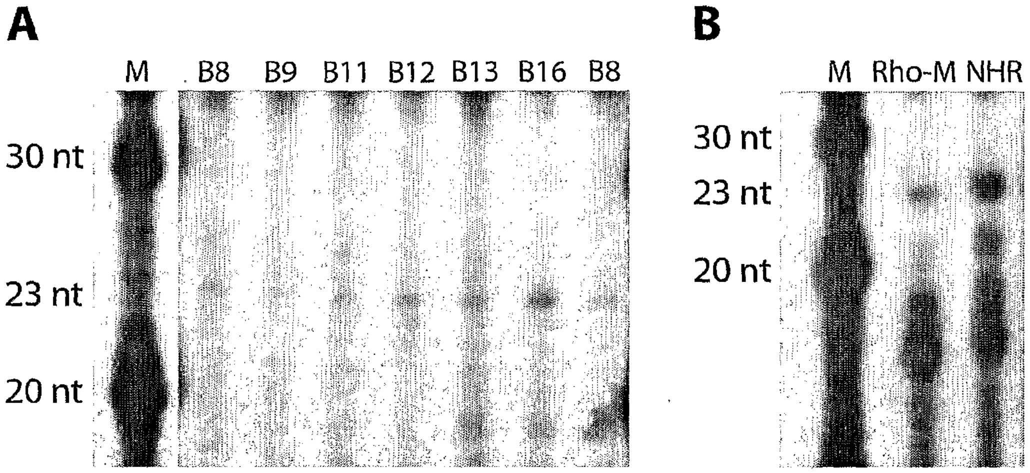

FIG. 10 illustrates a comparison of levels of expression from the Rho-M transgene versus that obtained from the suppression and replacement constructs in AAV2/5 and represented in FIG. 9, using RNAse protection. FIG. 10 illustrates that the suppression and replacement constructs (see FIG. 9) engineered into AAV2/5, AAV-BB8, AAV-BB10, AAV-BB11, AAV-BB12, AAV-BB13 and AAV-BB16 express the human rhodopsin replacement gene in RNA extracted from 129 wild type mice subretinally injected with suppression and or replacement constructs. (Lanes with material from mouse eyes injected with AAV-BB8 are indicated by BB8, AAV-BB10 by BB10, AAV-BB11 by BB11 etc. The plasmid constructs used to generate AAV vectors are written in the format pAAV as presented in FIG. 9). BB8, BB10 and BB11 express rhodopsin at lower levels than BB12, BB13 and BB16.

Figure 11:
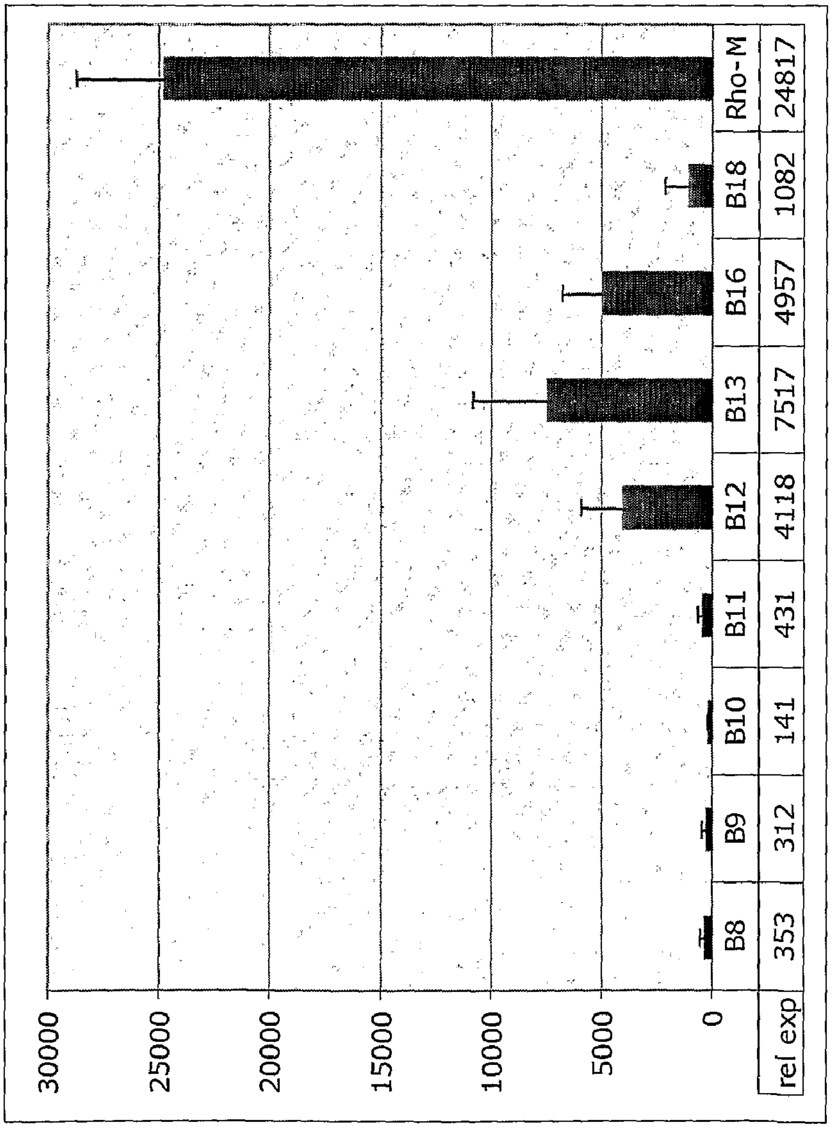

FIG. 11 provides a comparative analysis of rhodopsin expression from rAAV2/5 suppression and replacement vectors using real time RT-PCR. FIG. 11 illustrates replacement rhodopsin expression levels in RNA extracted from 129 wild type mice subretinally injected with suppression and/or replacement constructs. Expression levels were also determined in Rho-M transgenic mice which express a rhodopsin replacement construct rCC and display normal retinal function. Suppression and replacement constructs BB12, BB13, BB16 and BB18 express approximately in the same order of magnitude as levels of replacement rhodopsin transcript in Rho-M mice, indicating that enhanced replacement constructs with enhancer elements and conserved regions may express sufficient levels of rhodopsin to sustain a functional retina in vivo. (Lanes with material from mouse eyes injected with AAV-BB8 are indicated by BB8, AAV-BB10 by BB10, AAV-BB11 by BB11 etc.)

Figure 12:
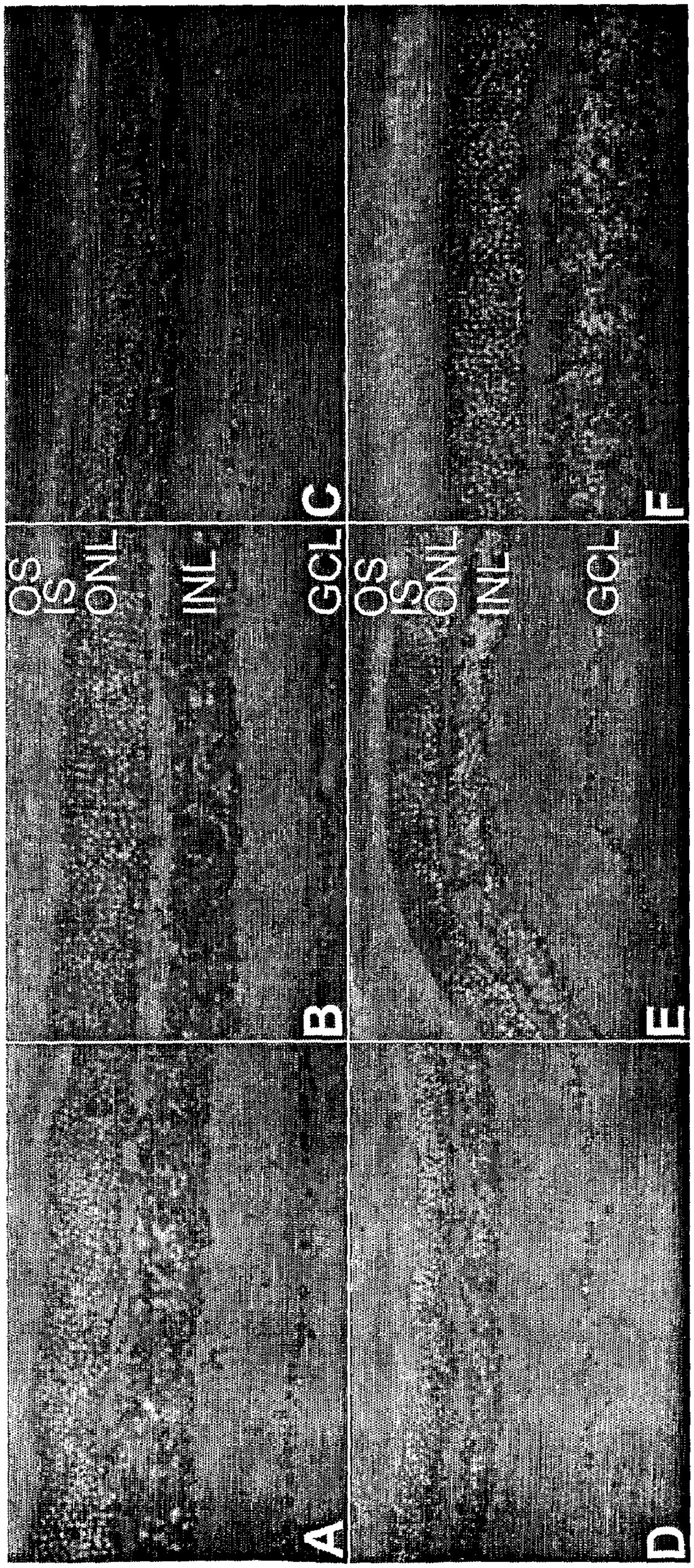

FIG. 12 illustrates retinal histology of adult wild type retinas were subretinally injected with 2 ul of $2\times10^{12}$ particle/ml of different replacement-RHO AAV vectors (see FIG. 9). Two weeks post-injection transduced eyes were removed, fixed in 4% paraformaldehyde and cryosectioned (12 um). Subsequently, sections were stained with human specific anti-RHO antibody to visualize expression of replacement-RHO using Cy3 label (red) on the secondary antibody; cell nuclei were counterstained with DAPI (blue). A: AAV-BB8, B: AAV-BB13, C: AAV-BB24, D: AAV-Q8, E: AAV-Q26, F: retina from uninjected RhoM transgenic mouse expressing RHO (positive control). Sections indicate different levels of RHO expression in the sections. OS: photoreceptor outer segments; IS: photoreceptor inner segments; ONL: outer nuclear layer; INL: inner nuclear layer; GCL: ganglion cell layer.

Figure 13:
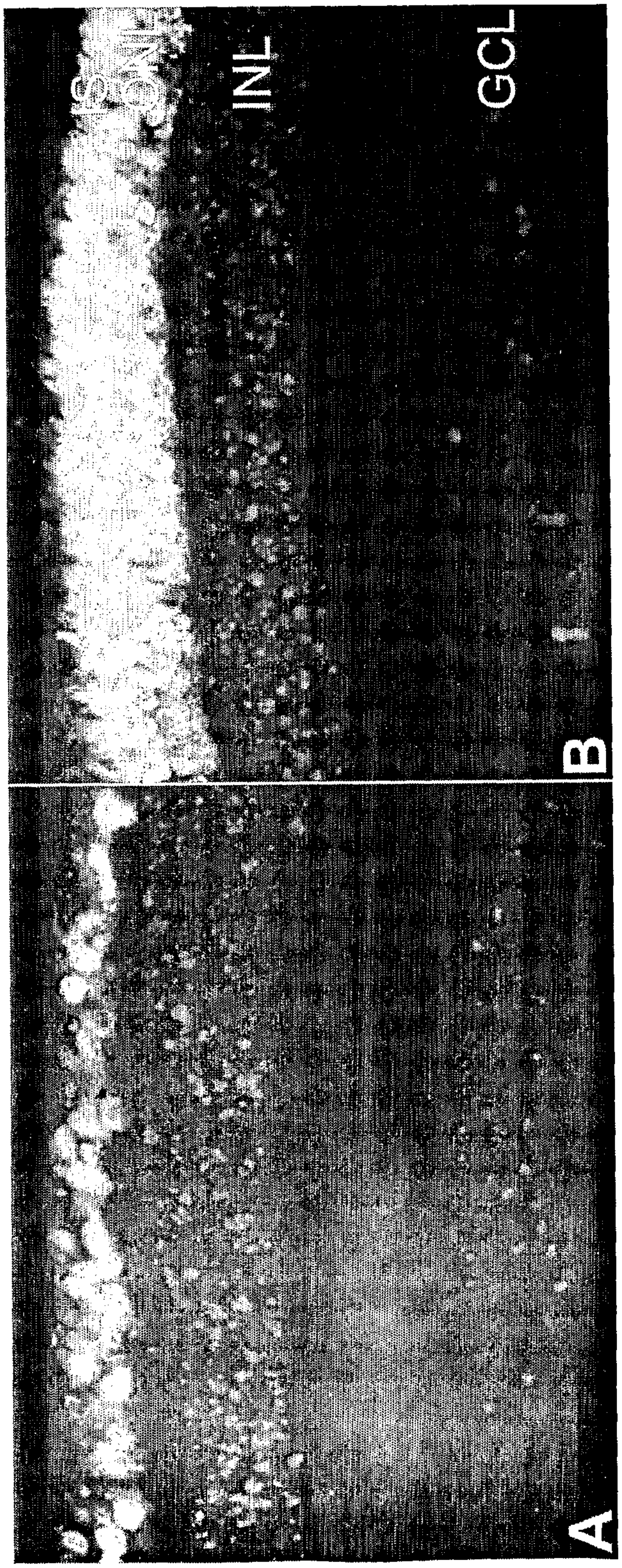

FIG. 13 illustrates retinal histology of adult NHR transgenic mice on a rho−/− background, therefore expressing normal human RHO but not mouse rho. These mice were transduced by subretinal injection of 2 ul of $2\times10^{12}$ particle/ml of AAV-shQ1-EGFP (A) or AAV-shNT-EGFP (B). Two weeks after injection, eyes were removed, fixed in 4% paraformaldehyde and cryosectioned AAV-shQ1-EGFP expresses shRNA-Q1, which targets RHO, while AAV-shNT-EGFP expresses a non-targeting shRNA (FIG. 9 illustrates exemplary constructs). Both constructs express EGFP allowing tracking the transduced cell populations (green). Sections were counterstained DAPI (blue) to label position of the nuclear layers. A significant reduction in the photoreceptor cell number in the transduced part of the outer nuclear layer is apparent in the AAV-shQ1-EGFP injected (A) retinas compared to those of injected with AAV-shNT-EGFP (B). IS: photoreceptor inner segments; ONL: outer nuclear layer; INL: inner nuclear layer; GCL: ganglion cell layer.

Figure 14D:
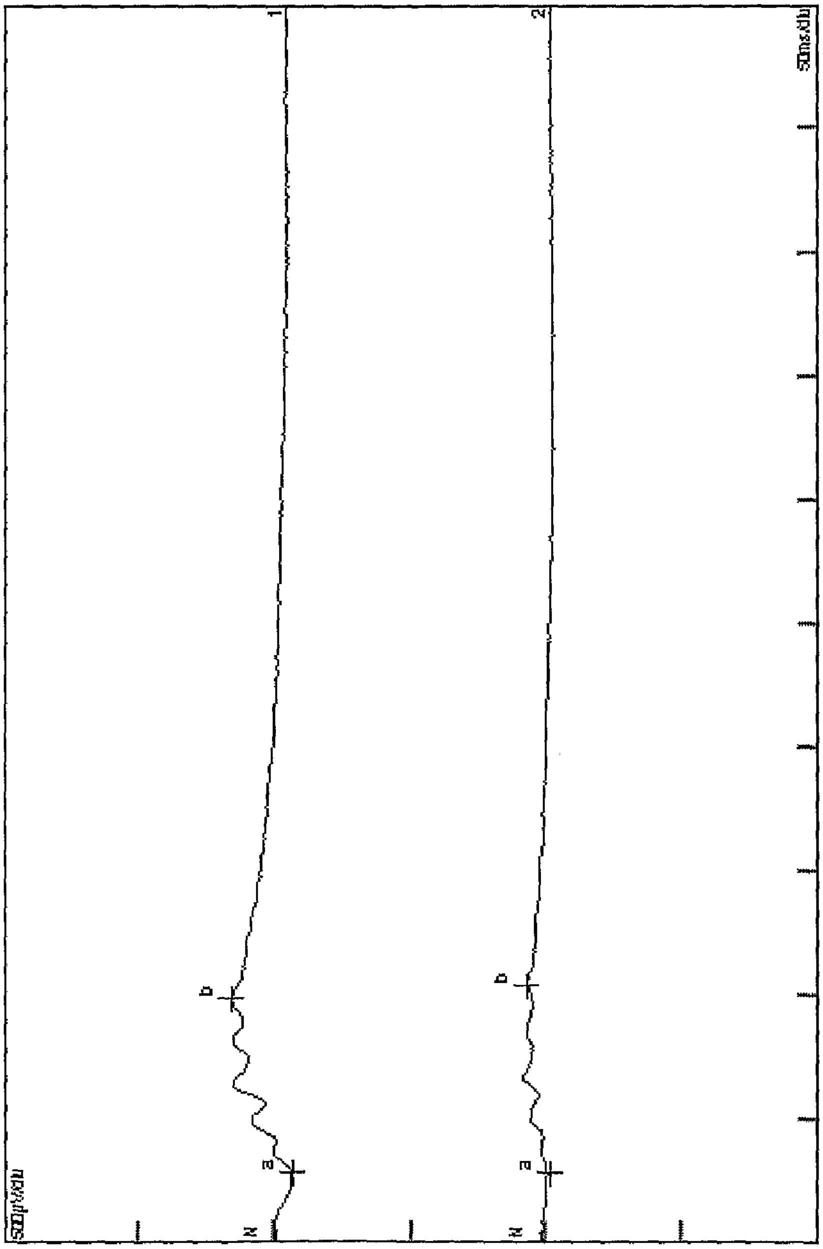

FIG. 14A-C illustrates retinal histology of adult RHO-347 transgenic mice carrying a dominant RHO mutation on a mouse rho+/+background causing retinal degeneration were subretinally injected with 2 ul of $2\times10^{12}$ particle/ml of AAV-shNT-EGFP (A) or AAV-shQ1-EGFP (B) vectors. Two weeks post-injection transduced eyes were removed, fixed in 4% paraformaldehyde and cryosectioned (12 um). AAV-shQ1-EGFP expresses shRNA-Q1-EGFP, which targets RHO, while AAV-shNT-EGFP expresses a non-targeting shRNA. Both constructs express EGFP allowing tracking of the transduced part of the retina (green). Sections were counterstained with DAPI (blue) to indicate positions of the nuclear layers. A significant reduction of the photoreceptor cell numbers in the transduced part of the outer nuclear layer in the AAV-shNT-EGFP injected or the uninjected (C) retinas are apparent due to the degenerative effects of RHO-347 transgene. A significantly preserved outer nuclear layer is detected in the AAV-shQ1-EGFP transduced retinas, where shRNA-Q1-EGFP effectively suppresses the RHO-347 transcript therefore reducing retinal degeneration. Note, that mouse rho (expressed in these retinas) is refractory to suppression by shRNA-Q1-EGFP due to the presence of nucleotide changes at the target site for Q1 siRNA suppression. Suppression and replacement using the degeneracy of the genetic code provided therapeutic benefit at a histological level. FIG. 14D provides evidence of an improvement in the electroretinogram (ERG) in RHO-347 eyes treated with AAV-shQ1-EGFP versus eyes treated with AAV-shNT-EGFP. FIG. 14D provides a representative maximum ERG response of a RHO-347 mouse, containing a human rhodopsin transgene with a mutation at codon 347, subretinally injected with AAV2/5 constructs. This RHO-347 mouse normally displays a phenotype similar to autosomal dominant RP. The top panel in FIG. 14D is the response of the right eye, which received an injection of AAV-shQ1, a AAV2/5 vector containing suppressor siRNA Q1 driven by an H1 promoter (shQ1) and a CMV-driven EGFP gene. The left eye received an AAV-shNT, a AAV2/5 containing a non-targeting (control) siRNA driven by an H1 promoter (shNT) and a CMV-driven EGFP gene. As can be seen in FIG. 14D, the maximum response is significantly greater in the treated right eye than in the control left eye, indicating that suppression of the mutant rhodopsin transgene leads to some rescue at the ERG level.

Figure 15:
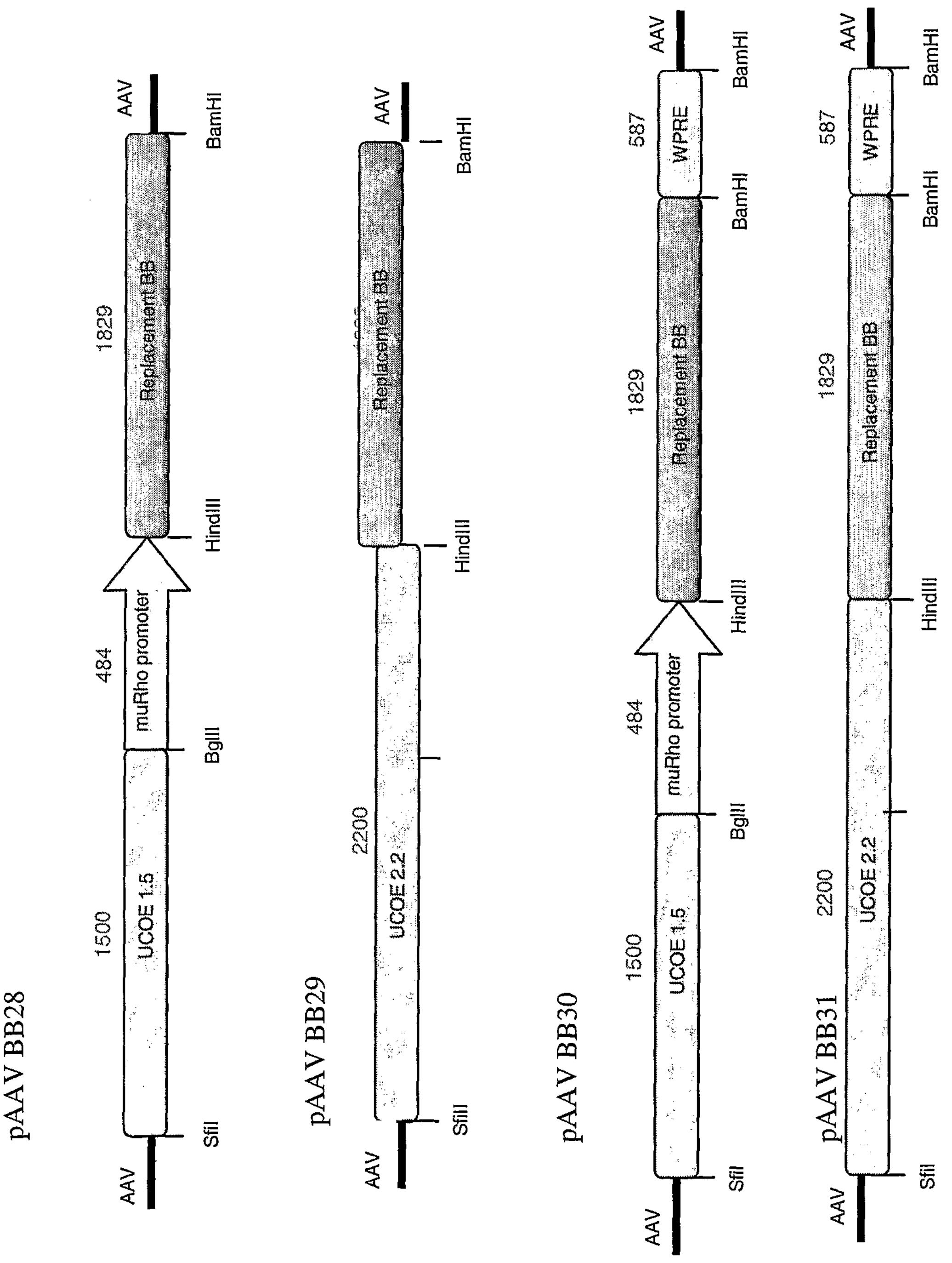

FIG. 15 illustrates exemplary constructs utilising chromatin opening elements to optimise expression are presented. Components utilised to enhance expression may be cloned into vectors such as AAV vectors. Elements to optimise expression of a given gene may be combined with other promoter elements such as the rhodopsin promoter and/or enhancer sequences or alternatively sequences that modulate chromatin structures and drive gene expression may be utilised alone to facilitate optimisation of expression of a target gene.

FIG. 16 shows sequences of exemplary elements that can facilitate modulation of chromatin structures.

FIG. 17 shows nucleotide and amino acid sequences of a number of exemplary neurotrophic factors.

Figure 18:
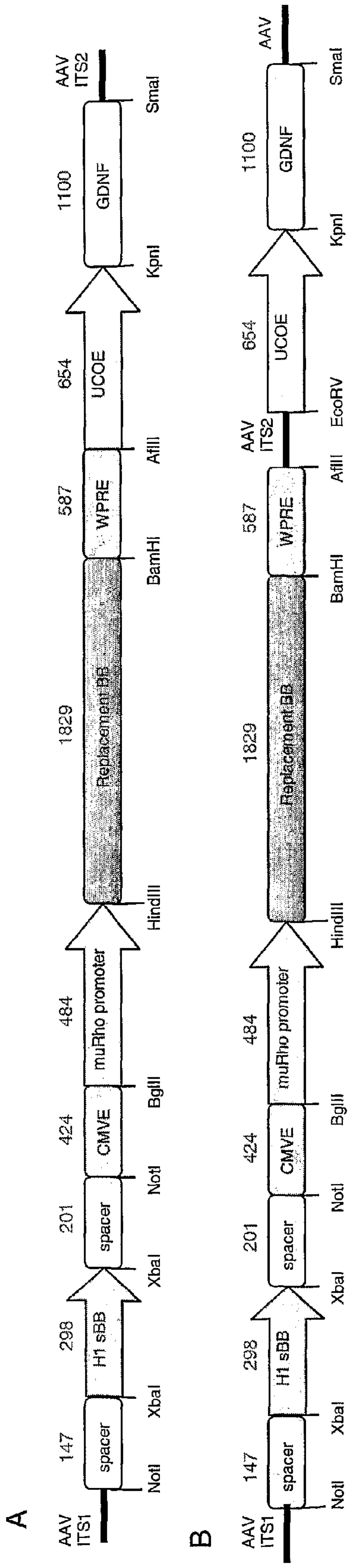

FIG. 18 illustrates exemplary suppression and replacement constructs containing other genetic elements which are beneficial for photoreceptor cell survival. In the example pAAV-BB18 has been combined with neurotrophic factor GDNF, driven by a small UCOE (chromatin opening element. A Thrasher, Abstract 36, British Society for Gene Therapy $5^{th}$ Annual Conference 2008) promoter). Other neurotrophic factors such as, for example, Neurturin may also be used in combination with any of the suppression and replacement constructs described. In addition, other beneficial genes, other than neurotrophic factors may also be combined with suppression and replacement constructs such as for example, a second suppression element, a second replacement element, VEGF and others. In example A, the additional element, in this case GDNF is co-located with the suppression and replacement construct within the two AAV inverted terminal repeat sequences, ITR1 and ITR2. In the second example, B, the GDNF gene and its promoter are not co-located with the suppression and replacement elements within ITR1 and ITR2, but are located within the backbone of the plasmid used to generate AAV. Since a small proportion of the backbone is packaged during AAV production, this would result in a mixed population of AAVs with the majority containing the suppression and replacement elements and a minority the GDNF elements. In this case, other beneficial genes, other than neurotrophic factors may also be combined with suppression and replacement constructs such as for example, a second suppression element, a second replacement element, VEGF and others.

DETAILED DESCRIPTION OF THE INVENTION

The instant invention utilises efficient gene suppression in conjunction with gene replacement to overcome the challenge of mutational heterogeneity. The suppression agent does not necessarily target a mutation (although it can encompass the site of a mutation), but is rather mutation independent. Suppression can involve one or both alleles of an endogenous gene. In conjunction with suppression, a replacement gene is provided that has been modified such that the replacement gene is refractory or partially refractory to suppression. The invention uses the degeneracy of the genetic code to modify the replacement gene. Alteration of "wobble" bases makes it possible for replacement nucleic acids to escape suppression at least in part, but does not change the protein product expressed from the replacement nucleic acids. Alternatively, replacement genes are modified in such a way that they encode altered amino acids but still encode a functional or partially functional protein that does not lead to pathology (e.g., because the amino acid changes are silent mutations or polymorphisms). Replacement has been demonstrated using rhodopsin nucleic acids, however, other genes or combinations of genes can be made and used in the practice of the invention. In particular, the invention relates to modulating and optimizing the expression levels of the suppression agents and/or replacement nucleic acids using one or more of the untranslated regions (UTRs) of a gene, intronic sequences, the degeneracy of the genetic code and/or polymorphisms to alter the sequence of replacement nucleic acids such that they are refractory or partially refractory to suppression.

In one aspect, the invention provides methods for preparing and using a suppression agent and replacement nucleic acid. The suppression agent binds to a coding region of a mature RNA or DNA encoding a mutant allele and inhibits expression of the mutant allele. The replacement nucleic acid encodes a wild-type or non-disease causing allele and comprises at least one degenerate/wobble nucleotide that is altered so that the replacement nucleic acid is not suppressed, or is only partially suppressed, by the suppression of one or both alleles of a gene.

The invention provides for replacement genes using sequences to enhance expression of replacement genes from viral and or non-viral vectors. In particular the invention relates to enhanced expression of suppression agent(s) and or replacement genes from viral or and non-viral vectors. The invention relates to use of conserved sequences from retinal genes to enhance expression of suppression agent(s) and or replacement genes. In a particular aspect the invention relates to use of conserved sequences from retinal genes to enhance expression of suppression agent(s) and or replacement genes from adeno associated virus (AAV) vectors. In another aspect the invention provides vectors for expression of suppression agent(s) and or replacement gene(s) using regulatory sequences from retinal gene(s) and or non-retinal gene(s) and or ubiquitously expressing genes such as those provided in the Tables below to enhance expression from viral and non-viral vectors.

In another aspect, the invention provides a composition comprising a suppression agent that binds to the coding region of a mature and/or immature RNA or DNA encoding a mutant allele to inhibit expression of the mutant allele and a replacement nucleic acid that encodes a wild-type or non-disease causing allele and comprises at least one degenerate/wobble nucleotide that is altered so that the replacement nucleic acid is not suppressed, or is only partially suppressed, by the suppression agent.

In yet another aspect, the invention provides a kit comprising a suppression agent that suppresses the expression of a mature and or immature RNA or DNA encoding a mutant allele and a replacement nucleic acid that encodes a wild-type or non-disease causing allele that is not Suppressed, or is only partially suppressed, by the suppression agent and differs from the mutant allele in at least one degenerate/wobble nucleotide.

Suppression is achieved using a wide variety of molecular tools, such as, for example, RNA interference (RNAi) including non-coding RNAs such as small interfering RNA (siRNA), short hairpin RNA (shRNA), microRNAs (miRNA), or other nucleotide-based molecules. In an embodiment, siRNAs in the order of 14-27 nucleotides in length are used for gene suppression. ShRNAs can be used to express functional siRNAs intracellularly and to achieve suppression in vitro and in vivo. Other suppression molecules include, for example, sense and antisense nucleic acids (single or double stranded), ribozymes, peptides, DNAzymes, peptide nucleic acids (PNAs), triple helix forming oligonucleotides, antibodies, and aptamers and modified form(s) thereof directed to sequences in gene(s), RNA transcripts, or proteins.

In an embodiment, the invention relates to vector(s) for supplying an endogenously generated suppression agent, such as, for example, a dsRNA in the form of a short hairpin (shRNA) which can be processed intracellularly into siRNA. dsRNA may be locally or systemically delivered. Expression vectors are used to generate functional siRNAs in cells and in animals typically using polymerase III promoters to drive expression, although polymerase II promoters are also used. For example, miRNA structures can be used to express double stranded RNAs from polymerase II promoters to enable tissue specific expression of double stranded RNA or polymerase II promoters can be juxtaposed to shRNA sequences to be expressed.

Suppression agents may be modified to alter the potency of the suppression agent, the target affinity of the suppression agent, the safety profile of the suppression agent and/or the stability of the suppression agent, for example, to render them resistant or partially resistant to intracellular degradation. Modifications, such as phosphorothioates, for example, can be made to oligonucleotides to increase resistance to nuclease degradation, binding affinity and/or uptake. In addition, hydrophobization and bioconjugation enhances siRNA delivery and targeting (De Paula et al., RNA. 13(4):431-56, 2007) and siRNAs with ribo-difluorotoluyl nucleotides maintain gene silencing activity (Xia et al., ASC Chem. Biol. 1(3):176-83, (2006). siRNAs with amide-linked oligoribonucleosides have been generated which are more resistant to Si nuclease degradation (Iwase R et al. 2006 Nucleic Acids Symp Ser 50: 175-176). In addition, modification of siRNA at the 2'-sugar position and phosphodiester linkage confers improved serum stability without loss of efficacy (Choung et al., Biochem. Biophys. Res. Commun. 342(3):919-26, 2006). In one study, 2'-deoxy-2'-fluoro-beta-D-arabinonucleic acid (FANA)-containing antisense oligonucleotides compared favourably to phosphorothioate oligonucleotides, 2'-O-methyl-RNA/DNA chimeric oligonucleotides and siRNAs in terms of suppression potency and resistance to degradation (Ferrari N et al. 2006 Ann N Y Acad Sci 1082: 91-102.)

Antisense and ribozyme suppression strategies have led to the reversal of a tumor phenotype by reducing expression of a gene product or by cleaving a mutant transcript at the site of the mutation (Carter and Lemoine Br. J. Cancer. 67(5):869-76, 1993; Lange et al., Leukemia. 6(11):1786-94, 1993; Valera et al., J. Biol. Chem. 269(46):28543-6, 1994; Dosaka-Akita et al., Am. J. Clin. Pathol. 102(5):660-4, 1994; Feng et al., Cancer Res. 55(10):2024-8, 1995; Quattrone et al., Cancer Res. 55(1):90-5, 1995; Lewin et al., Nat Med. 4(8):967-71, 1998). For example, neoplastic reversion was obtained using a ribozyme targeted to an H-ras mutation in bladder carcinoma cells (Feng et al., Cancer Res. 55(10):2024-8, 1995). Ribozymes have also been proposed as a means of both inhibiting gene expression of a mutant gene and of correcting the mutant by targeted trans-splicing (Sullenger and Cech Nature 371(6498):619-22, 1994; Jones et al., Nat. Med. 2(6):643-8, 1996). Ribozyme activity may be augmented by the use of, for example, non-specific nucleic acid binding proteins or facilitator oligonucleotides (Herschlag et al., Embo J. 13(12):2913-24, 1994; Jankowsky and Schwenzer Nucleic Acids Res. 24(3):423-9, 1996). Multitarget ribozymes (connected or shotgun) have been suggested as a means of improving efficiency of ribozymes for gene suppression (Ohkawa et al., Nucleic Acids Symp Ser. (29):121-2, 1993).

Triple helix approaches have also been investigated for sequence-specific gene suppression. Triplex forming oligonucleotides have been found in some cases to bind in a sequence-specific manner (Postel et al., Proc. Natl. Acad. Sci. U.S.A. 88(18):8227-31, 1991; Duval-Valentin et al., Proc. Natl. Acad. Sci. U.S.A. 89(2):504-8, 1992; Hardenbol and Van Dyke Proc. Natl. Acad. Sci. U.S.A. 93(7):2811-6, 1996; Porumb et al., Cancer Res. 56(3):515-22, 1996). Similarly, peptide nucleic acids have been shown to inhibit gene expression (Haney et al., Antisense Res. Dev. 1(4):307-17, 1991; Knudsen and Nielson Nucleic Acids Res. 24(3):494-500, 1996; Taylor et al., Arch. Surg. 132(11):1177-83, 1997). Minor groove binding polyamides can bind in a sequence-specific manner to DNA targets and hence may represent useful small molecules for future suppression at the DNA level (Trauger et al., Chem. Biol. 3(5):369-77, 1996). In addition, suppression has been obtained by interference at the protein level using dominant negative mutant peptides and antibodies (Herskowitz Nature 329(6136):219-22, 1987; Rimsky et al., Nature 341(6241):453-6, 1989; Wright et al., Proc. Natl. Acad. Sci. U.S.A. 86(9):3199-203, 1989). In some cases suppression strategies have lead to a reduction in RNA levels without a concomitant reduction in proteins, whereas in others, reductions in RNA have been mirrored by reductions in protein.

The diverse array of suppression strategies that can be employed includes the use of DNA and/or RNA aptamers that can be selected to target, for example, a protein of interest such as rhodopsin. In the case of age related macular degeneration (AMD), anti-VEGF aptamers have been generated and have been shown to provide clinical benefit in some AMD patients (Ulrich H, et al. Comb. Chem. High Throughput Screen 9: 619-632, 2006). Suppression and replacement using aptamers for suppression in conjunction with a modified replacement gene and encoded protein that is refractory or partially refractory to aptamer-based suppression could be used in the invention.

Recent evidence suggests that control of gene expression occurs endogenously in part by the activity of small non-coding RNAs, one broad category of which is termed microRNAs (miRNAs). miRNAs are expressed from polymerase II promoters, but can also be expressed from polymerase III promoters. miRNAs are processed intracellularly from larger transcripts to form small molecules approximately 20 nucleotides in length. miRNA structures can be used to express small double stranded RNAs and thus can be used to express the double stranded RNAs of the current invention.

Suppression targeted to coding sequence holds the advantage that such sequences are present in both precursor and mature RNAs, thereby enabling suppressor effectors to target all forms of RNA. A combined approach using a number of suppression effectors directed to multiple targets on an RNA or to multiple RNAs may also be used in the invention. As with suppression, multiple replacement nucleic acids can be used in the invention. For some disorders, it may be necessary to block expression of a disease allele completely to prevent disease symptoms whereas for others low levels of mutant protein may be tolerated. The invention can thus provide partial or complete suppression.

In one embodiment of the invention, suppressors are targeted to genes that are involved in the regulation of other genes. Suppression of these genes therefore may lead to up- or down-regulation of other genes.

In another embodiment, the invention relates to suppression of the expression of mutated genes that give rise to a dominant or deleterious effect or disease. A suppression effector may target either the disease allele or the normal allele. In another embodiment, the suppression effector targets both the disease allele and the normal allele.

In an embodiment of the invention, a replacement nucleic acid is provided that is altered at one or more degenerate or wobble bases from the endogenous wild type gene but that encodes the identical amino acids as the wild type or a non-disease causing gene. In another embodiment, the replacement nucleic acid encodes a beneficial replacement nucleic acid (e.g., a more active or stable product than that encoded by the wild-type gene). The replacement nucleic acid provides expression of a normal or non-disease causing protein product when required to ameliorate pathology associated with reduced levels of wild type protein. The same replacement nucleic acid can be used in conjunction with the suppression of many different disease mutations within a given gene. In addition, multiple replacement nucleic acids can be used in the invention.

Although the instant application provides numerous exemplary suppression agents and replacement nucleic acid sequences, these are only examples and other such sequences can be determined as described herein for the same targets or for any desired target. "Functional variant" includes any variant nucleic acid or other suppression agent that may have one or more nucleic acid substitutions but that does not have a materially different function than, or that can still hybridize under stringent hybridization conditions (0.2×SCC, 0.1% SDS) to, or that shares at least 70% identity, for example 80%, such as at least 90% or at least 95% sequence identity with the nucleic acid indicated.

In another embodiment of the invention, suppression effectors are targeted to the untranslated regions (either 5'UTR or 3'UTR) of at least one allele of a gene. In another embodiment of the invention replacement nucleic acids are provided that have been altered at the suppression site, such that replacement nucleic acids provide functional or partially functional protein and escape or partially escape from suppression by suppressors.

In another embodiment of the invention, suppression effectors are targeted to intronic sequences. In another embodiment, replacement nucleic acids are provided which have been altered at one or more nucleotides of the targeted site of the intron so that transcripts from the replacement nucleic acids escape or partially escape suppression by suppressors. In another embodiment the whole targeted intron may not be present in replacement nucleic acids.

In another embodiment of the invention, suppression effectors are targeted to polymorphic sites and at least one allele of the gene is suppressed or partially suppressed. In another embodiment, replacement nucleic acids are provided for the alternative polymorphic variant such that replacement nucleic acids encode functional or partially functional protein and escape or partially escape from suppression by suppressors.

In another embodiment of the invention the suppression agent and/or replacement nucleic acid is expressed from one or more promoter sequences. The invention provides promoter sequences that have been demonstrated to promote ubiquitous expression of nucleotides and/or promoters that have been demonstrated to exert tissue specific, temporal, inducible, and/or quantitative control of gene expression. The invention also provides enhancer sequences (Table 1) and/or post-translational regulatory elements and/or other regulatory elements and/or epigenetic elements that provide optimized expression of suppression agents and/or replacement nucleic acids.

TABLE 1

Exemplary Enhancer Elements

| Enhancer Element | Reference |
|---|---|
| Chicken ovalbumin upstream promoter transcription factor II | Eguchi et al., Biochimie 89(3): 278-88, 2007 |
| Mouse dystrophin muscle promoter/enhancer | Anderson et al., Mol. Ther. 14(5): 724-34, 2006 |
| Tobacco eIF4A-10 promoter elements | Tian et al., J. Plant Physiol. 162(12): 1355-66, 2005 |
| Immunoglobulin (Ig) enhancer element HS1, 2A | Frezza et al., Ann. Rheum. Dis. Mar. 28, 2007 |
| Col9a1 enhancer element | Genzer and Bridgewater Nucleic Acids Res. 35(4): 1178-86, 2007 |
| Gata2 intronic enhancer | Khandekar et al., Development Mar. 29, 2007 |
| TH promoter enhancer | Gao et al., Brain Res. 1130(1): 1-16, 2007 |
| CMV enhancer | InvivoGen cat# pdrive-cag 05A13-SV |
| Woodchuck hepatitis virus posttranscriptional regulatory element | Donello et al., J. Virol. 72(6): 5085-92, 1998 |
| Woodchuck hepatitis virus posttranscriptional regulatory element | Schambach et al., Gene Ther. 13(7): 641-5, 2006 |
| IRBP | Ying et al., Curr. Eye Res. 17(8): 777-82, 1998 |
| CMV enhancer and chicken β-actin promoter | InvivoGen cat# pdrive-cag 05A13-SV |
| CMV enhancer and chicken β-actin promoter and 5'UTR | InvivoGen cat# pdrive-cag 05A13-SV |
| CpG-island | Antoniou et al., Genomics 82: 269-279, 2003 |

In a particular embodiment, sequences that influence chromatin structure, such as but not exclusive to insulator, antirepressor, cis-acting modulators of nucleosome positioning and/or silencer elements, sometimes termed epigenetic elements, are used to modulate expression of suppression agents and/or replacement nucleic acids. Exemplary epigenetic elements such as insulator and antirepressor sequences are provided in Table 2. It is clear that chromatin structures influence gene expression, for example, chromatin structures influence the ability of the transcriptional machinery to access promoter and/or enhancer elements amongst other sequence motifs. The inclusion of sequences which influence chromatin structures in viral and/or non-viral vectors and/or administered in conjunction with suppression and/or replacement nucleic acids can be used to optimize expression of either or both suppressors and replacement nucleic acids. In addition, chemical entities which influence chromatin structures can be used to optimize expression such as histone deacetylase (HDAC) inhibitors and/or DNA methyl transferase inhibitors and/or histone methyl transferase inhibitors. Such entities can be supplied in the form of DNA and/or RNA and/or protein amongst other forms. Similarly attracting enzymes and/or supplying enzymes (in the form of DNA and/or RNA and or protein) involved in chromatin remodelling such as but not exclusive to histone acetyl transferases to nucleic acids to be expressed and their associated regulatory regions can be used to optimize expression of suppression and/or replacement nucleic acids.

TABLE 2

Exemplary Epigenetic Elements

| Epigenetic elements | Reference |
|---|---|
| Mcp Insulators | Kyrchanova et al., Mol. Cell Biol. 27(8): 3035-43, 2007 |
| CpG-island region of the HNRPA2B1 locus | Williams et al., BMC Biotechnol. 5: 17, 2005 |
| Chicken b-globin 5'hypersensitive site 4 (cHS4) | Kwaks and Otte 2006 Trends in Biotechnology 24: 137-142 |
| Ubiquitous chromatin opening elements (UCOEs) | Kwaks and Otte 2006 Trends in Biotechnology 24: 137-142 |
| Matrix associated regions (MARs) | Kwaks and Otte 2006 Trends in Biotechnology 24: 137-142 |
| Stabilising and antirepressor elements (STAR) | Kwaks and Otte 2006 Trends in Biotechnology 24: 137-142 |
| Human growth hormone gene silencer | Trujillo MA et al. 2006 Mol Endocrinol 20: 2559 |
| S/MAR | Liebich et al., Nucleic Acids Res. 30: 3433-42, 2002 |

In another embodiment, expression of a suppression agent and/or replacement nucleic acid is optimized to enable efficient suppression in conjunction with sufficient replacement. In an additional embodiment, suppression and/or replacement nucleic acids are provided with agents that aid vector transfection, transduction, and/or expression of suppression and replacement nucleic acids.

The invention circumvents the need for a specific therapy for every disease-causing mutation within a given gene. Notably, the invention has the advantage that the same suppression agents can be used to suppress many mutations in a gene. This is particularly relevant when any one of a large number of mutations within a single gene can cause disease pathology. The compositions and methods of the invention allow greater flexibility in choice of target sequence for suppression of expression of a disease allele. Furthermore, the compositions and methods of the invention allow greater flexibility in terms of controlling expression of the suppression and/or replacement of a given gene and or allele of a gene.

Suppression and replacement can be undertaken in conjunction with each other or separately. Suppression and replacement utilizing the degeneracy of the genetic code may be undertaken in test tubes, in cells, in animals, or in plants and may be used for experimental research (e.g., for the study of development or gene expression) or for therapeutic purposes. Suppression and replacement may be used in conjunction with agents to promote cell transfection or cell transduction such as, for example, lipids and polymers. Suppression and replacement may be provided to consumers in a kit.

The suppression and replacement agents of the invention can be delivered to a target cell and or tissue and or animal and or plant using 'naked' reagents such as DNA, RNA, peptides or other reagents. Alternatively viral and or non-viral vectors can be used with or without 'naked' reagents.

In an embodiment, suppression and/or replacement construct(s) can be delivered to a cell using an AAV2/5 recombinant virus, however, other viral and non-viral vectors, such as other AAV serotypes, adenovirus, herpes virus, SV40, HIV, SIV and other lentiviral vectors, RSV and non-viral vectors including naked DNA, plasmid vectors, peptide-guided gene delivery, terplex gene delivery systems, calcium phosphate nanoparticles, magnetic nanoparticles, colloidal microgels and/or the integrase system from bacteriophage phiC31 may be utilised in the invention, for example. Suppression and replacement components may be found on separate vectors or may be incorporated into the same vector. Viral vectors useful in the invention include, but are not limited to, those listed in Table 3. Non-viral vectors useful in the invention include, but are not limited to, those listed in Table 4. Cationic lipid-based non-viral vectors can include glycerol-based (e.g. DOTMA, DOTAP, DMRIE, DOSPA), non-glycerol-based (e.g. DOGS, DOTIM) and/or cholesterol-based cationic lipids (e.g. BGTC, CTAP; Karmali P P and Chaudhuri A 2006 Med Res Rev). Viral and non-viral vector delivery may be accompanied by other molecules such as cationic lipids and/or polymers and/or detergents and/or agents to alter pH, such as, for example, polyethelene glycol (PEG), to enhance cellular uptake of vectors and/or to enhance expression from vectors and/or to evade the immune system. For example, polycationic molecules have been generated to facilitate gene delivery including but not exclusive to cationic lipids, poly-amino acids, cationic block co-polymers, cyclodextrins amongst others. Pegylation of vectors with polyethelene glycol (PEG) can shield vectors from, for example, the extracellular environment. Vectors may be used in conjunction with agents to avoid or minimise cellular immune responses such as PEG or as a Polyplex with Poly(L-Lysine) Vector delivery may be undertaken using physical methodologies such as electroporation, nucleofection and/or ionotophoresis, either alone or in combination with molecules to enhance delivery. Vectors may be used in conjunction with agents to promote expression of suppression and/or replacement components incorporated into vectors, for example, using histone deacetylase inhibitors (HDAC) and/or DNA methyl transferase inhibitors and/or histone methyl transferase inhibitors to modulate chromatin structures thereby aiding expression. HDAC inhibitors include but are not exclusive to short chain fatty acids such as valproic acid and sodium butyrate, ketones, benzamides, cyclic and non-cyclic hydroxamates such as suberoyl anilide hydroxamic acids (SAHA), trichostatin A (TSA), cyclic peptides or tetrapeptides amongst others (Liu T et al. 2006 Cancer Treatment Reviews 32: 157-165). DNA methyl transfease inhibitors including, for example, 5-AC, decitabine and zebularine can be used to modulate chromatin structures. In addition, histone methyl transferase inhibitors can influence chromatin states, for example, BIX-01294 (diazepin-quinazolin-amine derivative). In addition, to the chemical entities referred to above, nucleic acids-based inhibitors can be used to suppress expression of proteins and/or non-coding RNAs involved in chromatin remodelling. In one embodiment of the invention vectors are optimized to specifically transduce target cell type(s) or target tissue type(s). Viral and/or non-viral vectors may be modified to target specific cell types and/or to prevent targeting of some cell types. For example, the inclusion of the capsid from AAV serotype 5 in an AAV2/5 hybrid virus facilitates transduction of photoreceptor cells. Similarly, for example, peptides may be included in viral vectors to facilitate targeting. Synthetic non-viral vectors can be modified to include ligands to facilitate targeting of vectors to specific cell and/or tissue types, for example, folate can be conjugated to liposomes to target tumour cells which over express the folate receptor (Hattori Y et al. 2005; Curr Drug Deliv 3: 243-52). In another embodiment of the invention, suppression and replacement vectors are designed to optimize the generation and/or production of vector, for example, to optimize viral titre and/or to optimize the number or type of nucleotides incorporated into vector(s). For example, vector genomes may be modified such that large transgenes may be incorporated into vectors, for example, 'gutless' adenovirus vectors have an increased capacity in terms of size than previous generations of adenovirus vectors. Components of vectors can be modified to optimize generation and production of vectors, for example, genes involved in replication of AAV can be modified to optimize replication and/or self complementary AAV vectors can be used to optimize rates of transgene expression. In an additional embodiment, vectors are designed to optimize suppression in conjunction with replacement, to enable optimal expression of all components of a therapeutic. For example, to optimize expression of both elements of suppression and replacement from a given vector, additional sequences can be included in the vector. For example, inclusion of nucleotides to separate the ITRs of AAV and the shRNA sequences of an RNAi-based suppression agent can result in optimisation of expression of the suppression component. Nucleotides encoding suppressors and/or replacement nucleic acids can be juxtaposed or separated from each other and/or can be in the same orientation or opposing orientations. In addition, the suppressor(s) can be 5' and/or 3' to the replacement nucleic acids. Nucleotides encoding suppressors and/or replacement nucleic acids can be juxtaposed to nucleotides comprising vector(s) or can be separated from nucleotides comprising vector(s). Nucleotides encoding suppressors and/or replacement nucleic acids may be cloned within the backbone of the plasmid used to generate AAV and or may be cloned between the AAV ITRs and not within the plasmid backbone of the plasmid, and/or may be cloned in a combination of these positions. Additional sequences, such as, for example, stuffer sequences can be included in vectors to optimize vector design. In addition, multiple suppressors and/or replacement nucleic acids may be used in one vector.

TABLE 3

Exemplary Viral Vectors

| Delivery Method | Serotype | Reference |
|---|---|---|
| AAV | All serotypes, including but not limited to 1, 2, 3, 4, 5, 6, 7, 8, 9, 10, 11, 12, | Lebkowski et al., Mol. Cell Biol. 8(10): 3988-96, 1988<br>Flannery et al., Proc. Natl. Acad. Sci. U.S.A. 94(13): 6916-21, 1997 |
| Lentivirus (for example but not exclusively Feline - FIV, Equine - EIAV, Bovine - BIV and Simian - SIV). | VSV-G<br>Rabies-G<br>Further serotypes** | Pang et al., Mol. Vis. 12: 756-67, 2006<br>Takahashi Methods Mol. Biol. 246: 439-49, 2004<br>Balaggan et al., J. Gene Med. 8(3): 275-85, 2006 |
| Adenovirus | Various | Bennett et al., Nat. Med. 2(6): 649-54, 1996 |
| Simian papovirius SV40 | Various | Kimchi-Sarfaty et al., Hum. Gene Ther. 13(2): 299-310, 2002 |
| Semliki Forest Virus | Various | DiCiommo et al., Invest. Ophthalmol. Vis. Sco. 45(9): 3320-9, 2004 |
| Sendai Virus | Various | Ikeda et al., Exp. Eye Res. 75(1): 39-48, 2002 |

The list provided is not exhaustive; other viral vectors and derivatives, natural or synthesized could be used in the invention.

TABLE 4

Exemplary Non-Viral Vectors or Delivery Methods

| Delivery Method | Reference |
|---|---|
| Cationic liposomes | Sakurai et al., Gene Ther. 8(9): 677-86, 2001 |
| HVJ liposomes | Hangai et al., Arch. Ophthalmol. 116(3): 342-8, 1998 |
| Polyethylenimine | Liao and Yau Biotechniques 42(3): 285-6, 2007 |
| DNA nanoparticles | Farjo et al., PloS ONE 1: e38, 2006 |
| Dendrimers | Marano et al., Gene Ther. 12(21): 1544-50, 2005 |
| Bacterial | Brown and Giaccia Cancer Res. 58(7): 1408-16, 1998 |
| Macrophages | Griffiths et al., Gene Ther. 7(3): 255-62, 2000 |
| Stem cells | Hall et al., Exp. Hematol. 34(4): 433-42, 2006 |
| Retinal transplant | Ng et al., Chem. Immunol. Allergy 92: 300-16, 2007 |
| Marrow/Mesenchymal stromal cells | Kicic et al., J. Neurosci. 23(21): 7742-9, 2003<br>Chng et al., J. Gene Med. 9(1): 22-32, 2007 |
| Implant (e.g., Poly(imide) uncoated or coated) | Montezuma et al., Invest. Ophthalmol. Vis. Sci. 47(8): 3514-22, 2006 |
| Electroporation | Featherstone A. Biotechnol. Lab. 11(8): 16, 1993 |
| Targeting peptides (for example but not exclusively Tat) | Trompeter et al., J. Immunol Methods. 274(1-2): 245-56, 2003 |
| Lipid mediated (e.g., DOPE, PEG) | Nagahara et al., Nat. Med. 4(12): 1449-52, 1998<br>Zeng et al., J. Virol. 81(5): 2401-17, 2007<br>Caplen et al., Gene Ther. 2(9): 603-13, 1995Manconi et al., Int. J. Pharm. 234(1-2): 237-48, 2006<br>Amrite et al., Invest. Ophthalmol. Vis. Sci. 47(3): 1149-60, 2006<br>Chalberg et al., Invest. Ophthalmol. Vis. Sci. 46(6): 2140-6, 2005 |

The list provided is not exhaustive. Other non-viral vectors and derivatives, natural or synthesized and other delivery methods could be used with the invention.

In an embodiment, the replacement nucleic acid encodes mammalian rhodopsin, collagen 1A1, collagen 1A2, collagen 7A1, or peripherin. In another embodiment, the replacement nucleic acid encodes a protein that has been mutated to cause an autosomal or X-linked dominant retinitis pigmentosa, such as those listed in Table 5. Suppression agents and replacement nucleic acids may be generated for one or more of these genes, for example.

TABLE 5

Genes known to be involved in retinitis pigmentosa (Table adapted from RETNET) (http://www.sph.uth.tmc.edu/Retnet/)

| Symbols; OMIM Numbers | Location | Diseases; Protein | References |
|---|---|---|---|
| LCA9 | 1p36 | recessive Leber congenital amaurosis | Keen et al., Hum. Mol. Genet. 3: 367-368 (1994) |
| NPHP4, SLSN4; | 1p36.31 | recessive Senior-Loken syndrome; recessive nephronophthisis, juvenile; protein: nephronophthisis 4 protein | Mollet et al., Nat. Genet. 32: 300-305 (2002); Otto et al., Am. J. Hum. Genet. 71: 1161-1167 (2002); Schuermann et al., Am. J. Hum. Genet. 70: 1240-1246 (2002) |
| RP32; | 1p34.3-p13.3 | recessive RP, severe | Zhang et al., Hum. Genet. 118: 356-365 (2005) |
| RPE65, LCA2, RP20; | 1p31.2 | recessive Leber congenital amaurosis; recessive RP; protein: retinal pigment epithelium-specific 65 kD protein | Acland Nat. Genet. 28: 92-95 (2001) |
| ABCA4, ABCR, RP19, STGD1; | 1p22.1 | recessive Stargardt disease, juvenile and late onset; recessive MD; recessive RP; recessive fundus flavimaculatus; recessive cone-rod dystrophy; protein: ATP-binding cassette transporter-retinal | Lewis et al., Am. J. Hum. Genet. 64: 422-434 (1999) |
| COL11A1, STL2; | 1p21.1 | dominant Stickler syndrome, type II; dominant Marshall syndrome; protein: collagen, type XI, alpha 1 | Annunen et al., Am. J. Hum. Genet. 65: 974-983 (1999) |
| GNAT2, ACHM4; | 1p13.3 | recessive achromatopsia; protein: guanine nucleotide binding protein (G protein) cone-specifc transducin alpha subunit | Aligianis et al., J. Med. Genet. 39: 656-660 (2002) |
| PRPF3, HPRP3, PRP3, RP18; | 1q21.2 | dominant RP; protein: human homolog of yeast pre-mRNA splicing factor 3 | Chakarova et al., Hum. Mol. Genet. 11: 87-92 (2002) |
| SEMA4A, SEMAB; | 1q22 | dominant RP; dominant cone-rod dystrophy; protein: semaphorin 4A | Abid et al., J. Med. Genet. 43: 378-381 (2005) |
| CORD8; | 1q23.1-q23.3 | recessive cone-rod dystrophy | Ismail et al., J. Hum. Genet. 51: 827-831 (2006) |
| AXPC1 | 1q31-q32 | recessive ataxia, posterior column with RP | Higgins et al., Neurol. 52: 146-150 (1999) |
| ARMD1, FIBL6, FBLN6; | 1q31.1 | dominant MD, age-related; protein: hemicentin 1 (fibulin 6) | Schultz et al., Hum. Mol. Genet. 12: 3315-3123 (2003) |

TABLE 5-continued

Genes known to be involved in retinitis pigmentosa (Table adapted from RETNET) (http://www.sph.uth.tmc.edu/Retnet/)

| Symbols; OMIM Numbers | Location | Diseases; Protein | References |
|---|---|---|---|
| CFH, HF1; | 1q31.3 | age-related macular degeneration, complex etiology; protein: complement factor H | Edwards et al., Science 308: 421-424 (2005) |
| CRB1, RP12 | 1q31.3 | recessive RP with para-arteriolar preservation of the RPE (PPRPE); recessive RP; recessive Leber congenital amaurosis; dominant pigmented paravenous chorioretinal atrophy; protein: crumbs homolog 1 | Jacobson et al., Hum. Mol. Genet. 9: 1073-1078 (2003) |
| RD3, C1ORF36; | 1q32.3 | recessive Leber congenital amaurosis; protein: RD3 protein | Friedman et al., Am. J. Hum. Genet. 79: 1059-1070 (2006) |
| USH2A; | 1q41 | recessive Usher syndrome, type 2a; recessive RP; protein: usherin | Seyedahmadi et al., Exp. Eye. Res. 79: 167-173 (2004) |
| RP28; | 2p16-p11 | recessive RP | Kumar et al., Mol. Vis. 10: 399-402 (2004) |
| EFEMP1, DHRD, MTLV, FBLN3; | 2p16.1 | dominant radial, macular drusen; dominant Doyne honeycomb retinal degeneration (Malattia Leventinese); protein: EGF-containing fibrillin-like extra-cellular matrix protein 1 (fibulin 3) | Kermani et al., Hum. Genet. 104: 77-82 (1999) |
| ALMS1, ALSS | 2p13.1 | recessive Alstrom syndrome; protein: ALMS1 protein | Hearn et al., Nat. Genet. 31: 79-83 (2002) |
| RP33 | 2cen-q12.1 | dominant RP | Zhao et al., Hum. Genet. 119: 617-623 (2006) |
| LOC619531 | 2q11 | recessive cone-rod dystrophy and amelogenesis imperfecta | Michaelides et al., J. Med. Genet. 41: 468-473 (2004) |
| CNGA3, ACHM2, CNCG3, RMCH2 | 2q11.2 | recessive achromatopsia; protein: cone photoreceptor cGMP-gated cation channel alpha subunit | Nishiguchi et al., Hum. Mutat. 25: 248-258 (2005) |
| MERTK | 2q13 | recessive RP; protein: c-mer protooncogene receptor tyrosine kinase | Vollrath et al., Proc. Natl. Acad. Sci. USA 98: 12584-12589 (2001) |
| NPHP1, JBTS4, SLSN1 | 2q13 | recessive Senior-Loken syndrome; recessive nephronophthisis, juvenile; recessive Joubert syndrome; protein: nephronophthisis 3 protein | Hildebrandt et al., Nat. Genet. 17: 149-153 (1997) |

TABLE 5-continued

Genes known to be involved in retinitis pigmentosa (Table adapted from RETNET) (http://www.sph.uth.tmc.edu/Retnet/)

| Symbols; OMIM Numbers | Location | Diseases; Protein | References |
|---|---|---|---|
| BBS5 | 2q31.1 | recessive Bardet-Biedl syndrome; protein: flagellar apparatus-basal body protein DKFZp7621194 | Li et al., Cell. 117: 541-552 (2004) |
| CERKL, RP26 | 2q31.3 | recessive RP; protein: ceramide kinase-like protein | Tuson et al., Am. J. Hum. Genet. 74: 128-138 (2004) |
| SVD | 2q36 | dominant vitreoretinal degeneration, snowflake | Jiao et al., Invest. Ophthalmol. Vis. Sci. 45: 4498-503 (2004) |
| SAG | 2q37.1 | recessive Oguchi disease; recessive RP; protein: arrestin (s-antigen) | Nakazawa et al., Arch. Ophthalmol. 116: 498-501 (1998) |
| USH2B DFNB6 | 3p24.2-p23 | recessive Usher syndrome, type 2; recessive sensorineural deafness without RP | Hmani et al., Eur. J. Hum. Genet. 7: 363-367 (1999) |
| CRV, HERNS, HVR | 3p21.3-p21.1 | dominant hereditary vascular retinopathy with Raynaud phenomenon and migraine | OPhoff et al., Am. J. Hum. Genet. 69: 447-453 (2001) |
| GNAT1 | 3p21.31 | dominant CSNB, Nougaret type; protein: rod transducin alpha subunit | Dryja et al., Nat. Genet. 13: 358-360 (1996) |
| ATXN7, ADCA2, OPCA3, SCA7 | 3p14.1 | dominant spinocerebellar ataxia w/ MD or retinal degeneration; protein: ataxin 7 | Aleman et al., Exp. Eye. Res. 74: 737-745 (2002) |
| ARL6, BBS3 | 3q11.2 | recessive Bardet-Biedl syndrome; protein: ADP-ribosylation factor-like 6 | Fan et al., Nat. Genet. 36: 989-993 (2004) |
| IQCB1, NPHP5, SLSN5 | 3q13.33 | recessive Senior-Loken syndrome; protein: IQ motif containing B1 protein | Otto et al., Nat. Genet. 37: 282-288 (2005) |
| NPHP3, SLSN3 | 3q22.1 | recessive Senior-Loken syndrome; recessive nephronophthisis, adolescent; protein: nephronophthisis 3 protein | Olbrich et al., Nat. Genet. 34: 455-459 (2003) |
| RHO, RP4 | 3q22.1 | dominant RP; dominant CSNB; recessive RP; protein: rhodopsin | Dryja et al., Nat. Genet. 4: 280-283 (1993) |
| RP5 | same as RHO | not distinct from RHO/RP4 | Farrar et al., Hum. Mol. Genet. 1: 769-771 (1992) |
| USH3A, USH3 | 3q25.1 | recessive Usher syndrome, type 3; protein: clarin-1 | Joensuu et al., Am. J. Hum. Genet. 69: 673-684 (2001) |
| OPA1 | 3q29 | dominant optic atrophy, Kjer type; dominant optic atrophy with sensorineural hearing loss; protein: OPA1 protein | Aung et al., Hum. Genet. 110: 52-56 (2002) |
| STGD4 | 4p | dominant Stargardt-like macular dystrophy | Kniazeva et al., Am. J. Hum. Genet. 64: 1394-1399 (1999) |
| MCDR2 | 4p16.3-p15.2 | dominant MD, bull's-eye | Michaelides et al., Invest. Ophthalmol. Vis. Sci. 44: 1657-1662 (2003) |
| PDE6B, CSNB3 | 4p16.3 | recessive RP; dominant CSNB; protein: rod cGMP phosphodiesterase beta subunit | Pearce-Kelling et al., Mol. Vis. 7: 42-47 (2001) |
| WFS1, DFNA38 | 4p16.1 | recessive Wolfram syndrome; dominant low frequency sensorineural hearing loss; protein: wolframin | Hum. Mol. Genet. 10: 2501-2508 (2001) |
| PROML1 | 4p15.32 | recessive retinal degeneration; protein: prominin (mouse)-like 1 | Maw et al., Hum. Mol. Genet. 9: 27-34 (2000) |
| CNGA1, CNCG, CNCG1 | 4p12 | recessive RP; protein: rod cGMP-gated channel alpha subunit | Dryja et al., Proc. Natl. Acad. Sci. USA 92: 10177-10181 (1995) |
| WFS2 | 4q22-q24 | recessive Wolfram syndrome; dominant | El-Shanti et al., Am. J. Hum. Genet. 66: 1229-1236 (2000) |
| MTP, ABL | 4q23 | recessive abetalipoproteinemia; protein: microsomal triglyceride transfer protein | Narcisi et al., Am. J. Hum. Genet. 57: 1298-1310 (1995) |
| BBS7, BBS2L1 | 4q27 | recessiveBardet Biedl syndrome; protein: BBS7 protein | Badano et al., Am. J. Hum. Genet. 72: 650-658 (2003) |
| BBS12, FLJ35630 | 4q27 | recessive Bardet-Biedl syndrome; protein: BBS12 protein | Stoetzel et al., Am. J. Hum. Genet. 80: 1-11 (2007) |
| RP29 | 4q32-q34 | recessive RP | Hameed et al., Invest. Ophthalmol. Vis. Sci. 42: 1436-1438 (2001) |
| LRAT | 4q32.1 | recessive RP, severe early-onset; recessive Leber congenital amaurosis; protein: lecithin retinol acyltransferase | Thompson et al., Nat. Genet. 128: 123-124 (2001) |
| CYP4V2, BCD | 4q35.2 | recessive Bietti crystalline corneoretinal dystrophy; protein: cytochrome P450 4V2 | Li et al., Am. J. Hum. Genet. 74: 817-826 (2004) |
| MCDR3 | 5p15.33-p13.1 | dominant MD | Michaelides et al., Invest. Ophthalmol. Vis. Sci. 44: 2178-2183 (2003) |
| CSPG2, WGN1, ERVR | 5q14.3 | dominant Wagner disease and erosive vitreoretinopathy; protein: chondroitin sulfate proteoglycan 2 (versican) | Kloeckener-Gruissem et al., Mol. Vis. 12: 350-355 (2006) |
| MASS1, USH2C, VLGR1 | 5q14.3 | recessive Usher syndrome, type 2; dominant/recessive febrile convulsions; | Weston et al., Am. J. Hum. Genet. 74: 357-366 (2004) |

TABLE 5-continued

Genes known to be involved in retinitis pigmentosa (Table adapted from RETNET) (http://www.sph.uth.tmc.edu/Retnet/)

| Symbols; OMIM Numbers | Location | Diseases; Protein | References |
|---|---|---|---|
| | | protein: monogenic audiogenic seizure susceptibility 1 homolog | |
| BSMD | 5q21.2-q33.2 | dominant MD, butterfly-shaped | den Hollander et al., J. Med. Genet. 41: 699-702 (2004) |
| PDE6A | 5q33.1 | recessive RP; protein: cGMP phosphodiesterase alpha subunit | Dryja et al., Invest. Ophthalmol. Vis. Sci. 40: 1859-1865 (1999). |
| GRM6 | 5q35.3 | recessive CSNB; protein: metabotropic glutamate receptor 6 | Dryja et al., Proc. Natl. Acad. Sci. USA 102: 4884-4889 (2005) |
| C2 | 6p21.32 | age-related macular degeneration, complex etiology; protein: complement component 2 | Gold et al., Nat. Genet. 38: 458-462 (2006) |
| CFB, BF, BFD | 6p21.32 | age-related macular degeneration, complex etiology; protein: complement factor B, properdin | Gold et al., Nat. Genet. 38: 458-462 (2006) |
| TULP1, RP14 | 6p21.31 | recessive RP; recessive Leber congenital amaurosis; protein: tubby-like protein 1 | Banerjee et al., Nat. Genet. 18: 177-179 (1998) |
| RDS, RP7 | 6p21.2 | dominant RP; dominant MD; digenic RP with ROM1; dominant adult vitelliform MD; protein: peripherin 2 | Hum. Mutat. 10: 301-309 (1997) |
| GUCA1A, COD3, GCAP1 | 6p21.1 | dominant cone dystrophy; dominant cone-rod dystrophy; protein: guanylate cyclase activating protein 1A | Payne et al., Am. J. Hum. Genet. 61: A290 (1997) |
| GUCA1B, GCAP2 | 6p21.1 | dominant RP; dominant MD; protein: guanylate cyclase activating protein 1B | Sato et al., Graefes Arch. Clin. Exp. Ophthalmol. 243: 235-242 (2004) |
| BCMAD | 6p12.3-q16 | dominant MD, benign concentric annular | van Lith-Verhoeven et al., Invest. Ophthalmol. Vis. Sci. 45: 30-35 (2004) |
| RP25 | 6cen-q15 | recessive RP | Abd El-Aziz et al., Ann. Hum. Genet. (2006) |
| LCA5 | 6q11-q16 | recessive Leber congenital amaurosis | Dharmaraj et al., Am. J. Hum. Genet. 66: 319-326 (2000) |
| COL9A1 | 6q13 | recessive Stickler syndrome; dominant multiple epiphyseal dysplasia (MED); protein: collagen, type IX, alpha-1 | Van Camp et al., Am. J. Hum. Genet. 79: 449-457 (2006) |
| RIMS1, CORD7, RIM1 | 6q13 | dominant cone-rod dystrophy; protein: regulating synaptic membrane exocytosis protein 1or rab3A-interacting molecule | Kelsell et al., Am. J. Hum. Genet. 63: 274-279 (1998) |
| MCDR1, PBCRA | 6q14-q16.2 | dominant MD, North Carolina type; dominant progressive bifocal chorioretinal atrophy | Small et al., Mol. Vis. 5: 38 (1999) |
| ELOVL4, STGD3 | 6q14.1 | dominant MD, Stargardt-like; protein: elongation of very long fatty acids protein | Edwards et al., Invest. Ophthalmol. Vis. Sci. 42: 2652-2663 (2001) |
| AHI1, JBTS3 | 6q23.3 | recessive Joubert syndrome; protein: Abelson helper integration site 1 | Parisi et al., J. Med. Genet. 43: 334-339 (2006) |
| PEX7, PTS2R, RCDP1, | 6q23.3 | recessive Refsum disease, adult form; protein: peroxisome biogenesis factor 7 | van den Brink 0et al., Am. J. Hum. Genet. 72: 471-477 (2003) |
| RCD1 | 6q25-q26 | dominant retinal-cone dystrophy 1 | OMIM 07 |
| MDDC, CYMD | 7p21-p15 | dominant MD, cystoid | Inglehearn et al., Am. J. Hum. Genet. 55: 581-582 (1994) |
| PTHB1, BBS9, PHTB1 | 7p14.3 | recessive Bardet Biedl syndrome; protein: parathyroid hormone-responsive B1 protein | Nishimura et al., Am. J. Hum. Genet. 77: 1021-1033 (2005) |
| RP9, PAP1, PIM1K | 7p14.3 | dominant RP; protein: RP9 protein or PIM1-kinase associated protein 1 | Sullivan et al., Invest. Ophthalmol. Vis. Sci. 47: 3052-3064 (2006) |
| PEX1, IRD | 7q21.2 | recessive Refsum disease, infantile form; protein: peroxisome biogenesis factor 1 | Portsteffen et al., Nat. Genet. 17: 449-452 (1997) |
| IMPDH1, RP10 | 7q32.1 | dominant RP; dominant Leber congenital amaurosis; protein: inosine monophosphate dehydrogenase 1 | Mortimer et al., Biochem. J. 390: 41-47 (2005) |
| OPN1SW, BCP, CBT | 7q32.1 | dominant tritanopia; protein: blue cone opsin | Fitzgibbon et al., Hum. Genet. 93: 79-80 (1994) |
| CORD9 | 8p11 | recessive cone-rod dystrophy | Danciger et al., Invest. Ophthalmol. Vis. Sci. 42: 2458-2465 (2001) |
| RP1 | 8q12.1 | dominant RP; recessive RP; protein: RP1 protein | Bowne et al., Hum. Mol. Genet. 11: 2121-2128 (1999) |
| TTPA | 8q12.3 | recessive RP and/or recessive or dominant ataxia; protein: alpha-tocopherol-transfer protein | Yokota et al., New Eng. J. Med. 335: 1770-1771 (1996) |
| ROA1 | 8q21-q22 | recessive optic atrophy | Barbet et al., Eur. J. Hum. Genet. 11: 966-971 (2003) |
| PXMP3, PAF1, PEX2, PMP35 | 8q21.13 | recessive Refsum disease, infantile form; protein: peroxisomal membrane protein 3 | Gartner et al., Nat. Genet. 1: 16-23 (1992) |
| CNGB3, ACHM3 | 8q21.3 | recessive achromatopsia Pingelapese; | Kohl et al., Eur. J. Hum. Genet. 13: |

TABLE 5-continued

Genes known to be involved in retinitis pigmentosa (Table adapted from RETNET) (http://www.sph.uth.tmc.edu/Retnet/)

| Symbols; OMIM Numbers | Location | Diseases; Protein | References |
|---|---|---|---|
| | | recessive, progressive cone dystrophy; protein: cone cyclic nucleotide-gated cation channel beta 3 subunit | 302-308 (2005) |
| VMD1 | not 8q24 | dominant MD, atypical vitelliform | Sohocki et al., Am. J. Hum. Genet. 61: 239-241 (1997) |
| RP31 | 9p22-p13 | dominant RP | Papaioannou et al., Hum. Mut. 118: 501-503 (2005) |
| KCNV2 | 9q24.2 | recessive cone dystrophy with super-normal rod electroretinogram; protein: potasium channel subfamily V member 2 | Wu et al., Am. J. Hum. Genet. 79: 574-579 (2006) |
| INVS, NPHP2 | 9q31.1 | recessive Senior-Loken syndrome; recessive nephronophthisis; protein: inverson | O'Toole et al., Nephrol. Dial. Transplant. 21: 1989-1991 (2006) |
| DFNB31 | 9q32 | recessive Usher syndrome, type 2; recessive deafness without RP; protein: whirlin | Ebermann et al., Hum. Genet. (2006) |
| TLR4 | 9q33.1 | age-related macular degeneration, complex etiology; protein: toll-like receptor 4 | Zareparsi et al., Hum. Mol. Genet. 14: 1449-1455 (2005) |
| TRIM32, BBS11, HT2A | 9q33.1 | recessive Bardet-Biedl syndrome; recessive limb-girdle muscular dystrophy; protein: tripartite motif-containing protein 32 | Chiang et al., Proc. Natl. Acad. Sci. USA 103: 6287-6292 (2006) |
| RP21, RP8 | not 9q34-qter | dominant RP with sensorineural deafness | Mansergh et al., Am. J. Hum. Genet. 64: 971-985 (1999) |
| JBTS1, CORS1 | 9q34 | recessive Joubert syndrome | Saar et al., Am. J. Hum. Genet. 65: 1666-1671 (1999) |
| PHYH, PAHX, RDPA | 10p13 | recessive Refsum disease, adult form; protein: phytanoyl-CoA hydroxyase | Jansen et al., Nat. Genet. 17: 190-193 (1997) |
| RNANC | 10q21 | recessive nonsyn-dromal congenital retinal nonattachmen | Ghiasvand et al., Am. J. Med. Genet. 90: 165-168 (2000) |
| PCDH15, DFNB23, USH1F | 10q21.1 | recessive Usher syndrome, type 1f; recessive deafness without RP; protein: protocadherin 15 | Ahmed et al., Hum. Mol. Genet. 12: 3215-3223 (2003) |
| CDH23, DFNB12, USH1D | 10q22.1 | recessive Usher syndrome, type 1d; recessive deafness without RP; protein: cadherin-like gene 23 | Astuto et al., Am. J. Hum. Genet. 71: 262-275 (2002) |
| RGR | 10q23.1 | recessive RP; dominant choroidal sclerosis; protein: RPE-retinal G protein-coupled receptor | Morimura et al., Nat. Genet. 23: 393-394 (1999) |
| RBP4 | 10q23.33 | recessive RPE degeneration; protein: retinol-binding protein 4 | Seeliger et al., Invest. Ophthalmol. Vis. Sci. 40: 3-11 (1999) |
| PAX2, ONCR | 10q24.31 | dominant renal-coloboma syndrome; protein: paired home-otic gene 2 protein | Favor et al., Proc. Natl. Acad. Sci. USA 93: 13870-13875 (1996) |
| HTRA1, PRSS11 | 10q26.13 | age-related macular degeneration, complex etiology; protein: HtrA serine peptidase 1 | DeWan et al., Science 314: 989-992 (2006) |
| LOC387715 | 10q26.13 | age-related macular degeneration, complex etiology; protein: hypothetical protein with Entrez ID 387715 | Jakobsdottir et al., Am. J. Hum. Genet. 77: 389-407 (2005) |
| OAT | 10q26.13 | recessive gyrate atrophy; protein: ornithine aminotransferase | D Valle, O Simell. In 'The Metabolic and Molecular Bases of Inherited Disease', 8th Ed. CR Schriver, et al. eds., McGraw-Hill. (2000) |
| TEAD1, AA, TCF13, TEF1 | 11p15.3 | dominant atrophia areata; protein: TEA domain family member 1 [Entrez] | Fossdal et al., Hum. Mol. Genet. 13: 975-981 (2004) |
| USH1C, DFNB18 | 11p15.1 | recessive Usher syndrome, Acadian; recessive deafness without RP; protein: harmonin | Ahmed et al., Hum. Genet. 110: 527-531 (2002) |
| EVR3 | 11p13-p12 | dominant familial exudative vitreoretinopathy | Downey et al., Am. J. Hum. Genet. 68: 778-781 (2001) |
| CORS2, JBTS2 | 11p12-q13.3 | recessive Joubert syndrome | Valente et al., Ann. Neurol. 57: 513-519 (2005) |
| ROM1 | 11q12.3 | dominant RP; digenic RP with RDS; protein: retinal outer segment membrane protein 1 | Dryja et al., Invest. Ophthalmol. Vis. Sci. 18: 1972-1982 (1997) |
| VMD2 | 11q12.3 | dominant MD, Best type; dominant vitreo-retinochoroidopathy; protein: bestrophin | Weber et al., Am. J. Hum. Genet. 55: 1182-1187 (1994a) |
| BBS1 | 11q13 | recessive Bardet-Biedl syndrome; protein: BBS1 protein | Mykytyn et al., Nat. Genet. 31: 435-438 (2002) |
| VRNI | 11q13 | dominant neovascular inflammatory vitreoretinopathy | Stone et al., Hum. Mol. Genet. 1: 685-689 (1992) |
| CABP4 | 11q13.1 | recessive CSNB; protein: calcium binding protein 4 | Zeitz et al., Am. J. Hum. Genet. 79: 657-667 (2006) |
| LRP5, EVR4, HBM, OPPG | 11q13.2 | dominant familial exudative vitreo-retinopathy; dominant high bone mass trait; recessive osteo-porosis-pseudoglioma syndrome; recessive | Jiao et al., Am. J. Hum. Genet. 75: 878-884 (2004) |

TABLE 5-continued

Genes known to be involved in retinitis pigmentosa (Table adapted from RETNET) (http://www.sph.uth.tmc.edu/Retnet/)

| Symbols; OMIM Numbers | Location | Diseases; Protein | References |
|---|---|---|---|
| | | FEVR; protein: low density lipoprotein receptor-related protein 5 | |
| MYO7A, DFNB2, USH1B | 11q13.5 | recessive Usher syndrome, type 1; recessive congenital deafness without RP; recessive atypical Usher syndrome (USH3-like); protein: myosin VIIA | Gibbs et al., Natl. Acad. Sci. USA 100: 6481-6486 (2003) |
| FZD4, EVR1, FEVR | 11q14.2 | dominant familial exudative vitreo-retinopathy; protein: frizzled-4 Wnt receptor homolog | Muller et al., Genomics 20: 317-319 (1994) |
| C1QTNF5, CTRP5 | 11q23.3 | dominant MD, late onset; dominant MD with lens zonules; protein: C1q and tumor necrosis-related protein 5 collagen | Ayyagari et at., Invest. Ophthalmol. Vis. Sci. 46: 3363-3371 (2005) |
| COL2A1, AOM, STL1 | 12q13.11 | dominant Stickler syndrome, type I; dominant Wagner syndrome; dominant epiphyseal dysplasia; protein: collagen, type II, alpha 1 | Snead et al., J. Med. Genet. 36: 353-659 (1999) |
| RDH5, RDH1 | 12q13.2 | recessive fundus albipunctatus; recessive cone dystrophy, late onset; protein: 11-cis retinol dehydrogenase 5 | Cideciyan et al., Vis. Neurosci. 17: 667-678 (2000) |
| BBS10, FLJ23560 | 12q21.2 | recessive Bardet-Biedl syndrome; protein: BBS10 (C12orf58) chaperonin | Stoetzel et al., Nat. Genet. 38: 521-524 (2006) |
| CEP290, JBTS5, NPHP6, SLSN6 | 12q21.32 | recessive Senior-Loken syndrome; recessive Joubert syndrome; recessive Leber congenital amaurosis; protein: centrosomal protein 290 kDa | Chang et al., Hum. Mol. Genet. 15: 1847-1857 (2006) |
| RB1 | 13q14.2 | dominant germline or somatic retino-blastoma; benign retinoma; pinealoma; osteogenic sarcoma; protein: retino-blastoma protein 1 | Lohmann et al., Am. J. Hum. Genet. 58: 940-949 (1996) |
| GRK1, RHOK, RK | 13q34 | recessive CSNB, Oguchi type; protein: rhodopsin kinase | Cideciyan et al., Proc. Natl. Acad. Sci. USA 95: 328-333 (1998) |
| STGD2 | not 13q34 | dominant MD, Stargardt type | Zhang et al., Nat. Genet. 27: 89-93 (2001) |
| ACHM1, RMCH | 14 | recessive rod monochromacy or achromatopsia | Pentao et al., Am. J. Hum. Genet. 50: 690-699 (1992) |
| RP16 | not 14 | recessive RP | Bruford et al., Am. J. Hum. Genet. 55: A181 (1994) |
| MCDR4 | 14q | dominant MD, North Carolina-like with progressive sensori-neural hearing loss | Francis et al., Br. J. Ophthalmol. 87: 893-898 (2003) |
| NRL, RP27 | 14q11.2 | dominant RP; recessive RP; protein: neural retina lucine zipper | Mears et al., Nat. Genet. 29: 447-452 (2001) |
| RPGRIP1, LCA6 | 14q11.2 | recessive Leber congenital amaurosis; protein: RPGR-interacting protein 1 | Mellersh et al., Genomics 88: 293-301 (2006) |
| LCA3 | 14q24 | recessive Leber congenital amaurosis | Stockton et al., Hum. Genet. 103: 328-333 (1998) |
| RDH12 | 14q24.1 | recessive Leber congenital amaurosis with severe childhood retinal dystrophy; protein: retinol dehydrogenase 12 | Janecke et al., Nat. Genet. 36: 850-854 (2004) |
| USH1A, USH1 | not 14q32 | recessive Usher syndrome, French | Gerber et al., Am. J. Hum. Genet. 78: 357-359 (2006) |
| TTC8, BBS8 | 14q32.11 | recessive Bardet-Biedl syndrome; pro-tein: tetratricopeptide repeat domain 8 | Ansley et al., Nat. 425: 628-633 (2003) |
| FBLN5 | 14q32.12 | familial MD, age-related; protein: fibulin 5 | Arch. Ophthalmol. 112: 765-772 (1994) |
| NR2E3, ESCS, PNR | 15q23 | recessive enhanced S-cone syndrome; recessive RP in Portuguese Crypto Jews; Goldmann-Favre syndrome; pro-tein: nuclear receptor subfamily 2 group E3 | Sharon et al., Arch. Ophthalmol. 121: 1316-1323 (2003) |
| MRST | 15q24 | recessive retardation, spasticity and retinal degeneration | Mitchell et al., Am. J. Hum. Genet. 62: 1070-1076 (1998) |
| BBS4 | 15q24.1 | recessive Bardet-Biedl syndrome; protein: BBS4 protein | Katsanis et al., Nat. Genet. 26: 67-70 (2000) |
| RLBP1, CRALBP | 15q26.1 | recessive RP; recessive Bothnia dystrophy; recessive retinitis punctata albescens; recessive Newfoundland rod-cone dystrophy; pro-tein: retinaldehyde-binding protein 1 | Burstedt et al., Invest. Ophthalmol. Vis. Sci. 40: 995-1000 (1999) |
| ABCC6, ARA, MRP6, PXE | 16p13.11 | recessive pseudo-xanthoma elasticum; dominant pseudo-xanthoma elasticum; protein: ATP-binding casette, subfamily C, member 6 | Bergen et al., Nat. Genet. 25: 228-231 (2000) |
| RP22 | 16p12.3-p12.1 | recessive RP | Finckh et al., Genomics 48: 341-345 (1998) |
| CLN3, JNCL | 16p11.2 | recessive Batten disease (ceroid-lipofuscinosis, neuronal 3), juvenile; protein: Batten disease protein | Kremmidiotis et al., Hum. Mol. Genet. 8: 523-531 (1999) |

TABLE 5-continued

Genes known to be involved in retinitis pigmentosa (Table adapted from RETNET) (http://www.sph.uth.tmc.edu/Retnet/)

| Symbols; OMIM Numbers | Location | Diseases; Protein | References |
|---|---|---|---|
| BBS2 | 16q12.2 | recessive Bardet-Biedl syndrome; protein: BBS2 protein | Beales et al., Am. J. Hum. Genet. 68: 606-616 (2001) |
| CNGB1, CNCG2, CNCG3L, GAR1, GARP | 16q13 | recessive RP; protein: rod cGMP-gated channel beta subunit | Bareil et al., Hum. Genet. 108: 328-334 (2001) |
| CDH3, CDHP, PCAD | 16q22.1 | recessive MD, juvenile with hypotrichosis; protein: cadherin 3, type 1, placental | Indelman et al., J. Invest. Dermatol. 119: 1210-1213 (2002) |
| FHASD | 16q23.2-q24.2 | recessive foveal hypoplasia and anterior segment dysgenesis | Pal et al., J. Med. Genet. 41: 772-777 (2004) |
| CACD | 17p13 | dominant central areolar choroidal dystrophy | Hughes et al., J. Med. Genet. 35: 770-772 (1998) |
| PRPF8, PRPC8, RP13 | 17p13.3 | dominant RP; protein: human homolog of yeast pre-mRNA splicing factor C8 | Kojis et al., Am. J. Hum. Genet. 58: 347-355 (1996) |
| AIPL1, LCA4 | 17p13.2 | recessive Leber congenital amaurosis; dominant cone-rod dystrophy; protein: arylhydrocarbon-interacting receptor protein-like 1 | Hanein et al., Hum. Mutat. 23: 306-317 (2004) |
| GUCY2D, CORD6, LCA1, RETGC, RETGC1 | 17p13.1 | recessive Leber congenital amaurosis; dominant cone-rod dystrophy; protein: retinal-specific guanylate cyclase | Hanein et al., Hum. Mutat. 23: 306-317 (2004) |
| CORD5, RCD2 | same as GUCY2D | dominant cone-rod dystrophy, progressive; recessive cone-rod dystrophy | Udar et al., Hum. Mut. 21: 170-171 (2003) |
| CORD4 | 17q | cone-rod dystrophy | Klystra et al., |
| UNC119, HRG4 | 17q11.2 | dominant cone-rod dystrophy; protein: human homolog of *C. elegans* unc119 protein | Kobayashi et al., Invest. Ophthalmol. Vis. Sci. 41: 3268-3277 (2000) |
| CA4, RP17 | 17q23.2 | dominant RP; protein: carbonic anhydrase IV | Rebello et al., Proc. Natl. Acad. Sci. USA 101: 6617-6622 (2004) |
| USH1G, SANS | 17q24-q25 | recessive Usher syndrome; protein: human homolog of mouse scaffold protein containing ankyrin repeats and SAM domain | Kikkawa et al., Hum. Mol. Genet. 12: 453-461 (2003) |
| RGS9 | 17q24.1 | recessive delayed cone adaptation; protein: regulator of G-protein signalling 9 | Nishiguchi et al., Nature 427: 75-78 (2004) |
| PRCD | 17q25.1 | recessive RP; protein: progressive rod-cone degneration protein | Zangerl et al., Genomics (2006) |
| FSCN2, RP30 | 17q25.3 | dominant RP; dominant MD; protein: retinal fascin homolog 2, actin bundling protein | Wada et al., Arch. Ophthalmol. 121: 1613-1620 (2003) |
| OPA4 | 18q12.2-q12.3 | dominant optic atrophy, Kjer type | Kerrison et al., Arch. Ophthalmol. 117: 805-810 (1999) |
| CORD1 | 18q21.1-q21.3 | cone-rod dystrophy; de Grouchy syndrome | Manhant et al., Am. J. Hum. Genet. 57: A96 (1995) |
| R9AP | 19q13.12 | recessive delayed cone adaptation; protein: regulator of G-protein signalling 9-binding protein | Nishiguchi et al., Nature 427: 75-78 (2004) |
| MCDR5 | 19q13.31-q13.32 | dominant macular dystrophy | Yang et al., Science 314: 992-993 (2006) |
| CRX, CORD2 | 19q13.32 | dominant cone-rod dystrophy; recessive, dominant and de novo Leber congenital amaurosis; dominant RP; protein: cone-rod otx-like photoreceptor homeobox transcription factor | Hanein et al., Hum. Mutat. 23: 306-317 (2004) |
| OPA3, MGA3 | 19q13.32 | recessive optic atrophy with ataxia and 3-methylglutaconic aciduria; protein: OPA3 protein | Anikster et al., Am. J. Hum. Genet. 69: 1218-1224 (2001) |
| PRPF31, PRP31, RP11 | 19q13.42 | dominant RP; protein: human homolog of yeast pre-mRNA splicing factor 31 | Sullivan et al., Invest. Ophthalmol. Vis. Sci. 47: 4579-4588 (2006) |
| JAG1, AGS | 20p12.2 | dominant Alagille syndrome; protein: Jagged protein 1 | Li et al., Nat. Genet. 16: 243-251 (1997) |
| MKKS, BBS6 | 20p12.2 | recessive Bardet-Biedl syndrome; protein: McKusick-Kaufman syndrome protein | Beales et al., Am. J. Hum. Genet. 68: 606-616 (2001) |
| PANK2, HARP, PKAN | 20p13 | recessive HARP (hypoprebetalipoproteinemia, acanthocytosis, RP, and palladial degeneration); recessive Hallervorden-Spatz syndrome; protein: pantothenate kinase 2 | Hartig et al., Ann. Neurol. 59: 248-256 (2006) |
| USH1E | 21q21 | recessive Usher syndrome, type 1 | Chaib et al., Hum. Mol. Genet. 6: 27-31 (1997) |
| OPA5 | 22q12.1-q12.3 | dominant optic atrophy | Rozet et al., Invest. Ophthalmol. Vis. Sci. 46: E-Abstract 2292 (2005) |
| TIMP3, SFD | 22q12.3 | dominant Sorsby's fundus dystrophy; protein: tissue inhibitor of metalloproteinases-3 | Felbor et al., Am. J. Hum. Genet. 60: 57-62 (1997) |
| RP23 | Xp22 | X-linked RP | Hardcastle et al., Invest. Ophthalmol. Vis. Sci. 41: 2080-2086 (2000) |
| RS1, XLRS1 | Xp22.13 | retinoschisis; protein: retinoschisin | Grayson et al., Hum. Mol. Genet. 9: 1873-1879 (2000) |

TABLE 5-continued

Genes known to be involved in retinitis pigmentosa (Table adapted from RETNET) (http://www.sph.uth.tmc.edu/Retnet/)

| Symbols; OMIM Numbers | Location | Diseases; Protein | References |
|---|---|---|---|
| (—) | Xp21-q21 | RP with mental retardation | Aldred et al., Am. J. Hum. Genet. 55: 916-922 (1994) |
| RP6 | Xp21.3-p21.2 | X-linked RP | Breuer et al., Invest. Ophthalmol. Vis. Sci. 41: S191 (2000) |
| DMD | Xp21.2-p21.1 | Oregon eye disease (probably); protein: dystrophin | D'Souza et al., Hum. Mol. Genet. 5: 837-842 (1995) |
| AIED, OA2 | Xp11.4-q21 | Åland island eye disease | Wutz et al., Eur. J. Hum. Genet. 10: 449-456 (2002) |
| COD4 | Xp11.4-q13.1 | X-linked progressive cone-rod dystrophy | Jalkanen et al., J. Med. Genet. 40: 418-423 (2003) |
| OPA2 | Xp11.4-p11.2 | X-linked optic atrophy | Assink et al., Am. J. Hum. Genet. 61: 934-939 (1997) |
| NYX, CSNB1 | Xp11.4 | X-linked CSNB; protein: nyctalopin | Bech-Hansen et al., Nat. Genet. 26: 319-323 (2000) |
| CSNB4 | same as NYX | X-linked CSNB | Pusch et al., Nat. Genet. 26: 324-327 (2000) |
| RPGR, RP3 | Xp11.4 | X-linked RP, recessive; X-linked RP, dominant; X-linked CSNB; X-linked cone dystrophy 1; X-linked atrophic MD, recessive; protein: retinitis pigmentosa GTPase regulator | Bader et al., Invest. Ophthalmol. Vis. Sci. 44: 1458-1463 (2003) |
| COD1 | same as RPGR | X-linked cone dystrophy 1 | Demirci et al., Am. J. Hum. Genet. 70: 1049-1053 (2002) |
| RP15 | same as RPGR | X-linked RP, dominant | Mears et al., Am. J. Hum. Genet. 67: 1000-1003 (2000) |
| PRD | Xp11.3-p11.23 | retinal dysplasia, primary | Ravia et al., Hum. Mol. Genet. 8: 1295-1297 (1993) |
| NDP, EVR2 | Xp11.3 | Norrie disease; familial exudative vitreoretinopathy; Coats disease; protein: Norrie disease protein | Black et al., Hum. Mol. Genet. 11: 2021-2035 (1999) |
| CACNA1F, CSNB2, CSNBX2 | Xp11.23 | X-linked CSNB, incomplete; ÅIED-like disease; severe CSNB; protein: L-type voltage-gated calcium channel alpha-1 subunit | Nakamura et al., Arch. Ophthalmol. 121: 1028-1033 (2003) |
| RP2 | Xp11.23 | X-linked RP; protein: novel XRP2 protein similar to human cofactor C | Hardcastle et al., Am. J. Hum. Genet. 64: 1210-1215 (1999) |
| PGK1 | Xq21.1 | RP with myopathy; protein: phospho-glycerate kinase, | Tonin et al., Neurol. 43: 387-391 (1993) |
| CHM | Xq21.2 | choroideremia; protein: geranyl-geranyl transferase Rab escort protein 1 | van den Hurk et al., Hum. Mutat. 9: 110-117 (1997) |
| TIMM8A, DDP, DDP2, DFN1 | Xq22.1 | optic atrophy with deafness-dystonia syndrome; protein: inner mitochondrial membrane translocase 8 homolog A | Koehler et al., Proc. Natl. Acad. Sci USA 96: 2141-1246 (1999) |
| RP24 | Xq26-q27 | X-linked RP | Gieser et al., Am. J. Hum. Genet. 63: 1439-1447 (1998) |
| COD2, XLPCD | Xq27 | X-linked progressive cone dystrophy, 2 | Bergen et al., |
| RP34 | Xq28-qter | X-linked RP | Melamud et al., J. Med. Genet. 43: e27 (2006) |
| OPN1LW, GCP, CBD | Xq28 | deuteranopia and rare macular dystrophy in blue cone mono-chromacy with loss of locus control element; protein: green cone opsin | Ayyagari et al., Mol. Vis. 58: 98-101 (1999) |
| OPN1MW, RCP, CBP | Xq28 | protanopia and rare macular dystrophy in blue cone mono-chromacy with loss of locus control element; protein: red cone opsin | Ayyagari et al., Mol. Vis. 58: 98-101 (1999) |
| KSS | mito-chondrion | Kearns-Sayre syndrome including retinal pigmentary degeneration; protein: several mitochondrial proteins | al., Science 283: 1482-1488 (1999) |
| LHON, MTND1, MTND4, MTND6 | mito-chondrion | Leber hereditary optic neuropathy; protein: complex I, III or IV proteins | Brown et al., Am. J. Hum. Genet. 60: 381-387 (1997) |
| MTTL1, DMDF, TRNL1 | mito-chondrion | macular pattern dystrophy with type II diabetes and deafness; protein: leucine tRNA 1 (UUA/G), nt 3230-3304 | Bonte et al., Retina 17: 216-221 (1997) |
| MTATP6, ATP6, NARP | mito-chondrion | RP with develop-mental and neuro-logical abnormalities; Leigh syndrome; LHON; protein: complex V ATPase 6 subunit, nt 8527-9207 | White et al., J. Inherit. Metab. Dis. 22: 899-914 (1999) |
| MTTH, TRNH | mito-chondrion | pigmentary retin-opathy and sensori-neural hearing loss; protein: histidine tRNA, nt 12138-12206 | Crimi et al., Neurology 60: 1200-1203 (2003) |
| MTTS2, TRNS2 | mito-chondrion | RP with progressive sensorineural hearing loss; protein: serine tRNA 2 (AGU/C), nt 12207-12265 | Mansergh et al., Am. J. Hum. Genet. 64: 971-985 (1999) |

In an embodiment of the invention, suppression agents are siRNAs or shRNAs targeting human rhodopsin. Exemplary siRNAs and replacement rhodopsin sequences are provided in Table 6A.

TABLE 6A

Exemplary siRNA Sequences Targeting Human Rhodopsin and Replacement Rhodopsin Sequences

| siRNA Target Site | SEQ ID NO | Replacement Site | SEQ ID NO |
|---|---|---|---|
| 1. TACGTCACCGTCCAGCACAAG | 1 | TATGTGACGGTGCAACATAA | 2 |
| 2. CTCAACTACATCCTGCTCAAC | 3 | CTGAATTATATTTTATTGAAT | 4 |
| 3. CAGCTCGTCTTCACCGTCAAG | 5 | CAATTGGTGTTTACGGTGAAA | 6 |
| 4. ATCTATATCATGATGAACAAG | 7 | ATTTACATTATGATGAATAAA | 8 |
| 5. GCCTACATGTTTCTGCTGATC | 9 | GCTTATATGTTCTTATTAATT | 10 |
| 6. TACATGTTTCTGCTGATCGTG | 11 | TATATGTTCTTATTAATTGTC | 12 |
| 7. CTGCGCACGCCTCTCAACTAC | 13 | TTACGGACCCCCTTGAATTAT | 14 |
| 8. CGCACGCCTCTCAACTACATC | 15 | CGGACCCCCTTGAATTATATT | 16 |
| 9. CTCAAGCCGGAGGTCAACAAC | 17 | TTGAAACCCGAAGTGAATAAT | 18 |
| 10. CAGCTCGTCTTCACCGTCA | 19 | CAATTGGTGTTTACGGTGA | 20 |
| 11. TACGCCAGCGTGGCATTCTAC | 21 | TATGCTTCTGTCGCCTTTTAC | 22 |
| 12. CCAGCGTTCTTTGCCAAGA | 23 | CCCGCCTTTTTCGCTAAAA | 24 |
| 13. GTCATCTATATCATGATGAAC | 25 | GTGATTTACATTATGATGAAT | 26 |
| 14. AACTGCATGCTCACCACCATC | 27 | AATTGTATGTTGACGACGATT | 28 |
| 15. ACCATCTGCTGCGGCAAGA | 29 | ACGATTTGTTGTGGGAAAA | 30 |
| 16. GACGATGAGGCCTCTGCTA | 31 | GAGGACGAAGCTAGCGCCA | 32 |
| 17. CACCTCTCTGCATGGATACT | 33 | CACGAGCTTACACGGGTATT | 34 |
| siRNAs Targeting 5' UTR | | | |
| 18. AGCTCAGGCCTTCGCAGCA | 35 | | |
| 19. CAGGCCTTCGCAGCATTCT | 36 | | |
| siRNAs Targeting 3' UTR | | | |
| 20. TCACTTTCTTCTCCTATAA | 37 | | |
| 21. TAGTTAATGTTGTGAATAA | 38 | | |
| 22. GCTCCTATGTTGGTATTAA | 39 | | |
| 23. AGTCACATAGGCTCCTTAA | 40 | | |
| 24. GATTCTTGCTTTCTGGAAA | 41 | | |
| 25. ACAGTAGGTGCTTAATAAA | 42 | | |
| 26. GAACATATCTATCCTCTCA | 43 | | |
| 27. CTGTACAGATTCTAGTTAA | 44 | | |
| 28. TGTGAATAACATCAATTAA | 45 | | |
| 29. CAATTAATGTAACTAGTTA | 46 | | |
| 30. TGATTATCACCTCCTGATA | 47 | | |
| 31. GCAGTCATCAGACCTGAAA | 48 | | |
| 32. TGTCATCCTTACTCGAAGA | 49 | | |

TABLE 6A-continued

| Exemplary siRNA Sequences Targeting Human Rhodopsin and Replacement Rhodopsin Sequences | | | |
|---|---|---|---|
| siRNA Target Site | SEQ ID NO | Replacement Site | SEQ ID NO |
| 33. GAATTAAGCTGCCTCAGTA | 50 | | |
| 34. GCCAGAAGCTCTAGCTTTA | 51 | | |
| 35. AGCTCTGCCTGGAGACTAA | 52 | | |
| siRNAs Targeting an Intron | | | |
| 36. GATCTTATTTGGAGCAATA | 53 | | |
| 37. TGGCTGTGATCCAGGAATA | 54 | | |
| 38. GATGCATTCTTCTGCTAAA | 55 | | |
| 39. GCAATATGCGCTTGTCTAA | 56 | | |
| 40. TTGTCTAATTTCACAGCAA | 57 | | |
| 41. TGTTTGTTGCATTCAATAA | 58 | | |
| 42. CCAGAGCGCTAAGCAAATA | 59 | | |
| 43. GTCTTGCATTTAACAGGAA | 60 | | |
| 44. GGCTGTGATCCAGGAATAT | 61 | | |
| 45. TGCAGGAGGAGACGCTAGA | 62 | | |
| 46. CTTTCACTGTTAGGAATGT | 63 | | |
| 47. TTTGGTTGATTAACTATAT | 64 | | |
| 48. TTAACTATATGGCCACTCT | 65 | | |
| 49. AGATGTTCGAATTCCATCA | 66 | | |
| siRNAs Targeting a Polymorphism | | | |
| 50. TCTTCACCGTCAAGGAGGTAT | 67 | TGTTTACGGTGAAAGAAGTAC | 68 |

siRNA sequences 1-17 target the human rhodopsin coding sequence. siRNA sequences 18 and 19 target the human rhodopsin 5'UTR. siRNA sequences 20-35 target the human rhodopsin 3'UTR. siRNA sequences 36-49 target human rhodopsin intronic sequence. The sequence of the sense strand of the siRNA is given. Notably, siRNAs may also target a combination of these. For example, an siRNA target site may be in the 5'UTR and exon 1. Or an siRNA target site may be in the coding region and an intron. Or an siRNA target site may be in an exon and the 3'UTR. siRNA sequence 50 is an example of an siRNA that has a target site that spans Exon 3/intron 3 of the human rhodopsin gene. The site contains a known polymorphism in intron 3. If this site was used as an siRNA target, the replacement gene would have the wildtype base at the polymorphic site but degeneracy of the genetic code could be used to change other bases at the replacement site. The siRNA(s) may comprise all or part of the sequence provided. The sequences of replacement human rhodopsin nucleic acids over the target for siRNA-mediated suppression are provided for siRNA sequences 1-17. Replacement nucleic acids include at least one altered nucleotide(s) at degenerate position(s) over the siRNA target site (highlighted in bold print). Thus, replacement sequences here provide one of multiple replacement options. Some replacement constructs contain nucleotide changes in the coding sequence. These replacement constructs while altered in nucleotide sequence encode the same amino acids as the wild type rhodopsin protein. Other replacement constructs are altered at either silent or non-silent polymorphic sites. These replacement constructs encode wild type protein, with wild type function. For siRNAs targeting the UTRs or intronic sequence, no replacement constructs have been suggested because the number of base changes within the site is not limited to degenerate positions (as is the case for sequence coding for amino acids).

It is notable that suppression of a given gene such as rhodopsin may be evaluated in a variety of animal species. The siRNA sequences provided in Table 6B represent examples of RNAi sequences that are homologous between porcine and human rhodopsin. In some transgenic animal models the presence of the human transgene enables direct evaluation of sequences that target the human gene in that animal model. In other instances suppressor sequences may be chosen to maximise the homology between the human gene (for example, rhodopsin) and the endogenous gene in the animal under evaluation.

TABLE 6B

Exemplary siRNA Sequences Targeting Homologous Sequences Between Human and Porcine Rhodopsin

| siRNA | Sequence | SEQ ID NO: | Position in NM_000539.2 | Suppression levels in HeLa Cells |
|---|---|---|---|---|
| P1 | ACCTCTCTGCATGG ATAGT-TT | 414 | 384-403 | 69% |
| P2 | CATGTTCGTGGTCC ACTTC-TT | 415 | 713-732 | 81% |

siRNA can be expressed in miR vectors using polymerase II promoters. For this purpose pcDNA6.2-GW/EmGFP-miR from Invitrogen is used where the cloned miR-155 gene is recombined in order to express the choice of siRNA. The antisense strand of the siRNA is kept intact followed by a modified terminal loop and the sense strand, which is modified by introducing a deletion of 2 central nucleotides in order to form an internal loop. See Catalogue no K4936-00, Block-IT, POLII, miR RNAi expression vector kits catalogue, Invitrogen, page 7 for figure showing the native miR-155 sequence and the converted sequence of siRNA-lacZ in the form of miR-lacZ.

Exemplary miRNA Sequences Targeting Human Rhodopsin:

CC miRNA oligos:

(SEQ ID NO: 416)
Top strand: 5'-
TGCTGCTTCTTGTGCTGGACGGTGACGTTTTGGCCACTGACTGACGTCAC
CGTAGCACAAGAAG-3'

(SEQ ID NO: 417)
Bottom strand: 5'-
CCTGCTTCTTGTGCTACGGTGACGTCAGTCAGTGGCCAAAACGTCACCGT
CCAGCACAAGAAGC-3'

Q1 miRNA oligos:

(SEQ ID NO: 418)
Top strand: 5'-
TGCTGGTAGTAGTCGATTCCACACGAGTTTTGGCCACTGACTGACTCGTG
TGGTCGACTACTAC-3'

(SEQ ID NO: 419)
Bottom strand: 5'-
CCTGGTAGTAGTCGACCACACGAGTCAGTCAGTGGCCAAAACTCGTGTGG
AATCGACTACTACC-3'

BB miRNA oligos:

(SEQ ID NO: 420)
Top strand: 5'-
TGCTGGTAGAGCGTGAGGAAGTTGATGTTTTGGCCACTGACTGACATCAA
CTTTCACGCTCTAC-3'

(SEQ ID NO: 421)
Bottom strand: 5'-
CCTGGTAGAGCGTGAAAGTTGATGTCAGTCAGTGGCCAAAACATCAACTT
CCTCACGCTCTACC-3'

In an embodiment of the invention, suppression agents and replacement genes are expressed in photoreceptor cells to alleviate disease pathology. In a further embodiment, replacement nucleic acids encode a gene which when mutated may cause retinal degeneration other than retinitis pigmentosa, for example, Stargarts Syndrome, glaucoma, cod-rod dystrophy, corneal dystrophy or Age-related Macular Degeneration (AMD) (Table 5).

In another aspect, the invention provides cells expressing a suppression effector such as a dsRNA, either transiently or stably, for experimental or therapeutic use. In an embodiment, the cells express an siRNA that targets rhodopsin. In another embodiment, the cells express a replacement nucleic acid expressing rhodopsin that is not targeted by the siRNA. In another embodiment, the cells comprise a vector encoding at least one or more siRNAs. In another embodiment, the cells comprise a vector encoding a replacement nucleic acid. In an additional embodiment, the cells comprise one or more vectors encoding siRNA(s) and replacement nucleic acid(s).

In another aspect, the invention provides transgenic animals and their experimental or therapeutic use. In an embodiment, the transgenic animal is a model for Retinitis Pigmentosa, for example, an animal with a mutation observed in humans such as the Pro23His and or Pro347ser mutations. In another embodiment, the transgenic animal expresses a dsRNA that targets human rhodopsin. In another embodiment, the transgenic animal expresses a replacement nucleic acid transgene that has been altered at one or more wobble position(s) such that it escapes suppression.

Suppression agents and replacement nucleic acids of the invention can be administered to cells, tissues, plants and/or animals, either separately or together. In yet another aspect administration of suppression agent and/or replacement nucleic acid may be systemic or local. In yet another aspect, administration of suppression agent and replacement nucleic acid may be used in conjunction with chemical and/or physical agents to aid administration. In another aspect, the invention provides methods for suppressing rhodopsin expression in an animal by intraocular (e.g., subretinal or intravitreal) injection of a suppression agent into the animal. In another aspect intraocular administration (e.g., subretinal injection, intravitreal) is used to administer a suppression agent and/or replacement nucleic acid to an animal. In another embodiment, ionthophoresis or electroporation is used to administer suppression agents and/or replacement nucleic acids. In another embodiment, suppression agents and/or replacement nucleic acids are administered using nanotechnology (Kawasaki and Player Nanomedicine 1(2):101-9, 2005; Silva Surg. Neurol. 67(2):113-6, 2007; Andrieu-Solar et al., Mol. Vis. 12:1334-47, 2006) or bacteria (Daudel et al., Expert Rev. Vaccines 6(1):97-110, 2007).

Suppression agents and replacement nucleic acids may be optimally combined with conserved regions A-I and/or transcription factor binding sites identified within conserved regions A-I and/or with enhancer elements and/or other regulatory elements (see Tables 1 and 2 above and Tables 9-12 below).

In one aspect of the invention, there is provided a vector for expression of a suppression agent for a disease causing gene and/or a replacement nucleic acid that is not recognized by the suppression agent, wherein the vector comprises at least one of the conserved regions selected from: conserved region B from the rhodopsin gene represented by SEQ ID NO: 93, or a variant or equivalent thereof; conserved region C from the rhodopsin gene represented by SEQ ID NO: 94, or a variant or equivalent thereof; conserved region F and G from the rhodopsin gene represented by SEQ ID NO: 97 or a variant or equivalent thereof; and conserved region A from the rhodopsin gene represented by SEQ ID NO: 92, or a variant or equivalent thereof. In a particular embodiment, the vector comprises at least one of the conserved regions selected from: conserved region B from the rhodopsin gene represented by SEQ ID NO: 93; conserved region C from the rhodopsin gene represented by SEQ ID NO: 94; conserved region F and G from the rhodopsin gene represented by SEQ ID NO: 97; and conserved region A from the rhodopsin gene represented by SEQ ID NO: 92.

In one embodiment of the invention the use of suppression and replacement constructs in combination with one or more factors to facilitate cell survival, cell viability and/or cell functioning is contemplated. In relation to neurons, a range of neurotrophic and/or neuroprotective factors may be used inter glia brain derived neurotrophic factor (BDNF), glial derived neurotrophic factor (GDNF), neurturin, ciliary derived neurotrophic factor (CNTF), nerve growth factor (NGF), fibroblast growth factors (FGF), insulin-like growth factors (IGF), pigment epithelium-derived factor (PEDG), hepatocyte growth factor (HGF), thyrotrophin releasing hormone (TRH) and rod derived cone viability factor (RDCVF) amongst others. There is substantial evidence in the literature that such factors may increase cell viability and/or cell survival for a range of cell types. For example, these factors have been shown to provide beneficial effects to a wide range of neuronal cell types including, for example, photoreceptors, when delivered either in protein or DNA forms (Buch et al., Mol. Ther., 2006; 14(5):700-709). The use of GDNF to augment gene-based therapies for recessive disease has been demonstrated in mice (Buch et al., Mol. Ther., 2006; 14(5):700-709). Genes encoding neurotrophic/neuroprotective factors may be expressed from general promoters such as the CBA promoter (Buch et al., Mol. Ther., 2006; 14(5):700-709) or from tissue specific promoters. Sequences to optimise expression of neurotrophic/neuroprotective factors such as those sequences identified in Tables 1, 2, 9-13 may be included in constructs.

Sequences of a number of exemplary neurotrophic factors are provided in FIG. 17. DNA encoding one or more neurotrophic and/or neuroprotective factors may be utilised in conjunction with suppression and replacement. FIG. 18 provides examples of constructs incorporating suppression and replacement sequences together with sequence encoding a factor promoting cell viability and/or cell functioning such as GDNF, neurturin, CNTF and/or RDCVF amongst others as described above. Well established art known methods involving DNA restriction digestion, DNA ligation into plasmids, bacterial transformation, characterization of transfected bacterial colonies, plasmid purification and DNA sequencing may be used to clone suppression and replacement and neuroprotection/neurotrophic sequences into DNA-based vectors. Examples of the design of such constructs are provided in FIG. 18

Constructs incorporating suppression and replacement and neurotrophic/neuroprotective factor(s) may be delivered using viral and/or non-viral vectors using art known methods (Andrieu-Soler et al., Mil. Vis., 2006; 12:1334-47). Naked DNA, lipids, polymers, nanoparticles, electrotransfer amongst other methods have been used to achieve gene/nucleotide delivery in cells and animals. For example, lentiviral vectors and/or adenoassociated viral (AAV) vectors may be used to deliver constructs incorporating the 3 components defined above (suppression, replacement and neurotrophism/neuroprotection). 3-component constructs in some instances may require vectors that have significant capacity in terms of size of DNA inserts. Many viral and non-viral vectors have been characterised that can facilitate large DNA fragments including inter alia lentiviral vectors and some of adenoassociated viral serotypes. For example, AAV serotype 2 capsid 5 vectors (AAV2/5) have been shown to accommodate 8-9 kilobases of DNA (Alberto Aurrichio; British Society of Gene Therapy, 2008). One or more components (suppression, replacement, neurotrophism/neuroprotection) may, for example, in the case of AAV be cloned between the AAV ITRS and or one or more components may be cloned into the backbone of the plasmid used to generate AAV. FIG. 18 provides key elements of the construct design (B). Utilisation of backbone plasmid sequences to carry components of a multi-component construct can be used to optimise the population of AAV vectors generated using that plasmid. Moreover, in relation to eye disease, it is notable that there is significant evidence that AAV2/5 transduces photoreceptor efficiently. Generation of AAV vectors carrying suppression and replacement sequences in conjunction with sequences encoding neurotrophic and/or neuroprotective agents is contemplated. While AAV may be of value as a vector to deliver 3-component constructs for some target tissues, a range of additional viral and non-viral vectors are available for this purpose, such as those described above, and vectors that are well know in the art.

While utilisation of a single vector to deliver 3-component constructs involving suppression and replacement and a neurotrophic/neuroprotective sequence to a cell, a tissue and or an animal is contemplated, the use of multiple vectors in combination to deliver all 3 components is also contemplated. The multivalent approach involving suppression, replacement and neuroprotection may involve the use of 1 or more vectors for delivery. In addition, the 3 components may be delivered using a combination of a vector or vectors incorporating DNA sequences together with RNA and or dsRNA and or protein. In the current invention, delivery of protein, of RNA encoding protein and/or of DNA encoding protein or a combination thereof to achieve delivery of all 3 components, suppression, replacement and neuroprotection, is contemplated.

In another embodiment of the invention the size of the backbone of the AAV plasmid vector is either increased or decreased so as to increase expression from the virus. For example, it has been described in the art that increasing the AAV virus backbone in size such that it is larger than the insert cloned within ITSI and ITS2 favours AAV packaging of the insert over packaging of the backbone, thereby increasing expression of DNA cloned within the ITR regions (Bennet et al., Reversal of visual defects in animal models of LCA within weeks of treatment with an optimized AAV. Molecular Therapy Vol. 15, supplement 1, s286).

In a further embodiment of the invention the size of the backbone is increased with a gene which is therapeutically beneficial driven by a promoter. In this embodiment a portion of packaged AAV consists of the backbone and hence a portion of AAV particles will express the gene encoded within the backbone. In one embodiment the therapeutically beneficial gene cloned in the backbone is a neurotrophic factor such GDNF, Neurturin or others.

While the invention can be used for dominant and or polygenic disorders, it may also be practised for recessive disorders. For example, the art describes that when treating the recessive disorder phenylketonuria (PKU) with replacement genes, endogenous protein expressed from mutant genes interfered with protein from replacement genes (Described in a thesis submitted to the University of Florida in partial fulfillment of the requirements for the degree of Doctor of Philosophy, by Catherine Elisabeth Charron, August 2005 and entitled “Gene therapy for phenylketonuria: dominant-negative interference in a recessive disease”). Thus, suppression and replacement constructs may be targeted to recessive disorders which like PKU require suppression and replacement.

Suppression and replacement technology provides a strategy that may be applicable to a wide range of genetic disorders including disorders characterized by either a recessive, dominant, polygenic, multifactorial or a dominant negative pathology. In a further embodiment of the invention conserved regions identified in the promoter region of mammalian rhodopsin genes and/or enhancer elements and/or other regulatory elements and/or epigenetic elements such as listed in Table 5 may be combined with suppressors targeting genes with mutations other than rhodopsin and providing replacement genes other than rhodopsin. Osteogenesis imperfecta, epidermolysis bullosa, autosomal dominant early onset Alzheimer's disease, autosomal dominant polycystic kidney disease, Rett syndrome, familial platelet disorder, dominant negative diabetes insipidus, autosomal dominant Stargardt like macular dystrophy, nemaline myopathy, familial pulmonary arterial hypertension, APC and p53 related cancers and several other disorders (OMIM) may potentially benefit from a suppression and replacement therapeutic approach. Triplet repeat disorders, 14 of which have been characterised to date, including Huntington's disease, spinocerebellar ataxia and myotonic dystrophy may benefit from a suppression and replacement approach. For each disorder, promoters of the endogenous gene or constitutive promoters or promotes from other genes, or inducible promoters may be used to express the suppression agent or replacement nucleic acid.

In another embodiment of the invention, promoter and/or enhancer elements and/or other regulatory elements and/or epigenetic elements may be combined with other promoters than rhodopsin in combination with suppression and/or replacement elements. For example, but not exclusively, promoter and enhancer elements can be combined with the COL1A1 and or COL1A2 and or COL7A1 and or Keratin 5 and or Keratin 14 and or peripherin and/or IMPDH1 promoters and/or genes. Depending upon the tissue in which the suppression agent and/or replacement nucleic acid is administered or active in vivo, tissue specific regulatory elements are used to enhance expression of the suppression agent and/or replacement nucleic acid.

The suppressors and/or replacement nucleic acids of the invention can be targeted to suppress and replace a gene where mutations in the gene can give rise, predispose or work in combination with other genetic factors and/or environmental factors to cause disease pathology. For example, in the case of dominant retinopathies the rhodopsin geen may be suppressed and replaced. For example, siRNAs targeting RHO-(NM_000539.2) can be designed and provided commercially. Likewise control siRNAs, for example, targeting EGFP (U57608) and or other reporter genes and or other non-targeting siRNAs can be designed and synthesized. siRNAs are chosen to target sequences which differed by at least one and preferable many more nucleotides from any known gene in mouse and human databases (http://www.ncbi.nlm-.nih.gov/blast, BLASTN2.2.6, Altschul et al., Nuc Acids Res. 25: (17:3389-402, 1997). siRNAs can be cloned downstream of, for example, polymerase III promoters such as the H1 or U6 promoters to generate short hairpin RNAs (shRNAs; Brummelkamp et al., Science 296: (5567:505-3, 2001). Alternatively, polymerase II promoters which drive expression in many or all cell or tissue types including the CMV promoter, ubquitin promoter and or the β-actin promoter, for example, may be used to express shRNAs. Likewise tissue specific promoters such as the rhodopsin promoter, peripherin promoter and or enolase promoter amongst others may be used to express shRNAs. shRNA sequences can be cloned into vectors with a reporter gene to facilitate monitoring expression from vectors, for example, shRNAs can be cloned in pEGFP-1 amongst other plasmids (BD Biosciences, Clontech, Palo Alto, Calif.). Suppressors can be delivered to cells, tissues and or animals with or without replacement nucleic acids.

Replacement nucleic acids with nucleotide sequence changes over the target site for siRNA-mediated suppression, for example, at degenerative nucleotides can be generated by primer directed mutagenesis and cloned into vectors such as pcDNA3.1-(Invitrogen). Replacement nucleic acids may also be modified at the UTRs and or at polymorphic sites within the target gene. Ubiquitous promoters such as the CMV promoter and or the ubiquitin promoter and or the β-actin promoter amongst others can be used to drive expression of replacement nucleic acids. Alternatively, tissue specific promoters such as the rhodopsin promoter, peripherin promoter, Col1A1 promoter, Col1A2 promoter, Col1A7 promoter, Keratin promoters and/or the enolase promoter amongst others and/or inducible promoters such as a tetracycline responsive promoter can be used to drive expression of replacement nucleic acids. Replacement human rhodopsin nucleic acids which have been altered in nucleotide sequence at degenerate positions over siRNA target sites for example, replacement nucleic acids for siRNA sequences 1-17 are provided in Table 5. Replacement nucleic acids can be delivered to cells, tissues and or animals with or without suppressor agents.

Suppression and Replacement in Cells and Tissues

Promoter driven replacement nucleic acids such as rhodopsin nucleic acids and siRNAs and/or shRNAs targeting rhodopsin can be co-transfected into cells, for example, HeLa and or Cos-7 cells amongst other cell types using art known methods. For example, 24 hours post-transfection of suppressor agents and/or replacement nucleic acids, RNA and cytoplasmic protein can be isolated from cells using well established methodologies. Additionally, suppression and replacement can be evaluated in tissues. In the case of retinal genes, for example, organotypic retinal explant cultures from mouse or rat, for example, can be prepared and maintained using art known methods and suppressor agents and or replacement nucleic acids can be delivered to organotypic cultures. For example, electroporation can be used to deliver siRNA and/or shRNA constructs and/or shRNA constructs and replacement nucleic acids to retinal explants as described in Palfi et al., Hum. Mutat. 27(3):260-8, 2006. Subsequent to electroporation of retinal explants, retinas can be treated with trypsin to expedite dissociation of cells. Retinal cell subpopulations within the dissociated cell population which have a particular feature, for example, that express a reporter gene such as EGFP can be identified. One method of identification that can be invoked is FACS (Palfi et al., Hum. Mutat. 27(3): 260-8, 2006). Levels of suppression and replacement of a target gene can be evaluated in FACS isolated cell populations. For example, suppression and/or suppression and replacement can be evaluated in electroporated EGFP positive cells from retinal explants.

Evaluation of Suppression and Replacement Using RNA Assays

Suppression and replacement can be evaluated in cells, tissues and/or animals using RNA assays including real time RT-PCR, northern blotting, RNA in situ hybridisation and or RNAse protection assays. RNA expression levels of suppressors and/or of endogenous genes and or replacement nucleic acids can be assessed by real time RT-PCR using, for example, a 7300 Real Time PCR System (Applied Biosystems, Foster City, Calif., USA) and using, for example, a QuantiTect SYBR Green RT-PCR kit (Qiagen Ltd). RT-PCR assays are undertaken using levels of expression of housekeeping controls such as β-actin or GAPDH, for example, for comparative purposes. Levels of RNA expression can be evaluated using sets of primers targeting the nucleic acids of interest including suppressors, target genes and/or replacements, for example, the following primers can be used for the evaluation of levels of expression of human rhodopsin, β-actin and GAPDH.

TABLE 7

PCR Primers for measuring rhodopsin, β-actin, and GAPDH

| Primer | Sequence | SEQ ID NO |
|---|---|---|
| RHO forward primer | 5' CTTTCCTGATCTGCTGGGTG 3' | 69 |
| RHO reverse primer | 5' GGCAAAGAACGCTGGGATG 3' | 70 |
| β-actin forward primer | 5' TCACCCACACTGTGCCCATCTACGA 3' | 71 |
| β-actin reverse primer | 5' CAGCGGAACCGCTCATTGCCAATGG 3' | 72 |
| GAPDH forward primer: | 5'-CAGCCTCAAGATCATCAGCA-3' | 73 |
| GAPDH reverse primer: | 5'-CATGAGTCCTTCCACGATAC-3' | 74 |

Expression of replacement constructs and/or shRNAs may be confirmed, for example, by Northern blotting. RNA may also be detected by in situ hybridisations using single stranded RNA probes that have been labelled with, for example, DIG. To evaluate levels of expression of suppression agents and/or replacement nucleic acids and/or endogenous target genes, RNase protections assays can be performed using art known methods, such as that described in the Ambion mirVana™ Probe and Marker kit manual (catalogue number 1554) and the Ambion RPAIII™ Ribonuclease protection assay kit manual (catalogue number 1414). For example, RNA probes approximately 15-25 nucleotides in length specific for transcripts from, for example, an endogenous target gene and/or a suppressor and/or a replacement nucleic acid can be synthesized. For example, RNA probes targeting mouse rhodopsin and/or human rhodopsin and/or suppression agents targeting rhodopsin and/or rhodopsin replacement nucleic acids can be synthesized using companies such as Sigma-Proligo or Ambion. RNA probes and size standards can be labelled to aid visualization after separation of samples on denaturing polyacrylamide gels. For example, RNA probes and Decade™ size marker (Ambion Inc) can be 5' end-labelled with $P^{32}$-γATP (GE Healthcare) using the mirVana™ probe and marker kit according to the manufacturer's protocol (Ambion Inc.). RNase protection assays can be performed using art known methods, for example, using the RPA III™ Ribonuclease Protection Assay Kit and the manufacturer's protocol (Ambion Inc.).

Expression of suppressors and/or replacement nucleic acids and/or endogenous genes can be undertaken and determined in cells, in tissues and or in animals using, for example, the assays and associated methodologies provided above.

Evaluation of Suppression and Replacement Using Protein Assays

Suppression and replacement can be evaluated in cells, tissues and/or animals using protein assays including ELISA, western blotting and immunocytochemistry assays. ELISAs can be undertaken to evaluate levels of suppression by assessing levels of expression of a target endogenous gene and/or can be used to evaluate levels expression of replacement nucleic acids—such proteins assays are well know in the art and methods are provided in, for example, Palfi et al., Hum. Mutat. 27(3):260-8, 2006. For example, in the case of retinal genes such as the rhodopsin gene, ELISA is undertaken using a rhodopsin primary antibody which is typically used in a diluted form, for example, using a 1/10-1/10000 dilution (but possibly outside of this range) of an antibody for the target protein. In addition, Western Blotting may be undertaken to determine relative quantities of a specific protein, for example rhodopsin. Briefly, protein samples are separated using SDS-PAGE and transferred to a membrane. The membrane is incubated with generic protein (for example milk proteins) to bind to "sticky" places on the membrane. A primary antibody is added to a solution which is able to bind to its specific protein and a secondary antibody-enzyme conjugate, which recognizes the primary antibody is added to find locations where the primary antibody bound.

In addition to the protein assays referred to above, assays using antibodies in conjunction with microscopy can be used to evaluate protein levels. For example, in the case of rhodopsin immunocytochemistry (for example, using a 1/10-1:1000 dilution of a primary rhodopsin antibody) and fluorescent microscopy can be carried out as has been documented in Kiang et al., 2005 Mol. Ther. 12(3):555-61, 2005. Immunocytochemistry can be undertaken on cells and/or tissues. In the case of the retina, various modes of sectioning can be implemented to evaluate retinal sections. For example, frozen sections, agar embedded sections and/or resin embedded sections can be used. To obtain thin sections, for example of the retina, epon embedding and semi-thin sectioning can be performed using art known methods such as those provided in McNally et al., Hum. Mol. Genet. 11(9):1005-16, 2002. Immunocytochemistry may be used to evaluate suppression of a target gene and or expression of replacement nucleic acids. Additionally, histological analyses can be used to evaluate the histological effect(s) associated with the administration of suppressors and or replacement nucleic acids. In animal models of retinal degenerations such as the rho−/−, rds, rhodopsin Pro23His, rhodopsin Pro2347Ser mice and others there is a degeneration of the photoreceptor cell layer over time. Histological analyses can be used to evaluate if this degeneration has been modulated subsequent to administration of suppression agents and/or replacement nucleic acids.

Delivery of Suppression and Replacement

Both non-viral and/or viral vectors can be used in the invention to deliver the suppression agents and/or replacement nucleic acids. For example, in the case of retina, recombinant adenoassociated virus (AAV) and more specifically AAV2/5 has previously been found to elicit efficient transduction of photoreceptopr cells. Other AAV serotypes may also be used to deliver to retina, for example, AAV2/2 elicits efficient delivery to the retinal pigment epithelium (RPE) as does AAV4. AAV vectors can be generated using protocols with and without helper virus. For example, a helper virus free protocol using a triple transfection approach is well documented (Xiao et al., J. Virol. 72(3):2224-32, 1998). Expression cassettes carrying suppression and/or replacement elements can be cloned into plasmids such as pAAV-MCS provided by Stratagene Inc. Suppressors and/or replacement nucleic acids are cloned between the inverted terminal repeats of AAV2 and transfected into 293 cells (Stratagene; ATACC cat no CRL-1573) with two other plasmids, hence the term triple transfection. For example, the pRep2/Cap5 plasmid (Hildinger et al., J. Virol. 75(13):6199-203, 2001) together with the pHelper plasmid (Stratagene), at, for example, a ratio of 1:1:2, can be used to generate AAV2/5 vectors. Virus can be generated using a variety of art known procedures including the method outlined below. For example, to generate virus fifty 150 mm plates of confluent HEK293 cells were transfected (50 μg DNA/plate) with polyethyleminine (Reed et al., J. Virol. Methods 138(1-2):85-98, 2006). 48 hrs post-transfection crude viral lysates were cleared (Auricchio et al., 2001) and purified by $CsCl_2$ gradient centrifugation (Zolotukhin et al., Gene Ther. 6(6):973-85, 1999). The AAV containing fraction was dialyzed against PBS. Genomic titres, viral particles (vp/ml), were determined by quantitative real-time PCR using art known methods (Rohr et al., J. Virol. Methods 106(1):81-8, 2002). AAVs can be generated that contain, for example, either targeting shRNAs or control shRNAs and/or replacement nucleic acids such as rhodopsin and/or reporter nucleic acids such as EGFP and/or stuffer sequences and/or sequences aiding expression of suppression agents and/or replacement nucleic acids such as promoter and/or enhancer sequences and/or other regulatory sequences and/or epigenetic elements.

Administration of Suppression and Replacement Vectors

Animal models can be used to mirror human disorders. For example, animal models of human retinopathies or that express a human retinal gene have been generated, for example, rho−/− mice (Humphries et al., Nat. Genet. 15(2): 216-9, 1997), NHR +/− mice (Olsson et al., Neuron 9(5):815-30, 1992), Pro23His mice (Olsson et al., Neuron 9(5):815-30, 1992), Pro347Ser mice (Li et al., Proc. Natl. Acad. Sci. U.S.A. 95(20):11933-8, 1998) and RHO-M mice (see below). Mice typically are maintained under specific pathogen free (SPF) housing conditions and in a controlled light environment. The suppression agents and/or replacement nucleic acids of the invention can be administered to animals either locally and/or systemically. Local administration can include direct injection to the target tissues and/or in the proximity of the target tissue as has been described in detail in the art in, for example, Xia et al. (ACS Chem. Biol. 1(3):176-83, 2004) delivered AAV vectors with shRNAs to brain to treat spinocerebellar ataxia. In the case of the retina, subretinal injection can be used to administer suppression agents and/or replacement nucleic acids according to the following procedure. For example, mice can be anaesthetised by intraperitoneal injection of Domitor and Ketalar (10 and 50 μg/g of body weight respectively). The pupils are dilated with phenylephrine and under local analgesia (amethocaine) a small puncture is made in the sclera. A micro-needle attached to a 10 μl syringe (Hamilton Company Europe) is inserted through the puncture to the subretinal space and 1-3 μl of vector is administered. For example, in the case of AAV 1-411 of a $10^{12-14}$ vp/ml AAV vector preparation in PBS is administered. A reverse anaesthetic (antisedan, 50 μg/g of body weight) can be applied by intraperitoneal injection post-delivery. Body temperature during the procedure is sustained using a homeothermic heating device. In addition newborn mice can be prepared for subretinal injection according to Matsuda and Cepko (Proc. Natl. Acad. Sci. U.S.A. 101(1):16-22, 2004).

Assay for Function

To evaluate if suppression and/or replacement modulates the function of a target tissue and/or cell type, one or more assays may be employed that are well described in the prior art. In the case of the retina, functional assays include but are not limited to electrophysiology, such as pattern electroretinogram (ERG), full field ERG, and visual evoked potentials. In addition, visual field assessments, color vision assessments, and pupilometry may be performed. For example, electroretinography can be used to evaluate the response of the retina to light. This can be performed using, for example, the following procedure or an adapted procedure. Animals can be dark-adapted overnight and prepared for ERG under dim red light. Pupils are dilated with 1% cyclopentalate and 2.5% phenylephrine. Animals are anesthetized with ketamine and xylazine (16 and 1.6 μg/10 g body weight respectively) injected intraperitoneally. Standardized flashes of light are presented to the animal, for example a mouse, in a Ganzfeld bowl. ERG responses are recorded simultaneously from both eyes by means of contact lens electrodes (Medical Workshop, Netherlands) using 1% amethocaine as topical anesthesia. Reference and ground electrodes are positioned subcutaneously, approximately one mm from the temporal canthus and anterior to the tail respectively. Responses are analysed using a RetiScan RetiPort electrophysiology unit (Roland Consulting Gmbh). The protocol is based on that approved by the International Clinical Standards Committee for human electroretinography. Rod-isolated responses are recorded using a dim white flash (−25 dB maximal intensity where maximal flash intensity was 3 candelas/$m^2$/s) presented in the dark-adapted state. Maximal combined rod-cone responses to the maximal intensity flash are then recorded. Following a 10 minute light adaptation to a background illumination of 30 candelas/$m^2$, cone-isolated responses are recorded to the maximal intensity flash presented initially as a single flash and subsequently as 10 Hz flickers. A-waves are measured from the baseline to the trough and b-waves from the baseline (in the case of rod-isolated responses) or from the a-wave to the trough.

The agents of the invention are administered in effective amounts. An effective amount is a dosage of the agent sufficient to provide a medically desirable result. An effective amount means that amount necessary to delay the onset of, inhibit the progression of or halt altogether the onset or progression of the particular condition or disease being treated. An effective amount may be an amount that reduces one or more signs or symptoms of the disease. When administered to a subject, effective amounts will depend, of course, on the particular condition being treated; the severity of the condition; individual patient parameters including age, physical condition, size and weight, concurrent treatment, frequency of treatment, and the mode of administration. These factors are well known to those of ordinary skill in the art and can be addressed with no more than routine experimentation.

Actual dosage levels of active ingredients in the pharmaceutical compositions of the invention can be varied to obtain an amount of the agent(s) that is effective to achieve the desired therapeutic response for a particular patient, compositions, and mode of administration. The selected dosage level depends upon the activity of the particular agent, the route of administration, the severity of the condition being treated, the condition, and prior medical history of the patient being treated. However, it is within the skill of the art to start doses of the agent(s) at levels lower than required to achieve the desired therapeutic effort and to gradually increase the dosage until the desired effect is achieved.

The agents and pharmaceutical compositions of the invention can be administered to a subject by any suitable route. For example, the compositions can be administered orally, including sublingually, rectally, parenterally, intracisternally, intravaginally, intraperitoneally, topically and transdermally (as by powders, ointments, or drops), bucally, or nasally. The term "parenteral" administration as used herein refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation also is contemplated, including, for example, embedding a composition of the invention in the body such as, for example, in the brain, in the abdominal cavity, under the splenic capsule, brain, or in the cornea.

Agents of the present invention also can be administered in the form of liposomes. As is known in the art, liposomes generally are derived from phospholipids or other lipid substances. Liposomes are formed by mono- or multi-lamellar hydrated liquid crystals that are dispersed in an aqueous medium. Any nontoxic, physiologically acceptable, and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33, et seq.

Dosage forms for topical administration of an agent of this invention include powders, sprays, ointments, and inhalants as described herein. The agent is mixed under sterile conditions with a pharmaceutically acceptable carrier and any needed preservatives, buffers, or propellants which may be required. Ophthalmic formulations, eye ointments, powders, and solutions also are contemplated as being within the scope of this invention.

Pharmaceutical compositions of the invention for parenteral injection comprise pharmaceutically acceptable sterile aqueous or nonaqueous solutions, dispersions, suspensions, or emulsions, as well as sterile powders for reconstitution into sterile injectable solutions or dispersions just prior to use. Examples of suitable aqueous and nonaqueous carriers, diluents, solvents, or vehicles include water ethanol, polyols (such as, glycerol, propylene glycol, polyethylene glycol, and the like), and suitable mixtures thereof, vegetable oils (such, as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions also can contain adjuvants such as preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It also may be desirable to include isotonic agents such as sugars, sodium chloride, and the like. Prolonged absorption of the injectable pharmaceutical form can be brought about by the inclusion of agents which delay absorption, such as aluminum monostearate and gelatin.

In some cases, in order to prolong the effect of the agent, it is desirable to slow the absorption of the drug from subcutaneous or intramuscular injection. This result can be accomplished by the use of a liquid suspension of crystalline or amorphous materials with poor water solubility. The rate of absorption of the agent then depends upon its rate of dissolution which, in turn, may depend upon crystal size and crystalline form. Alternatively, delayed absorption of a parenterally administered drug from is accomplished by dissolving or suspending the agent in an oil vehicle.

Injectable depot forms are made by forming microencapsule matrices of the agent in biodegradable polymers such a polylactide-polyglycolide. Depending upon the ratio of agent to polymer and the nature of the particular polymer employed, the rate of agent release can be controlled. Examples of other biodegradable polymers include poly (orthoesters) and poly(anhydrides). Depot injectable formulations also are prepared by entrapping the drug in liposomes or microemulsions which are compatible with body tissue.

The injectable formulations can be sterilized, for example, by filtration through a bacterial- or viral-retaining filter, or by incorporating sterilizing agents in the form of sterile solid compositions which can be dissolved or dispersed in sterile water or other sterile injectable medium just prior to use.

The invention provides methods for oral administration of a pharmaceutical composition of the invention. Oral solid dosage forms are described generally in Remington's Pharmaceutical Sciences, 18th Ed., 1990 (Mack Publishing Co. Easton Pa. 18042) at Chapter 89. Solid dosage forms for oral administration include capsules, tablets, pills, powders, troches or lozenges, cachets, pellets, and granules. Also, liposomal or proteinoid encapsulation can be used to formulate the present compositions (as, for example, proteinoid microspheres reported in U.S. Pat. No. 4,925,673). Liposomal encapsulation may include liposomes that are derivatized with various polymers (e.g., U.S. Pat. No. 5,013,556). In general, the formulation includes an agent of the invention and inert ingredients which protect against degradation in the stomach and which permit release of the biologically active material in the intestine.

In such solid dosage forms, the agent is mixed with, or chemically modified to include, a least one inert, pharmaceutically acceptable excipient or carrier. The excipient or carrier preferably permits (a) inhibition of proteolysis, and (b) uptake into the blood stream from the stomach or intestine. In a most preferred embodiment, the excipient or carrier increases uptake of the agent, overall stability of the agent and/or circulation time of the agent in the body. Excipients and carriers include, for example, sodium citrate or dicalcium phosphate and/or (a) fillers or extenders such as starches, lactose, sucrose, glucose, cellulose, modified dextrans, mannitol, and silicic acid, as well as inorganic salts such as calcium triphosphate, magnesium carbonate and sodium chloride, and commercially available diluents such as FAST-FLO®, EMDEX®, STA-RX 1500®, EMCOMPRESS® and AVICEL®, (b) binders such as, for example, methylcellulose ethylcellulose, hydroxypropyhnethyl cellulose, carboxymethylcellulose, gums (e.g., alginates, acacia), gelatin, polyvinylpyrrolidone, and sucrose, (c) humectants, such as glycerol, (d) disintegrating agents, such as agar-agar, calcium carbonate, potato or tapioca starch, alginic acid, certain silicates, sodium carbonate, starch including the commercial disintegrant based on starch, EXPLOTAB®, sodium starch glycolate, AMBERLITE®, sodium carboxymethylcellulose, ultramylopectin, gelatin, orange peel, carboxymethyl cellulose, natural sponge, bentonite, insoluble cationic exchange resins, and powdered gums such as agar, karaya or tragacanth; (e) solution retarding agents such a paraffm, (f) absorption accelerators, such as quaternary ammonium compounds and fatty acids including oleic acid, linoleic acid, and linolenic acid (g) wetting agents, such as, for example, cetyl alcohol and glycerol monosterate, anionic detergent surfactants including sodium lauryl sulfate, dioctyl sodium sulfosuccinate, and dioctyl sodium sulfonate, cationic detergents, such as benzalkonium chloride or benzethonium chloride, nonionic detergents including lauromacrogol 400, polyoxyl 40 stearate, polyoxyethylene hydrogenated castor oil 10, 50 and 60, glycerol monostearate, polysorbate 40, 60, 65, and 80, sucrose fatty acid ester, methyl cellulose and carboxymethyl cellulose; (h) absorbents, such as kaolin and bentonite clay, (i) lubricants, such as talc, calcium sterate, magnesium stearate, solid polyethylene glycols, sodium lauryl sulfate, polytetrafluoroethylene (PTFE), liquid paraffin, vegetable oils, waxes, CARBOWAX® 4000, CARBOWAX® 6000, magnesium lauryl sulfate, and mixtures thereof; (j) glidants that improve the flow properties of the drug during formulation and aid rearrangement during compression that include starch, talc, pyrogenic silica, and hydrated silicoaluminate. In the case of capsules, tablets, and pills, the dosage form also can comprise buffering agents.

Solid compositions of a similar type also can be employed as fillers in soft and hard-filled gelatin capsules, using such excipients as lactose or milk sugar, as well as high molecular weight polyethylene glycols and the like.

The solid dosage forms of tablets, dragees, capsules, pills, and granules can be prepared with coatings and shells, such as enteric coatings and other coatings well known in the pharmaceutical formulating art. They optionally can contain opacifying agents and also can be of a composition that they release the active ingredients(s) only, or preferentially, in a part of the intestinal tract, optionally, in a delayed manner. Exemplary materials include polymers having pH sensitive solubility, such as the materials available as EUDRAGIT® Examples of embedding compositions which can be used include polymeric substances and waxes.

The active compounds also can be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms can contain inert diluents commonly used in the art, such as, for example, water or other solvents, solubilizing agents and emulsifiers, such as ethyl alcohol, isopropyl alcohol ethyl carbonate ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydroflirfuryl alcohol, polyethylene glycols, fatty acid esters of sorbitan, and mixtures thereof.

Besides inert diluents, the oral compositions also can include adjuvants, such as wetting agents, emulsifying and suspending agents, sweetening, coloring, flavoring, and perfuming agents. Oral compositions can be formulated and further contain an edible product, such as a beverage.

Suspensions, in addition to the agent(s), can contain suspending agents such as, for example ethoxylated isostearyl alcohols, polyoxyethylene sorbitol and sorbitan esters, microcrystalline cellulose, aluminum metahydroxide, bentonite, agar-agar, tragacanth, and mixtures thereof.

Also contemplated herein is pulmonary delivery of the agent(s) of the invention. The agent(s) is delivered to the lungs of a mammal while inhaling, thereby promoting the traversal of the lung epithelial lining to the blood stream. See, Adjei et al., Pharmaceutical Research 7:565-569 (1990); Adjei et al., International Journal of Pharmaceutics 63:135-144 (1990) (leuprolide acetate); Braquet et al., Journal of Cardiovascular Pharmacology 13 (suppl.5): s.143-146 (1989)(endothelin-1); Hubbard et al., Annals of Internal Medicine 3:206-212 (1989) (α1-antitrypsin); Smith et al., J. Clin. Invest. 84:1145-1146 (1989) (α1-proteinase); Oswein et al., "Aerosolization of Proteins," Proceedings of Symposium on Respiratory Drug Delivery II, Keystone, Colo., March, 1990 (recombinant human growth hormone); Debs et al., The Journal of Immunology 140:3482-3488 (1988) (interferon-γ and tumor necrosis factor α) and Platz et al., U.S. Pat. No. 5,284,656 (granulocyte colony stimulating factor).

Contemplated for use in the practice of this invention are a wide range of mechanical devices designed for pulmonary delivery of therapeutic products, including, but not limited to, nebulizers, metered dose inhalers, and powder inhalers, all of which are familiar to those skilled in the art.

Some specific examples of commercially available devices suitable for the practice of the invention are the ULTRAVENT® nebulizer, manufactured by Mallinckrodt, Inc., St. Louis, Mo.; the ACORN II® nebulizer, manufactured by Marquest Medical Products, Englewood, Colo.; the VENTOL® metered dose inhaler, manufactured by Glaxo Inc., Research Triangle Park, N.C.; and the SPINHALER® powder inhaler, manufactured by Fisons Corp., Bedford, Mass.

All such devices require the use of formulations suitable for the dispensing of a agent(s) of the invention. Typically, each formulation is specific to the type of device employed and can involve the use of an appropriate propellant material, in addition to diluents, adjuvants, and/or carriers useful in therapy.

The composition is prepared in particulate form, preferably with an average particle size of less than 10 μm, and most preferably 0.5 to 5 μm, for most effective delivery to the distal lung.

Carriers include carbohydrates such as trehalose, mannitol, xylitol, sucrose, lactose, and sorbitol. Other ingredients for use in formulations may include lipids, such as DPPC, DOPE, DSPC and DOPC, natural or synthetic surfactants, polyethylene glycol (even apart from its use in derivatizing the inhibitor itself), dextrans, such as cyclodextran, bile salts, and other related enhancers, cellulose and cellulose derivatives, and amino acids.

Also, the use of liposomes, microcapsules or microspheres, inclusion complexes, or other types of carriers is contemplated.

Formulations suitable for use with a nebulizer, either jet or ultrasonic, typically comprise a compound of the invention dissolved in water at a concentration of about 0.1 to 25 mg of biologically active protein per mL of solution. The formulation also can include a buffer and a simple sugar (e.g., for protein stabilization and regulation of osmotic pressure). The nebulizer formulation also can contain a surfactant to reduce or prevent surface-induced aggregation of the inhibitor composition caused by atomization of the solution in forming the aerosol.

Formulations for use with a metered-dose inhaler device generally comprise a finely divided powder containing the agent suspended in a propellant with the aid of a surfactant. The propellant can be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid also can be useful as a surfactant.

Formulations for dispensing from a powder inhaler device comprise a finely divided dry powder containing the agent and also can include a bulking agent, such as lactose, sorbitol, sucrose, mannitol, trehalose, or xylitol, in amounts which facilitate dispersal of the powder from the device, e.g., 50 to 90% by weight of the formulation.

Nasal delivery of the agent(s) and composition of the invention also is contemplated. Nasal delivery allows the passage of the agent or composition to the blood stream directly after administering the therapeutic product to the nose, without the necessity for deposition of the product in the lung. Formulations for nasal delivery include those with dextran or cyclodextran. Delivery via transport across other mucous membranes also is contemplated.

Compositions for rectal or vaginal administration are preferably suppositories which can be prepared by mixing the agent(s) of the invention with suitable nonirritating excipients or carriers, such as cocoa butter, polyethylene glycol, or suppository wax, which are solid at room temperature, but liquid at body temperature, and therefore melt in the rectum or vaginal cavity and release the active compound.

In order to facilitate delivery of the agent(s) across cell and/or nuclear membranes, compositions of relatively high hybrophobicity are preferred. The agent(s) can be modified in a manner which increases hydrophobicity, or the agent(s) can be encapsulated in hydrophobic carriers or solutions which result in increased hydrophobicity.

Practice of the invention will be still more fully understood from the following examples, which are presented herein for illustration only and should not be construed as limiting the invention in any way.

EXEMPLIFICATION

Figure 1:
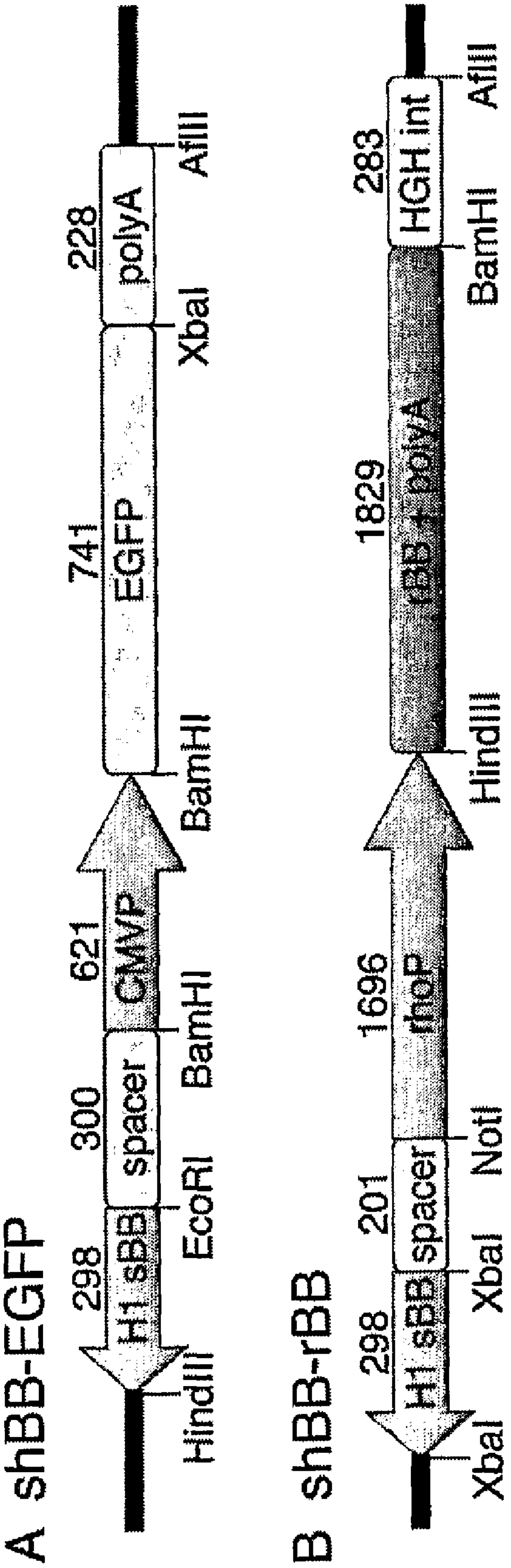
FIG. 1 illustrates RHO suppression and replacement constructs.

Example 1 siRNAs Targeting Human Rhodopsin and Rhodopsin Replacement Nucleic Acids siRNAs targeting human rhodopsin were synthesized and evaluated for RNAi-mediated suppression (listed in Table 8). Suppression and replacement constructs with suppressors targeting the human rhodopsin mRNA sequence and replacement rhodopsin genes that escape suppression by the suppressor due to subtle changes in the sequence were subsequently designed. These changes, while enabling replacement nucleic acids to escape suppression at least in part, did not change the protein product expressed from the replacement genes. Short hairpin RNAs (shRNAs) were used to demonstrate suppression in vivo (FIG. 1). The sequence of the sense and antisense strands of the shRNAs is the same as the sequence used for the siRNAs. An intervening loop is included between the sense and antisense strands in the same manner as Brummelkamp et al., Science 296(5567):550-3, 2001. Notably, the number of nucleotides and the make up of the nucleotides in the intervening loop can vary. The construct(s) were delivered using an AAV2/5 recombinant virus. Non-targeting siRNA can be used as controls, for example, a non-targeting siRNA directed towards an EGFP reporter gene can be used—for example.

siRNAs were designed according to the method of Elbashir et al., Nature 411(6836):494-8, 2001, or by using the HiPerformance siRNA design algorithm (Qiagen Ltd. Crawley, UK). siRNA target sequences differed by at least 4 nucleotides from any non-rhodopsin sequences in mouse and human databases (http://www.ncbi.nlm.nih.gov/blast, BLAST2.2.6 (Altschul et al., Nucleic Acids Res. 25(17): 3389-402, 1997). siBB, siQ1 and a non-targeting siRNA siNT (5' UUCUCCGAACGUGUCACGU 3'; SEQ ID NO:75) or EGFP (U57608), siEGFP (nt 256-277) were initially cloned downstream of the H1 promoter using BglII/BamH1 and Hind III restriction sites to generate shRNAs and subsequently in pEGFP-1 (BD Biosciences, Clontech, Palo Alto, Calif.) using EcoRI and Hind III sites generating shBB-EGFP, shQ1-EGFP and shNT-EGFP (FIG. 1A). The EGFP gene enabled viral transduction to be monitored. Six siRNAs sequences targeted the coding region of human rhodopsin. Replacement nucleic acids were cloned into pCDNA3.1-plasmid (Invitrogen, Karlsruhe, Germany). The CMV promoter was replaced with either the human ubiquitin C promoter (pUB6/V5-His, Invitrogen) or a 1.7 kb fragment of the mouse rho promoter (rhoP). Sequence alterations were introduced into replacement nucleic acids using primer directed PCR-based mutagenesis using art known methods. Replacement nucleic acids with sequence alterations over the target sites for siB, siBB, siC, siCC, siQ1 and siQ2 were termed rB, rBB, rC, rCC, rQ1, and rQ2. Altered nucleotides in the replacement rhodopsin sequences are at wobble positions (highlighted in bold print). These replacement genes were designed to avoid suppression by the siRNAs yet encode wild type protein. Table 8 provides one replacement example for each siRNA target site; however, in each case there are several alternative possible replacement sequences because some amino acids have as many as six codons and others have four or three codons.

TABLE 8 siRNA Sequence and Replacement Rhodopsin Sequence

| siRNA | Sequence | SEQ ID NO | Replacement rhodopsin sequence | SEQ ID NO | Position in NM_000539.2 |
|---|---|---|---|---|---|
| siB | TCAACTTCCTCACGCTCTA | 75 | ATAAATTTTTTGACCCTGTAT | 76 | 256-277 |
| siBB | TCACCGTCCAGCACAAGAA | 77 | CTGTATGTGACGGTGCAGCAC | 78 | 254-274 |
| siC | CGTGTGGAATCGACTACTA | 79 | AGCTGCGGTATAGATTATTA | 80 | 270-292 |
| siCC | CGCTCAAGCCGGAGGTCAA | 81 | ACCTTGAAACCCGAAGTGAA | 82 | 274-294 |
| siQ1 | TCAACTTCCTCACGCTCTACGT | 83 | CTGTATGTGACGGTGCAGCAC | 84 | 650-670 |
| siQ2 | CTCTACGTCACCGTCCAGCACAA | 85 | CTGTATGTGACGGTGCAGCAC | 86 | 671-694 |

Suppression of RHO in HeLa Cells

Figure 2:
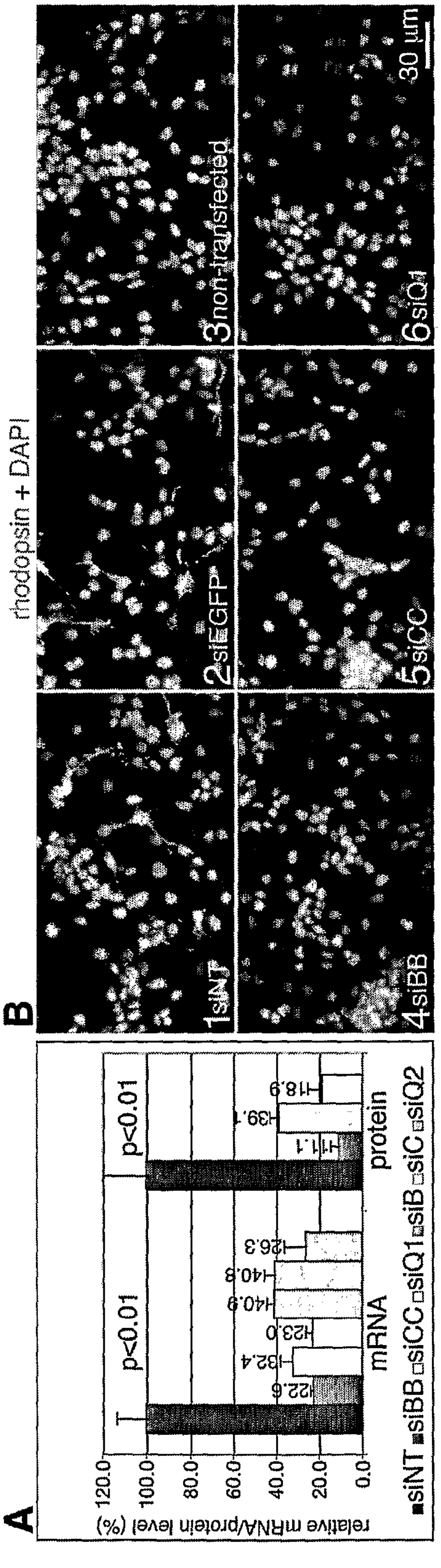
FIG. 2 illustrates RHO suppression in HeLa cells. HeLa cells were transiently co-transfected three times in triplicate with wild type RHO and RHO-targeting siRNAs (siB, siBB, siC, siCC, siQ1 or siQ2) or control siRNAs (siEGFP or siNT). Following transfection, RHO mRNA and protein levels were evaluated by real time RT-PCR (A), ELISA (A) and Alexa Fluor 568-labeled immunocytochemistry (B). Cell nuclei were counterstained with DAPI. Error bars represent SD values.
Figure 3:
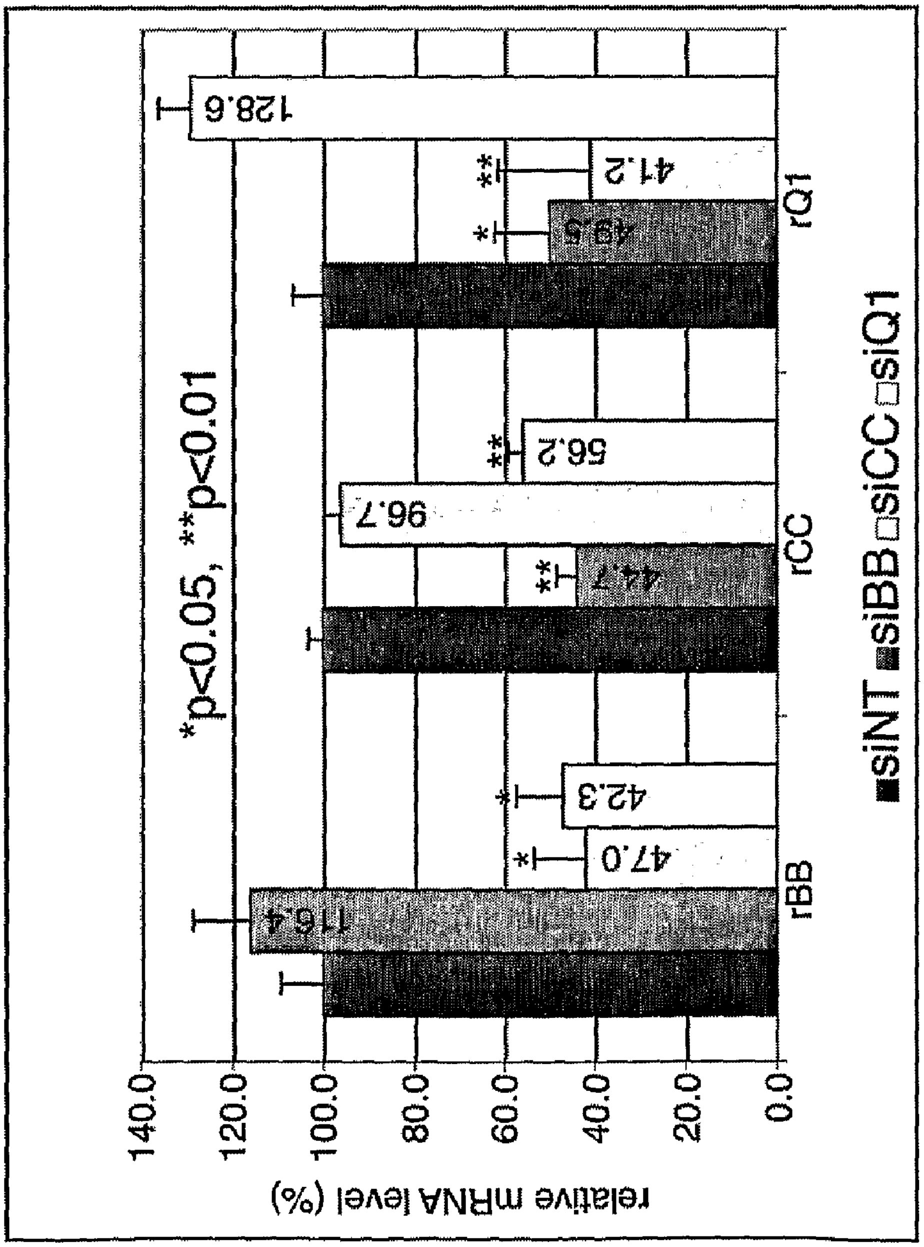
FIG. 3 illustrates replacement of RHO expression in conjunction with suppression in HeLa cells. Replacement RHO sequences were generated with altered degenerate nucleotides at siRNA target sites. HeLa cells were transiently co-transfected three times in triplicate with a replacement RHO expression vector (rBB, rCC or rQ1) and a RHO-targeting siRNA (siBB, siCC or siQ1) or a non-targeting siRNA (siNT). Replacement RHO mRNA levels were evaluated by real time RT-PCR. Error bars represent SD values.

RNAi-mediated suppression of RHO was initially evaluated in HeLa cells. siRNAs targeting RHO were co-transfected with a CMV promoter-driven wild type RHO. Transfections were carried out three times in quadruplicate using lipofectamine 2000 to aid transfections (Gibco-BRL). Real time RT-PCRs, performed on RNAs extracted from transfected cells 24 hours post-transfection, demonstrated up to 87% suppression ($p<0.01$, FIG. 2A) (see Table 7 for primer sequences). siRNAs siBB, siCC and siQ1 were selected for further analysis. Similar levels of rhodopsin protein suppression were quantified by ELISA (up to 88%, $p<0.01$, FIG. 2A) and demonstrated by immunocytochemistry 24 hours post-transfection (FIG. 2B). Subsequently, replacement RHO constructs, rBB, rCC and rQ1, were generated incorporating nucleotide changes at degenerate positions over the target sites for siRNAs, siBB, siQ1 and siCC as described above and shown in Table 8. Transfections were performed three times in quadruplicate in HeLa cells according to art known methods as described above. Results indicated that replacement RHO constructs were not suppressed by corresponding siRNAs, for example, rBB by siBB (FIG. 3). However, significant levels of suppression were obtained with other non-corresponding siRNAs, for example siQ1 suppressed rBB and rCC (FIG. 3).

Long Term Suppression of RHO in Retinal Explants

Figure 4:
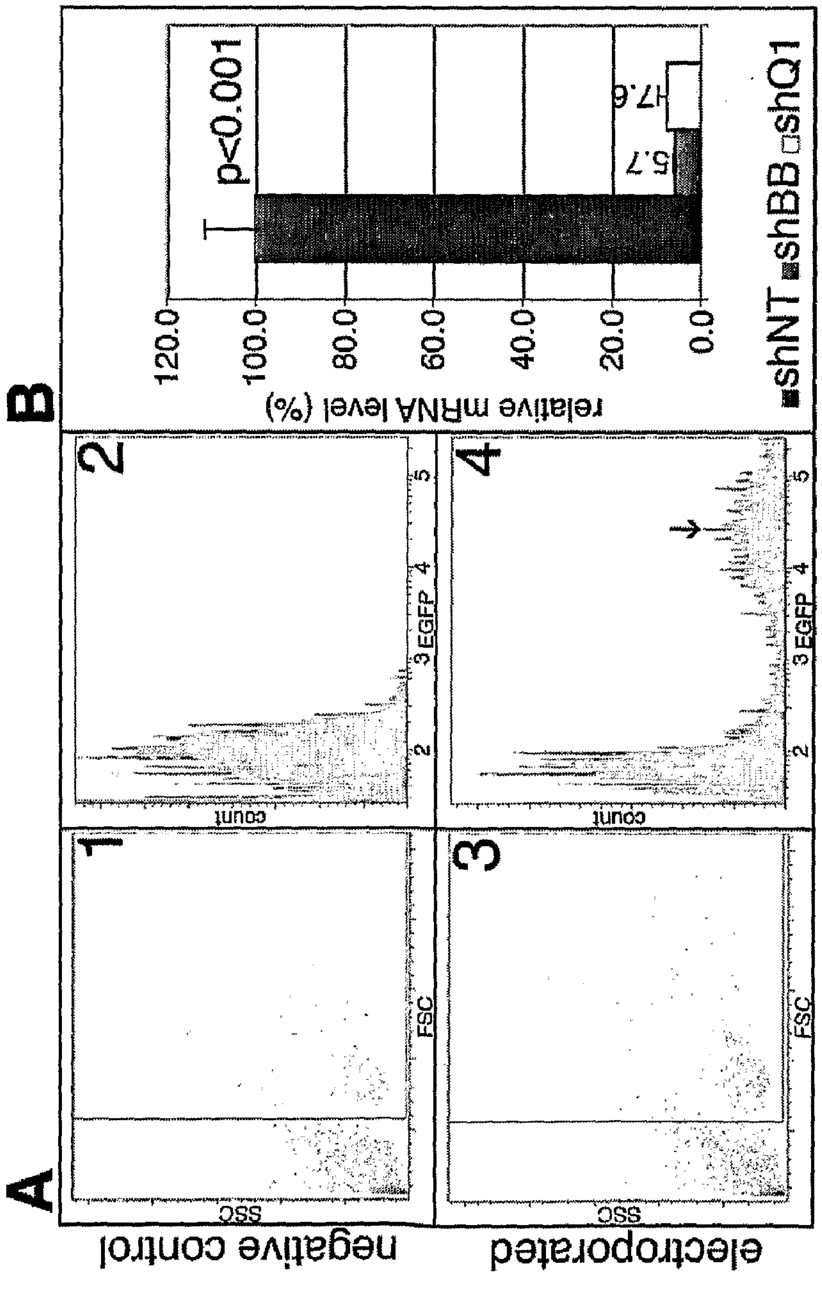
FIG. 4 illustrates RHO suppression in retinal explants. Mouse retinas (n=6), dissected from newborn NHR+/− rho−/− pups (transgenic mice expressing a human rhodopsin transgene NHR on a mouse rhodopsin knockout background rho−/−), were electroporated with a construct co-expressing a shRNA targeting RHO or a non-targeting shRNA and EGFP (shBB-EGFP, shQ1-EGFP or shNT-EGFP). Negative control explants were not electroporated. Two week organotypic cultures were dissociated with trypsin and FACS analysed. Red and blue dots (right and left populations respectively in each of A1 and A2) represent gated and ungated populations of dissociated explants. Scatterplots of forward-(FSC) versus side-scatter (SSC) and histograms of EGFP fluorescence of the gated population of non-electroporated (A1 and A2, EGFP-negative) and electroporated (A3 and A4, EGFP-positive) retinas are given.

To provide long term RHO suppression, siBB and siQ1 were cloned as shRNAs into an EGFP expressing vector (shBB-EGFP and shQ1-EGFP, FIG. 1A). Plasmids were electroporated into retinal explants from newborn NBR+/− rho−/− mice using the methods described in Matsuda and Cepko (2004) Proc. Natl. Acad. Sci. USA 101: 16-22. NHR+/− mice express a wild type human RHO gene and display a wild type phenotype. Cells from retinal explants (n=6) were dissociated two weeks post-electroporation and EGFP-positive cells isolated by FACS (FIG. 4A). Real time RT-PCR was performed on RNA extracted from EGFP-positive FACS-isolated cells using the primers described in Table 8 and results obtained in explants mirrored those found in HeLa cells. Results indicated that RHO suppression of greater than 85% was achieved (p<0.001, FIG. 4B).

Long Term Suppression Using AAV Vectors

Long-term expression of therapies will be required for a progressive retinopathy such as adRP. To achieve long-term suppression in vivo, shBB-EGFP and the non-targeting shNT-EGFP were engineered into AAV vectors (AAV-shBB-EGFP and AAV-shNT-EGFP) (FIG. 1A). Recombinant AAV2/5 viruses were generated using a helper virus free system. Expression cassettes were cloned into pAAV-MCS (Stratagene, La Jolla, Calif., USA), between the inverted terminal repeats of AAV2, and transfected into HEK-293 cells (ATCC no. CRL-1573) with pRep2/Cap5 and pHelper (Stratagene), at a ratio of 1:1:2. Fifty 150 mm plates of confluent cells were transfected (50 µg DNA/plate) with polyethyleminine. Forty eight hours post-transfection crude viral lysates were cleared and purified by $CsCl_2$ gradient centrifugation. AAV-containing fractions were dialysed against PBS. Genomic titres, i.e., viral particles (vp/ml), were determined by quantitative real time PCR. AAVs generated contained the shBB-EGFP and shNT-EGFP constructs (AAV-shBB-EGFP and AAV-shNT-EGFP, FIG. 1A).

Figure 5:
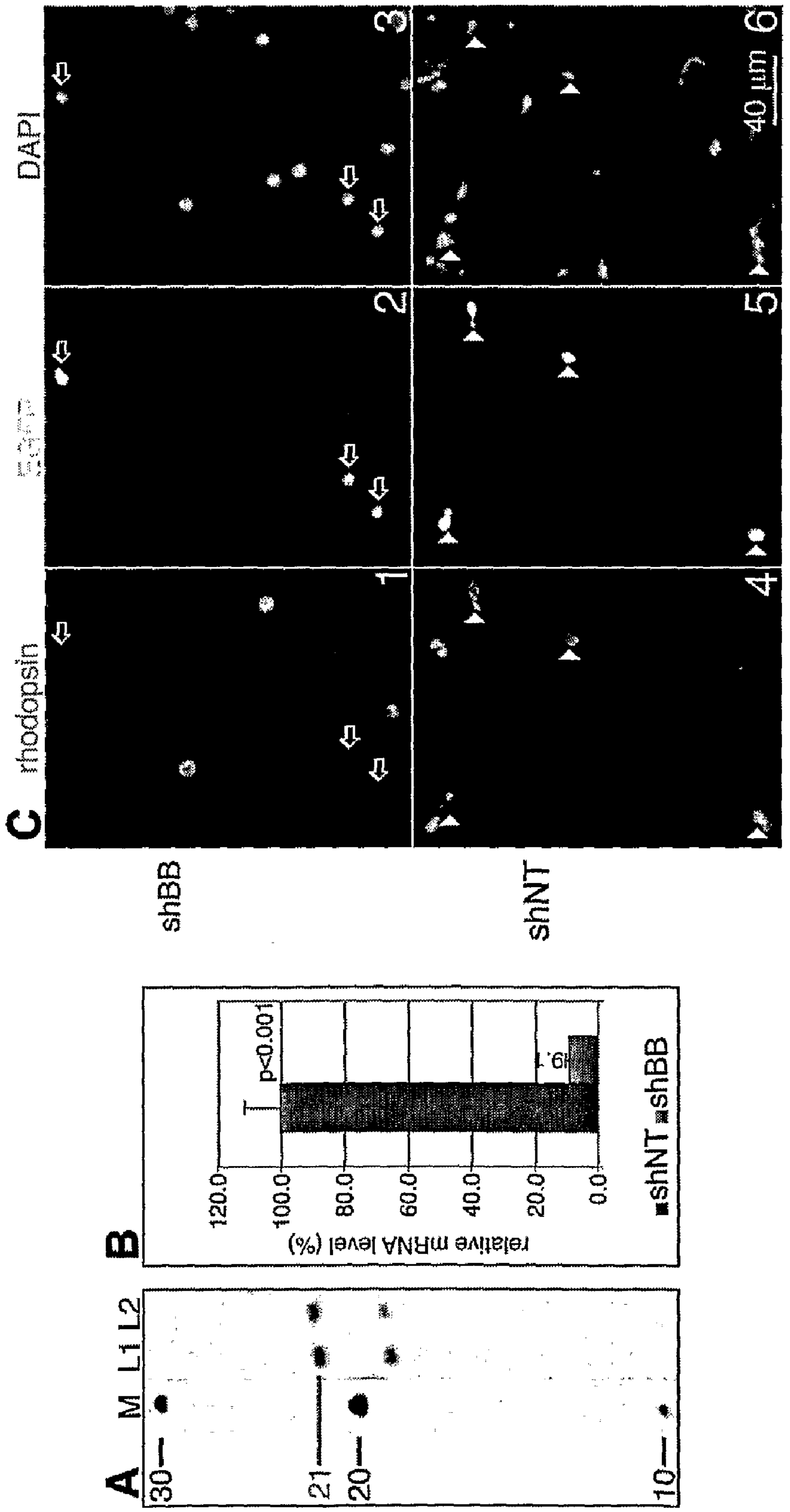
FIG. 5 illustrates RHO suppression in photoreceptor cells in vivo. Adult transgenic NHR+/− rho−/− mice were subretinally injected with 3 μl $2\times10^{12}$ vp/ml AAV co-expressing a RHO-targeting or non-targeting shRNA and EGFP (AAV-shBB-EGFP or AAV-shNT-EGFP). Retinas were analysed two weeks post-injection. Expression of the 21 nucleotide (nt) shRNA BB, detected by RNase protection in two transduced retinas, is depicted in lanes L1 and L2 (A). RHO RNA probes were labelled with $P^{32}$-γATP and protected RNA separated on 15% denaturing acrylamide gels (A). M: size marker indicates 10, 20 and 30 nt. Bars represent RHO mRNA levels in FACS sorted cells from dissociated retinas (n=6) transduced with either AAV-shBB-EGFP or AAV-shNT-EGFP (B). Suppression levels were determined by real time RT-PCR. Error bars represent SD values. Rhodopsin immunocytochemistry (Cy3-labeled) and EGFP protein expression in cells from dissociated retinas, transduced with either AAV-shBB-EGFP (arrows) or AAV-shNT-EGFP (arrow heads), are depicted (C). Cell nuclei were counterstained with DAPI.

The EGFP gene enabled viral transduction to be monitored. Three µl of AAV-shBB-EGFP ($2\times10^{12}$ vp/ml) or AAV-shNT-EGFP ($3\times10^{12}$ vp/ml) were subretinally injected into adult NHR+/− rho−/− mice. Two weeks post-injection two animals were sacrificed and expression of the 21 nucleotide shBB shown in two retinas using RNase protection (FIG. 5A). Retinas were dissociated and EGFP-positive cells collected by FACS. RNAi-mediated suppression of RHO, as evaluated by real time RT-PCR (see Table 8 for primer sequences) two weeks post-injection (n=6), was approximately 90% (p<0.001) in AAV-shBB-EGFP-transduced photoreceptor cells (FIG. 5B). Four retinas were dissociated and significant suppression of rhodopsin protein expression was demonstrated in vivo in EGFP-positive transduced cells by immunocytochemistry (FIG. 5C).

Suppression in Transgenic Animals

A transgenic mouse expressing a sequence-modified RHO gene was generated (RHO-M). RHO-M+/− rho−/− were evaluated at two months of age for rescue of the retinal pathology present in rho−/− mice by histology (FIG. 6A-C) and ERG (FIG. 6D). Rhodopsin immunolabeling in rod outer segments and the thickness of outer nuclear layers were similar in wild type rho+/+ (FIG. 6A), NHR+/− rho−/− (FIG. 6B) and RHO-M+/− rho−/− (FIG. 6C) mice. Additionally, ERG responses were similar in wild type rho+/+, rho+/−, NHR+/− rho−/− and RHO-M+/− rho−/− mice. ERG b-waves of rod-isolated responses of 500-700 µV were observed in mice of all genotypes (FIG. 6D). The amplitudes and timings of the combined rod and cone responses to the maximal intensity flash presented in the dark-adapted state, as well as the light adapted cone-isolated responses both to single flash and 10 Hz flickers, were equivalent in all the genotypes examined (data not shown). These results validate the use of the degeneracy of the genetic code to engineer codon-modified human RHO genes which can provide functional human rhodopsin protein.

AAV-Delivered Suppression and Replacement of Human RHO In Vivo

Having established shBB and shQ1 as potent suppressors and rBB and rQ1 as being refractory to their corresponding suppressors, shBB-rBB and shQ1-rQ1 were cloned into AAV vectors using the triple plasmid system detailed above and viruses containing both elements of the therapeutics were generated (AAV-shBB-rBB (also termed AAV-BB8) and AAV-shQ1-rQ1 (also termed AAV-Q1)) using the method detailed above. Three µl of AAV-shBB-rBB was subretinally injected into adult wild type rho+/+ mice (n=12) and replacement RHO mRNA expression confirmed by RT-PCR and RNase protection using RNA extracted 10 days post-injection (data not shown). To demonstrate that AAV-delivered rBB is translated into protein, 2 µl of a 1:1 mix of AAV-shBB-rBB and AAV-CMV-EGFP was subretinally injected into 10 day old rho−/− mice (n=6). Two weeks post-injection rhodopsin and EGFP protein expression were determined using fluorescent microscopy. Marked rhodopsin expression, overlapping with EGFP, was observed in transduced areas (FIG. 7).

Subsequently, 1 µl of AAV-shBB-rBB or AAV-shQ1-rQ1 was subretinally injected into newborn Pro23His+/− rho+/− mice (n=10) that present with a retinal degeneration resulting in complete loss of photoreceptors by two weeks of age. In all animals one eye was injected with therapeutic virus (either AAV-shBB-rBB or AAV-shQ1-rQ1) and the other with a control virus (AAV-EGFP). The early onset and rapid nature of the retinopathy in young Pro23His pups precluded use of ERG as a readout for benefit. However, at ten days of age retinal histology was evaluated in semi-thin resin embedded sections cut at approximately 50 µm intervals throughout the central meridian of the eye (n=10). From each section approximately 40 measurements of ONL thickness were taken. Since only a part of the retina is transduced by a single subretinal injection of AAV (particularly in newborn pups), to identify the transduced area ONL measurements were ordered by thickness and the 15% highest and lowest values grouped for analysis. Lowest values represent thinnest ONL readings, most likely corresponding to peripheral areas of the retina and thus not in close proximity to injection sites. Highest values represent thickest ONL readings, most likely corresponding to central areas of the retina and thus in closer proximity to injection sites. Significant differences in ONL thickness between AAV-shBB-rBB- and AAV-EGFP-treated eyes were observed. The ONL of treated eyes was found to be approximately 33% (p<0.001) thicker than control injected counterparts for the highest value groupings (FIG. 8A-C). In the lowest value groupings a difference of approximately 10% was observed (FIG. 8A). These data provide evidence at the histological level that AAV2/5-delivered RNAi in conjunction with provision of a codon-modified replacement gene can beneficially modulate the retinopathy in Pro23His+/− rho−/− mice.

RNAi-mediated suppression was evaluated in retinal tissue after sub-retinal injection of AAV vectors expressing either a suppressor targeting rhodopsin (AAV-shBB-EGFP, AAV-shCC-EGFP and AAV-shQ1-EGFP) or a non-targeting control (AAV-shNT-EGFP). Mice expressing a human rhodopsin replacement gene (referred to as RHO-M mice and detailed in the section on suppression in transgenic animals) were sub-retinally injected with AAV vectors (AAV2/5), containing shRNA sequences for BB, CC and Q1 and an EGFP reporter gene (AAV-shBB-EGFP, AAV-shCC-EGFP and AAV-shQ1-EGFP). The presence of the EGFP reporter gene enabled isolation of the population of retinal cells that are EGFP positive and therefore have received AAV using FACS to isolate these cell populations. AAV-delivered RNAi-mediated suppression with each suppressor (BB, CC and Q1) was evaluated using real-time RT-PCR in cell populations characterised by FACS and was compared to suppression obtained using AAV with non-targeting control shRNA sequences (AAV-shNT-EGFP). Significant rhodopsin suppression was obtained with BB and Q1 suppressors, however, significantly lower levels of suppression were obtained with the CC suppressor (FIG. 6E). The replacement gene in RHO-M mice was partially protected from suppression due to the presence of two nucleotide mismatches between the CC suppressor sequence and the target site for suppression in the human rhodopsin replacement gene. The replacement gene is partially protected from siRNA CC-based suppression by the introduction of two nucleotide changes at degenerate sites in the replacement gene. FIG. 6F illustrates depression of the ERG response in RHO-M eyes that have received AAV-shBB-EGFP (panel 1) or AAV-shQ1-EGFP (panel 2) when compared to eyes subretinally injected with AAV-shNT-EGFP. The top tracing in each panel represents the right eye which received the targeting AAV-shRNA vector and the bottom tracing in each panel represents the left eye which received the control non-targeting AAV-shNT vector. In contrast no reduction/depression of the ERG was observed in RHO-M mice subretinally injected with AAV-shCC-EGFP (panel 3) vector; this is likely due to the reduced levels of rhodopsin suppression observed with AAV-shCC-EGFP (see FIG. 6E above).

Example 2

Optimization of Expression of Suppression Agents and Replacement Nucleic Acids Expression of suppression and/or replacement vectors was optimized by including in the vectors sequences that enhanced and/or modulate expression levels at the RNA and/or protein level. A list of exemplary sequence elements is provided in Table 1, however, the enhancing and/or modulating elements of the invention are not exclusive to this list. For example, one or more of a promoter, a stuffer, an insulator, a silencer, a chromatin remodelling sequence, an intron sequence, a poly adenylation signal, a post translational regulatory element, and a transcription factor binding site can be included in suppression and/or replacement constructs to modulate expression of suppression and/or replacement components relating to the invention. Such elements and derivatives thereof can be used to modulate levels of expression, tissue specificity, timing of expression, and/or induction of expression. Table 9 provides some exemplary sequences that can be used to modulate expression of suppression and/or replacement constructs relating to the invention. The sequences provided are within conserved regions as evaluated by comparison of sequences from multiple species. At any one position a nucleotide may not be conserved between all species the sequences represent regions where overall there is a high degree of conservation. Such conserved sequences from any species such as human, mouse, rat, bacteria, virus and/or indeed a hybrid sequence from more than one species could be used in the invention.

TABLE 9

| Exemplary Enhancer Sequences |
|---|
| CMV enhancer element amplified from pCDNA3.1 Invitrogen nt 308-734 http://www.invitrogen.com/ (SEQ ID NO: 87) |
| CCGCGTTACATAACTTACGGTAAATGGCCCGCCTGGCTGACCGCCCAACGACCCCCG |
| CCCATTGACGTCAATAATGACGTATGTTCCCATAGTAACGCCAATAGGGACTTTCCA |
| TTGACGTCAATGGGTGGAGTATTTACGGTAAACTGCCCACTTGGCAGTACATCAAGT |
| GTATCATATGCCAAGTACGCCCCCTATTGACGTCAATGACGGTAAATGGCCCGCCTG |
| GCATTATGCCCAGTACATGACCTTATGGGACTTTCCTACTTGGCAGTACATCTACGTA |
| TTAGTCATCGCTATTACCATGGTGATGCGGTTTTGGCAGTACATCAATGGGCGTGGA |
| TAGCGGTTTGACTCACGGGGATTTCCAAGTCTCCACCCCATTGACGTCAATGGGAGT |
| TTG TTTTGGCACC AAAATCAACG GGAC |
| pAAV.BB11 The WPR element from pSin11 CMV GFPpre mut FL (Gene Therapy (7): 641-5 (2006)) (SEQ ID NO: 88) |
| GAGCAT CTTACCGCCATTTATTCCCA TATTTGTTCT GTTTTTCTTG ATTTGGGTAT |
| ACATTTAAATGTTAATAAAA CAAAATGGTG GGGCAATCAT TTACATTTTT |
| AGGGATATGTAATTACTAGT TCAGGTGTAT TGCCACAAGA CAAACATGTT |
| AAGAAACTTTCCCGTTATTT ACGCTCTGTT CCTGTTAATC AACCTCTGGA |

TABLE 9-continued

| Exemplary Enhancer Sequences |
|---|
| TTACAAAATTTGTGAAAGAT TGACTGATAT TCTTAACTAT GTTGCTCCTT |
| TTACGCTGTGTGGATATGCT GCTTTATAGC CTCTGTATCT AGCTATTGCT |
| TCCCGTACGGCTTTCGTTTT CTCCTCCTTG TATAAATCCT GGTTGCTGTC |
| TCTTTTAGAGGAGTTGTGGC CCGTTGTCCG TCAACGTGGC GTGGTGTGCT |
| CTGTGTTTGCTGACGCAACC CCCACTGGCT GGGGCATTGC CACCACCTGT |
| CAACTCCTTTCTGGGACTTT CGCTTTCCCC CTCCCGATCG CCACGGCAGA |
| ACTCATCGCCGCCTGCCTTG CCCGCTGCTG GACAGGGGCT AGGTTGCTGG |
| GCACTGATAATTCCGTGGTG TTGTC |
| pAAV.BB13 The WPR element from pBSK11 (Donello JE, et al. J. Virol. 1998 72(6): 5085-92.) (SEQ ID NO: 89) |
| AATCAACCTCTGGATTACAAAATTTGTGAAAGATTGACTGGTATTCTTAACTATGTT |
| GCTCCTTTTACGCTATGTGGATACGCTGCTTTAATGCCTTTGTATCATGCTATTGCTTC |
| CCGTATGGCTTTCATTTTCTCCTCCTTGTATAAATCCTGGTTGCTGTCTCTTTATGAGG |
| AGTTGTGGCCCGTTGTCAGGCAACGTGGCGTGGTGTGCACTGTGTTTGCTGACGCAA |
| CCCCCACTGGTTGGGGCATTGCCACCACCTGTCAGCTCCTTTCCGGGACTTTCGCTTT |
| CCCCCTCCCTATTGCCACGGCGGAACTCATCGCCGCCTGCCTTGCCCGCTGCTGGAC |
| AGGGGCTCGGCTGTTGGGCACTGACAATTCCGTGGTGTTGTCGGGGAAGCTGACGTC |
| CTTTCCATGGCTGCTCGCCTGTGTTGCCACCTGGATTCTGCGCGGGACGTCCTTCTGC |
| TACGTCCCTTCGGCCCTCAATCCAGCGGACCTTCCTTCCCGCGGCCTGCTGCCGGCTC |
| TGCGGCCTCTTCCGCGTCTTCGCCTTCGCCCTCAGACGAGTCGGATCTCCCTTTGGGC |
| CGCCTCCCC |

(Wild type woodchuck hepatitis B virus genome sequence ACCESSION J04514)

Example 3

Comparison of Rhodopsin Genes

In addition to adding enhancing and/or modulating elements to suppression and/or replacement vectors, the rhodopsin promoter was studied in detail. A comparison of rhodopsin genes present in different mammals resulted in identification of 9 highly conserved regions in the rhodopsin gene (conserved regions A though I, Sequence 1, Table 10). Regions A, B, C and D are in the rhodopsin promoter region, conserved region E is in intron 2 of the gene and conserved regions F, G, H and I are in the 3' region.

The following sequence (Sequence 1; Table 10) shows the conserved regions within the mouse promoter human intronic and exonic and 3' sequence. Notably, conserved sequences in the mouse promoter are nearly the same in the human rhodopsin promoter and it is contemplated that the human or other mammalian rhodopsin promoters and/or derivatives and/or hybrids thereof may be used in suppression and replacement constructs. Additionally, it is contemplated that other promoters could be combined with some or all of conserved regions A though I and used in suppression and/or replacement constructs, for example, other retinal promoter sequences may be used.

TABLE 10

| Conserved Regions of Rhodopsin |
|---|
| GTTCCAGGGC CCAGGGGCTT CCAGCCATGA GGGCACCTAG ACTTGTAATC |
| CCTAGAGTCC TCCTGATGCC ACTGCCCAGG GACAGACAGC ACACAGCACC |
| CCTCCCCCAC TCTCTTAACA GGCAGAAGCA GGGAGATGGA GGCATGCTGA |
| AGATGTCCAT GTGAGGCTGG TGGTAGCATG CCCACTGCTG GGATGAAGAG |
| ATGGGGGCAA AGTGAGTGGC AGAGGCCAGG CCAGGTCCAG GCCCTTCCAG |
| GCTTCCTCTG CCACTGTGGA GATGAAAGAG GGAGCCAGGC AAGGTCCAGG |

TABLE 10-continued

| Conserved Regions of Rhodopsin |
|---|
| CCCTCCCCAC CCCCTCTGCC TCTATGGAGA TGAAGGGGGA ATGAAGAAGG |
| GAGCCAGACA GTTGTGCCAA CACAACTCCT CCGTC**GAGTG TCTAATTGCT** |
| **TATGATCATG CATGCTCTCT CTCCCACTAA ACATTTATTA ATGTGTTAGG** cons reg A |
| **ATTTCCATTA GCGCGTGCCT TGAACTGAAA TCATTTGCAT ATGGCTGGGA** |
| **AAAAGTGGGG TGAGGGAGGA AACAGTGCCA GCTCCCCAAC AGGCGTCAAT** |
| **CACAGTGACA GATCAGATGG** TTTCTGGCTG GAGGCAGGGG GGCTGTCTGA |
| GATGGCGGCA TGCATCCTTT CAGTGCATAT CACAGAAATT CAGGTGACTC |
| CTGCTGGGAG CCAAGACCCT GAGGCTGAGC CTGGCCACAG CTCCAATAGC |
| TGCTGGATAT CATCATGTCT GGGCTGAGCA GCCTCTAGAG GTACCCTTTT |
| ACAGATAGTA AAACTGAGGC TCAGTGACTG CTGAGCCAAA GTTGGACCCA |
| CCCACACTCA TTTGCAGACT GCCGTGGGCC ATGTTCTGAT CTCTTCCCTA |
| CCTGGACTCA GCCCAGCACA CTCGGCACAC AAGGCCCTTC TTCAGCTTGA |
| ATACAGCGTC CTCAGCTATA GCCAGCATCT ATGAATGGAG CTCAGTGACC |
| CTGACTGGAG GAAGTTAGGA CAGGGATTTT TTCTGGAGTT TTGGCAGGAA |
| GAGGCCAGGG TCAGGTGACT GCTGGAGCAC ACAGCTTGGT AAGACTAGTC |
| AGGACCTGCG TCCTGAGGCT ACATGTCATA TCCACAGTAA GGAAGTGGAA |
| GATGGGAGAT GACTGGCTGG GCCACAACCA GTGAGTGGAA TGTCCTTGTG |
| CATCTTTGTT TCCTAACCTT CCCCTCTGTA GCTGCTGAAA CACACACACA |
| CCCCATGCTC TGTTATGCCT CTTCCCTGGC CTGGGATTTC CATGGCTGAG |
| GTGATGGGGC ACTGAGGCAC CGCCAGGAAA GGCTGTAACC CATCTGCTCC |
| CCCATCCTTC ACCAGACTTC AAGCACCTAC CTAGAGCACA GGTGCAATTT |
| TGTACCCTCC CTGTCTGGGA CCCACAGTGG TTCCTCAATG CCGGCCAACC |
| AGACTCATAG GCCTGCCCAC AAGGCCCTTG GGGCTATCTG TCTGAGGCCT |
| GCAGGTGCCC TCCTGGCCAC CTAGGCTCCT GTGAGACTTA GACTTCCATA |
| GATTCTTCCT GAAAGACTAC TGAGGGCAGG AGCCCCCAAG CCTCAGGGTT |
| AGCTTTCCTC AGCCCTGCCT CTTTGCTAGC TCCGTTTCCA CATTGAAGGC |
| AGGGCTGAGC AGGGCAGGCG CAGCGAGGAG CTAACTGCTG CTTCTCTCTC |
| GTTCATTTGT CTGCTGCCCT GAGACGCCAC AGCACCTAAT AAGAGCATGT |
| TATGTGTAGC AAACATTAGG CCTGTAAGGA AGGAAAGGAG TGACGTCCCT |
| TGACGTCCTC AGCTAGGCTG TGGTGACACA AGCAAGAGGA CTAAGCCACA |
| GGTGAGGAGA AAGGGGGGGG GGGG**TCTGCT GACCCAGCAA CACTCTTTCC** cons reg B |
| **TTCTGAGGCT TAAGAGCTAT TAGCGTAGGT GACTCAGTCC CTAATCCTCC** |
| ATTCAATGCC CTGTGACTGC CCCTGCTTCT GAAGGGCCAA CATGGCTACA |
| GCTAGCTCCA GAGACAGCTT TTCAGGGCCC CAGCATCCAA GCATCTCACA |
| GTTCTCCACT GACCACACTC CTGTGCAGCA CTGGGCTTTT CAATGCCCCT |
| GACTTGAAGA GAACTCAAAC TGCAGGTCAA CTAGACTCTG CAAACTTCAC |
| CTGTGCTGGG GGTTCCTAGC CTGTGGGGAC AGTGTATCTT GAATACCTGC |
| TGCTATGGAC CAAGAGCTGA ACACACAGAC AAACAGGCTC AGCTGGCCGG |
| CATTCTGGAA CCACAAATGA GTGTGGATGA GCAGGAGGGC AACAAAATGG |

TABLE 10-continued

| Conserved Regions of Rhodopsin |
|---|
| TCTGGGTGTT GTCAACACAG TCAGTAAACA ATGCACGCAG TGGGGCTGGG |
| CCCTGATGTG GAGCTAGGTG GGGTTGGCTC TCCTTGGAAA CCTGAAGGGA |
| GAAGGAGAGG GAGCGAGATG ATGAGGTTTA TCAGCCTGCA GAGGCAGGGG |
| GTCAGGAAGG AGTGCCACTG TACTGACCCA GGACCTCTGT GGGACATCAA |
| GCCATGCCAA GGAGCCATGG AGCCTCGATT GCACTGGCAG GGACAGGTTG |
| TGATGCCCCA GAGTCCCCAG ACCCAGCAAA CAGAGGCCCA GAGTGGGAAG |
| TGGAGCTTTC CAGGGTATCG GGGTGACTCA GAGACACAGG GTAGAATCTG |
| CCTTGGGTGC TCACTGCCCT ATCTGAGTCC ACATGGCTCA GTCCCCAGGC |
| CCTGTTCTCT AGTGACTGTT GCTTTGATGA GGTAGAGACA GGCAGCCCTC |
| TTCTAAGAAC TATGTTTTGA TGGGGGACTC AGAGTTGGGG TGGGGTGGCA |
| ATGAAATTCT GTAGACTGTG TGGTTATAAC CCTGGCTGTT ACTAGCTAGT |
| TCTGTGACCT TGGTGACCCA CTTCAGACTC TAGGCCTCAG CCTCTGTAAG |
| TGCAGATACA CAGCGCCAAT CAGCCGATGA CTTCTAACAA TACTCTTAAC |
| TCACACAGAG CTTGTCTCAC TGAGCCAACA CCCTGTACCC TCAGCTCAGT |
| GACGGCTTTC AACCTGTGGG GCTGCCTCTG TTACCCAAGT GAGAGAGGGC |
| CAGTGCTCCC AGAGGTGACC TTGTTTGCCC ATTCTCTCCC TGGGTCAGCC |
| AGTGTTTATC TGTTGTATAC CCAGTCCACC CTGCAGGCTC ACATCAGAGC |
| CTAGGAGATG GCTAGTGTCC CCGCGGAGAC CACGATG**AAG CTT**CCCAGCT HindIII |
| GTCTCAAGCA CAAGCTGGCT GCAGAGGCTG CTGAGGCACT GCTAGCTGGG start 1.734kb |
| GATGGGGGCA GGGTAGATCT GGGGCTGACC ACCAGGG**TCA GAATCAGAAC** |
| **CTCCACCTTG ACCTCATTAA CGCTGGTCTT AATCACCAAG CCAAGCTCCT** cons reg C |
| **TAAACT**GCTA GTGGCCAACT CCCAGGCCCT GACACACATA CCTGCCCTGT |
| GTTCCCAAAC AAGACACCTG CATGGAAGGA AGGGGGTTGC TTTTCTAAGC |
| AAACATCTAG GAATCCCGGG TGCAGTGTGA GGAGACTAGG CGAGGGAGTA |
| CTTTAAGGGC CTCAAGGCTC AGAGAGGAAT ACTTCTTCCC TGGTTAGCCT |
| CGTGCCTAGG CTCCAGGGTC TTTGTCCTGC CTGGATACCT ATGTGGCAAG |
| GGGCATAGCA TTTCCCCCAC CATCAGCTCT TAGCTCAACC TTATCTTCTC |
| GGAAAGACTG CGCAGTGTAA CAACACAGCA GAGACTTTTC TTTTGTCCCC |
| TGTCTACCCC TGTAACTGCT ACTCAGAAGC ATCTTTCTCA CAGGGTACTG |
| GCTTCTTGCA TCCAGAGTTT TTTGTCTCCC TCGGGCCCCC AGAATCAAAT |
| TCTTCCTCTG GGACTCAGTG GATGTTTCAC ACACGTATCG GCCTGACAGT |
| CATCCTGGAG CATCCTACAC AGGGGCCATC ACAGCTGCAT GTCAGAAATG |
| CTGGCCTCAC ATCCTCAGAC ACCAGGCCTA GTGCTGGTCT TCCTCAGACT |
| GGCGTCCCCA GCAGGCCAGT AGGATCATCT TTTAGCCTAC AGAGTTCTGA |
| AGCCTCAGAG CCCCAGGTCC CTGGTCATCT TCTCTGCCCC TGAGATTTTT |
| CCAAGTTGTA TGCCTTCTAG GTAAGGCAAA ACTTCTTACG CCCCTCCTCG |
| TGGCCTCCAG GCCCCACATG CTCACCTGAA TAACCTGGCA GCCTGCTCCC |
| TCATGCAGGG ACCACGTCCT GCTGCACCCA GCAGGCCATC CCGTCTCCAT |
| AGCCCATGGT CATCCCTCCC TGGACAGGAA TGTGTCTCCT CCCCGGGCTG |

TABLE 10-continued

Conserved Regions of Rhodopsin

AGTCTTGCTC AAGCTAGAAG CACTCCGAAC AGGGTTATGG GCGCCTCCTC

CATCTCCCAA GTGGCTGGCT TATGAATGTT TAATGTACAT GTGAGTGAAC

AAATTCCAAT TGAACGCAAC AAATAGTTAT CGAGCCGCTG AGCCGGGGGG

CGGGGGGTGT GAGACTGGAG GCGATGGACG GAGCTGACGG CACACACAGC

TCAGATCTGT CAAGTGAGCC ATTGTCAGGG CTTGGGGACT GGATAAGTCA

GGGGGTCTCC TGGGAAGAGA TGGGATAGGT GAGTTCAGGA GGAGACATTG

TCAACTGGAG CCATGTGGAG AAGTGAATTT AGGGCCCAAA GGTTCCAGTC

GCAGCCTGAG GCCACCAGAC TGACATGGGG AGGAATTCCC AGAGGACTCT

GGGGCAGACA AGATGAGACA CCCTTTCCTT TCTTTACCTA AGGGCCTCCA

CCCGATGTCA CCTTGGCCCC TCTGCAAGCC AATTAGGCCC CGGTGGCAGC

AGTGGGATTA GCGTTAGTAT GATATCTCGC GGATGCTGAA TCAGCCTCTG

GCTTAGGGAG AGAAGGTCAC TTTATAAGGG TCTGGGGGGG GTCAGTGCCT

GGAGTTGCGC TGTGGGAGCC GTCAGTGGCT GAGCTCGCCA AGCAGCCTTG

GTCTCTGTCT ACGAAGAGCC CGTGGGGCAG CCTCGAG XhoI ggatcctgag tacctctcct ccctgacctc aggcttcctc ctagtgtcac cttggcccct conserved region D cttagaagcc aattaggccc tcagtttctg cagcggggat taatatgatt atgaacaccc ccaatctccc agatgctgat tcagccagga gcttaggagg gggaggtcac tttataaggg tctggggggg tcagaaccca gagtcatcca gctggagccc tgagtggctg agctcaggcc ttcgcagcat tcttgggtgg gagcagccac gggtcagcca caagggccac agccatgaat ggcacagaag gccctaactt ctacgtgccc ttctccaatg cgacgggtgt ggtacgcagc cccttcgagt acccacagta ctacctggct gagccatggc agttctccat gctggccgcc tacatgtttc tgctgatcgt gctgggcttc cccatcaact tcctcacgct ctacgtcacc gtccagcaca agaagctgcg cacgcctctc aactacatcc tgctcaacct agccgtggct gacctcttca tggtcctagg tggcttcacc agcaccctct acacctctct gcatggatac ttcgtcttcg ggcccacagg atgcaatttg gagggcttct ttgccaccct gggcggtatg agccgggtgt gggtggggtg tgcaggagcc cgggagcatg gaggggtctg ggagagtccc gggcttggcg gtggtggctg agaggccttc tcccttctcc tgtcctgtca atgttatcca aagccctcat atattcagtc aacaaacacc attcatggtg atagccgggc tgctgtttgt gcagggctgg cactgaacac tgccttgatc ttatttggag caatatgcgc ttgtctaatt tcacagcaag aaaactgagc tgaggctcaa aggccaagtc aagcccctgc tggggcgtca cacagggacg ggtgcagagt tgagttggaa gcccgcatct atctcgggcc atgtttgcag caccaagcct ctgtttccct tggagcagct gtgctgagtc agacccaggc tgggcactga gggagagctg ggcaagccag acccctcctc tctgggggcc caagctcagg gtgggaagtg gattttccat tctccagtca ttgggtcttc cctgtgctgg gcaatgggct cggtcccctc tggcatcctc tgcctcccct ctcagcccct gtcctcaggt gcccctccag cctccctgcc gcgttccaag tctcctggtg ttgagaaccg caagcagccg ctctgaagca gttccttttt gctttagaat aatgtcttgc atttaacagg aaaacagatg gggtgctgca gggataacag atcccactta acagagagga aaactgaggc agggagaggg gaagagactc atttagggat gtggccaggc agcaacaaga gcctaggtct cctggctgtg atccaggaat atctctgctg TABLE 10-continued

| Conserved Regions of Rhodopsin |
| --- |
| agatgcagga ggagacgcta gaagcagcca ttgcaaagct gggtgacggg gagagcttac |
| cgccagccac aagcgtctct ctgccagcct tgccctgtct cccccatgtc caggctgctg |
| cctcggtccc attctcaggg aatctctggc cattgttggg tgtttgttgc attcaataat |
| cacagatcac tcagttctgg ccagaaggtg ggtgtgccac ttacgggtgg ttgttctctg |
| cagggtcagt cccagtttac aaatattgtc cctttcactg ttaggaatgt cccagtttgg |
| ttgattaact atatggccac tctccctatg aaacttcatg gggtggtgag caggacagat |
| gttcgaattc catcatttcc ttcttcttcc tctgggcaaa acattgcaca ttgcttcatg |
| gctcctagga gaggccccca catgtccggg ttatttcatt tcccgagaag ggagagggag |
| gaaggactgc caattctggg tttccaccac ctctgcattc cttcccaaca aggaactctg |
| ccccacatta ggatgcattc ttctgctaaa cacacacaca cacacacaca cacacaacac |
| acacacacac acacacacac acacacacac aaaactccct accgggttcc cagttcaatc |
| ctgacccccct gatctgattc gtgtccctta tgggcccaga gcgctaagca aataacttcc |
| cccattccct ggaatttctt tgcccagctc tcctcagcgt gtggtccctc tgccccttcc |
| ccctcctccc agcaccaagc tctctccttc cccaaggcct cctcaaatcc ctctcccact |
| cctggttgcc ttcctagcta ccctctccct gtctaggggg gagtgcaccc tccttaggca |
| gtggggtctg tgctgaccgc ctgctgactg ccttgcaggt gaaattgccc tgtggtcctt |
| ggtggtcctg gccatcgagc ggtacgtggt ggtgtgtaag cccatgagca acttccgctt |
| cggggagaac catgccatca tgggcgttgc cttcacctgg gtcatggcgc tggcctgcgc |
| cgcaccccca ctcgccggct ggtccaggta atggcactga gcagaaggga agaagctccg |
| ggggctcttt gtagggtcct ccagtcagga ctcaaaccca gtagtgtctg gttccaggca |
| ctgaccttgt atgtctcctg gcccaaatgc ccactcaggg taggggtgta gggcagaaga |
| agaaacagac tctaatgttg ctacaagggc tggtcccatc tcctgagccc catgt**caaac** conserved region E |
| **agaatcc**aag acatc**ccaac ccttcacctt ggctgtgccc ctaatcctca actaagc**tag |
| **gcgcaaattc caatcctctt tggtctagt**a ccc**cggg**ggc agcc**ccctct aaccttgggc** |
| **ctca**gc**agca** ggggaggcca caccttccta gtgcaggtgg ccatattgtg gccccttgga |
| actgggtccc actcagcctc taggcgattg tctcctaatg gggctgagat gagactcagt |
| ggggacagtg gtttggacaa taggactggt gactctggtc cccagaggcc tcatgtccct |
| ctgtctccag aaaattccca ctctcacttc cctttcctcc tcagtcttgc tagggtccat |
| ttctacccct tgctgaattt gagcccaccc cctggacttt ttccccatct tctccaatct |
| ggcctagttc tatcctctgg aagcagagcc gctggacgct ctgggtttcc tgaggcccgt |
| ccactgtcac caatatcagg aaccattgcc acgtcctaat gacgtgcgct ggaagcctct |
| agtttccaga agctgcacaa agatccctta gatactctgt gtgtccatct ttggcctgga |
| aaatactctc accctggggc taggaagacc tcggtttgta caaacttcct caaatgcaga |
| gcctgagggc tctccccacc tcctcaccaa ccctctgcgt ggcatagccc tagcctcagc |
| gggcagtgga tgctggggct gggcatgcag ggagaggctg ggtggtgtca tctggtaacg |
| cagccaccaa acaatgaagc gacactgatt ccacaaggtg catctgcatc cccatctgat |
| ccattccatc ctgtcaccca gccatgcaga cgtttatgat ccccttttcc agggagggaa |
| tgtgaagccc cagaaagggc cagcgctcgg cagccacctt ggctgttccc aagtccctca |
| caggcagggt ctccctacct gcctgtcctc aggtacatcc ccgagggcct gcagtgctcg |

TABLE 10-continued

Conserved Regions of Rhodopsin tgtggaatcg actactacac gctcaagccg gaggtcaaca acgagtcttt tgtcatctac atgttcgtgg tccacttcac catccccatg attatcatct ttttctgcta tgggcagctc gtcttcaccg tcaaggaggt acgggccggg gggtgggcgg cctcacggct ctgagggtcc agcccccagc atgcatctgc ggctcctgct ccctggagga gccatggtct ggacccgggt cccgtgtcct gcaggccgct gcccagcagc aggagtcagc caccacacag aaggcagaga aggaggtcac ccgcatggtc atcatcatgg tcatcgcttt cctgatctgc tgggtgccct acgccagcgt ggcattctac atcttcaccc accagggctc caacttcggt cccatcttca tgaccatccc agcgttcttt gccaagagcg ccgccatcta caaccctgtc atctatatca tgatgaacaa gcaggtgcct actgcgggtg ggagggcccc agtgccccag gccacaggcg ctgcctgcca aggacaagct actcccaggg caggggaggg gctccatcag ggttactggc agcagtcttg ggtcagcagt cccaatgggg agtgtgtgag aaatgcagat tcctggcccc actcagaact gctgaatctc agggtgggcc caggaacctg catttccagc aagccctcca caggtggctc agatgctcac tcaggtggga gaagctccag tcagctagtt ctggaagccc aatgtcaaag tcagaaggac ccaagtcggg aatgggatgg gccagtctcc ataaagctga ataaggagct aaaaagtctt attctgaggg gtaaaggggt aaagggttcc tcggagaggt acctccgagg ggtaaacagt tgggtaaaca gtctctgaag tcagctctgc cattttctag ctgtatggcc ctgggcaagt caatttcctt ctctgtgctt tggtttcctc atccatagaa aggtagaaag ggcaaaacac caaactcttg gattacaaga gataatttac agaacaccct tggcacacag agggcaccat gaaatgtcac gggtgacaca gccccccttgt gctcagtccc tggcatctct aggggtgagg agcgtctgcc tagcaggttc ccaccaggaa gctggatttg agtggatggg gcgctggaat cgtgaggggc agaagcaggc aaagggtcgg ggcgaacctc actaacgtgc cagttccaag cacactgtgg gcagccctgg ccctgactca agcctcttgc cttccagttc cggaactgca tgctcaccac catctgctgc ggcaagaacc cactgggtga cgatgaggcc tctgctaccg tgtccaagac ggagacgagc caggtggccc cggcctaaga cctgcctagg actctgtggc cgactatagg cgtctcccat cccctacacc ttcccccagc cacagccatc ccaccaggag cagcgcctgt gcagaatgaa cgaagtcaca taggctcctt conserved region F aatttttttt ttttttttaa gaaataatta atgaggctcc tcactcacct gggacagcct gagaagggac B atccaccaag acctactgat ctggagtccc acgttcccca aggccagcgg gatgtgtgcc cctcctcctc ccaactcatc tttcaggaac acgaggattc ttgctttctg gaaaagtgtc ccagcttagg gataagtgtc tagcacagaa tggggcacac agtaggtgct conserved region G taataaatgc tggatggatg caggaaggaa tggaggaatg aatgggaagg gagaacatat ctatcctctc agaccctcgc agcagcagca actcatactt ggctaatgat atggagcagt tgtttttccc tccctgggcc tcactttctt ctcctataaa atggaaatcc cagatccctg gtcctgccga cacgcagcta ctgagaagac caaaagaggt gtgtgtgtgt ctatgtgtgt gtttcagcac tttgtaaata gcaagaagct gtacagattc tagttaatgt tgtgaataac atcaattaat gtaactagtt aattactatg attatcacct cctgatagtg aacattttga gattgggcat tcagatgatg gggtttcacc caaccttggg gcaggttttt aaaaattagc taggcatcaa ggccagacca gggctggggg ttgggctgta ggcagggaca gtcacaggaa tgcaggatgc agtcatcaga cctgaaaaaa caacactggg ggagggggac ggtgaaggcc TABLE 10-continued

| Conserved Regions of Rhodopsin |
|---|
| aagttcccaa tgagggtgag attgggcctg gggtctcacc cctagtgtgg ggccccaggt |
| cccgtgcctc cccttcccaa tgtggcctat ggagagacag gcctttctct cagcctctgg |
| aagccacctg ctcttttgct ctagcacctg ggtcccagca tctagagcat **ggagcctcta** |
| **gaagccatgc tcacccgccc acatttaatt aacagctgag tccctgatgt catccttact** conserved region H |
| cgaagagctt agaaacaaag agtgggaaat tccactgggc ctaccttcct tggggatgtt |
| catgggcccc agtttccagt ttcccttgcc agacaagccc atcttcagca gttgctagtc |
| cattctccat tctggagaat ctgctccaaa aagctggcca catctctgag gtgtcagaat |
| taagctgcct cagtaactgc tccccttct ccatataagc aaagccagaa gctctagctt |
| **tacccagctc tgcctggaga ctaaggcaaa ttgggccatt aaaagctcag ctcctatgtt** |
| **ggtattaacg gtggtgggtt ttgttgcttt cacactctat ccacaggata gattgaaact** conserved region I |
| **gccagcttcc acctgatccc tgaccctggg atggctggat tgagcaatga gcagagccaa** |
| **gcagcacaga gtcccctggg gctagaggtg gaggaggcag tcctgggaat gggaaaaacc** |
| **cca**actttgg ggtcatagag gcacaggtaa cccataaaac tgcaaacaag ctt |

Sequence 1: Mouse rhodopsin promoter sequence (upper case) ending at the Xho I site (highlighted in bold print), followed by the human rhodopsin 5'UTR, human rhodopsin exons and introns and human rhodopsin 3' region sequence (lower case). Conserved regions A-I are highlighted in bold print. (SEQ ID NO: 90).

Conserved regions A through I and some sequence flanking the regions (5' and 3', were combined (Table 11, SEQ ID NO: 92 through SEQ ID NO: 99, Sequence 2). This sequence was analyzed using MatInspector Release Professional 7.4.1 to identify other regions that may be involved in transcriptional and/or translational control of rhodopsin gene expression. (A small portion of the Matinspector results are presented in Table 12). This table illustrates some sequences within conserved regions A through I that are thought to be involved in the transcription and/or translation and/or stability of rhodopsin. Some of these sequences, such as the CRX binding element in conserved region D and the TATA box in region G are known in the art. Others, such as the CRX binding region in E, are not. The complete set of results from MatInspector are presented in Table 13. 302 putative transcription binding sites and/or regulatory sequences were identified and some are highlighted in bold. On the basis of the conserved nature of regions A though I and the important transcription factor binding sites thought to be located within these regions, the constructs in FIG. 9 were generated. Construct BB16 contains conserved regions A, B, C, D, F and G. In addition an artificial CRX-NRL element (below) was inserted between conserved regions A and B. The components of the artificial CRX-NRL enhancer element include the CRX motif from conserved region D, the CRX motif from conserved region E and NRL binding sites are underlined.

(SEQ ID NO: 91)

TTTCTGCAGCGGGGATTAATATGATTATGAACACCCCCAATCTCCCAGA

TGCTGATTCAGCCAGGAGGTACC

All these constructs contain transcription binding sites identified within conserved regions A though I.

Sequence 2: Conserved regions A through I in the rhodopsin gene are highlighted in bold below. The nucleotides of these sequences and a small section of 5' and 3' sequence surrounding conserved regions have been numbered 1-1600. This sequence was analysed with MatInspector and the nucleotide numbering system of sequence 2 (1-1600) relates to the nucleotide numbering system in Table 13.

TABLE 11

| Conserved region A 1-210 (SEQ ID NO: 92) |
|---|
| CACAACTCCT CCGTC**GAGTG TCTAATTGCT TATGATCATG** |
| **CATGCTCTCT CTCCCACTAA ACATTTATTA ATGTGTTAGG** |
| **ATTTCCATTA GCGCGTGCCT TGAACTGAAA TCATTTGCAT** |
| **ATGGCTGGGA AAAAGTGGGG TGAGGGAGGA AACAGTGCCA** |
| **GCTCCCCAAC AGGCGTCAAT CACAGTGACA GATCAGATGG** |
| TTTCTGGCTG 210 |
| Conserved region B 210-310 (SEQ ID NO: 93) |
| AAGGGGGGGG GGGG**TCTGCT GACCCAGCAA CACTCTTTCC** |
| **TTCTGAGGCT TAAGAGCTAT TAGCGTAGGT GACTCAGTCC** |

TABLE 11-continued

CTAATCCTCC ATTCAATGCC 310

Conserved region C 310-410 (SEQ ID NO: 94)

GGGGCTGACC ACCAGGGTCA GAATCAGAAC CTCCACCTTG

ACCTCATTAA CGCTGGTCTT AATCACCAAG CCAAGCTCCT

TAAACTGCTA GTGGCCAACT 410

Conserved region D 410-690 (SEQ ID NO: 95)

aggcttcctc ctagtgtcac cttggcccct cttagaagcc aattaggccc tcagtttctg cagcggggat taatatgatt atgaacaccc ccaatctccc agatgctgat tcagccagga gcttaggagg gggaggtcac tttataaggg tctggggggg tcagaaccca gagtcatcca gctggagccc tgagtggctg agctcaggcc ttcgcagcat tcttgggtgg gagcagccac gggtcagcca caagggccac agccatgaat ggcacagaag 690

Conserved region E 690-850 (SEQ ID NO: 96)

tcctgagccc catgtcaaac agaatccaag acatcccaac ccttcacctt ggctgtgccc ctaatcctca actaagctag gcgcaaattc caatcctctt tggtctagta ccccgggggc agcccctct aaccttgggc ctcagcagca ggggaggcca 850

Conserved regions F and G 850-1220 (SEQ ID NO: 97)

cccctacacc ttccccagc cacagccatc ccaccaggag cagcgcctgt gcagaatgaa cgaagtcaca taggctcctt aatttttttt ttttttttaa gaaataatta atgaggctcc tcactcacct gggacagcct gagaagggac atccaccaag acctactgat ctggagtccc acgttcccca aggccagcgg gatgtgtgcc cctcctcctc ccaactcatc tttcaggaac acgaggattc ttgctttctg gaaaagtgtc ccagcttagg gataagtgtc tagcacagaa tggggcacac agtaggtgct taataaatgc tggatggatg caggaaggaa tggaggaatg aatgggaagg 1220

Conserved region H 1220 1230-1316 1330 (SEQ ID NO: 98)

tctagagcat ggagcctcta gaagccatgc tcacccgccc acatttaatt aacagctgag tccctgatgt catccttact cgaagagctt agaaacaaag agtgggaaat 1330

Conserved region I 1330 1342-1425 1600 (SEQ ID NO: 99)

gctctagctt tacccagctc tgcctggaga ctaaggcaaa ttgggccatt aaaagctcag ctcctatgtt ggtattaacg gtggtgggtt ttgttgcttt cacactctat ccacaggata gattgaaact gccagcttcc acctgatccc tgaccctggg atggctggat tgagcaatga gcagagccaa gcagcacaga gtcccctggg gctagaggtg gaggaggcag tcctgggaat gggaaaaacc ccaactttgg ggtcatagag 1600

(Conserved regions are in bold)

TABLE 12

Conserved sequence motifs in Rhodopsin

| Conserved region | Position | Name |
|---|---|---|
| B | 288-304 | CRX |
| C | 366-382 | CRX |
| D | 470-486 | CRX |
| E | 784-764 | CRX |
| G | 1172-1177 | TATA box |
| D | 500-520 | Neuron-restrictive silencer factor |
| E | 794-814 | Neuron-restrictive silencer factor |
| E | 831-851 | Neuron-restrictive silencer factor |

TABLE 13

Putative Rhodopsin Transcription Regulatory Factors

| Family/matrix | Further Information | Opt. | Position | Str. | Core sim. | Matrix sim. | Sequence (red: ci-value >60 capitals: core sequence) | SEQ ID NO |
|---|---|---|---|---|---|---|---|---|
| V$PDX1/ISL1.01 | Pancreatic and intestinal lim-homeodomain factor | 0.82 | 14-34 | (+) | 1.000 | 0.860 | tcgagtgtcTAA Ttgcttatg | 100 |
| V$HOMF/MSX.01 | Homeodomain proteins MSX-1 and MSX-2 | 0.97 | 18-30 | (+) | 1.000 | 0.995 | gtgtcTAATtgct | 101 |
| V$HOXF/GSH2.01 | Homeodomain transcription factor Gsh-2 | 0.95 | 19-35 | (+) | 1.000 | 0.975 | tgtcTAATtgctt atga | 102 |
| V$GABF/GAGA.01 | GAGA-Box | 0.78 | 33-57 | (-) | 1.000 | 0.825 | gtgggAGAGag agcatgcatgatca | 103 |
| V$FKHD/FREAC2.01 | Fork head related activator-2 (FOXF2) | 0.84 | 52-68 | (+) | 1.000 | 0.884 | tcccacTAAAc atttat | 104 |
| V$HOXF/HOXC13.01 | Homeodomain transcription factor HOXC13 | 0.91 | 58-74 | (-) | 1.000 | 0.914 | acattaaTAAAt gttta | 105 |
| V$NKXH/HMX2.02 | Hmx2/Nkx5-2 homeodomain transcription factor | 0.82 | 58-72 | (-) | 0.750 | 0.835 | attaatAAATgtt ta | 106 |
| V$SATB/SATB1.01 | Special AT-rich sequence-binding protein 1, predominantly expressed in thymocytes, binds to matrix attachment regions (MARs) | 0.94 | 58-72 | (-) | 1.000 | 0.956 | attAATAaatgtt ta | 107 |
| V$BRNF/BRN3.02 | Brn-3, POU-IV protein class | 0.89 | 59-77 | (-) | 1.000 | 0.892 | aacacatTAATa aatgttt | 108 |
| V$PDX1/PDX1.01 | Pdx1 (IDX1/IPF1) pancreatic and intestinal homeodomain TF | 0.74 | 59-79 | (-) | 1.000 | 0.744 | ctaacacatTAA Taaatgttt | 109 |
| V$PIT1/PIT1.01 | Pit1, GHF-1 pituitary specific pou domain transcription factor | 0.84 | 61-73 | (+) | 1.000 | 0.857 | acatTTATtaatg | 110 |
| V$BRNF/BRN3.02 | Brn-3, POU-IV protein class | 0.89 | 62-80 | (+) | 1.000 | 0.893 | catttatTAATgt gttagg | 111 |
| V$LHXF/LMX1B.01 | LIM-homeodomain transcription factor | 0.91 | 62-76 | (-) | 1.000 | 0.946 | acacatTAATaa atg | 112 |
| V$HOXH/MEIS1B_HOXA9.01 | Meis1b and Hoxa9 form heterodimeric binding complexes on target DNA | 0.78 | 64-78 | (-) | 0.750 | 0.823 | TAACacattaat aaa | 113 |
| V$HOXF/HOX1-3.01 | Hox-1.3, vertebrate | 0.82 | 65-81 | (+) | 1.000 | 0.826 | ttatTAATgtgtt agga | 114 |

TABLE 13-continued

Putative Rhodopsin Transcription Regulatory Factors

| Family/matrix | Further Information | Opt. | Position | Str. | Core sim. | Matrix sim. | Sequence (red: ci-value >60 capitals: core sequence) | SEQ ID NO |
|---|---|---|---|---|---|---|---|---|
| | homeobox protein | | | | | | | |
| V$OCT1/OCT1.04 | Octamer-binding factor 1 | 0.80 | 77-91 | (-) | 0.846 | 0.866 | ctAATGgaaatc cta | 115 |
| V$HOXF/PHOX2.01 | Phox2a (ARIX) and Phox2b | 0.87 | 78-94 | (-) | 1.000 | 0.969 | gcgcTAATgga aatcct | 116 |
| V$AHRR/AHRARNT.01 | Aryl hydrocarbon receptor/Arnt heterodimers | 0.92 | 83-107 | (+) | 1.000 | 0.932 | ttccattagcgCG TGccttgaactg | 117 |
| V$MOKF/MOK2.02 | Ribonucleoprotein associated zinc finger protein MOK-2 (human) | 0.98 | 85-105 | (+) | 1.000 | 0.988 | ccattagcgcgtg CCTTgaac | 118 |
| V$EBOX/MYCMAX.03 | MYC-MAX binding sites | 0.91 | 87-101 | (-) | 1.000 | 0.918 | aaggcaCGCGc taat | 119 |
| V$HESF/HELT.01 | Hey-like bHLH-transcriptional repressor | 0.91 | 87-101 | (-) | 1.000 | 0.947 | aaggCACGcgc taat | 120 |
| V$HOMF/EN1.01 | Homeobox protein engrailed (en-1) | 0.77 | 97-109 | (+) | 0.782 | 0.776 | gccTTGAactg aa | 121 |
| V$OCT1/OCT1.02 | Octamer-binding factor 1 | 0.85 | 109-123 | (-) | 1.000 | 0.992 | catATGCaaatg att | 122 |
| V$OCTP/OCT1P.01 | Octamer-binding factor 1, POU-specific domain | 0.86 | 113-125 | (-) | 1.000 | 0.910 | gccATATgcaa at | 123 |
| V$AIRE/AIRE.01 | Autoimmune regulator | 0.86 | 119-145 | (+) | 0.916 | 0.862 | atatggctgggaaa aagTGGGgtga gg | 124 |
| V$RBPF/RBPJK.02 | Mammalian transcriptional repressor RBP-Jkappa/CBF1 | 0.94 | 122-136 | (+) | 1.000 | 0.941 | tggcTGGGaaa aagt | 125 |
| V$RXRF/VDR_RXR.06 | Bipartite binding site of VDR/RXR heterodimers: 4 spacer nucleotides between the two directly repeated motifs | 0.75 | 123-147 | (+) | 0.812 | 0.760 | ggctgggaaaaag tgGGGTgaggga | 126 |
| V$NKXH/HMX3.01 | H6 homeodomain HMX3/Nkx5.1 transcription factor | 0.89 | 127-141 | (+) | 1.000 | 0.910 | gggaaaAAGTg gggt | 127 |
| V$CIZF/NMP4.01 | NMP4 (nuclear matrix protein 4)/ CIZ (Cas-interacting zinc finger protein) | 0.97 | 128-138 | (+) | 1.000 | 0.998 | ggAAAAagtgg | 128 |
| V$EBOX/SREBP.01 | Sterol regulatory element binding protein 1 and 2 | 0.90 | 132-146 | (-) | 1.000 | 0.960 | cccTCACccca cttt | 129 |

TABLE 13-continued

Putative Rhodopsin Transcription Regulatory Factors

| Family/matrix | Further Information | Opt. | Position | Str. | Core sim. | Matrix sim. | Sequence (red: ci-value >60 capitals: core sequence) | SEQ ID NO |
|---|---|---|---|---|---|---|---|---|
| V$RXRF/VDR_RXR.02 | VDR/RXR Vitamin D receptor RXR heterodimer site | 0.86 | 134-158 | (+) | 1.000 | 0.878 | agtggggtgagg GAGGaaacagt gc | 130 |
| V$ETSF/PU1.01 | Pu.1 (Pu120)Ets-like transcription factor identified in lymphoid B-cells | 0.89 | 141-157 | (+) | 1.000 | 0.895 | tgagggaGGAA acagtg | 131 |
| V$NFAT/NFAT.01 | Nuclear factor of activated T-cells | 0.95 | 145-155 | (+) | 1.000 | 0.989 | ggaGGAAacag | 132 |
| V$AREB/AREB6.04 | AREB6 (Atp1a1 regulatory element binding factor 6) | 0.98 | 146-158 | (−) | 1.000 | 0.991 | gcactGTTTcctc | 133 |
| V$COMP/COMP1.01 | COMP1, cooperates with myogenic proteins in multicomponent complex | 0.77 | 163-185 | (−) | 1.000 | 0.811 | ctgtgATTGacg cctgttgggga | 134 |
| V$PAX6/PAX6.01 | Pax-6 paired domain binding site | 0.77 | 163-181 | (−) | 0.808 | 0.781 | gaTTGAcgcct gttgggga | 135 |
| V$MYBL/CMYB.01 | c-Myb, important in hematopoesis, cellular equivalent to avian myoblastosis virus oncogene v-myb | 0.90 | 165-177 | (+) | 1.000 | 0.945 | ccCAACaggcg tc | 136 |
| V$CREB/CREB.02 | cAMP-responsive element binding protein | 0.89 | 167-187 | (−) | 1.000 | 0.902 | cactgtgatTGA Cgcctgttg | 137 |
| V$WHZF/WHN.01 | Winged helix protein, involved in hair keratinization and thymus epithelium differentiation | 0.95 | 169-179 | (−) | 1.000 | 0.955 | ttgACGCctgt | 138 |
| V$HOXC/PBX1.01 | Homeo domain factor Pbx-1 | 0.78 | 170-186 | (−) | 1.000 | 0.840 | actgtGATTgac gcctg | 139 |
| V$PBXC/PBX1_MEIS1.02 | Binding site for a Pbx1/Meis1 heterodimer | 0.77 | 170-186 | (−) | 1.000 | 0.875 | actgTGATtgac gcctg | 140 |
| V$AP1R/TCF11MAFG.01 | TCF11/MafG heterodimers, binding to subclass of AP1 sites | 0.81 | 177-201 | (+) | 1.000 | 0.838 | caatcacagTGA Cagatcagatggt | 141 |
| V$TALE/MEIS1.01 | Binding site for monomeric Meis1 homeodomain protein | 0.95 | 183-193 | (−) | 1.000 | 0.971 | atcTGTCactg | 142 |

TABLE 13-continued

Putative Rhodopsin Transcription Regulatory Factors

| Family/matrix | Further Information | Opt. | Position | Str. | Core sim. | Matrix sim. | Sequence (red: ci-value >60 capitals: core sequence) | SEQ ID NO |
|---|---|---|---|---|---|---|---|---|
| V$HOXH/MEIS1A_HOXA9.01 | Meis1a and Hoxa9 form heterodimeric binding complexes on target DNA | 0.77 | 186-200 | (+) | 1.000 | 0.770 | TGACagatcag atgg | 143 |
| V$GATA/GATA3.02 | GATA-binding factor 3 | 0.91 | 187-199 | (+) | 1.000 | 0.950 | gacAGATcaga tg | 144 |
| V$AP4R/TAL1BETAE47.01 | Tal-1beta/E47 heterodimer | 0.87 | 189-205 | (+) | 1.000 | 0.955 | cagatCAGAtg gtttct | 145 |
| V$NEUR/NEUROG.01 | Neurogenin 1 and 3 (ngn1/3) binding sites | 0.92 | 191-203 | (−) | 1.000 | 0.925 | aaaCCATctgatc | 146 |
| V$ZBPF/ZBP89.01 | Zinc finger transcription factor ZBP-89 | 0.93 | 205-227 | (−) | 1.000 | 0.966 | agacccccccCC CCcttcagcca | 147 |
| V$ZBPF/ZNF219.01 | Kruppel-like zinc finger protein 219 | 0.91 | 207-229 | (−) | 1.000 | 0.997 | gcagaccCCCC cccccttcagc | 148 |
| V$INSM/INSM1.01 | Zinc finger protein insulinoma-associated 1 (IA-1) functions as a transcriptional repressor | 0.90 | 209-221nc | (+) | 1.000 | 0.914 | tgaagGGGGgg gg | 149 |
| V$EKLF/KKLF.01 | Kidney-enriched kruppel-like factor, KLF15 | 0.91 | 210-226nc | (+) | 1.000 | 0.934 | gaagggGGGG gggggtc | 150 |
| V$EGRF/WT1.01 | Wilms Tumor Suppressor | 0.92 | 211-227nc | (+) | 0.837 | 0.945 | aagggGGGGg ggggtct | 151 |
| V$SP1F/GC.01 | GC box elements | 0.88 | 211-225nc | (+) | 0.819 | 0.897 | aagggGGGGg ggggt | 152 |
| V$EKLF/KKLF.01 | Kidney-enriched kruppel-like factor, KLF15 | 0.91 | 212-228nc | (+) | 1.000 | 0.949 | agggggGGGG gggtctg | 153 |
| V$SP1F/GC.01 | GC box elements | 0.88 | 213-227nc | (+) | 0.819 | 0.908 | gggggGGGGg ggtct | 154 |
| V$EGRF/WT1.01 | Wilms Tumor Suppressor | 0.92 | 214-230nc | (+) | 0.837 | 0.932 | gggggGGGGg gtctgct | 155 |
| V$GLIF/ZIC2.01 | Zinc finger transcription factor, Zic family member 2 (odd-paired homolog, *Drosophila*) | 0.89 | 214-228 | (−) | 1.000 | 0.967 | cagacccCCCC cccc | 156 |
| V$MAZF/MAZR.01 | MYC-associated zinc finger protein related transcription factor | 0.88 | 215-227nc | (+) | 1.000 | 0.972 | ggggggGGGG tct | 157 |
| V$AP1R/BACH2.01 | Bach2 bound TRE | 0.89 | 221-245 | (−) | 0.813 | 0.897 | gagtgttgcTGG Gtcagcagacccc | 158 |
| V$AP1R/VMAF.01 | v-Maf | 0.82 | 221-245 | (+) | 1.000 | 0.957 | ggggtctgcTGA Cccagcaacactc | 159 |

TABLE 13-continued

Putative Rhodopsin Transcription Regulatory Factors

| Family/matrix | Further Information | Opt. | Position | Str. | Core sim. | Matrix sim. | Sequence (red: ci-value >60 capitals: core sequence) | SEQ ID NO |
|---|---|---|---|---|---|---|---|---|
| V$XBBF/MIF1.01 | MIBP-1/RFX1 complex | 0.76 | 225-243 | (-) | 0.800 | 0.778 | gtgttgctggGTC Agcaga | 160 |
| V$XBBF/RFX1.01 | X-box binding protein RFX1 | 0.89 | 227-245 | (+) | 1.000 | 0.907 | tgctgacccaGC AAcactc | 161 |
| V$NFAT/NFAT.01 | Nuclear factor of activated T-cells | 0.95 | 243-253 | (-) | 1.000 | 0.971 | gaaGGAAagag | 162 |
| V$NKXH/HMX2.01 | Hmx2/Nkx5-2 homeodomain transcription factor | 0.83 | 253-267 | (-) | 1.000 | 0.911 | gctCTTAagcct cag | 163 |
| V$PAX8/PAX8.01 | PAX 2/5/8 binding site | 0.88 | 254-266 | (-) | 0.800 | 0.901 | ctcTTAAgcctca | 164 |
| V$NKXH/HMX2.01 | Hmx2/Nkx5-2 homeodomain transcription factor | 0.83 | 256-270 | (+) | 1.000 | 0.931 | aggCTTAagag | 165 |
| V$HOXF/PHOX2.01 | Phox2a (ARIX) and Phox2b | 0.87 | 260-276 | (-) | 1.000 | 0.898 | acgcTAATagc tcttaa | 166 |
| V$CLOX/CDPCR3.01 | Cut-like homeodomain protein | 0.73 | 266-284 | (-) | 0.880 | 0.770 | agtcacctacgcta ATAGc | 167 |
| V$EGRF/NGFIC.01 | Nerve growth factor-induced protein C | 0.80 | 269-285 | (+) | 1.000 | 0.855 | attaGCGTaggt gactc | 168 |
| V$AP1R/BACH2.01 | Bach2 bound TRE | 0.89 | 271-295 | (-) | 1.000 | 0.957 | attagggacTGA Gtcacctacgcta | 169 |
| V$CREB/TAXCREB.02 | Tax/CREB complex | 0.71 | 274-294 | (+) | 1.000 | 0.744 | cgtaggTGACtc agtccctaa | 170 |
| V$AP1F/AP1.01 | Activator protein 1 | 0.94 | 278-288 | (+) | 0.904 | 0.967 | ggtgACTCagt | 171 |
| V$AP1F/AP1.03 | Activator protein 1 | 0.94 | 278-288 | (-) | 1.000 | 0.976 | acTGAGtcacc | 172 |
| V$HOXF/CRX.01 | Cone-rod B homeobox-containing transcription factor/otx-like homeobox gene | 0.94 | 288-304 | (+) | 1.000 | 0.972 | tcccTAATcctc cattc | 173 |
| V$SORY/HBP1.01 | HMG box-containing protein 1 | 0.86 | 298-310 | (-) | 1.000 | 0.905 | ggcattgAATG ga | 174 |
| V$IRFF/IRF7.01 | Interferon regulatory factor 7 (IRF-7) | 0.86 | 329-347 | (+) | 0.936 | 0.865 | caGAATcagaa cctccacc | 175 |
| V$RORA/RORA1.01 | RAR-related orphan receptor alpha1 | 0.93 | 342-360 | (-) | 1.000 | 0.953 | ttaatgaGGTCa aggtgga | 176 |
| V$CSEN/DREAM.01 | Downstream regulatory element-antagonist modulator, Ca2+-binding protein of the neuronal calcium sensors family that | 0.95 | 344-354 | (-) | 1.000 | 0.960 | agGTCAaggtg | 177 |

TABLE 13-continued

| Putative Rhodopsin Transcription Regulatory Factors | | | | | | | | |
|---|---|---|---|---|---|---|---|---|
| Family/matrix | Further Information | Opt. | Position | Str. | Core sim. | Matrix sim. | Sequence (red: ci-value >60 capitals: core sequence) | SEQ ID NO |
| | binds DRE (downstream regulatory element) sites as a tetramer | | | | | | | |
| V$E4FF/E4F.01 | GLI-Krueppel-related transcription factor, regulator of adenovirus E4 promoter | 0.82 | 345-357 | (−) | 0.789 | 0.824 | atgAGGTcaaggt | 178 |
| V$HOXF/BARX2.01 | Barx2, homeobox transcription factor that preferentially binds to paired TAAT motifs | 0.95 | 347-363 | (−) | 1.000 | 0.980 | gcgtTAATgaggtcaag | 179 |
| V$MYBL/VMYB.04 | v-Myb, AMV v-myb | 0.85 | 356-368 | (+) | 1.000 | 0.881 | attAACGctggtc | 180 |
| V$HOXF/CRX.01 | Cone-rod (C) homeobox-containing transcription factor/otx-like homeobox gene | 0.94 | 366-382 | (+) | 1.000 | 0.962 | gtctTAATcaccaagcc | 181 |
| V$RCAT/CLTR_CAAT.01 | Mammalian C-type LTR CCAAT box | 0.71 | 375-399 | (+) | 1.000 | 0.718 | aCCAAgccaagctccttaaactgct | 182 |
| V$ETSF/ETS1.01 | c-Ets-1 binding site | 0.92 | 409-425 | (−) | 1.000 | 0.921 | actaggaGGAAgcctag | 183 |
| V$SF1F/FTF.01 | Alpha (1)-fetoprotein transcription factor (FTF), liver receptor homologue-1 (LRH-1) | 0.94 | 426-438 | (−) | 1.000 | 0.940 | gggcCAAGgtgac | 184 |
| V$BCL6/BCL6.02 | POZ/zinc finger protein, transcriptional repressor, translocations observed in diffuse large cell lymphoma | 0.77 | 436-452 | (+) | 1.000 | 0.785 | cccctctTAGAagccaa | 185 |
| V$HOXF/GSH2.01 | Homeodomain transcription factor Gsh-2 | 0.95 | 443-459 | (−) | 1.000 | 1.000 | ggccTAATtggcttcta | 186 |
| V$CAAT/CAAT.01 | Cellular and viral CCAAT box | 0.90 | 445-459 | (+) | 1.000 | 0.949 | gaagCCAAttaggcc | 187 |
| V$NKXH/NKX25.02 | Homeo domain factor Nkx-2.5/Csx, tinman homolog low affinity sites | 0.88 | 446-460 | (−) | 1.000 | 0.938 | gggccTAATtggctt | 188 |
| V$HOMF/S8.01 | Binding site for S8 type homeodomains | 0.97 | 448-460 | (−) | 1.000 | 0.999 | gggccTAATtggc | 189 |

TABLE 13-continued

| Putative Rhodopsin Transcription Regulatory Factors | | | | | | | | |
|---|---|---|---|---|---|---|---|---|
| Family/matrix | Further Information | Opt. | Position | Str. | Core sim. | Matrix sim. | Sequence (red: ci-value >60 capitals: core sequence) | SEQ ID NO |
| V$HOXF/CRX.01 | Cone-rod (D) homeobox-containing transcription factor/otx-like homeobox gene | 0.94 | 470-486 | (-) | 1.000 | 0.985 | atatTAATccccgctgc | 190 |
| V$MZF1/MZF1.01 | Myeloid zinc finger protein MZF1 | 0.99 | 473-481 | (+) | 1.000 | 0.991 | gcGGGGatt | 191 |
| V$OCTB/TST1.01 | POU-factor Tst-1/Oct-6 | 0.90 | 475-487 | (+) | 1.000 | 0.947 | ggggATTAatatg | 192 |
| V$CART/CART1.01 | Cart-1 (cartilage homeoprotein 1) | 0.86 | 477-493 | (-) | 1.000 | 0.926 | caTAATcatattaatcc | 193 |
| V$CART/CART1.01 | Cart-1 (cartilage homeoprotein 1) | 0.86 | 479-495 | (+) | 1.000 | 0.914 | atTAATatgattatgaa | 194 |
| V$SATB/SATB1.01 | Special AT-rich sequence-binding protein 1, predominantly expressed in thymocytes, binds to matrix attachment regions (MARs) | 0.94 | 479-493 | (+) | 1.000 | 0.957 | attAATAtgattatg | 195 |
| V$PDX1/PDX1.01 | Pdx1 (IDX1/IPF1) pancreatic and intestinal homeodomain TF | 0.74 | 480-500 | (+) | 0.826 | 0.775 | ttaatatgaTTATgaacaccc | 196 |
| V$GLIF/ZIC2.01 | Zinc finger transcription factor, Zic family member 2 (odd-paired homolog, *Drosophila*) | 0.89 | 491-505 | (+) | 1.000 | 0.932 | atgaacaCCCCcaat | 197 |
| V$CAAT/ACAAT.01 | Avian C-type LTR CCAAT box | 0.83 | 497-511 | (+) | 1.000 | 0.905 | acccCCAAtctccca | 198 |
| V$RREB/RREB1.01 | Ras-responsive element binding protein 1 | 0.80 | 499-513 | (+) | 1.000 | 0.841 | cCCCAatctcccaga | 199 |
| V$NRSF/NRSF.01 | Neuron-restrictive silencer factor | 0.69 | 500-520 | (-) | 1.000 | 0.696 | atcAGCAtctgggagattggg | 200 |
| V$IKRS/LYF1.01 | LyF-1 (Ikaros 1), enriched in B and T lymphocytes | 0.98 | 502-514 | (-) | 1.000 | 1.000 | atcTGGGagattg | 201 |
| V$AP4R/TAL1ALPHAE47.01 | Tal-1alpha/E47 heterodimer | 0.87 | 505-521 | (+) | 1.000 | 0.905 | tctcccCAGAtgctgatt | 202 |
| V$RP58/RP58.01 | Zinc finger protein RP58 (ZNF238), associated preferentially with heterochromatin | 0.84 | 507-519 | (-) | 1.000 | 0.865 | tcagCATCtggga | 203 |
| V$AP1R/NFE2.01 | NF-E2 p45 | 0.85 | 508-532 | (+) | 1.000 | 0.904 | cccagatgCTGAttcagccaggagc | 204 |

TABLE 13-continued

Putative Rhodopsin Transcription Regulatory Factors

| Family/matrix | Further Information | Opt. | Position | Str. | Core sim. | Matrix sim. | Sequence (red: ci-value >60 capitals: core sequence) | SEQ ID NO |
|---|---|---|---|---|---|---|---|---|
| V$AP1R/NFE2.01 | NF-E2 p45 | 0.85 | 508-532 | (-) | 1.000 | 0.882 | gctcctggCTGA atcagcatctggg | 205 |
| V$BEL1/BEL1.01 | Bel-1 similar region (defined in Lentivirus LTRs) | 0.81 | 510-532 | (-) | 1.000 | 0.818 | gctcctggctgaaT CAGcatctg | 206 |
| V$NRLF/NRL.01 | Neural retinal basic leucine zipper factor (bZIP) | 0.85 | 511-529 | (-) | 1.000 | 0.991 | cctggCTGAatc agcatct | 207 |
| V$AP1F/AP1.03 | Activator protein 1 | 0.94 | 515-525 | (+) | 0.885 | 0.970 | gcTGATtcagc | 208 |
| V$AP1F/AP1.03 | Activator protein 1 | 0.94 | 515-525 | (-) | 0.857 | 0.963 | gcTGAAtcagc | 209 |
| V$HOXF/PTX1.01 | Pituitary Homeobox 1 (Ptx1, Pitx-1) | 0.94 | 523-539 | (-) | 1.000 | 0.944 | ctcCTAAgctcc tggct | 210 |
| V$ZBPF/ZNF219.01 | Kruppel-like zinc finger protein 219 | 0.91 | 528-550 | (-) | 1.000 | 0.926 | gtgacctCCCCc tcctaagctcc | 211 |
| V$RXRF/VDR_RXR.01 | VDR/RXR Vitamin D receptor RXR heterodimer site | 0.85 | 531-555 | (+) | 1.000 | 0.889 | gcttaggaggggG AGGtcactttat | 212 |
| V$ZBPF/ZBP89.01 | Zinc finger transcription factor ZBP-89 | 0.93 | 531-553 | (-) | 1.000 | 0.958 | aaagtgacctCC CCctcctaagc | 213 |
| V$EKLF/KKLF.01 | Kidney-enriched kruppel-like factor, KLF15 | 0.91 | 534-550 | (+) | 1.000 | 0.913 | taggagGGGGa ggtcac | 214 |
| V$GLIF/ZIC2.01 | Zinc finger transcription factor, Zic family member 2 (odd-paired homolog, *Drosophila*) | 0.89 | 536-550 | (-) | 1.000 | 0.945 | gtgacctCCCCc tcc | 215 |
| V$RORA/TR2.01 | Nuclear hormone receptor TR2, half site | 0.92 | 538-556 | (+) | 1.000 | 0.950 | agggggaGGTC actttata | 216 |
| V$TBPF/TATA.01 | Cellular and viral TATA box elements | 0.90 | 543-559 | (-) | 1.000 | 0.915 | ccttaTAAAgtg acctc | 217 |
| V$SRFF/SRF.01 | Serum response factor | 0.66 | 545-563 | (-) | 1.000 | 0.722 | agaccctTATAa agtgacc | 218 |
| V$SRFF/SRF.01 | Serum response factor | 0.66 | 546-564 | (+) | 1.000 | 0.712 | gtcactttTATAa gggtctg | 219 |
| V$TBPF/LTATA.01 | Lentivirus LTR TATA box | 0.82 | 550-566 | (+) | 1.000 | 0.829 | cttTATAagggt ctggg | 220 |
| V$MOKF/MOK2.01 | Ribonucleoprotein associated zinc finger protein MOK-2 (mouse) | 0.74 | 552-572 | (-) | 1.000 | 0.772 | gacccccccagac CCTTataa | 221 |
| V$ZBPF/ZNF219.01 | Kruppel-like zinc finger protein 219 | 0.91 | 553-575 | (-) | 1.000 | 0.948 | tctgaccCCCCc agacccttata | 222 |

TABLE 13-continued

Putative Rhodopsin Transcription Regulatory Factors

| Family/matrix | Further Information | Opt. | Position | Str. | Core sim. | Matrix sim. | Sequence (red: ci-value >60 capitals: core sequence) | SEQ ID NO |
|---|---|---|---|---|---|---|---|---|
| V$GLIF/ZIC2.01 | Zinc finger transcription factor, Zic family member 2 (odd-paired homolog, *Drosophila*) | 0.89 | 560-574 | (-) | 1.000 | 0.967 | ctgacccCCCCa gac | 223 |
| V$MAZF/MAZR.01 | MYC-associated zinc finger protein related transcription factor | 0.88 | 561-573 | (+) | 1.000 | 0.919 | tctgggGGGGtca | 224 |
| V$ZNFP/SZF1.01 | SZF1, hematopoietic progenitor-restricted KRAB-zinc finger protein | 0.82 | 579-603 | (-) | 0.801 | 0.829 | tcaGGGCtccag ctggatgactctg | 225 |
| V$AP4R/AP4.01 | Activator protein 4 | 0.85 | 584-600UTR | (+) | 1.000 | 0.916 | tcatcCAGCtgg agccc | 226 |
| V$EBOX/ATF6.01 | Member of b-zip family, induced by ER damage/stress, binds to the ERSE in association with NF-Y | 0.93 | 596-610 | (-) | 1.000 | 0.970 | cagCCACtcag ggct | 227 |
| V$CAAT/CAAT.01 | Cellular and viral CCAAT box | 0.90 | 597-611 | (-) | 0.826 | 0.937 | tcagCCACtcag ggc | 228 |
| V$HEAT/HSF1.01 | Heat shock factor 1 | 0.84 | 621-645 | (-) | 1.000 | 0.857 | tgctcccacccaA GAAtgctgcgaa | 229 |
| V$OAZF/ROAZ.01 | Rat C2H2 Zn finger protein involved in olfactory neuronal differentiation | 0.73 | 625-641 | (+) | 0.750 | 0.779 | caGCATtcttgg gtggg | 230 |
| V$OAZF/ROAZ.01 | Rat C2H2 Zn finger protein involved in olfactory neuronal differentiation | 0.73 | 626-642nc | (-) | 0.750 | 0.744 | tcCCACccaag aatgct | 231 |
| V$EGRF/EGR2.01 | Egr-2/Krox-20 early growth response gene product | 0.79 | 631-647UTR | (+) | 0.766 | 0.828 | tcttGGGTggga gcagc | 232 |
| V$EGRF/WT1.01 | Wilms Tumor Suppressor | 0.92 | 633-649 | (+) | 1.000 | 0.930 | ttgggTGGGag cagcca | 233 |
| V$RBPF/RBPJK.01 | Mammalian transcriptional repressor RBP-Jkappa/CBF1 | 0.84 | 634-648UTR | (+) | 1.000 | 0.847 | tgggTGGGagc agcc | 234 |
| V$OAZF/ROAZ.01 | Rat C2H2 Zn finger protein involved in olfactory neuronal differentiation | 0.73 | 641-657 | (+) | 0.750 | 0.818 | gaGCAGccacg ggtcag | 235 |

TABLE 13-continued

Putative Rhodopsin Transcription Regulatory Factors

| Family/matrix | Further Information | Opt. | Position | Str. | Core sim. | Matrix sim. | Sequence (red: ci-value >60 capitals: core sequence) | SEQ ID NO |
|---|---|---|---|---|---|---|---|---|
| V$EBOX/USF.03 | Upstream stimulating factor | 0.89 | 643-657 | (-) | 1.000 | 0.904 | ctgaccCGTGg ctgc | 236 |
| V$EBOX/MYCMAX.03 | MYC-MAX binding sites | 0.91 | 644-658 | (+) | 0.842 | 0.919 | cagccaCGGGt cagc | 237 |
| V$PAX5/PAX5.03 | PAX5 paired domain protein | 0.80 | 659-687gen | (+) | 0.894 | 0.833 | cacaagggCCA Cagccatgaatgg cacag | 238 |
| V$CLOX/CDPCR3.01 | Cut-like homeodomain protein | 0.73 | 665-683gen | (+) | 1.000 | 0.735 | ggccacagccatg aATGGc | 239 |
| V$PAX5/PAX5.03 | PAX5 paired domain protein | 0.80 | 674-702gen | (+) | 1.000 | 0.800 | catgaatgGCAC agaagtcctgagcc cca | 240 |
| V$ZNFP/ZBRK1.01 | Transcription factor with 8 central zinc fingers and an N-terminal KRAB domain | 0.77 | 680-704 | (-) | 0.813 | 0.847 | catggggcTCA Ggacttctgtgcca | 241 |
| V$PBXC/PBX1_MEIS1.02 | Binding site for a Pbx1/Meis1 heterodimer | 0.77 | 699-715 | (-) | 0.750 | 0.860 | attcTGTTtgaca tggg | 242 |
| V$TALE/TGIF.01 | TG-interacting factor belonging to TALE class of homeodomain factors | 1.00 | 700-710nc | (+) | 1.000 | 1.000 | ccatGTCAaac | 243 |
| V$SNAP/PSE.02 | Proximal sequence element (PSE) of RNA polymerase III-transcribed genes | 0.73 | 745-763 | (+) | 1.000 | 0.734 | gtgccCCTAatc ctcaact | 244 |
| V$HOXF/CRX.01 | Cone-rod (E) homeobox-containing transcription factor/otx-like homeobox gene | 0.94 | 748-764 | (+) | 1.000 | 0.965 | ccccTAATcctc aacta | 245 |
| V$FAST/FAST1.01 | FAST-1 SMAD interacting protein | 0.81 | 749-763 | (-) | 0.983 | 0.829 | agttgagGATTa ggg | 246 |
| V$NR2F/HPF1.01 | HepG2-specific P450 2C factor-1 | 0.78 | 767-787 | (+) | 0.750 | 0.801 | ctaggcgcAAA Ttccaatcct | 247 |
| V$SORY/HMGIY.01 | HMGI(Y) high-mobility-group protein I (Y), architectural transcription factor organizing the framework of a nuclear protein-DNA transcriptional complex | 0.92 | 770-782 | (-) | 1.000 | 0.938 | tggAATTtgcgcc | 248 |
| V$HMTB/MTBF.01 | Muscle-specific Mt binding site | 0.90 | 774-782 | (-) | 1.000 | 0.953 | tggaATTTg | 249 |

TABLE 13-continued

Putative Rhodopsin Transcription Regulatory Factors

| Family/matrix | Further Information | Opt. | Position | Str. | Core sim. | Matrix sim. | Sequence (red: ci-value >60 capitals: core sequence) | SEQ ID NO |
|---|---|---|---|---|---|---|---|---|
| V$LEFF/LEF1.01 | TCF/LEF-1, involved in the Wnt signal transduction pathway | 0.86 | 783-799 | (−) | 1.000 | 0.889 | actagacCAAA gaggat | 250 |
| V$NRSE/NRSF.01 | Neural-restrictive-silencer-element | 0.67 | 794-814nc | (+) | 0.782 | 0.762 | tctagtacccCGG Gggcagcc | 251 |
| V$ZBPF/ZF9.01 | Core promoter-binding protein (CPBP) with 3 Krueppel-type zinc fingers | 0.87 | 803-825nc | (+) | 0.769 | 0.878 | ccgggggCAG Cccctctaacct | 252 |
| V$HICF/HIC1.01 | Hypermethylated in cancer 1, transcriptional repressor containing five Kruppel-like C2H2 zinc fingers, for optimal binding multiple binding sites are required. | 0.93 | 804-816 | (−) | 1.000 | 0.970 | ggggcTGCCcc cg | 253 |
| V$NFKB/NFKAPPAB50.01 | NF-kappaB (p50) | 0.83 | 806-818 | (−) | 0.750 | 0.865 | aggGGGCtgcc cc | 254 |
| V$STAF/ZNF76_143.01 | ZNF143 is the human ortholog of *Xenopus* Staf, ZNF76 is a DNA binding protein related to ZNF143 and Staf | 0.76 | 810-832 | (+) | 0.809 | 0.761 | cagcCCCCtcta accttgggcct | 255 |
| V$SF1F/SF1.01 | SF1 steroidogenic factor 1 | 0.95 | 819-831 | (−) | 1.000 | 0.966 | ggccCAAGgtt ag | 256 |
| V$RXRF/VDR_RXR.06 | Bipartite binding site of VDR/RXR heterodimers: 4 spacer nucleotides between the two directly repeated motifs | 0.75 | 825-849nc | (+) | 0.812 | 0.787 | ttgggcctcagcag cAGGGgaggcc | 257 |
| V$MYOD/MYF5.01 | Myf5 myogenic bHLH protein | 0.90 | 831-847nc | (+) | 1.000 | 0.903 | ctcagCAGCag gggagg | 258 |
| V$NRSF/NRSF.01 | Neuron-restrictive silencer factor | 0.69 | 831-851nc? | (+) | 1.000 | 0.705 | ctcAGCAgcag gggaggccac | 259 |
| V$ZBPF/ZF9.01 | Core promoter-binding protein (CPBP) with 3 Krueppel-type zinc fingers | 0.87 | 832-854 | (−) | 0.820 | 0.890 | ggggtggCCTC ccctgctgctga | 260 |
| V$ZBPF/ZF9.01 | Core promoter-binding protein (CPBP) with 3 Krueppel-type zinc fingers | 0.87 | 841-863nc | (+) | 0.923 | 0.937 | ggggaggCCA Cccctacaccttc | 261 |

TABLE 13-continued

Putative Rhodopsin Transcription Regulatory Factors

| Family/matrix | Further Information | Opt. | Position | Str. | Core sim. | Matrix sim. | Sequence (red: ci-value >60 capitals: core sequence) | SEQ ID NO |
|---|---|---|---|---|---|---|---|---|
| V$PLAG/PLAG1.01 | Pleomorphic adenoma gene (PLAG) 1, a developmentally regulated C2H2 zinc finger protein | 0.88 | 847-867 | (-) | 0.958 | 0.929 | GGGGgaaggtg taggggtggc | 262 |
| V$ZBPF/ZNF202.01 | Transcriptional repressor, binds to elements found predominantly in genes that participate in lipid metabolism | 0.73 | 859-881 | (+) | 1.000 | 0.776 | ccttccCCCAgc cacagccatcc | 263 |
| V$INSM/INSM1.01 | Zinc finger protein insulinoma-associated 1 (IA-1) functions as a transcriptional repressor | 0.90 | 860-872 | (-) | 1.000 | 0.965 | tggctGGGGga ag | 264 |
| V$MZF1/MZF1.02 | Myeloid zinc finger protein MZF1 | 0.99 | 860-868 | (-) | 1.000 | 0.994 | tgGGGGaag | 265 |
| V$HAML/AML3.01 | Runt-related transcription factor 2/CBFA1 (core-binding factor, runt domain, alpha subunit 1) | 0.84 | 863-877 | (-) | 1.000 | 0.845 | ggctGTGGctg gggg | 266 |
| V$NRF1/NRF1.01 | Nuclear respiratory factor 1 (NRF1), bZIP transcription factor that acts on nuclear genes encoding mitochondrial proteins | 0.78 | 889-905nc | (-) | 0.750 | 0.828 | tctGCACaggc gctgct | 267 |
| V$NRF1/NRF1.01 | Nuclear respiratory factor 1 (NRF1), bZIP transcription factor that acts on nuclear genes encoding mitochondrial proteins | 0.78 | 890-906nc | (+) | 1.000 | 0.801 | gcaGCGCctgt gcagaa | 268 |
| V$SORY/HBP1.01 | HMG box-containing protein 1 | 0.86 | 898-910nc | (+) | 1.000 | 0.862 | tgtgcagAATG aa | 269 |
| V$BRNF/BRN2.03 | Brn-2, POU-III protein class | 0.92 | 923-941 | (+) | 1.000 | 0.932 | ggctccttaATT Tttttt | 270 |
| V$NKXH/NKX25.02 | Homeo domain factor Nkx-2.5/Csx, tinman homolog low affinity sites | 0.88 | 925-939 | (+) | 1.000 | 0.956 | ctcctTAATtttttt | 271 |

TABLE 13-continued

Putative Rhodopsin Transcription Regulatory Factors

| Family/matrix | Further Information | Opt. | Position | Str. | Core sim. | Matrix sim. | Sequence (red: ci-value >60 capitals: core sequence) | SEQ ID NO |
|---|---|---|---|---|---|---|---|---|
| V$CDXF/CDX1.01 | Intestine specific homeodomain factor CDX-1 | 0.94 | 939-957 | (+) | 1.000 | 0.948 | ttttttTTTAaga aataa | 272 |
| V$HOXF/HOXB9.01 | Abd-B-like homeodomain protein Hoxb-9 | 0.88 | 940-956 | (−) | 1.000 | 0.888 | tatttctTAAAaa aaaa | 273 |
| V$CEBP/CEBPB.01 | CCAAT/enhancer binding protein beta | 0.94 | 943-957nc | (+) | 1.000 | 0.942 | ttttttaaGAAAt aa | 274 |
| V$HNF1/HNF1.01 | Hepatic nuclear factor 1 | 0.80 | 947-963 | (−) | 0.790 | 0.824 | cATTAattatttct taa | 275 |
| V$HOXF/BARX2.01 | Barx2, homeobox transcription factor that preferentially binds to paired TAAT motifs | 0.95 | 948-964 | (−) | 1.000 | 0.967 | tcatTAATtatttc tta | 276 |
| V$BRNF/BRN3.01 | Brn-3, POU-IV protein class | 0.78 | 949-967 | (−) | 1.000 | 0.990 | gcctcattaATT Atttctt | 277 |
| V$BRNF/BRN4.01 | POU domain transcription factor brain 4 | 0.89 | 949-967nc | (+) | 1.000 | 0.894 | aagaaataatTA ATgaggc | 278 |
| V$LHXF/LMX1B.01 | LIM-homeodomain transcription factor | 0.91 | 949-963nc | (+) | 1.000 | 0.962 | aagaaaTAATta atg | 279 |
| V$HOMF/S8.01 | Binding site for S8 type homeodomains | 0.97 | 950-962nc | (+) | 1.000 | 0.997 | agaaaTAATtaat | 280 |
| V$HOXF/GSH1.01 | Homeobox transcription factor Gsh-1 | 0.85 | 952-968nc | (+) | 1.000 | 0.863 | aaataatTAATg aggct | 281 |
| V$LHXF/LMX1B.01 | LIM-homeodomain transcription factor | 0.91 | 952-966 | (−) | 1.000 | 0.946 | cctcatTAATtat tt | 282 |
| V$RBIT/BRIGHT.01 | Bright, B cell regulator of IgH transcription | 0.92 | 952-964nc | (+) | 1.000 | 0.961 | aaataATTAatga | 283 |
| V$HOMF/S8.01 | Binding site for S8 type homeodomains | 0.97 | 953-965 | (−) | 1.000 | 0.992 | ctcatTAATtatt | 284 |
| V$LHXF/LHX3.01 | Homeodomain binding site in LIM/Homeodomain factor LHX3 | 0.81 | 953-967nc | (+) | 1.000 | 0.851 | aataaTTAAtga ggc | 285 |
| V$SORY/HBP1.01 | HMG box-containing protein 1 | 0.86 | 953-965nc | (+) | 1.000 | 0.876 | aataattAATGag | 286 |
| V$HOXF/BARX2.01 | Barx2, homeobox transcription factor that preferentially | 0.95 | 955-971nc | (+) | 1.000 | 0.987 | taatTAATgagg ctcct | 287 |

TABLE 13-continued

Putative Rhodopsin Transcription Regulatory Factors

| Family/matrix | Further Information | Opt. | Position | Str. | Core sim. | Matrix sim. | Sequence (red: ci-value >60 capitals: core sequence) | SEQ ID NO |
|---|---|---|---|---|---|---|---|---|
| | binds to paired TAAT motifs | | | | | | | |
| V$RXRF/VDR_RXR.02 | VDR/RXR Vitamin D receptor RXR heterodimer site | 0.86 | 960-984 | (-) | 1.000 | 0.871 | tcccaggtgagtG AGGagcctcatt | 288 |
| V$AP1F/AP1.03 | Activator protein 1 | 0.94 | 969-979 | (-) | 1.000 | 0.940 | ggTGAGtgagg | 289 |
| V$AREB/AREB6.01 | AREB6 (Atp1a1 regulatory element binding factor 6) | 0.93 | 972-984nc | (+) | 1.000 | 0.933 | cactcACCTgg ga | 290 |
| V$PAX6/PAX6.02 | PAX6 paired domain and homeodomain are required for binding to this site | 0.89 | 973-991 | (-) | 1.000 | 0.893 | caggctgtcCCA Ggtgagt | 291 |
| V$AP2F/AP2.01 | Activator protein 2 | 0.90 | 1033-1047 | (-) | 1.000 | 0.911 | ctgGCCTtggg gaac | 292 |
| V$EREF/ERR.01 | Estrogen related receptor | 0.87 | 1033-1051nc | (+) | 1.000 | 0.897 | gttccccAAGG ccagcggg | 293 |
| V$MZF1/MZF1.02 | Myeloid zinc finger protein MZF1 | 0.99 | 1033-1041 | (-) | 1.000 | 0.994 | ttGGGGaac | 294 |
| V$SF1F/SF1.01 | SF1 steroidogenic factor 1 | 0.95 | 1035-1047nc | (+) | 1.000 | 0.992 | tccccAAGgcc ag | 295 |
| V$TEAF/TEF.01 | Thyrotrophic embryonic factor | 0.88 | 1044-1060 | (-) | 0.968 | 0.894 | ggcacaCATCc cgctgg | 296 |
| V$SP1F/TIEG.01 | TGFbeta-inducible early gene (TIEG)/ Early growth response gene alpha (EGRalpha) | 0.83 | 1046-1060nc | (+) | 0.750 | 0.878 | agcGGGAtgtgt gcc | 297 |
| V$MAZF/MAZ.01 | Myc associated zinc finger protein (MAZ) | 0.90 | 1056-1068 | (-) | 1.000 | 0.909 | ggagGAGGgg cac | 298 |
| V$RXRF/VDR_RXR.03 | Bipartite binding site of VDR/RXR heterodimers without a spacer between directly repeated motifs | 0.74 | 1056-1080 | (-) | 0.823 | 0.750 | gatgAGTTggg aggaggaggggc ac | 299 |
| V$EVI1/MEL1.02 | MEL1 (MDS1/EVI1-like gene 1) DNA-binding domain 2 | 0.99 | 1071-1087 | (-) | 1.000 | 0.997 | cctgaaaGATG agttgg | 300 |
| V$HEAT/HSF1.01 | Heat shock factor 1 | 0.84 | 1073-1097 | (-) | 0.857 | 0.849 | tcctcgtgttccTG AAagatgagtt | 301 |
| V$MYT1/MYT1L.01 | Myelin transcription factor 1-like, neuronal C2HC | 0.92 | 1073-1085 | (-) | 0.818 | 0.927 | tgaaAGATgag tt | 302 |

TABLE 13-continued

| Putative Rhodopsin Transcription Regulatory Factors | | | | | | | | |
|---|---|---|---|---|---|---|---|---|
| Family/matrix | Further Information | Opt. | Position | Str. | Core sim. | Matrix sim. | Sequence (red: ci-value >60 capitals: core sequence) | SEQ ID NO |
| | zinc finger factor 1 | | | | | | | |
| V$STAT/STAT1.01 | Signal transducer and activator of transcription 1 | 0.77 | 1075-1093 | (−) | 0.767 | 0.774 | cgtgttcctGAA Agatgag | 303 |
| V$STAT/STAT.01 | Signal transducers and activators of transcription | 0.87 | 1077-1095 | (+) | 1.000 | 0.911 | catctttcaGGA Acacgag | 304 |
| V$EBOX/NMYC.01 | N-Myc | 0.92 | 1085-1099 | (−) | 1.000 | 0.923 | aatcctCGTGttc ct | 305 |
| V$HEAT/HSF2.02 | Heat shock factor 2 | 0.95 | 1089-1113 | (−) | 1.000 | 0.967 | ttccagaaagcaA GAAtcctcgtgt | 306 |
| V$HEAT/HSF1.01 | Heat shock factor 1 | 0.84 | 1097-1121 | (−) | 1.000 | 0.874 | ggacacttttccA GAAagcaagaat | 307 |
| V$STAT/STAT1.01 | Signal transducer and activator of transcription 1 | 0.77 | 1099-1117 | (−) | 0.767 | 0.798 | acttttccaGAA Agcaaga | 308 |
| V$STAT/STAT.01 | Signal transducers and activators of transcription | 0.87 | 1101-1119 | (+) | 1.000 | 0.895 | ttgctttctGGAA aagtgt | 309 |
| V$BCL6/BCL6.02 | POZ/zinc finger protein, transcriptional repressor, translocations observed in diffuse large cell lymphoma | 0.77 | 1102-1118 | (+) | 0.800 | 0.808 | tgctttcTGGAa aagtg | 310 |
| V$BNCF/BNC.01 | Basonuclin, cooperates with USF1 in rDNA PolI transcription) | 0.85 | 1107-1125 | (+) | 1.000 | 0.852 | tctggaaaagTG TCccagc | 311 |
| V$GATA/GATA2.01 | GATA-binding factor 2 | 0.92 | 1127-1139 | (+) | 1.000 | 0.938 | taggGATAagt gt | 312 |
| V$NKXH/NKX32.01 | Homeodomain protein NKX3.2 (BAPX1, NKX3B, Bagpipe homolog) | 0.96 | 1128-1142 | (+) | 1.000 | 0.962 | agggataAGTG tcta | 313 |
| V$PAX1/PAX1.01 | Pax1 paired domain protein, expressed in the developing vertebral column of mouse embryos | 0.62 | 1135-1153 | (−) | 0.750 | 0.696 | cCATTctgtgct agacact | 314 |
| V$SORY/HBP1.01 | HMG box-containing protein 1 | 0.86 | 1142-1154nc | (+) | 1.000 | 0.860 | agcacagAATG gg | 315 |
| V$NKXH/NKX25.02 | Homeo domain factor Nkx-2.5/Csx, tinman homolog low affinity sites | 0.88 | 1166-1180 | (+) | 1.000 | 0.898 | gtgctTAATaaa tgc | 316 |

TABLE 13-continued

Putative Rhodopsin Transcription Regulatory Factors

| Family/matrix | Further Information | Opt. | Position | Str. | Core sim. | Matrix sim. | Sequence (red: ci-value >60 capitals: core sequence) | SEQ ID NO |
|---|---|---|---|---|---|---|---|---|
| V$HOXF/HOXC13.01 | Homeodomain transcription factor HOXC13 | 0.91 | 1167-1183 | (+) | 1.000 | 0.944 | tgcttaaTAAAt gctgg | 317 |
| V$HOXC/HOX_PBX0.1 | HOX/PBX binding sites | 0.81 | 1178-1194 | (+) | 0.944 | 0.862 | tgctGGATggat gcagg | 318 |
| V$AIRE/AIRE.01 | Autoimmune regulator | 0.86 | 1184-1210 | (+) | 1.000 | 0.877 | atggatgcaggaa ggaaTGGAgga atg | 319 |
| V$ETSF/ELF2.01 | Ets - family member ELF-2 (NERF1a) | 0.90 | 1186-1202 | (+) | 1.000 | 0.933 | ggatgcaGGAA ggaatg | 320 |
| V$GKLF/GKLF.01 | Gut-enriched Krueppel-like factor | 0.86 | 1191-1203 | (+) | 0.779 | 0.864 | caggaaggaAT GG | 321 |
| V$SORY/HBP1.01 | HMG box-containing protein 1 | 0.86 | 1192-1204 | (+) | 1.000 | 0.904 | aggaaggAATG ga | 322 |
| V$TEAF/TEF1.01 | TEF-1 related muscle factor | 0.84 | 1192-1208 | (−) | 1.000 | 0.859 | ttcctcCATTcct tcct | 323 |
| V$ETSF/PU1.01 | Pu.1 (Pu120) Ets-like transcription factor identified in lymphoid B-cells | 0.89 | 1198-1214 | (+) | 1.000 | 0.899 | gaatggaGGAA tgaatg | 324 |
| V$SORY/HBPI.01 | HMG box-containing protein 1 | 0.86 | 1200-1212 | (+) | 1.000 | 0.916 | atggaggAATG aa | 325 |
| V$TEAF/TEF1.01 | TEF-1 related muscle factor | 0.84 | 1200-1216 | (−) | 1.000 | 0.884 | cccattCATTcct ccat | 326 |
| V$SORY/HBP1.01 | HMG box-containing protein 1 | 0.86 | 1204-1216 | (+) | 1.000 | 0.949 | aggaatgAATG gg | 327 |
| V$IRFF/IRF7.01 | Interferon regulatory factor 7 (IRF-7) | 0.86 | 1208-1226nc | (+) | 0.936 | 0.885 | atGAATgggaa ggtctaga | 328 |
| V$RBPF/RBPJK.02 | Mammalian transcriptional repressor RBP-Jkappa/CBF1 | 0.94 | 1209-1223nc | (+) | 1.000 | 0.942 | tgaaTGGGaag gtct | 329 |
| V$IKRS/IK1.01 | Ikaros 1, potential regulator of lymphocyte differentiation | 0.92 | 1210-1222nc | (+) | 1.000 | 0.925 | gaatGGGAagg tc | 330 |
| V$RORA/NBRE.01 | Monomers of the nur subfamily of nuclear receptors (nur77, nurr1, nor-1) | 0.89 | 1212-1230nc | (+) | 1.000 | 0.947 | atgggAAGGtct agagcat | 331 |
| V$ZFIA/ZID.01 | Zinc finger with interaction domain | 0.85 | 1225-1237 | (−) | 1.000 | 0.916 | agGCTCcatgctc | 332 |
| V$AIRE/AIRE.01 | Autoimmune regulator | 0.86 | 1238-1264 | (−) | 0.916 | 0.863 | atgtgggcgggtg agcaTGGCttct ag | 333 |

TABLE 13-continued

| Family/matrix | Further Information | Opt. | Position | Str. | Core sim. | Matrix sim. | Sequence (red: ci-value >60 capitals: core sequence) | SEQ ID NO |
|---|---|---|---|---|---|---|---|---|
| Putative Rhodopsin Transcription Regulatory Factors | | | | | | | | |
| V$EGRF/WT1.01 | Wilms Tumor Suppressor | 0.92 | 1246-1262 | (-) | 0.953 | 0.930 | gtgggCGGGtg agcatg | 334 |
| V$SP1F/SP1.01 | Stimulating protein 1, ubiquitous zinc finger transcription factor | 0.88 | 1250-1264 | (-) | 1.000 | 0.907 | atgtGGGCgggt gag | 335 |
| V$NKXH/HMX3.02 | Hmx3/Nkx5-1 homeo domain transcription factor | 0.92 | 1258-1272 | (-) | 1.000 | 0.933 | ttaaTTAAatgtg gg | 336 |
| V$CREB/E4BP4.01 | E4BP4, bZIP domain, transcriptional repressor | 0.80 | 1259-1279 | (+) | 0.758 | 0.801 | ccacatttaaTTA Acagctga | 337 |
| V$BRNF/BRN3.02 | Brn-3, POU-IV protein class | 0.89 | 1260-1278 | (-) | 1.000 | 0.940 | cagctgtTAATt aaatgtg | 338 |
| V$LHXF/LHX3.01 | Homeodomain binding site in LIM/Homeodomain factor LHX3 | 0.81 | 1260-1274 | (+) | 1.000 | 0.944 | cacatTTAAtta aca | 339 |
| V$OCT1/OCT1.05 | Octamer-binding factor 1 | 0.89 | 1260-1274 | (+) | 0.900 | 0.942 | caCATTtaattaa ca | 340 |
| V$HOMF/S8.01 | Binding site for S8 type homeodomains | 0.97 | 1261-1273 | (+) | 1.000 | 0.997 | acattTAATtaac | 341 |
| V$HOXF/PHOX2.01 | Phox2a (ARIX) and Phox2b | 0.87 | 1262-1278 | (+) | 1.000 | 0.877 | cattTAATtaac agctg | 342 |
| V$NKXH/NKX25.02 | Homeo domain factor Nkx-2.5/Csx, tinman homolog low affinity sites | 0.88 | 1262-1276 | (-) | 1.000 | 0.898 | gctgtTAATtaa atg | 343 |
| V$PBXC/PBX1_MEIS1.02 | Binding site for a Pbx1/Meis1 heterodimer | 0.77 | 1262-1278 | (+) | 0.750 | 0.781 | cattTAATtaac agctg | 344 |
| V$RBIT/BRIGHT.01 | Bright, B cell regulator of IgH transcription | 0.92 | 1262-1274 | (-) | 1.000 | 0.967 | tgttaATTAaatg | 345 |
| V$FAST/FAST1.01 | FAST-1 SMAD interacting protein | 0.81 | 1263-1277 | (-) | 0.850 | 0.845 | agctgttAATTa aat | 346 |
| V$LHXF/LHX3.01 | Homeodomain binding site in LIM/Homeodomain factor LHX3 | 0.81 | 1263-1277 | (-) | 1.000 | 0.870 | agctgTTAAtta aat | 347 |
| V$RBIT/BRIGHT.01 | Bright, B cell regulator of IgH transcription | 0.92 | 1263-1275 | (+) | 1.000 | 0.941 | atttaATTAacag | 348 |
| V$ZNFP/SZF1.01 | SZF1, hematopoietic progenitor-restricted KRAB-zinc finger protein | 0.82 | 1263-1287 | (-) | 0.875 | 0.866 | tcaGGGActca gctgttaattaaat | 349 |

TABLE 13-continued

| Putative Rhodopsin Transcription Regulatory Factors | | | | | | | | |
|---|---|---|---|---|---|---|---|---|
| Family/matrix | Further Information | Opt. | Position | Str. | Core sim. | Matrix sim. | Sequence (red: ci-value >60 capitals: core sequence) | SEQ ID NO |
| V$ATBF/ATBF1.01 | AT-binding transcription factor 1 | 0.79 | 1264-1280 | (-) | 1.000 | 0.812 | ctcagctgttAAT Taaa | 350 |
| V$HOMF/S8.01 | Binding site for S8 type homeodomains | 0.97 | 1264-1276 | (-) | 1.000 | 0.997 | gctgtTAATtaaa | 351 |
| V$HEN1/HEN1.02 | HEN1 | 0.81 | 1265-1285 | (-) | 1.000 | 0.845 | agggactcaGCT Gttaattaa | 352 |
| V$NKXH/HMX3.02 | Hmx3/Nkx5-1 homeodomain transcription factor | 0.92 | 1265-1279 | (+) | 1.000 | 0.927 | ttaaTTAAcagc tga | 353 |
| V$AP4R/AP4.02 | Activator protein 4 | 0.92 | 1267-1283 | (-) | 1.000 | 0.950 | ggactcAGCTgt taatt | 354 |
| V$AP1R/NFE2.01 | NF-E2 p45 | 0.85 | 1268-1292 | (+) | 1.000 | 0.865 | attaacagCTGA gtccctgatgtca | 355 |
| V$BEL1/BEL1.01 | Bel-1 similar region (defined in Lentivirus LTRs) | 0.81 | 1270-1292- | (-) | 1.000 | 0.842 | tgacatcagggac TCAGctgtta | 356 |
| V$CREB/CREBP1.01 | cAMP-responsive element binding protein 1 | 0.85 | 1278-1298 | (-) | 1.000 | 0.851 | taaggaTGACat cagggactc | 357 |
| V$CREB/ATF2.01 | Activating transcription factor 2 | 0.87 | 1279-1299 | (+) | 0.814 | 0.871 | agtcccTGATgt catccttac | 358 |
| V$E4FF/E4F.01 | GLI-Krueppel-related transcription factor, regulator of adenovirus E4 promoter | 0.82 | 1284-1296 | (+) | 0.842 | 0.824 | ctgATGTcatcct | 359 |
| V$HOXF/PTX1.01 | Pituitary Homeobox 1 (Ptx1, Pitx-1) | 0.94 | 1299-1315 | (-) | 1.000 | 0.949 | tttCTAAgctctt cgag | 360 |
| V$TBPF/ATATA.01 | Avian C-type LTR TATA box | 0.78 | 1302-1318 | (-) | 1.000 | 0.781 | ttgtttcTAAGct cttc | 361 |
| V$XBBF/RFX1.01 | X-box binding protein RFX1 | 0.89 | 1302-1320 | (+) | 0.881 | 0.890 | gaagagcttaGA AAcaaag | 362 |
| V$LEFF/LEF1.01 | TCF/LEF-1, involved in the Wnt signal transduction pathway | 0.86 | 1309-1325nc | (+) | 1.000 | 0.884 | ttagaaaCAAA gagtgg | 363 |
| V$RBPF/RBPJK.02 | Mammalian transcriptional repressor RBP-Jkappa/CBF1 | 0.94 | 1319-1333 nc | (+) | 1.000 | 0.977 | agagTGGGaaa tgct | 364 |
| V$CP2F/CP2.01 | CP2 | 0.90 | 1331-1349 | (-) | 1.000 | 0.932 | agCTGGgtaaa gctagagc | 365 |
| V$SRFF/SRF.02 | Serum response factor | 0.84 | 1362-1380 | (+) | 0.888 | 0.842 | taaggCAAAttg ggccatt | 366 |

TABLE 13-continued

| Putative Rhodopsin Transcription Regulatory Factors | | | | | | | | |
|---|---|---|---|---|---|---|---|---|
| Family/matrix | Further Information | Opt. | Position | Str. | Core sim. | Matrix sim. | Sequence (red: ci-value >60 capitals: core sequence) | SEQ ID NO |
| V$CART/XVENT2.01 | *Xenopus* homeodomain factor Xvent-2; early BMP signaling response | 0.82 | 1366-1382 | (+) | 0.750 | 0.882 | gcAAATtgggc cattaa | 367 |
| V$CART/XVENT2.01 | *Xenopus* homeodomain factor Xvent-2; early BMP signaling response | 0.82 | 1367-1383 | (−) | 1.000 | 0.835 | ttTAATggccca atttg | 368 |
| V$PDX1/ISL1.01 | Pancreatic and intestinal lim-homeodomain factor | 0.82 | 1370-1390 | (−) | 1.000 | 0.875 | ctgagctttTAAT ggcccaat | 369 |
| V$NKXH/HMX3.02 | Hmx3/Nkx5-1 homeodomain transcription factor | 0.92 | 1372-1386 | (−) | 1.000 | 0.946 | gcttTTAAtggc cca | 370 |
| V$HOXF/HOXC13.01 | Homeodomain transcription factor HOXC13 | 0.91 | 1373-1389 | (+) | 1.000 | 0.932 | gggccatTAAA agctca | 371 |
| V$NKXH/HMX3.02 | Hmx3/Nkx5-1 homeodomain transcription factor | 0.92 | 1375-1389 | (+) | 1.000 | 0.953 | gccaTTAAaag ctca | 372 |
| V$MYBL/VMYB.05 | v-Myb, variant of AMV v-myb | 0.90 | 1404-1416 | (+) | 1.000 | 0.990 | attAACGgtggtg | 373 |
| V$AHRR/AHRARNT.02 | Aryl hydrocarbon/ Arnt heterodimers, fixed core | 0.77 | 1423-1447 | (−) | 0.750 | 0.781 | cctgtggataGA GTgtgaaagcaac | 374 |
| V$EVI1/IEVI1.06 | Ecotropic viral integration site 1 encoded factor, amino-terminal zinc finger domain | 0.83 | 1440-1456 | (+) | 0.750 | 0.835 | tccacaGGATa gattga | 375 |
| V$HOXC/HOX_PBX.01 | HOX/PBX binding sites | 0.81 | 1442-1458 | (+) | 0.944 | 0.814 | cacaGGATaga ttgaaa | 376 |
| V$HOXC/PBX1.01 | Homeo domain factor Pbx-1 | 0.78 | 1446-1462 | (+) | 1.000 | 0.809 | ggataGATTga aactgc | 377 |
| V$IRFF/ISRE.01 | Interferon-stimulated response element | 0.81 | 1447-1465 | (+) | 1.000 | 0.829 | gatagattGAAA ctgccag | 378 |
| V$HOXH/MEIS1B_HOXA9.01 | Meis1b and Hoxa9 form heterodimeric binding complexes on target DNA | 0.78 | 1450-1464 | (−) | 0.750 | 0.781 | TGGCagtttcaat ct | 379 |
| V$NR2F/ARP1.01 | Apolipoprotein AI regulatory protein 1, NR2F2 | 0.82 | 1469-1489 | (−) | 0.857 | 0.897 | ccagggtcaggG ATCaggtgg | 380 |
| V$MEF3/MEF3.01 | MEF3 binding site, present in | 0.89 | 1474-1486 | (−) | 1.000 | 0.943 | gggTCAGggat ca | 381 |

TABLE 13-continued

| Putative Rhodopsin Transcription Regulatory Factors | | | | | | | | |
|---|---|---|---|---|---|---|---|---|
| Family/matrix | Further Information | Opt. | Position | Str. | Core sim. | Matrix sim. | Sequence (red: ci-value >60 capitals: core sequence) | SEQ ID NO |
| | skeletal muscle-specific transcriptional enhancers | | | | | | | |
| V$RORA/TR4.01 | Nuclear hormone receptor TR4 homodimer binding site | 0.84 | 1474-1492 | (-) | 1.000 | 0.841 | atcccagGGTC agggatca | 382 |
| V$CSEN/DREAM.01 | Downstream regulatory element-antagonist modulator, Ca2+-binding protein of the neuronal calcium sensors family that binds DRE (downstream regulatory element) sites as a tetramer | 0.95 | 1476-1486 | (-) | 1.000 | 0.974 | ggGTCAgggat | 383 |
| V$CP2F/CP2.01 | CP2 | 0.90 | 1493-1511 | (+) | 1.000 | 0.969 | ggCTGGattga gcaatgag | 384 |
| V$HOXC/PBX1.01 | Homeo domain factor Pbx-1 | 0.78 | 1493-1509 | (+) | 1.000 | 0.811 | ggctgGATTga gcaatg | 385 |
| V$CEBP/CEBPB.01 | CCAAT/enhancer binding protein beta | 0.94 | 1496-1510 | (+) | 1.000 | 0.984 | tggattgaGCAA tga | 386 |
| V$CAAT/NFY.03 | Nuclear factor Y (Y-box binding factor) | 0.81 | 1513-1527 | (+) | 1.000 | 0.873 | agagCCAAgca gcac | 387 |
| V$STAF/ZNF76_143.01 | ZNF143 is the human ortholog of *Xenopus* Staf, ZNF76 is a DNA binding protein related to ZNF143 and Staf | 0.76 | 1522-1544 | (-) | 1.000 | 0.765 | tagcCCCAggg gactctgtgctg | 388 |
| V$NOLF/OLF1.01 | Olfactory neuron-specific factor | 0.82 | 1526-1548 | (+) | 1.000 | 0.879 | acagagTCCCct ggggctagagg | 389 |
| V$AP2F/AP2.02 | Activator protein 2 alpha | 0.92 | 1531-1545 | (-) | 0.905 | 0.941 | ctaGCCCcagg ggac | 390 |
| V$ZBPF/ZNF202.01 | Transcriptional repressor, binds to elements found predominantly in genes that participate in lipid metabolism | 0.73 | 1536-1558 | (-) | 0.761 | 0.739 | gcctccTCCAcc tctagccccag | 391 |
| V$IKRS/IK1.01 | Ikaros 1, potential regulator of lymphocyte differentiation | 0.92 | 1561-1573 | (+) | 1.000 | 0.933 | tcctGGGAatggg | 392 |
| V$TEAF/TEF1.01 | TEF-1 related muscle factor | 0.84 | 1561-1577 | (-) | 1.000 | 0.855 | ttttccCATTccc agga | 393 |

TABLE 13-continued

Putative Rhodopsin Transcription Regulatory Factors

| Family/matrix | Further Information | Opt. | Position | Str. | Core sim. | Matrix sim. | Sequence (red: ci-value >60 capitals: core sequence) | SEQ ID NO |
|---|---|---|---|---|---|---|---|---|
| V$IRFF/IRF7.01 | Interferon regulatory factor 7 (IRF-7) | 0.86 | 1565-1583nc | (+) | 0.936 | 0.895 | ggGAATggga aaaacccca | 394 |
| V$LTUP/TAACC.01 | Lentiviral TATA upstream element | 0.71 | 1565-1587nc | (+) | 1.000 | 0.721 | gggaatgggaaa AACCccaactt | 395 |
| V$RBPF/RBPJK.02 | Mammalian transcriptional repressor RBP-Jkappa/CBF1 | 0.94 | 1566-1580nc | (+) | 1.000 | 0.947 | ggaaTGGGaaa aacc | 396 |
| V$IKRS/IK1.01 | Ikaros 1, potential regulator of lymphocyte differentiation | 0.92 | 1567-1579nc | (+) | 1.000 | 0.927 | gaatGGGAaaa ac | 397 |
| V$NFKB/CREL.01 | c-Rel | 0.91 | 1571-1583 | (−) | 1.000 | 0.971 | tggggtttTTCCc | 398 |
| V$CIZF/NMP4.01 | NMP4 (nuclear matrix protein 4)/ CIZ (Cas-interacting zinc finger protein) | 0.97 | 1572-1582nc | (+) | 1.000 | 0.986 | ggAAAAacccc | 399 |
| V$SRFF/SRF.02 | Serum response factor | 0.84 | 1576-1594 | (−) | 0.888 | 0.881 | gacccCAAAgt tggggttt | 400 |
| V$MYT1/MYT1.02 | MyT1 zinc finger transcription factor involved in primary neurogenesis | 0.88 | 1578-1590 | (−) | 1.000 | 0.882 | ccaAAGTtggg gt | 401 |

Cartharius K, et al. (2005) Bioinformatics 21, 2933-42.

Example 4

Utilising the data from Examples 2 and 3, a suite of constructs are generated containing various shRNA suppressors and/or replacement rhodopsin nucleic acids enhanced with additional promoter sequences, known to be conserved between vertebrate species and various sequences known to enhance expression at RNA and/or protein levels. FIGS. 9 and 16 represents diagrammatically sequences cloned in suppression and/or replacement constructs. Notably, any combination of the elements and conserved regions outlined and indeed other elements that can modulate gene expression could be used in the invention to control expression of suppression and/or replacement components.

Suppression and/or replacement constructs (FIG. 9) were then used to generate recombinant AAV2/5 viruses using the procedures provided in Example 1. AAV2/5 suppression and/or replacement vectors were evaluated in 129 wild type (WT) mice for levels of expression of suppressors and/or replacement nucleic acids at the RNA and protein levels as detailed in Example 1. FIG. 10A illustrates a comparison using an RNAse protection assay of levels of human rhodopsin expression from the RHO-M transgene in RHO-M mice (lane M) versus the rhodopsin expression obtained from the suppression and replacement constructs in rAAV2/5 subretinally injected into wild type 129 mice (lanes B8, B9, B11, B12, B13, B16, B8). FIG. 10A illustrates that AAV-BB8, AAV-BB10, AAV-BB11, AAV-BB12, AAV-BB13 and AAV-BB16 express the human rhodopsin replacement gene in RNA extracted from 129 wild type mice subretinally injected with these suppression and or replacement constructs. AAV-BB8, AAV-BB10 and AAV-BB11 express human rhodopsin at lower levels than AAV-BB12, AAV-BB13 and AAV-BB16.

Further evaluation of suppression and replacement vectors was undertaken. FIG. 11 provides a comparative analysis of human rhodopsin expression from rAAV2/5 suppression and replacement vectors using real time RT-PCR. FIG. 11 illustrates replacement rhodopsin expression levels in RNA extracted from 129 wild type mice subretinally injected with suppression and/or replacement constructs. Expression levels were also determined in Rho-M transgenic mice which express a rhodopsin replacement construct termed rCC and display normal retinal function. Suppression and replacement vectors AAV-BB12, AAV-BB13, AAV-BB16 and AAV-BB18 express approximately in the same order of magnitude as levels of replacement rhodopsin transcript in Rho-M mice, indicating that enhanced replacement constructs with enhancer elements and conserved regions may express sufficient levels of rhodopsin to sustain a functional retina in vivo.

FIG. 12 illustrates retinal histology of adult wild type mouse retinas subretinally injected with 2 ul of $2\times10^{12}$ particle/ml of different suppression and replacement rhodopsin AAV vectors (see FIG. 9). Two weeks post-injection of AAV vectors transduced eyes were removed, fixed in 4% paraformaldehyde and cryosectioned (12 um). Subsequently, sections were stained with human specific anti-RHO antibody to visualise expression of replacement-RHO using Cy3 label (red) on the secondary antibody; cell nuclei were counterstained with DAPI (blue). A: AAV-BB8, B: AAV-BB13, C: AAV-BB24, D: AAV-Q8, E: AAV-Q26, F: retina from uninjected Rho-M transgenic mouse expressing RHO (positive control). Clear evidence of human rhodopsin expression from AAV suppression and replacement vectors was obtained. Sections indicate different levels of human RHO expression from the AAV suppression and replacement vectors under evaluation. OS: photoreceptor outer segments; IS: photoreceptor inner segments; ONL: outer nuclear layer; INL: inner nuclear layer; GCL: ganglion cell layer.

To explore efficacy of the suppression component of the suppression and replacement approach delivered using AAV, a variety of suppression only vectors were generated with an EGFP reporter gene (see FIG. 9). Adult NHR transgenic mice on a rho−/− background, therefore expressing normal human RHO but not mouse rho, were transduced by subretinal injection of 2 ul of $2\times10^{12}$ particle/ml of AAV-shQ1-EGFP (A) or AAV-shNT-EGFP (B). Two weeks after injection, eyes were removed, fixed in 4% paraformaldehyde and cryosectioned (FIG. 13). AAV-shQ1-EGFP expresses shRNA-Q1, which targets RHO, while AAV-shNT-EGFP expresses a non-targeting shRNA (see FIG. 9 for constructs). Both constructs express EGFP allowing tracking of the transduced cell populations (green). Sections were counterstained with DAPI (blue) to label the position of the nuclear layers. A significant reduction in the photoreceptor cell number in the transduced part of the outer nuclear layer was apparent in the AAV-shQ1-EGFP injected (A) retinas compared to those of injected with AAV-shNT-EGFP (B) (FIG. 13). IS: photoreceptor inner segments; ONL: outer nuclear layer; INL: inner nuclear layer; GCL: ganglion cell layer.

Adult RHO-347 transgenic mice carrying a dominant RHO mutation causing retinal degeneration akin to human RP, were subretinally injected with 2 ul of $2\times10^{12}$ particle/ml of AAV-shNT (A) or AAV-shQ1 (B) vectors (FIG. 14A). Two weeks post-injection transduced eyes were removed, fixed in 4% paraformaldehyde and cryosectioned (12 um). AAV-shQ1 expresses shRNA-Q1, which targets RHO, while AAV-shNT expresses a non-targeting shRNA. Both constructs express EGFP allowing tracking of the transduced part of the retina (green). Sections were counterstained with DAPI (blue) to indicate positions of the nuclear layers. A significant reduction of the photoreceptor cell numbers in the transduced part of the outer nuclear layer in the AAV-shNT injected or the uninjected (C) retinas was apparent due to the degenerative effects of RHO-347 transgene (FIG. 14A). A significantly preserved outer nuclear layer is detected in the AAV-shQ1 transduced retinas, where shRNA-Q1 effectively suppresses the RHO-347 transcript therefore reducing retinal degeneration (FIG. 14A). Note that the mouse rhodopsin gene (expressed in these retinas) was refractory to suppression by shRNA-Q1 due to the presence of nucleotide changes at the target site for Q1 siRNA-based suppression. Suppression of human rhodopsin and replacement using the degeneracy of the genetic code provided therapeutic benefit at a histological level in RHO-347 mice.

In addition, FIG. 14D provides evidence of an improvement in the electroretinogram (ERG) in RHO-347 eyes treated with AAV-shQ1-EGFP versus eyes treated with AAV-shNT-EGFP. In FIG. 14D a representative maximum ERG response of a RHO-347 mouse, containing a human rhodopsin transgene with a mutation at codon 347, subretinally injected with AAV2/5 constructs is presented. This RHO-347 mouse normally displays a phenotype similar to autosomal dominant RP. The top figure is the response of the right eye, which received an injection of AAV-shQ1-EGFP, a AAV2/5 vector containing suppressor siRNA Q1 driven by an H1 promoter (shQ1) and a CMV-driven EGFP gene. The left eye received an AAV-shNT-EGFP, a AAV2/5 containing a non-targeting (control) siRNA driven by an H1 promoter (shNT) and a CMV-driven EGFP gene. As can be seen above, the maximum response is significantly greater in the treated right eye than in the control left eye, indicating that suppression of the mutant rhodopsin transgene leads to some rescue at the ERG level.

Example 5

Sequences of Various Elements Designed to Enhance Expression of Replacement Constructs As described, enhancer elements, conserved regions A through I and/or transcription factor binding sites and/or other regulatory elements and/or epigenetic elements may be combined to improve expression of replacement constructs (see FIGS. 9 and 15 and Tables 1, 2, 9-13). These elements can be used in many different combinations to achieve optimum expression, as demonstrated in the Examples provided above. Additional examples include inter alia a construct comprising a human rhodopsin gene expressed from a composite promoter element containing the 484 by mouse rhodopsin promoter together with the CMV enhancer, the rhodopsin promoter enhancer element, the rhodopsin promoter conserved region B and flanked at the 3' end of the gene by a woodchuck posttranscriptional regulatory element and a minimal poly A sequence. Another example is similar to the one above but instead of the CMV enhancer, it contains multiples of the CRX and/or NRL binding sites.

Example 6

Utilisation of Neuroprotective/Neurotrophic Factors in Conjunction with Suppression and Replacement As described above, there is evidence from the prior art that neurotrophic/neuroprotective factors can improve cell viability and or cell functioning, the sequences encoding a number of these factors are provided in FIG. 17. FIG. 18 provides suppression and replacement constructs containing genetic elements that are beneficial for neuronal cell survival. In the example, the suppression and replacement construct pAAV-BB18 (FIG. 9) has been combined with the gene encoding the neurotrophic factor GDNF, driven by a small UCOE (chromatin opening element. A Thrasher, Abstract 36, British Society for Gene Therapy $5^{th}$ Annual Conference 2008) promoter. Notably other neurotrophic factors and or genes encoding neurotrophic factors such as, for example, Neurturin may also be used in combination with any of the suppression and replacement constructs described. In example A (FIG. 18), the additional element, in this case sequence encoding GDNF is co-located with the suppression and replacement construct within the two AAV inverted terminal repeat sequences, ITS1 and ITS2. In the second example, B (FIG. 18), the GDNF gene and its promoter are not co-located with the suppression and replacement elements within ITS1 and ITS2, but are located within the backbone of the plasmid used to generate AAV. Since a small proportion of the backbone is packaged during AAV production, this results in a mixed population of AAVs with the majority containing the suppression and replacement elements and a minority the GDNF elements.

AAV vectors generated to contain suppression, replacement and neurotrophic/neuroprotection components can be subretinally injected into wild type mice and or into mice with inherited retinal degenerations such as the RHO-347 and Pro23His mice described in the Examples above.

TABLE 14

| Enhancers |
|---|
| CMV Enhancer (SEQ ID NO: 402) |
| CCGCGTTACA TAACTTACGG TAAATGGCCC GCCTGGCTG A |
| CCGCCCAACG ACCCCCGCCC ATTGACGTCA ATAATGACGT ATGTTCCCAT |
| AGTAACGCCA ATAGGGACTT TCCATTGACG TCAATGGGTG GAGTATTTAC |
| GGTAAACTGC CCACTTGGCA GTACATCAAG TGTATCATAT GCCAAGTACG |
| CCCCCTATTG ACGTCAATGA CGGTAAATGG CCCGCCTGGC ATTATGCCCA |
| GTACATGACC TTATGGGACT TTCCTACTTG GCAGTACATC TACGTATTAG |
| TCATCGCTAT TACCATGGTG ATGCGGTTTT GGCAGTACAT CAATGGGCGT |
| GGATAGCGGT TTGACTCACG GGGATTTCCA AGTCTCCACC CCATTGACGT |
| CAATGGGAGT TTGTTTTGGC ACCAAAATCA ACGGGAC |
| Rhodopsin promoter conserved REGION A (SEQ ID NO: 403) |
| GAGTGTCTAATTGCTTATGATCATGCATGCTCTCTCTCCCACTAAACATTT |
| ATTAATGTGTTAGGATTTCCATTAGCGCGTGCCTTGAACTGAAATCATTT |
| GCATATGGCTGGGAAAAAGTGGGGTGAGGGAGGAAACAGTGCCAGCTCCC |
| CAACAGGCGTCAATCACAGTGACAGATCAGATGG |
| Rhodopsin Promoter Enhancer Element (contains Crx D(-) & CrxE (+) & NRL binding sites) (SEQ ID NO: 404 |
| TTTCTGCAGCGGGGATTAATATGATTATG |
| AACACCCCCAATCTCCCAGATGCTGATTCAGCCAGGAGGTACC |
| Crx D(-) (SEQ ID NO: 405) |
| GCGGGGATTAATAT |
| CrxE (+)(SEQ ID NO: 406) |
| TGAACACCCCCAATCTC |
| NRL (SEQ ID NO: 407) |
| TGCTGATTCAGC |
| Rhodopsin promoter conserved region B (SEQ ID NO: 408) |
| TCTGCTGACCCAGCAACACTCTTTCCTTCTGAGGCTTAAGAGCTATTAGCGTAGGTG |
| ACTCAGTCCCTAATCCTCC |
| Human rhodopsin polyA region F (SEQ ID NO: 409) |
| GACCTGCCTAGGACTCTGTGGCCGACTATAGGCGTCTCCCATCCCCTACACCTTCCCC |
| CAGCCACAGCCATCCCACCAGGAGCAGCGCCTGTGCAGAATGAACGAAGT |
| CACATAGGCTCCTTAATTTTTTTTTTTTTTTTAAGAAATAATTAATGAGG |
| CTCCTCACTC |
| Human rhodopsin polyA region G (SEQ ID NO: 410) |
| ACCTGGGACAGCCTGAGAAGGGACATCCACCAAGACCTAC |
| TGATCTGGAGTCCCACGTTCCCCAAGGCCAGCGGGATGTGTGCCCCTCCT |
| CCTCCCAACTCATCTTTCAGGAACACGAGGATTCTTGCTTTCTGGAAAAG |

TABLE 14-continued

| Enhancers |
|---|
| TGTCCCAGCTTAGGGATAAGTGTCTAGCACAGAATGGGGCACACAGTAGG |
| TGCTTAATAAATGCTGGATGGATGCAGGAAGGAATGGAGGAATGAATGGG |
| AAGGGAGAACATAGGATCC |
| SV40 Minimal polyA (SEQ ID NO: 411) |
| AATAAAGGAAATTTATTTTCATGCAATAGTGTGTTGGTTTTTTGTGTG |
| WPRE from pSK11 (SEQ ID NO: 412) |
| GGATCC AATCAACCTC |
| TGGATTACAA AATTTGTGAA AGATTGACTG GTATTCTTAA CTATGTTGCT |
| CCTTTTACGC TATGTGGATA CGCTGCTTTA ATGCCTTTGT ATCATGCTAT |
| TGCTTCCCGT ATGGCTTTCA TTTTCTCCTC CTTGTATAAA TCCTGGTTGC |
| TGTCTCTTTA TGAGGAGTTG TGGCCCGTTG TCAGGCAACG TGGCGTGGTG |
| TGCACTGTGT TTGCTGACGC AACCCCCACT GGTTGGGGCA TTGCCACCAC |
| CTGTCAGCTC CTTTCCGGGA CTTTCGCTTT CCCCCTCCCT ATTGCCACGG |
| CGGAACTCAT CGCCGCCTGC CTTGCCCGCT GCTGGACAGG GGCTCGGCTG |
| TTGGGCACTG ACAATTCCGT GGTGTTGTCG GGGAAGCTGA CGTCCTTTCC |
| ATGGCTGCTG GCCTGTGTTG CCACCTGGAT TCTGCGCGGG ACGTCCTTCT |
| GCTACGTCCC TTCGGCCCTC AATCCAGCGG ACCTTCCTTC CCGCGGCCTG |
| CTGCCGGCTC TGCGGCCTCT TCCGCGTCTT CGCCTTCGCC CTCAGACGAG |
| TCGGATCTCC CTTTGGGCCG CCTCCCC |
| WPRE from pSin11 (SEQ ID NO: 413) |
| GAGCAT CTTACCGCCA |
| TTTATTCCCA TATTTGTTCT GTTTTTCTTG ATTTGGGTAT ACATTTAAAT |
| GTTAATAAAA CAAAATGGTG GGGCAATCAT TTACATTTTT AGGGATATGT |
| AATTACTAGT TCAGGTGTAT TGCCACAAGA CAAACATGTT AAGAAACTTT |
| CCCGTTATTT ACGCTCTGTT CCTGTTAATC AACCTCTGGA TTACAAAATT |
| TGTGAAAGAT TGACTGATAT TCTTAACTAT GTTGCTCCTT TTACGCTGTG |
| TGGATATGCT GCTTTATAGC CTCTGTATCT AGCTATTGCT TCCCGTACGG |
| CTTTCGTTTT CTCCTCCTTG TATAAATCCT GGTTGCTGTC TCTTTTAGAG |
| GAGTTGTGGC CCGTTGTCCG TCAACGTGGC GTGGTGTGCT CTGTGTTTGC |
| TGACGCAACC CCCACTGGCT GGGGCATTGC CACCACCTGT CAACTCCTTT |
| CTGGGACTTT CGCTTTCCCC CTCCCGATCG CCACGGCAGA ACTCATCGCC |
| GCCTGCCTTG CCCGCTGCTG GACAGGGGCT AGGTTGCTGG GCACTGATAA |
| TTCCGTGGTG TTGTC |

INCORPORATION BY REFERENCE

The contents of all cited references (including literature references, patents, patent applications, and websites) that maybe cited throughout this application are hereby expressly incorporated by reference. The practice of the present invention will employ, unless otherwise indicated, conventional techniques of molecular biology, which are well known in the art.

EQUIVALENTS

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes that come within the meaning and range of equivalency of the claims are therefore intended to be embraced herein.

The invention claimed is:

1. An enhanced viral expression vector comprising (i) conserved region B from the rhodopsin gene having the nucleic acid sequence set forth in SEQ ID NO: 93, and optionally (ii) at least one of the conserved regions selected from conserved region C from the rhodopsin gene having the nucleic acid sequence set forth in SEQ ID NO: 94; conserved region F and G from the rhodopsin gene having the nucleic acid sequence set forth in SEQ ID NO: 97; and conserved region A from the rhodopsin gene having the nucleic acid sequence set forth in SEQ ID NO: 92.

2. The vector according to claim 1, wherein the vector additionally comprises:

(i) conserved region D from the rhodopsin gene having the nucleic acid sequence set forth in SEQ ID NO: 95; and/or (ii) at least one of conserved regions H and I from the rhodopsin gene having the nucleic acid sequence set forth in SEQ ID NOs: 98 and 99 respectively.

3. The vector according to claim 1, wherein the vector comprises at least one of each of conserved regions B, C, D, E, F and G, H, I and A, from the rhodopsin gene having the nucleic acid sequence set forth in SEQ ID NOs: 93, 94, 95, 96, 97, 98, 99 and 92.

4. The vector according to claim 1, wherein the viral vector is an AAV vector.

5. The vector according to claim 1, wherein the vector comprises at least one sequence selected from the group consisting of a stuffer, an insulator, a silencer, an intron sequence, a post translational regulatory element, a transcription factor binding site, and an enhancer.

6. The vector of claim 5, wherein said sequence(s) is:

(i) an enhancer selected from the group consisting of SEQ ID NOs: 87-89 and 91; or (ii) a sequence selected from the group consisting of SEQ ID NOs: 402-413.

7. The vector according to claim 5, wherein the vector comprises at least one transcription factor binding site sequence selected from the group consisting of SEQ ID NOs: 100-401.

8. The vector according to claim 1, wherein the vector comprises a chromatin opening element and/or a sequence encoding a neurotrophic or neuroprotective factor.

9. The vector according to claim 1, wherein the vector comprises at least one suppression agent and/or at least one replacement nucleic acid.

10. The vector according to claim 1, wherein the replacement nucleic acid encodes a rhodopsin gene.

11. The vector according to claim 1, wherein said vector comprises at least one suppression agent, wherein said suppression agent comprises:

(i) a nucleotide sequence selected from the group consisting of SEQ ID NOs: 75, 77, 79, 81, 83, 85, 414, 415, 416, 417, 418, 419, 420 and 421;

(ii) a nucleotide sequence selected from the group consisting of SEQ ID NOs: 1, 3, 5, 7, 9, 11, 13, 15, 17, 19, 21, 23, 25, 27, 29, 31, and 33; or (iii) a nucleotide sequence selected from the group consisting of SEQ ID NOs: 35-67.

12. The vector according to claim 1, wherein said vector comprises at least one replacement nucleic acid, wherein said replacement nucleic acid comprises:

(i) a nucleotide sequence selected from the group consisting of SEQ ID NOs: 2, 4, 6, 8, 10, 12, 14, 16, 18, 20, 22, 24, 26, 28, 30, 32, 34, and 68; or (ii) a nucleotide sequence selected from the group consisting of SEQ ID NOs: 76, 78, 80, 82, 84, and 86.

13. The vector according to claim 11, wherein said vector comprises at least one replacement nucleic acid, wherein said replacement nucleic acid comprises:

(i) a nucleotide sequence selected from the group consisting of SEQ ID NOs: 2, 4, 6, 8, 10, 12, 14, 16, 18, 20, 22, 24, 26, 28, 30, 32, 34, and 68; or (ii) a nucleotide sequence selected from the group consisting of SEQ ID NOs: 76, 78, 80, 82, 84, and 86.

14. A composition comprising at least one vector according to claim 1.

15. A cell comprising the vector of claim 1.

16. A method of suppressing the expression of a mutant gene and replacing expression of the mutant gene with a replacement nucleic acid, the method comprising the steps of administering to a mammal the composition of claim 13.

17. A kit comprising (i) the vector according to claim 11 and (ii) the vector according to claim 12.

18. The vector according to claim 1, wherein the vector comprises each of conserved regions B and C from the rhodopsin gene having the nucleic acid sequence set forth in SEQ ID NOs: 93 and 94.

19. The vector according to claim 1, wherein the vector comprises (i) at least one of each of conserved regions B, C, D, F and G from the rhodopsin gene having the nucleic acid sequence set forth in SEQ ID NOs: 93, 94, 95, and 97;

(ii) the nucleic acid sequence having the nucleic acid sequence set forth in SEQ ID NO: 411;

(iii) the enhancer having the nucleic acid sequence set forth in SEQ ID NO: 91; and (iv) replacement nucleic acid having the nucleic acid sequence set forth in SEQ ID NO: 76.

20. A kit comprising (i) the vector according to claim 19 and (ii) a vector comprising a suppression agent comprising a nucleotide sequence having the nucleic acid sequence set forth in SEQ ID NO: 75.

* * * * *

SEQUENCE LISTING

```
<160> NUMBER OF SEQ ID NOS: 432

<210> SEQ ID NO 1
<211> LENGTH: 21
<212> TYPE: DNA
<213> ORGANISM: Artificial Sequence
<220> FEATURE:
<223> OTHER INFORMATION: siRNA sequence targeting human rhodopsin

<400> SEQUENCE: 1

tacgtcaccg tccagcacaa g                                              21


<210> SEQ ID NO 2
<211> LENGTH: 20
<212> TYPE: DNA
<213> ORGANISM: Artificial Sequence
<220> FEATURE:
<223> OTHER INFORMATION: Replacement rhodopsin sequence

<400> SEQUENCE: 2

tatgtgacgg tgcaacataa                                                20


<210> SEQ ID NO 3
<211> LENGTH: 21
<212> TYPE: DNA
<213> ORGANISM: Artificial Sequence
<220> FEATURE:
<223> OTHER INFORMATION: siRNA sequence targeting human rhodopsin

<400> SEQUENCE: 3

ctcaactaca tcctgctcaa c                                              21


<210> SEQ ID NO 4
<211> LENGTH: 21
<212> TYPE: DNA
<213> ORGANISM: Artificial Sequence
<220> FEATURE:
<223> OTHER INFORMATION: Replacement rhodopsin sequence

<400> SEQUENCE: 4

ctgaattata ttttattgaa t                                              21


<210> SEQ ID NO 5
<211> LENGTH: 21
<212> TYPE: DNA
<213> ORGANISM: Artificial Sequence
<220> FEATURE:
<223> OTHER INFORMATION: siRNA sequence targeting human rhodopsin

<400> SEQUENCE: 5

cagctcgtct tcaccgtcaa g                                              21
```

<210> SEQ ID NO 6
<211> LENGTH: 21
<212> TYPE: DNA
<213> ORGANISM: Artificial Sequence
<220> FEATURE:
<223> OTHER INFORMATION: Replacement rhodopsin sequence

<400> SEQUENCE: 6
caattggtgt ttacggtgaa a 21

<210> SEQ ID NO 7
<211> LENGTH: 21
<212> TYPE: DNA
<213> ORGANISM: Artificial Sequence
<220> FEATURE:
<223> OTHER INFORMATION: siRNA sequence targeting human rhodopsin

<400> SEQUENCE: 7
atctatatca tgatgaacaa g 21

<210> SEQ ID NO 8
<211> LENGTH: 21
<212> TYPE: DNA
<213> ORGANISM: Artificial Sequence
<220> FEATURE:
<223> OTHER INFORMATION: Replacement rhodopsin sequence

<400> SEQUENCE: 8
atttacatta tgatgaataa a 21

<210> SEQ ID NO 9
<211> LENGTH: 21
<212> TYPE: DNA
<213> ORGANISM: Artificial Sequence
<220> FEATURE:
<223> OTHER INFORMATION: siRNA sequence targeting human rhodopsin

<400> SEQUENCE: 9
gcctacatgt ttctgctgat c 21

<210> SEQ ID NO 10
<211> LENGTH: 21
<212> TYPE: DNA
<213> ORGANISM: Artificial Sequence
<220> FEATURE:
<223> OTHER INFORMATION: Replacement rhodopsin sequence

<400> SEQUENCE: 10
gcttatatgt tcttattaat t 21

<210> SEQ ID NO 11
<211> LENGTH: 21
<212> TYPE: DNA
<213> ORGANISM: Artificial Sequence
<220> FEATURE:
<223> OTHER INFORMATION: siRNA sequence targeting human rhodopsin

<400> SEQUENCE: 11
tacatgtttc tgctgatcgt g 21

<210> SEQ ID NO 12
<211> LENGTH: 21
<212> TYPE: DNA
<213> ORGANISM: Artificial Sequence
<220> FEATURE:
<223> OTHER INFORMATION: Replacement rhodopsin sequence

<400> SEQUENCE: 12
tatatgttct tattaattgt c 21

<210> SEQ ID NO 13
<211> LENGTH: 21
<212> TYPE: DNA
<213> ORGANISM: Artificial Sequence
<220> FEATURE:
<223> OTHER INFORMATION: siRNA sequence targeting human rhodopsin

<400> SEQUENCE: 13
ctgcgcacgc ctctcaacta c 21

<210> SEQ ID NO 14
<211> LENGTH: 21
<212> TYPE: DNA
<213> ORGANISM: Artificial Sequence
<220> FEATURE:
<223> OTHER INFORMATION: Replacement rhodopsin sequence

<400> SEQUENCE: 14
ttacggaccc ccttgaatta t 21

<210> SEQ ID NO 15
<211> LENGTH: 21
<212> TYPE: DNA
<213> ORGANISM: Artificial Sequence
<220> FEATURE:
<223> OTHER INFORMATION: siRNA sequence targeting human rhodopsin

<400> SEQUENCE: 15
cgcacgcctc tcaactacat c 21

<210> SEQ ID NO 16
<211> LENGTH: 21
<212> TYPE: DNA
<213> ORGANISM: Artificial Sequence
<220> FEATURE:
<223> OTHER INFORMATION: Replacement rhodopsin sequence

<400> SEQUENCE: 16
cggaccccct tgaattatat t 21

<210> SEQ ID NO 17
<211> LENGTH: 21
<212> TYPE: DNA
<213> ORGANISM: Artificial Sequence
<220> FEATURE:
<223> OTHER INFORMATION: siRNA sequence targeting human rhodopsin

<400> SEQUENCE: 17
ctcaagccgg aggtcaacaa c 21

<210> SEQ ID NO 18
<211> LENGTH: 21
<212> TYPE: DNA
<213> ORGANISM: Artificial Sequence
<220> FEATURE:
<223> OTHER INFORMATION: Replacement rhodopsin sequence

<400> SEQUENCE: 18
ttgaaacccg aagtgaataa t 21

<210> SEQ ID NO 19
<211> LENGTH: 19

-continued

<212> TYPE: DNA
<213> ORGANISM: Artificial Sequence
<220> FEATURE:
<223> OTHER INFORMATION: siRNA sequence targeting human rhodopsin

<400> SEQUENCE: 19
cagctcgtct tcaccgtca 19

<210> SEQ ID NO 20
<211> LENGTH: 19
<212> TYPE: DNA
<213> ORGANISM: Artificial Sequence
<220> FEATURE:
<223> OTHER INFORMATION: Replacement rhodopsin sequence

<400> SEQUENCE: 20
caattggtgt ttacggtga 19

<210> SEQ ID NO 21
<211> LENGTH: 21
<212> TYPE: DNA
<213> ORGANISM: Artificial Sequence
<220> FEATURE:
<223> OTHER INFORMATION: siRNA sequence targeting human rhodopsin

<400> SEQUENCE: 21
tacgccagcg tggcattcta c 21

<210> SEQ ID NO 22
<211> LENGTH: 21
<212> TYPE: DNA
<213> ORGANISM: Artificial Sequence
<220> FEATURE:
<223> OTHER INFORMATION: Replacement rhodopsin sequence

<400> SEQUENCE: 22
tatgcttctg tcgcctttta c 21

<210> SEQ ID NO 23
<211> LENGTH: 19
<212> TYPE: DNA
<213> ORGANISM: Artificial Sequence
<220> FEATURE:
<223> OTHER INFORMATION: siRNA sequence targeting human rhodopsin

<400> SEQUENCE: 23
ccagcgttct ttgccaaga 19

<210> SEQ ID NO 24
<211> LENGTH: 19
<212> TYPE: DNA
<213> ORGANISM: Artificial Sequence
<220> FEATURE:
<223> OTHER INFORMATION: Replacement rhodopsin sequence

<400> SEQUENCE: 24
cccgcctttt tcgctaaaa 19

<210> SEQ ID NO 25
<211> LENGTH: 21
<212> TYPE: DNA
<213> ORGANISM: Artificial Sequence
<220> FEATURE:
<223> OTHER INFORMATION: siRNA sequence targeting human rhodopsin

<400> SEQUENCE: 25
gtcatctata tcatgatgaa c 21

<210> SEQ ID NO 26
<211> LENGTH: 21
<212> TYPE: DNA
<213> ORGANISM: Artificial Sequence
<220> FEATURE:
<223> OTHER INFORMATION: Replacement rhodopsin sequence

<400> SEQUENCE: 26
gtgatttaca ttatgatgaa t 21

<210> SEQ ID NO 27
<211> LENGTH: 21
<212> TYPE: DNA
<213> ORGANISM: Artificial Sequence
<220> FEATURE:
<223> OTHER INFORMATION: siRNA sequence targeting human rhodopsin

<400> SEQUENCE: 27
aactgcatgc tcaccaccat c 21

<210> SEQ ID NO 28
<211> LENGTH: 21
<212> TYPE: DNA
<213> ORGANISM: Artificial Sequence
<220> FEATURE:
<223> OTHER INFORMATION: Replacement rhodopsin sequence

<400> SEQUENCE: 28
aattgtatgt tgacgacgat t 21

<210> SEQ ID NO 29
<211> LENGTH: 19
<212> TYPE: DNA
<213> ORGANISM: Artificial Sequence
<220> FEATURE:
<223> OTHER INFORMATION: siRNA sequence targeting human rhodopsin

<400> SEQUENCE: 29
accatctgct gcggcaaga 19

<210> SEQ ID NO 30
<211> LENGTH: 19
<212> TYPE: DNA
<213> ORGANISM: Artificial Sequence
<220> FEATURE:
<223> OTHER INFORMATION: Replacement rhodopsin sequence

<400> SEQUENCE: 30
acgatttgtt gtgggaaaa 19

<210> SEQ ID NO 31
<211> LENGTH: 19
<212> TYPE: DNA
<213> ORGANISM: Artificial Sequence
<220> FEATURE:
<223> OTHER INFORMATION: siRNA sequence targeting human rhodopsin

<400> SEQUENCE: 31
gacgatgagg cctctgcta 19

<210> SEQ ID NO 32
<211> LENGTH: 19
<212> TYPE: DNA
<213> ORGANISM: Artificial Sequence
<220> FEATURE:
<223> OTHER INFORMATION: Replacement rhodopsin sequence

<400> SEQUENCE: 32
gaggacgaag ctagcgcca 19

<210> SEQ ID NO 33
<211> LENGTH: 20
<212> TYPE: DNA
<213> ORGANISM: Artificial Sequence
<220> FEATURE:
<223> OTHER INFORMATION: siRNA sequence targeting human rhodopsin

<400> SEQUENCE: 33
cacctctctg catggatact 20

<210> SEQ ID NO 34
<211> LENGTH: 20
<212> TYPE: DNA
<213> ORGANISM: Artificial Sequence
<220> FEATURE:
<223> OTHER INFORMATION: Replacement rhodopsin sequence

<400> SEQUENCE: 34
cacgagctta cacgggtatt 20

<210> SEQ ID NO 35
<211> LENGTH: 19
<212> TYPE: DNA
<213> ORGANISM: Artificial Sequence
<220> FEATURE:
<223> OTHER INFORMATION: siRNA sequence targeting 5' UTR

<400> SEQUENCE: 35
agctcaggcc ttcgcagca 19

<210> SEQ ID NO 36
<211> LENGTH: 19
<212> TYPE: DNA
<213> ORGANISM: Artificial Sequence
<220> FEATURE:
<223> OTHER INFORMATION: siRNA sequence targeting 5' UTR

<400> SEQUENCE: 36
caggccttcg cagcattct 19

<210> SEQ ID NO 37
<211> LENGTH: 19
<212> TYPE: DNA
<213> ORGANISM: Artificial Sequence
<220> FEATURE:
<223> OTHER INFORMATION: siRNA sequence targeting 3' UTR

<400> SEQUENCE: 37
tcactttctt ctcctataa 19

<210> SEQ ID NO 38
<211> LENGTH: 19
<212> TYPE: DNA
<213> ORGANISM: Artificial Sequence
<220> FEATURE:
<223> OTHER INFORMATION: siRNA sequence  targeting 3' UTR

<400> SEQUENCE: 38
tagttaatgt tgtgaataa 19

<210> SEQ ID NO 39
<211> LENGTH: 19

-continued

```
<212> TYPE: DNA
<213> ORGANISM: Artificial Sequence
<220> FEATURE:
<223> OTHER INFORMATION: siRNA sequence targeting 3' UTR

<400> SEQUENCE: 39

gctcctatgt tggtattaa                                              19


<210> SEQ ID NO 40
<211> LENGTH: 19
<212> TYPE: DNA
<213> ORGANISM: Artificial Sequence
<220> FEATURE:
<223> OTHER INFORMATION: siRNA sequence  targeting 3' UTR

<400> SEQUENCE: 40

agtcacatag gctccttaa                                              19


<210> SEQ ID NO 41
<211> LENGTH: 19
<212> TYPE: DNA
<213> ORGANISM: Artificial Sequence
<220> FEATURE:
<223> OTHER INFORMATION: siRNA sequence targeting 3' UTR

<400> SEQUENCE: 41

gattcttgct ttctggaaa                                              19


<210> SEQ ID NO 42
<211> LENGTH: 19
<212> TYPE: DNA
<213> ORGANISM: Artificial Sequence
<220> FEATURE:
<223> OTHER INFORMATION: siRNA sequence targeting 3' UTR

<400> SEQUENCE: 42

acagtaggtg cttaataaa                                              19


<210> SEQ ID NO 43
<211> LENGTH: 19
<212> TYPE: DNA
<213> ORGANISM: Artificial Sequence
<220> FEATURE:
<223> OTHER INFORMATION: siRNA sequence  targeting 3' UTR

<400> SEQUENCE: 43

gaacatatct atcctctca                                              19


<210> SEQ ID NO 44
<211> LENGTH: 19
<212> TYPE: DNA
<213> ORGANISM: Artificial Sequence
<220> FEATURE:
<223> OTHER INFORMATION: siRNA sequence targeting 3' UTR

<400> SEQUENCE: 44

ctgtacagat tctagttaa                                              19


<210> SEQ ID NO 45
<211> LENGTH: 19
<212> TYPE: DNA
<213> ORGANISM: Artificial Sequence
<220> FEATURE:
<223> OTHER INFORMATION: siRNA sequence targeting 3' UTR

<400> SEQUENCE: 45

tgtgaataac atcaattaa                                              19
```

<210> SEQ ID NO 46
<211> LENGTH: 19
<212> TYPE: DNA
<213> ORGANISM: Artificial Sequence
<220> FEATURE:
<223> OTHER INFORMATION: siRNA targeting 3' UTR

<400> SEQUENCE: 46
caattaatgt aactagtta 19

<210> SEQ ID NO 47
<211> LENGTH: 19
<212> TYPE: DNA
<213> ORGANISM: Artificial Sequence
<220> FEATURE:
<223> OTHER INFORMATION: siRNA sequence targeting 3' UTR

<400> SEQUENCE: 47
tgattatcac ctcctgata 19

<210> SEQ ID NO 48
<211> LENGTH: 19
<212> TYPE: DNA
<213> ORGANISM: Artificial Sequence
<220> FEATURE:
<223> OTHER INFORMATION: siRNA sequence targeting 3' UTR

<400> SEQUENCE: 48
gcagtcatca gacctgaaa 19

<210> SEQ ID NO 49
<211> LENGTH: 19
<212> TYPE: DNA
<213> ORGANISM: Artificial Sequence
<220> FEATURE:
<223> OTHER INFORMATION: siRNA sequence targeting 3' UTR

<400> SEQUENCE: 49
tgtcatcctt actcgaaga 19

<210> SEQ ID NO 50
<211> LENGTH: 19
<212> TYPE: DNA
<213> ORGANISM: Artificial Sequence
<220> FEATURE:
<223> OTHER INFORMATION: siRNA sequence targeting 3' UTR

<400> SEQUENCE: 50
gaattaagct gcctcagta 19

<210> SEQ ID NO 51
<211> LENGTH: 19
<212> TYPE: DNA
<213> ORGANISM: Artificial Sequence
<220> FEATURE:
<223> OTHER INFORMATION: siRNA sequence targeting 3' UTR

<400> SEQUENCE: 51
gccagaagct ctagcttta 19

<210> SEQ ID NO 52
<211> LENGTH: 19
<212> TYPE: DNA
<213> ORGANISM: Artificial Sequence
<220> FEATURE:
<223> OTHER INFORMATION: siRNA sequence targeting 3' UTR

<400> SEQUENCE: 52
agctctgcct ggagactaa 19

<210> SEQ ID NO 53
<211> LENGTH: 19
<212> TYPE: DNA
<213> ORGANISM: Artificial Sequence
<220> FEATURE:
<223> OTHER INFORMATION: siRNA sequence targeting an intron

<400> SEQUENCE: 53
gatcttattt ggagcaata 19

<210> SEQ ID NO 54
<211> LENGTH: 19
<212> TYPE: DNA
<213> ORGANISM: Artificial Sequence
<220> FEATURE:
<223> OTHER INFORMATION: siRNA sequence targeting an intron

<400> SEQUENCE: 54
tggctgtgat ccaggaata 19

<210> SEQ ID NO 55
<211> LENGTH: 19
<212> TYPE: DNA
<213> ORGANISM: Artificial Sequence
<220> FEATURE:
<223> OTHER INFORMATION: siRNA sequence targeting an intron

<400> SEQUENCE: 55
gatgcattct tctgctaaa 19

<210> SEQ ID NO 56
<211> LENGTH: 19
<212> TYPE: DNA
<213> ORGANISM: Artificial Sequence
<220> FEATURE:
<223> OTHER INFORMATION: siRNA sequence targeting an intron

<400> SEQUENCE: 56
gcaatatgcg cttgtctaa 19

<210> SEQ ID NO 57
<211> LENGTH: 19
<212> TYPE: DNA
<213> ORGANISM: Artificial Sequence
<220> FEATURE:
<223> OTHER INFORMATION: siRNA sequence targeting an intron

<400> SEQUENCE: 57
ttgtctaatt tcacagcaa 19

<210> SEQ ID NO 58
<211> LENGTH: 19
<212> TYPE: DNA
<213> ORGANISM: Artificial Sequence
<220> FEATURE:
<223> OTHER INFORMATION: siRNA sequence targeting an intron

<400> SEQUENCE: 58
tgtttgttgc attcaataa 19

<210> SEQ ID NO 59
<211> LENGTH: 19

<212> TYPE: DNA
<213> ORGANISM: Artificial Sequence
<220> FEATURE:
<223> OTHER INFORMATION: siRNA sequence targeting an intron

<400> SEQUENCE: 59
ccagagcgct aagcaaata 19

<210> SEQ ID NO 60
<211> LENGTH: 19
<212> TYPE: DNA
<213> ORGANISM: Artificial Sequence
<220> FEATURE:
<223> OTHER INFORMATION: siRNA sequence targeting an intron

<400> SEQUENCE: 60
gtcttgcatt taacaggaa 19

<210> SEQ ID NO 61
<211> LENGTH: 19
<212> TYPE: DNA
<213> ORGANISM: Artificial Sequence
<220> FEATURE:
<223> OTHER INFORMATION: siRNA sequence targeting an intron

<400> SEQUENCE: 61
ggctgtgatc caggaatat 19

<210> SEQ ID NO 62
<211> LENGTH: 19
<212> TYPE: DNA
<213> ORGANISM: Artificial Sequence
<220> FEATURE:
<223> OTHER INFORMATION: siRNA sequence targeting an intron

<400> SEQUENCE: 62
tgcaggagga gacgctaga 19

<210> SEQ ID NO 63
<211> LENGTH: 19
<212> TYPE: DNA
<213> ORGANISM: Artificial Sequence
<220> FEATURE:
<223> OTHER INFORMATION: siRNA sequence targeting an intron

<400> SEQUENCE: 63
ctttcactgt taggaatgt 19

<210> SEQ ID NO 64
<211> LENGTH: 19
<212> TYPE: DNA
<213> ORGANISM: Artificial Sequence
<220> FEATURE:
<223> OTHER INFORMATION: siRNA sequence targeting an intron

<400> SEQUENCE: 64
tttggttgat taactatat 19

<210> SEQ ID NO 65
<211> LENGTH: 19
<212> TYPE: DNA
<213> ORGANISM: Artificial Sequence
<220> FEATURE:
<223> OTHER INFORMATION: siRNA sequence targeting an intron

<400> SEQUENCE: 65
ttaactatat ggccactct 19

<210> SEQ ID NO 66
<211> LENGTH: 19
<212> TYPE: DNA
<213> ORGANISM: Artificial Sequence
<220> FEATURE:
<223> OTHER INFORMATION: siRNA sequence targeting an intron

<400> SEQUENCE: 66
agatgttcga attccatca 19

<210> SEQ ID NO 67
<211> LENGTH: 21
<212> TYPE: DNA
<213> ORGANISM: Artificial Sequence
<220> FEATURE:
<223> OTHER INFORMATION: siRNA sequence targeting a polymorphism

<400> SEQUENCE: 67
tcttcaccgt caaggaggta t 21

<210> SEQ ID NO 68
<211> LENGTH: 21
<212> TYPE: DNA
<213> ORGANISM: Artificial Sequence
<220> FEATURE:
<223> OTHER INFORMATION: siRNA sequence targeting a polymorphism

<400> SEQUENCE: 68
tgtttacggt gaaagaagta c 21

<210> SEQ ID NO 69
<211> LENGTH: 20
<212> TYPE: DNA
<213> ORGANISM: Artificial Sequence
<220> FEATURE:
<223> OTHER INFORMATION: Forward primer for rhodopsin

<400> SEQUENCE: 69
ctttcctgat ctgctgggtg 20

<210> SEQ ID NO 70
<211> LENGTH: 19
<212> TYPE: DNA
<213> ORGANISM: Artificial Sequence
<220> FEATURE:
<223> OTHER INFORMATION: Reverse primer for rhodopsin

<400> SEQUENCE: 70
ggcaaagaac gctgggatg 19

<210> SEQ ID NO 71
<211> LENGTH: 25
<212> TYPE: DNA
<213> ORGANISM: Artificial Sequence
<220> FEATURE:
<223> OTHER INFORMATION: Forward primer for beta-actin

<400> SEQUENCE: 71
tcacccacac tgtgcccatc tacga 25

<210> SEQ ID NO 72
<211> LENGTH: 25
<212> TYPE: DNA
<213> ORGANISM: Artificial Sequence
<220> FEATURE:
<223> OTHER INFORMATION: Reverse primer for beta-actin

<400> SEQUENCE: 72
cagcggaacc gctcattgcc aatgg 25

<210> SEQ ID NO 73
<211> LENGTH: 20
<212> TYPE: DNA
<213> ORGANISM: Artificial Sequence
<220> FEATURE:
<223> OTHER INFORMATION: Forward primer for GAPDH

<400> SEQUENCE: 73
cagcctcaag atcatcagca 20

<210> SEQ ID NO 74
<211> LENGTH: 20
<212> TYPE: DNA
<213> ORGANISM: Artificial Sequence
<220> FEATURE:
<223> OTHER INFORMATION: Reverse primer for GAPDH

<400> SEQUENCE: 74
catgagtcct tccacgatac 20

<210> SEQ ID NO 75
<211> LENGTH: 19
<212> TYPE: DNA
<213> ORGANISM: Artificial Sequence
<220> FEATURE:
<223> OTHER INFORMATION: siRNA sequence targeting rhodopsin (siB)

<400> SEQUENCE: 75
tcaacttcct cacgctcta 19

<210> SEQ ID NO 76
<211> LENGTH: 21
<212> TYPE: DNA
<213> ORGANISM: Artificial Sequence
<220> FEATURE:
<223> OTHER INFORMATION: siRNA replacement rhodopsin sequence (rB)

<400> SEQUENCE: 76
ataaattttt tgaccctgta t 21

<210> SEQ ID NO 77
<211> LENGTH: 19
<212> TYPE: DNA
<213> ORGANISM: Artificial Sequence
<220> FEATURE:
<223> OTHER INFORMATION: siRNA sequence targeting rhodopsin (siBB)

<400> SEQUENCE: 77
tcaccgtcca gcacaagaa 19

<210> SEQ ID NO 78
<211> LENGTH: 21
<212> TYPE: DNA
<213> ORGANISM: Artificial Sequence
<220> FEATURE:
<223> OTHER INFORMATION: siRNA replacement rhodopsin sequence (rBB)

<400> SEQUENCE: 78
ctgtatgtga cggtgcagca c 21

<210> SEQ ID NO 79
<211> LENGTH: 19

<212> TYPE: DNA
<213> ORGANISM: Artificial Sequence
<220> FEATURE:
<223> OTHER INFORMATION: siRNA sequence targeting rhodopsin (siC)

<400> SEQUENCE: 79
cgtgtggaat cgactacta 19

<210> SEQ ID NO 80
<211> LENGTH: 20
<212> TYPE: DNA
<213> ORGANISM: Artificial Sequence
<220> FEATURE:
<223> OTHER INFORMATION: Replacement rhodopsin sequence (rC)

<400> SEQUENCE: 80
agctgcggta tagattatta 20

<210> SEQ ID NO 81
<211> LENGTH: 19
<212> TYPE: DNA
<213> ORGANISM: Artificial Sequence
<220> FEATURE:
<223> OTHER INFORMATION: siRNA sequence targeting rhodopsin (siCC)

<400> SEQUENCE: 81
cgctcaagcc ggaggtcaa 19

<210> SEQ ID NO 82
<211> LENGTH: 20
<212> TYPE: DNA
<213> ORGANISM: Artificial Sequence
<220> FEATURE:
<223> OTHER INFORMATION: Replacement rhodopsin sequence (rCC)

<400> SEQUENCE: 82
accttgaaac ccgaagtgaa 20

<210> SEQ ID NO 83
<211> LENGTH: 22
<212> TYPE: DNA
<213> ORGANISM: Artificial Sequence
<220> FEATURE:
<223> OTHER INFORMATION: siRNA sequence targeting rhodopsin (siQ1)

<400> SEQUENCE: 83
tcaacttcct cacgctctac gt 22

<210> SEQ ID NO 84
<211> LENGTH: 21
<212> TYPE: DNA
<213> ORGANISM: Artificial Sequence
<220> FEATURE:
<223> OTHER INFORMATION: Replacement rhodopsin sequence (rQ1)

<400> SEQUENCE: 84
ctgtatgtga cggtgcagca c 21

<210> SEQ ID NO 85
<211> LENGTH: 23
<212> TYPE: DNA
<213> ORGANISM: Artificial Sequence
<220> FEATURE:
<223> OTHER INFORMATION: siRNA sequence targeting rhodopsin (siQ2)

<400> SEQUENCE: 85
ctctacgtca ccgtccagca caa 23

<210> SEQ ID NO 86
<211> LENGTH: 21
<212> TYPE: DNA
<213> ORGANISM: Artificial Sequence
<220> FEATURE:
<223> OTHER INFORMATION: Replacement rhodopsin sequence (rQ2)

<400> SEQUENCE: 86
ctgtatgtga cggtgcagca c 21

<210> SEQ ID NO 87
<211> LENGTH: 427
<212> TYPE: DNA
<213> ORGANISM: Artificial Sequence
<220> FEATURE:
<223> OTHER INFORMATION: CMV enhancer element amplified from pCDNA3.1 (Invitrogen nt 308 - 734 )

<400> SEQUENCE: 87
ccgcgttaca taacttacgg taaatggccc gcctggctga ccgcccaacg acccccgccc 60
attgacgtca ataatgacgt atgttcccat agtaacgcca atagggactt tccattgacg 120
tcaatgggtg gagtatttac ggtaaactgc ccacttggca gtacatcaag tgtatcatat 180
gccaagtacg ccccctattg acgtcaatga cggtaaatgg cccgcctggc attatgccca 240
gtacatgacc ttatgggact ttcctacttg gcagtacatc tacgtattag tcatcgctat 300
taccatggtg atgcggtttt ggcagtacat caatgggcgt ggatagcggt ttgactcacg 360
gggatttcca agtctccacc ccattgacgt caatgggagt ttgttttggc accaaaatca 420
acgggac 427

<210> SEQ ID NO 88
<211> LENGTH: 581
<212> TYPE: DNA
<213> ORGANISM: Artificial Sequence
<220> FEATURE:
<223> OTHER INFORMATION: pAAV.BB11 - the WPR element from pSin11 CMV GFPpre mut FL

<400> SEQUENCE: 88
gagcatctta ccgccattta ttcccatatt tgttctgttt ttcttgattt gggtatacat 60
ttaaatgtta ataaaacaaa atggtggggc aatcatttac atttttaggg atatgtaatt 120
actagttcag gtgtattgcc acaagacaaa catgttaaga aactttcccg ttatttacgc 180
tctgttcctg ttaatcaacc tctggattac aaaatttgtg aaagattgac tgatattctt 240
aactatgttg ctccttttac gctgtgtgga tatgctgctt tatagcctct gtatctagct 300
attgcttccc gtacggcttt cgttttctcc tccttgtata aatcctggtt gctgtctctt 360
ttagaggagt tgtggcccgt tgtccgtcaa cgtggcgtgg tgtgctctgt gtttgctgac 420
gcaaccccca ctggctgggg cattgccacc acctgtcaac tcctttctgg gactttcgct 480
ttccccctcc cgatcgccac ggcagaactc atcgccgcct gccttgcccg ctgctggaca 540
ggggctaggt tgctgggcac tgataattcc gtggtgttgt c 581

<210> SEQ ID NO 89
<211> LENGTH: 587
<212> TYPE: DNA
<213> ORGANISM: Artificial Sequence
<220> FEATURE:
<223> OTHER INFORMATION: pAAV.BB13 - the WPR element from pBSK11

<400> SEQUENCE: 89
aatcaacctc tggattacaa aatttgtgaa agattgactg gtattcttaa ctatgttgct 60
ccttttacgc tatgtggata cgctgcttta atgcctttgt atcatgctat tgcttcccgt 120
atggctttca ttttctcctc cttgtataaa tcctggttgc tgtctcttta tgaggagttg 180
tggcccgttg tcaggcaacg tggcgtggtg tgcactgtgt ttgctgacgc aacccccact 240
ggttggggca ttgccaccac ctgtcagctc ctttccggga ctttcgcttt ccccctccct 300
attgccacgg cggaactcat cgccgcctgc cttgcccgct gctggacagg ggctcggctg 360
ttgggcactg acaattccgt ggtgttgtcg gggaagctga cgtcctttcc atggctgctc 420
gcctgtgttg ccacctggat tctgcgcggg acgtccttct gctacgtccc ttcggccctc 480
aatccagcgg accttccttc ccgcggcctg ctgccggctc tgcggcctct tccgcgtctt 540
cgccttcgcc ctcagacgag tcggatctcc ctttgggccg cctcccc 587

<210> SEQ ID NO 90
<211> LENGTH: 11840
<212> TYPE: DNA
<213> ORGANISM: Artificial Sequence
<220> FEATURE:
<223> OTHER INFORMATION: Conserved regions A-I showing mouse rhodopsin promoter sequence (conserved regions A-D) followed by human rhodopsin 5'UTR, human rhodopsin exons and introns (conserved region E) and human rhodopsin 3' region sequence (conserved region F-I)

<400> SEQUENCE: 90
gttccagggc ccaggggctt ccagccatga gggcacctag acttgtaatc cctagagtcc 60
tcctgatgcc actgcccagg gacagacagc acacagcacc cctcccccac tctcttaaca 120
ggcagaagca gggagatgga ggcatgctga agatgtccat gtgaggctgg tggtagcatg 180
cccactgctg ggatgaagag atgggggcaa agtgagtggc agaggccagg ccaggtccag 240
gcccttccag gcttcctctg ccactgtgga gatgaaagag ggagccaggc aaggtccagg 300
ccctccccac cccctctgcc tctatggaga tgaaggggga atgaagaagg gagccagaca 360
gttgtgccaa cacaactcct ccgtcgagtg tctaattgct tatgatcatg catgctctct 420
ctcccactaa acatttatta atgtgttagg atttccatta gcgcgtgcct tgaactgaaa 480
tcatttgcat atggctggga aaaagtgggg tgagggagga aacagtgcca gctccccaac 540
aggcgtcaat cacagtgaca gatcagatgg tttctggctg gaggcagggg ggctgtctga 600
gatggcggca tgcatccttt cagtgcatat cacagaaatt caggtgactc ctgctgggag 660
ccaagaccct gaggctgagc ctggccacag ctccaatagc tgctggatat catcatgtct 720
gggctgagca gcctctagag gtaccctttt acagatagta aaactgaggc tcagtgactg 780
ctgagccaaa gttggaccca cccacactca tttgcagact gccgtgggcc atgttctgat 840
ctcttcccta cctggactca gcccagcaca ctcggcacac aaggcccttc ttcagcttga 900
atacagcgtc ctcagctata gccagcatct atgaatggag ctcagtgacc ctgactggag 960
gaagttagga cagggatttt ttctggagtt ttggcaggaa gaggccaggg tcaggtgact 1020
gctggagcac acagcttggt aagactagtc aggacctgcg tcctgaggct acatgtcata 1080
tccacagtaa ggaagtggaa gatgggagat gactggctgg gccacaacca gtgagtggaa 1140
tgtccttgtg catctttgtt tcctaacctt cccctctgta gctgctgaaa cacacacaca 1200
ccccatgctc tgttatgcct cttccctggc ctgggatttc catggctgag gtgatggggc 1260
actgaggcac cgccaggaaa ggctgtaacc catctgctcc cccatccttc accagacttc 1320
aagcacctac ctagagcaca ggtgcaattt tgtaccctcc ctgtctggga cccacagtgg 1380

-continued

```
ttcctcaatg ccggccaacc agactcatag gcctgcccac aaggcccttg gggctatctg   1440
tctgaggcct gcaggtgccc tcctggccac ctaggctcct gtgagactta gacttccata   1500
gattcttcct gaaagactac tgagggcagg agcccccaag cctcagggtt agctttcctc   1560
agccctgcct ctttgctagc tccgtttcca cattgaaggc agggctgagc agggcaggcg   1620
cagcgaggag ctaactgctg cttctctctc gttcatttgt ctgctgccct gagacgccac   1680
agcacctaat aagagcatgt tatgtgtagc aaacattagg cctgtaagga aggaaaggag   1740
tgacgtccct tgacgtcctc agctaggctg tggtgacaca agcaagagga ctaagccaca   1800
ggtgaggaga aagggggggg ggggtctgct gacccagcaa cactctttcc ttctgaggct   1860
taagagctat tagcgtaggt gactcagtcc ctaatcctcc attcaatgcc ctgtgactgc   1920
ccctgcttct gaagggccaa catggctaca gctagctcca gagacagctt ttcagggccc   1980
cagcatccaa gcatctcaca gttctccact gaccacactc ctgtgcagca ctgggctttt   2040
caatgcccct gacttgaaga gaactcaaac tgcaggtcaa ctagactctg caaacttcac   2100
ctgtgctggg ggttcctagc ctgtggggac agtgtatctt gaatacctgc tgctatggac   2160
caagagctga acacacagac aaacaggctc agctggccgg cattctggaa ccacaaatga   2220
gtgtggatga gcaggagggc aacaaaatgg tctgggtgtt gtcaacacag tcagtaaaca   2280
atgcacgcag tggggctggg ccctgatgtg gagctaggtg gggttggctc tccttggaaa   2340
cctgaaggga gaaggagagg gagcgagatg atgaggttta tcagcctgca gaggcagggg   2400
gtcaggaagg agtgccactg tactgaccca ggacctctgt gggacatcaa gccatgccaa   2460
ggagccatgg agcctcgatt gcactggcag ggacaggttg tgatgcccca gagtccccag   2520
acccagcaaa cagaggccca gagtgggaag tggagctttc cagggtatcg gggtgactca   2580
gagacacagg gtagaatctg ccttgggtgc tcactgccct atctgagtcc acatggctca   2640
gtccccaggc cctgttctct agtgactgtt gctttgatga ggtagagaca ggcagccctc   2700
ttctaagaac tatgttttga tgggggactc agagttgggg tggggtggca atgaaattct   2760
gtagactgtg tggttataac cctggctgtt actagctagt tctgtgacct tggtgaccca   2820
cttcagactc taggcctcag cctctgtaag tgcagataca cagcgccaat cagccgatga   2880
cttctaacaa tactcttaac tcacacagag cttgtctcac tgagccaaca ccctgtaccc   2940
tcagctcagt gacggctttc aacctgtggg gctgcctctg ttacccaagt gagagagggc   3000
cagtgctccc agaggtgacc ttgtttgccc attctctccc tgggtcagcc agtgtttatc   3060
tgttgtatac ccagtccacc ctgcaggctc acatcagagc ctaggagatg gctagtgtcc   3120
ccgcggagac cacgatgaag cttcccagct gtctcaagca caagctggct gcagaggctg   3180
ctgaggcact gctagctggg gatgggggca gggtagatct ggggctgacc accagggtca   3240
gaatcagaac ctccaccttg acctcattaa cgctggtctt aatcaccaag ccaagctcct   3300
taaactgcta gtggccaact cccaggccct gacacacata cctgccctgt gttcccaaac   3360
aagacacctg catggaagga agggggttgc ttttctaagc aaacatctag gaatcccggg   3420
tgcagtgtga ggagactagg cgagggagta ctttaagggc ctcaaggctc agagaggaat   3480
acttcttccc tggttagcct cgtgcctagg ctccagggtc tttgtcctgc ctggatacct   3540
atgtggcaag gggcatagca tttcccccac catcagctct tagctcaacc ttatcttctc   3600
ggaaagactg cgcagtgtaa caacacagca gagacttttc ttttgtcccc tgtctacccc   3660
tgtaactgct actcagaagc atctttctca cagggtactg gcttcttgca tccagagttt   3720
tttgtctccc tcgggccccc agaatcaaat tcttcctctg ggactcagtg gatgtttcac   3780
```

-continued

```
acacgtatcg gcctgacagt catcctggag catcctacac aggggccatc acagctgcat   3840
gtcagaaatg ctggcctcac atcctcagac accaggccta gtgctggtct tcctcagact   3900
ggcgtcccca gcaggccagt aggatcatct tttagcctac agagttctga agcctcagag   3960
ccccaggtcc ctggtcatct tctctgcccc tgagattttt ccaagttgta tgccttctag   4020
gtaaggcaaa acttcttacg cccctcctcg tggcctccag gccccacatg ctcacctgaa   4080
taacctggca gcctgctccc tcatgcaggg accacgtcct gctgcaccca gcaggccatc   4140
ccgtctccat agcccatggt catccctccc tggacaggaa tgtgtctcct ccccgggctg   4200
agtcttgctc aagctagaag cactccgaac agggttatgg gcgcctcctc catctcccaa   4260
gtggctggct tatgaatgtt taatgtacat gtgagtgaac aaattccaat tgaacgcaac   4320
aaatagttat cgagccgctg agccgggggg cggggggtgt gagactggag gcgatggacg   4380
gagctgacgg cacacacagc tcagatctgt caagtgagcc attgtcaggg cttggggact   4440
ggataagtca gggggtctcc tgggaagaga tgggataggt gagttcagga ggagacattg   4500
tcaactggag ccatgtggag aagtgaattt agggcccaaa ggttccagtc gcagcctgag   4560
gccaccagac tgacatgggg aggaattccc agaggactct ggggcagaca agatgagaca   4620
ccctttcctt tctttaccta agggcctcca cccgatgtca ccttggcccc tctgcaagcc   4680
aattaggccc cggtggcagc agtgggatta gcgttagtat gatatctcgc ggatgctgaa   4740
tcagcctctg gcttagggag agaaggtcac tttataaggg tctggggggg gtcagtgcct   4800
ggagttgcgc tgtgggagcc gtcagtggct gagctcgcca agcagccttg gtctctgtct   4860
acgaagagcc cgtggggcag cctcgaggga tcctgagtac ctctcctccc tgacctcagg   4920
cttcctccta gtgtcacctt ggcccctctt agaagccaat taggccctca gtttctgcag   4980
cggggattaa tatgattatg aacaccccca atctcccaga tgctgattca gccaggagct   5040
taggaggggg aggtcacttt ataagggtct gggggggtca gaacccagag tcatccagct   5100
ggagccctga gtggctgagc tcaggccttc gcagcattct tgggtgggag cagccacggg   5160
tcagccacaa gggccacagc catgaatggc acagaaggcc ctaacttcta cgtgcccttc   5220
tccaatgcga cgggtgtggt acgcagcccc ttcgagtacc cacagtacta cctggctgag   5280
ccatggcagt tctccatgct ggccgcctac atgtttctgc tgatcgtgct gggcttcccc   5340
atcaacttcc tcacgctcta cgtcaccgtc cagcacaaga agctgcgcac gcctctcaac   5400
tacatcctgc tcaacctagc cgtggctgac ctcttcatgg tcctaggtgg cttcaccagc   5460
accctctaca cctctctgca tggatacttc gtcttcgggc ccacaggatg caatttggag   5520
ggcttctttg ccaccctggg cggtatgagc cgggtgtggg tggggtgtgc aggagcccgg   5580
gagcatggag ggtctggga gagtcccggg cttggcggtg gtggctgaga ggccttctcc   5640
cttctcctgt cctgtcaatg ttatccaaag ccctcatata ttcagtcaac aaacaccatt   5700
catggtgata gccgggctgc tgtttgtgca gggctggcac tgaacactgc cttgatctta   5760
tttggagcaa tatgcgcttg tctaatttca cagcaagaaa actgagctga ggctcaaagg   5820
ccaagtcaag cccctgctgg ggcgtcacac agggacgggt gcagagttga gttggaagcc   5880
cgcatctatc tcgggccatg tttgcagcac caagcctctg tttcccttgg agcagctgtg   5940
ctgagtcaga cccaggctgg gcactgaggg agagctgggc aagccagacc cctcctctct   6000
gggggcccaa gctcagggtg ggaagtggat tttccattct ccagtcattg ggtcttccct   6060
gtgctgggca atgggctcgg tcccctctgg catcctctgc ctcccctctc agcccctgtc   6120
ctcaggtgcc cctccagcct ccctgccgcg ttccaagtct cctggtgttg agaaccgcaa   6180
```

-continued gcagccgctc tgaagcagtt cctttttgct ttagaataat gtcttgcatt taacaggaaa 6240
acagatgggg tgctgcaggg ataacagatc ccacttaaca gagaggaaaa ctgaggcagg 6300
gagaggggaa gagactcatt tagggatgtg gccaggcagc aacaagagcc taggtctcct 6360
ggctgtgatc caggaatatc tctgctgaga tgcaggagga gacgctagaa gcagccattg 6420
caaagctggg tgacggggag agcttaccgc cagccacaag cgtctctctg ccagccttgc 6480
cctgtctccc ccatgtccag gctgctgcct cggtcccatt ctcagggaat ctctggccat 6540
tgttgggtgt ttgttgcatt caataatcac agatcactca gttctggcca gaaggtgggt 6600
gtgccactta cgggtggttg ttctctgcag ggtcagtccc agtttacaaa tattgtccct 6660
ttcactgtta ggaatgtccc agtttggttg attaactata tggccactct ccctatgaaa 6720
cttcatgggg tggtgagcag gacagatgtt cgaattccat catttccttc ttcttcctct 6780
gggcaaaaca ttgcacattg cttcatggct cctaggagag gcccccacat gtccgggtta 6840
tttcatttcc cgagaaggga gagggaggaa ggactgccaa ttctgggttt ccaccacctc 6900
tgcattcctt cccaacaagg aactctgccc cacattagga tgcattcttc tgctaaacac 6960
acacacacac acacacacac acaacacaca cacacacaca cacacacaca cacacacaaa 7020
actccctacc gggttcccag ttcaatcctg accccctgat ctgattcgtg tcccttatgg 7080
gcccagagcg ctaagcaaat aacttccccc attccctgga atttctttgc ccagctctcc 7140
tcagcgtgtg gtccctctgc cccttccccc tcctcccagc accaagctct ctccttcccc 7200
aaggcctcct caaatccctc tcccactcct ggttgccttc ctagctaccc tctccctgtc 7260 tagggggggag tgcaccctcc ttaggcagtg gggtctgtgc tgaccgcctg ctgactgcct 7320
tgcaggtgaa attgccctgt ggtccttggt ggtcctggcc atcgagcggt acgtggtggt 7380
gtgtaagccc atgagcaact tccgcttcgg ggagaaccat gccatcatgg gcgttgcctt 7440
cacctgggtc atggcgctgg cctgcgccgc acccccactc gccggctggt ccaggtaatg 7500
gcactgagca gaagggaaga agctccgggg gctctttgta gggtcctcca gtcaggactc 7560
aaacccagta gtgtctggtt ccaggcactg accttgtatg tctcctggcc caaatgccca 7620
ctcagggtag gggtgtaggg cagaagaaga aacagactct aatgttgcta caagggctgg 7680
tcccatctcc tgagccccat gtcaaacaga atccaagaca tcccaaccct tcaccttggc 7740
tgtgccccta atcctcaact aagctaggcg caaattccaa tcctctttgg tctagtaccc 7800
cgggggcagc cccctctaac cttgggcctc agcagcaggg gaggccacac cttcctagtg 7860
caggtggcca tattgtggcc ccttggaact gggtcccact cagcctctag gcgattgtct 7920
cctaatgggg ctgagatgag actcagtggg gacagtggtt tggacaatag gactggtgac 7980
tctggtcccc agaggcctca tgtccctctg tctccagaaa attcccactc tcacttccct 8040
ttcctcctca gtcttgctag ggtccatttc taccccttgc tgaatttgag cccacccccct 8100 ggactttttc cccatcttct ccaatctggc ctagttctat cctctggaag cagagccgct 8160
ggacgctctg ggtttcctga ggcccgtcca ctgtcaccaa tatcaggaac cattgccacg 8220
tcctaatgac gtgcgctgga agcctctagt ttccagaagc tgcacaaaga tcccttagat 8280
actctgtgtg tccatctttg gcctggaaaa tactctcacc ctggggctag gaagacctcg 8340
gtttgtacaa acttcctcaa atgcagagcc tgagggctct ccccacctcc tcaccaaccc 8400
tctgcgtggc atagccctag cctcagcggg cagtggatgc tggggctggg catgcaggga 8460
gaggctgggt ggtgtcatct ggtaacgcag ccaccaaaca atgaagcgac actgattcca 8520
caaggtgcat ctgcatcccc atctgatcca ttccatcctg tcacccagcc atgcagacgt 8580
ttatgatccc cttttccagg gagggaatgt gaagccccag aaagggccag cgctcggcag 8640
ccaccttggc tgttcccaag tccctcacag gcagggtctc cctacctgcc tgtcctcagg 8700
tacatccccg agggcctgca gtgctcgtgt ggaatcgact actacacgct caagccggag 8760
gtcaacaacg agtcttttgt catctacatg ttcgtggtcc acttcaccat ccccatgatt 8820
atcatctttt tctgctatgg gcagctcgtc ttcaccgtca aggaggtacg ggccgggggg 8880
tgggcggcct cacggctctg agggtccagc ccccagcatg catctgcggc tcctgctccc 8940
tggaggagcc atggtctgga cccgggtccc gtgtcctgca ggccgctgcc cagcagcagg 9000
agtcagccac cacacagaag gcagagaagg aggtcacccg catggtcatc atcatggtca 9060
tcgctttcct gatctgctgg gtgccctacg ccagcgtggc attctacatc ttcacccacc 9120
agggctccaa cttcggtccc atcttcatga ccatcccagc gttctttgcc aagagcgccg 9180
ccatctacaa ccctgtcatc tatatcatga tgaacaagca ggtgcctact gcgggtggga 9240
gggccccagt gccccaggcc acaggcgctg cctgccaagg acaagctact cccagggcag 9300
gggaggggct ccatcagggt tactggcagc agtcttgggt cagcagtccc aatggggagt 9360
gtgtgagaaa tgcagattcc tggccccact cagaactgct gaatctcagg gtgggcccag 9420
gaacctgcat ttccagcaag ccctccacag gtggctcaga tgctcactca ggtgggagaa 9480
gctccagtca gctagttctg gaagcccaat gtcaaagtca gaaggaccca agtcgggaat 9540
gggatgggcc agtctccata aagctgaata aggagctaaa aagtcttatt ctgaggggta 9600
aaggggtaaa gggttcctcg gagaggtacc tccgaggggt aaacagttgg gtaaacagtc 9660
tctgaagtca gctctgccat tttctagctg tatggccctg ggcaagtcaa tttccttctc 9720
tgtgctttgg tttcctcatc catagaaagg tagaaagggc aaaacaccaa actcttggat 9780
tacaagagat aatttacaga acacccttgg cacacagagg gcaccatgaa atgtcacggg 9840
tgacacagcc cccttgtgct cagtccctgg catctctagg ggtgaggagc gtctgcctag 9900
caggttccca ccaggaagct ggatttgagt ggatggggcg ctggaatcgt gaggggcaga 9960
agcaggcaaa gggtcggggc gaacctcact aacgtgccag ttccaagcac actgtgggca 10020
gccctggccc tgactcaagc ctcttgcctt ccagttccgg aactgcatgc tcaccaccat 10080
ctgctgcggc aagaacccac tgggtgacga tgaggcctct gctaccgtgt ccaagacgga 10140
gacgagccag gtggccccgg cctaagacct gcctaggact ctgtggccga ctataggcgt 10200
ctcccatccc ctacaccttc cccagccac agccatccca ccaggagcag cgcctgtgca 10260
gaatgaacga agtcacatag gctccttaat tttttttttt tttttaagaa ataattaatg 10320
aggctcctca ctcacctggg acagcctgag aagggacatc caccaagacc tactgatctg 10380
gagtcccacg ttccccaagg ccagcgggat gtgtgcccct cctcctccca actcatcttt 10440
caggaacacg aggattcttg ctttctggaa aagtgtccca gcttagggat aagtgtctag 10500
cacagaatgg ggcacacagt aggtgcttaa taaatgctgg atggatgcag gaaggaatgg 10560
aggaatgaat gggaagggag aacatatcta tcctctcaga ccctcgcagc agcagcaact 10620
catacttggc taatgatatg gagcagttgt ttttccctcc ctgggcctca ctttcttctc 10680
ctataaaatg gaaatcccag atccctggtc ctgccgacac gcagctactg agaagaccaa 10740
aagaggtgtg tgtgtgtcta tgtgtgtgtt tcagcacttt gtaaatagca agaagctgta 10800
cagattctag ttaatgttgt gaataacatc aattaatgta actagttaat tactatgatt 10860
atcacctcct gatagtgaac attttgagat tgggcattca gatgatgggg tttcacccaa 10920
ccttggggca ggtttttaaa aattagctag gcatcaaggc cagaccaggg ctggggggttg 10980 ggctgtaggc agggacagtc acaggaatgc aggatgcagt catcagacct gaaaaaacaa 11040
cactggggga gggggacggt gaaggccaag ttcccaatga gggtgagatt gggcctgggg 11100
tctcacccct agtgtggggc cccaggtccc gtgcctcccc ttcccaatgt ggcctatgga 11160
gagacaggcc tttctctcag cctctggaag ccacctgctc ttttgctcta gcacctgggt 11220
cccagcatct agagcatgga gcctctagaa gccatgctca cccgcccaca tttaattaac 11280
agctgagtcc ctgatgtcat ccttactcga agagcttaga aacaaagagt gggaaattcc 11340
actgggccta ccttccttgg ggatgttcat gggccccagt ttccagtttc ccttgccaga 11400
caagcccatc ttcagcagtt gctagtccat tctccattct ggagaatctg ctccaaaaag 11460
ctggccacat ctctgaggtg tcagaattaa gctgcctcag taactgctcc cccttctcca 11520
tataagcaaa gccagaagct ctagctttac ccagctctgc ctggagacta aggcaaattg 11580
ggccattaaa agctcagctc ctatgttggt attaacggtg gtgggttttg ttgctttcac 11640
actctatcca caggatagat tgaaactgcc agcttccacc tgatccctga ccctgggatg 11700
gctggattga gcaatgagca gagccaagca gcacagagtc ccctggggct agaggtggag 11760
gaggcagtcc tgggaatggg aaaaacccca actttggggt catagaggca caggtaaccc 11820
ataaaactgc aaacaagctt 11840

<210> SEQ ID NO 91
<211> LENGTH: 72
<212> TYPE: DNA
<213> ORGANISM: Artificial Sequence
<220> FEATURE:
<223> OTHER INFORMATION: CRX-NRL element including the CRX motif from conserved region D, the CRX motif from conserved region E and NRL binding sites
<400> SEQUENCE: 91
tttctgcagc ggggattaat atgattatga acacccccaa tctcccagat gctgattcag 60
ccaggaggta cc 72

<210> SEQ ID NO 92
<211> LENGTH: 210
<212> TYPE: DNA
<213> ORGANISM: Artificial Sequence
<220> FEATURE:
<223> OTHER INFORMATION: DNA sequence (1-210) of conserved region A of the rhodopsin gene
<400> SEQUENCE: 92
cacaactcct ccgtcgagtg tctaattgct tatgatcatg catgctctct ctcccactaa 60
acatttatta atgtgttagg atttccatta gcgcgtgcct tgaactgaaa tcatttgcat 120
atggctggga aaaagtgggg tgagggagga aacagtgcca gctccccaac aggcgtcaat 180
cacagtgaca gatcagatgg tttctggctg 210

<210> SEQ ID NO 93
<211> LENGTH: 100
<212> TYPE: DNA
<213> ORGANISM: Artificial Sequence
<220> FEATURE:
<223> OTHER INFORMATION: Conserved region B of the rhodopsin gene (210-310)

<400> SEQUENCE: 93
aagggggggg ggggtctgct gacccagcaa cactctttcc ttctgaggct taagagctat 60
tagcgtaggt gactcagtcc ctaatcctcc attcaatgcc 100

<210> SEQ ID NO 94
<211> LENGTH: 100
<212> TYPE: DNA
<213> ORGANISM: Artificial Sequence
<220> FEATURE:
<223> OTHER INFORMATION: Conserved region C of the rhodopsin gene (310-410)

<400> SEQUENCE: 94
ggggctgacc accagggtca gaatcagaac ctccaccttg acctcattaa cgctggtctt 60
aatcaccaag ccaagctcct taaactgcta gtggccaact 100

<210> SEQ ID NO 95
<211> LENGTH: 280
<212> TYPE: DNA
<213> ORGANISM: Artificial Sequence
<220> FEATURE:
<223> OTHER INFORMATION: Conserved region D of the rhodopsin gene (410-690)

<400> SEQUENCE: 95
aggcttcctc ctagtgtcac cttggcccct cttagaagcc aattaggccc tcagtttctg 60
cagcggggat taatatgatt atgaacaccc ccaatctccc agatgctgat tcagccagga 120
gcttaggagg gggaggtcac tttataaggg tctggggggg tcagaaccca gagtcatcca 180
gctggagccc tgagtggctg agctcaggcc ttcgcagcat tcttgggtgg gagcagccac 240
gggtcagcca caagggccac agccatgaat ggcacagaag 280

<210> SEQ ID NO 96
<211> LENGTH: 160
<212> TYPE: DNA
<213> ORGANISM: Artificial Sequence
<220> FEATURE:
<223> OTHER INFORMATION: Conserved region E of the rhodopsin gene (690-850)

<400> SEQUENCE: 96
tcctgagccc catgtcaaac agaatccaag acatcccaac ccttcacctt ggctgtgccc 60
ctaatcctca actaagctag gcgcaaattc caatcctctt tggtctagta ccccgggggc 120
agccccctct aaccttgggc ctcagcagca ggggaggcca 160

<210> SEQ ID NO 97
<211> LENGTH: 370
<212> TYPE: DNA
<213> ORGANISM: Artificial Sequence
<220> FEATURE:
<223> OTHER INFORMATION: Conserved region F & G of the rhodopsin gene (850-1220)

<400> SEQUENCE: 97
cccctacacc ttcccccagc cacagccatc ccaccaggag cagcgcctgt gcagaatgaa 60
cgaagtcaca taggctcctt aatttttttt ttttttttaa gaaataatta atgaggctcc 120
tcactcacct gggacagcct gagaagggac atccaccaag acctactgat ctggagtccc 180
acgttcccca aggccagcgg gatgtgtgcc cctcctcctc ccaactcatc tttcaggaac 240
acgaggattc ttgctttctg gaaaagtgtc ccagcttagg gataagtgtc tagcacagaa 300
tggggcacac agtaggtgct taataaatgc tggatggatg caggaaggaa tggaggaatg 360
aatgggaagg 370

<210> SEQ ID NO 98
<211> LENGTH: 110
<212> TYPE: DNA
<213> ORGANISM: Artificial Sequence
<220> FEATURE:
<223> OTHER INFORMATION: Conserved region H of the rhosopsin gene (1220 1230-1316 1330)

<400> SEQUENCE: 98
tctagagcat ggagcctcta gaagccatgc tcacccgccc acatttaatt aacagctgag 60
tccctgatgt catccttact cgaagagctt agaaacaaag agtgggaaat 110

<210> SEQ ID NO 99
<211> LENGTH: 270
<212> TYPE: DNA
<213> ORGANISM: Artificial Sequence
<220> FEATURE:
<223> OTHER INFORMATION: Conserved region I of the rhodopsin gene (1330 1342-1425 1600)

<400> SEQUENCE: 99
gctctagctt tacccagctc tgcctggaga ctaaggcaaa ttgggccatt aaaagctcag 60
ctcctatgtt ggtattaacg gtggtgggtt ttgttgcttt cacactctat ccacaggata 120
gattgaaact gccagcttcc acctgatccc tgaccctggg atggctggat tgagcaatga 180
gcagagccaa gcagcacaga gtcccctggg gctagaggtg gaggaggcag tcctgggaat 240
gggaaaaacc ccaactttgg ggtcatagag 270

<210> SEQ ID NO 100
<211> LENGTH: 21
<212> TYPE: DNA
<213> ORGANISM: Unknown
<220> FEATURE:
<223> OTHER INFORMATION: Putative Rhodopsin transcription regulatory factors

<400> SEQUENCE: 100
tcgagtgtct aattgcttat g 21

<210> SEQ ID NO 101
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 101
gtgtctaatt gct 13

<210> SEQ ID NO 102
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 102
tgtctaattg cttatga 17

<210> SEQ ID NO 103
<211> LENGTH: 25
<212> TYPE: DNA
<213> ORGANISM: Unknown
<220> FEATURE:

<223> OTHER INFORMATION: Putative Rhodopsin transcription regulatory factors

<400> SEQUENCE: 103
gtgggagaga gagcatgcat gatca 25

<210> SEQ ID NO 104
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 104
tcccactaaa catttat 17

<210> SEQ ID NO 105
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 105
acattaataa atgttta 17

<210> SEQ ID NO 106
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 106
attaataaat gttta 15

<210> SEQ ID NO 107
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 107
attaataaat gttta 15

<210> SEQ ID NO 108
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 108
aacacattaa taaatgttt 19

<210> SEQ ID NO 109
<211> LENGTH: 21
<212> TYPE: DNA
<213> ORGANISM: Unknown
<220> FEATURE:
<223> OTHER INFORMATION: Putative Rhodopsin transcription regulatory factors

<400> SEQUENCE: 109
ctaacacatt aataaatgtt t 21

<210> SEQ ID NO 110
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 110
acatttatta atg 13

<210> SEQ ID NO 111
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 111
catttattaa tgtgttagg 19

<210> SEQ ID NO 112
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 112
acacattaat aaatg 15

<210> SEQ ID NO 113
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 113
taacacatta ataaa 15

<210> SEQ ID NO 114
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 114
ttattaatgt gttagga 17

<210> SEQ ID NO 115
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 115
ctaatggaaa tccta 15

<210> SEQ ID NO 116
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 116
gcgctaatgg aaatcct 17

<210> SEQ ID NO 117
<211> LENGTH: 25
<212> TYPE: DNA
<213> ORGANISM: Unknown
<220> FEATURE:
<223> OTHER INFORMATION: Putative Rhodopsin transcription regulatory factors

<400> SEQUENCE: 117
ttccattagc gcgtgccttg aactg 25

<210> SEQ ID NO 118
<211> LENGTH: 21
<212> TYPE: DNA
<213> ORGANISM: Homo sapiens

<400> SEQUENCE: 118
ccattagcgc gtgccttgaa c 21

<210> SEQ ID NO 119
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 119
aaggcacgcg ctaat 15

<210> SEQ ID NO 120
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 120
aaggcacgcg ctaat 15

<210> SEQ ID NO 121
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 121
gccttgaact gaa 13

<210> SEQ ID NO 122

<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 122
catatgcaaa tgatt 15

<210> SEQ ID NO 123
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 123
gccatatgca aat 13

<210> SEQ ID NO 124
<211> LENGTH: 27
<212> TYPE: DNA
<213> ORGANISM: Unknown
<220> FEATURE:
<223> OTHER INFORMATION: Putative Rhodopsin transcription regulatory factors

<400> SEQUENCE: 124
atatggctgg gaaaaagtgg ggtgagg 27

<210> SEQ ID NO 125
<211> LENGTH: 15
<212> TYPE: DNA
<213> ORGANISM: Unknown
<220> FEATURE:
<223> OTHER INFORMATION: Putative Rhodopsin transcription regulatory factor

<400> SEQUENCE: 125
tggctgggaa aaagt 15

<210> SEQ ID NO 126
<211> LENGTH: 25
<212> TYPE: DNA
<213> ORGANISM: Unknown
<220> FEATURE:
<223> OTHER INFORMATION: Putative Rhodopsin transcription regulatory factors

<400> SEQUENCE: 126
ggctgggaaa aagtggggtg aggga 25

<210> SEQ ID NO 127
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 127
gggaaaaagt ggggt 15

<210> SEQ ID NO 128
<211> LENGTH: 11
<212> TYPE: DNA

<213> ORGANISM: Unknown
<220> FEATURE:
<223> OTHER INFORMATION: Putative Rhodopsin transcription regulatory
factors

<400> SEQUENCE: 128
ggaaaaagtg g 11

<210> SEQ ID NO 129
<211> LENGTH: 15
<212> TYPE: DNA
<213> ORGANISM: Unknown
<220> FEATURE:
<223> OTHER INFORMATION: Putative Rhodopsin transcription regulatory
factors

<400> SEQUENCE: 129
ccctcacccc acttt 15

<210> SEQ ID NO 130
<211> LENGTH: 25
<212> TYPE: DNA
<213> ORGANISM: Unknown
<220> FEATURE:
<223> OTHER INFORMATION: Putative Rhodopsin transcription regulatory
factors

<400> SEQUENCE: 130
agtggggtga gggaggaaac agtgc 25

<210> SEQ ID NO 131
<211> LENGTH: 17
<212> TYPE: DNA
<213> ORGANISM: Unknown
<220> FEATURE:
<223> OTHER INFORMATION: Putative Rhodopsin transcription regulatory
factors

<400> SEQUENCE: 131
tgagggagga aacagtg 17

<210> SEQ ID NO 132
<211> LENGTH: 11
<212> TYPE: DNA
<213> ORGANISM: Unknown
<220> FEATURE:
<223> OTHER INFORMATION: Putative Rhodopsin transcription regulatory
factors

<400> SEQUENCE: 132
ggaggaaaca g 11

<210> SEQ ID NO 133
<211> LENGTH: 13
<212> TYPE: DNA
<213> ORGANISM: Unknown
<220> FEATURE:
<223> OTHER INFORMATION: Putative Rhodopsin transcription regulatory
factors

<400> SEQUENCE: 133
gcactgtttc ctc 13

<210> SEQ ID NO 134
<211> LENGTH: 23
<212> TYPE: DNA
<213> ORGANISM: Unknown
<220> FEATURE:

<223> OTHER INFORMATION: Putative Rhodopsin transcription regulatory factors

<400> SEQUENCE: 134
ctgtgattga cgcctgttgg gga 23

<210> SEQ ID NO 135
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 135
gattgacgcc tgttgggga 19

<210> SEQ ID NO 136
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 136
cccaacaggc gtc 13

<210> SEQ ID NO 137
<211> LENGTH: 21
<212> TYPE: DNA
<213> ORGANISM: Unknown
<220> FEATURE:
<223> OTHER INFORMATION: Putative Rhodopsin transcription regulatory factors

<400> SEQUENCE: 137
cactgtgatt gacgcctgtt g 21

<210> SEQ ID NO 138
<211> LENGTH: 11
<212> TYPE: DNA
<213> ORGANISM: Unknown
<220> FEATURE:
<223> OTHER INFORMATION: Putative Rhodopsin transcription regulatory factors

<400> SEQUENCE: 138
ttgacgcctg t 11

<210> SEQ ID NO 139
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 139
actgtgattg acgcctg 17

<210> SEQ ID NO 140
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 140
actgtgattg acgcctg 17

<210> SEQ ID NO 141
<211> LENGTH: 25
<212> TYPE: DNA
<213> ORGANISM: Unknown
<220> FEATURE:
<223> OTHER INFORMATION: Putative Rhodopsin transcription regulatory factors

<400> SEQUENCE: 141
caatcacagt gacagatcag atggt 25

<210> SEQ ID NO 142
<211> LENGTH: 11
<212> TYPE: DNA
<213> ORGANISM: Unknown
<220> FEATURE:
<223> OTHER INFORMATION: Putative Rhodopsin transcription regulatory factors

<400> SEQUENCE: 142
atctgtcact g 11

<210> SEQ ID NO 143
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 143
tgacagatca gatgg 15

<210> SEQ ID NO 144
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 144
gacagatcag atg 13

<210> SEQ ID NO 145
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 145
cagatcagat ggtttct 17

<210> SEQ ID NO 146
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 146
aaaccatctg atc 13

<210> SEQ ID NO 147
<211> LENGTH: 23
<212> TYPE: DNA
<213> ORGANISM: Unknown
<220> FEATURE:
<223> OTHER INFORMATION: Putative Rhodopsin transcription regulatory factors

<400> SEQUENCE: 147
agaccccccc ccccttcag cca 23

<210> SEQ ID NO 148
<211> LENGTH: 23
<212> TYPE: DNA
<213> ORGANISM: Unknown
<220> FEATURE:
<223> OTHER INFORMATION: Putative Rhodopsin transcription regulatory factors

<400> SEQUENCE: 148
gcagaccccc cccccccttc agc 23

<210> SEQ ID NO 149
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 149
tgaagggggg ggg 13

<210> SEQ ID NO 150
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 150
gaaggggggg gggggtc 17

<210> SEQ ID NO 151
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 151
aagggggggg ggggtct 17

<210> SEQ ID NO 152
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 152
aagggggggg ggggt 15

<210> SEQ ID NO 153
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 153
aggggggggg gggtctg 17

<210> SEQ ID NO 154
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 154
gggggggggg ggtct 15

<210> SEQ ID NO 155
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 155
gggggggggg gtctgct 17

<210> SEQ ID NO 156
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 156
cagacccccc ccccc 15

<210> SEQ ID NO 157
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 157
gggggggggg tct 13

<210> SEQ ID NO 158
<211> LENGTH: 25
<212> TYPE: DNA
<213> ORGANISM: Unknown
<220> FEATURE:
<223> OTHER INFORMATION: Putative Rhodopsin transcription regulatory factors

<400> SEQUENCE: 158
gagtgttgct gggtcagcag acccc 25

-continued

<210> SEQ ID NO 159
<211> LENGTH: 25
<212> TYPE: DNA
<213> ORGANISM: Unknown
<220> FEATURE:
<223> OTHER INFORMATION: Putative Rhodopsin transcription regulatory factors

<400> SEQUENCE: 159
ggggtctgct gacccagcaa cactc 25

<210> SEQ ID NO 160
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 160
gtgttgctgg gtcagcaga 19

<210> SEQ ID NO 161
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 161
tgctgaccca gcaacactc 19

<210> SEQ ID NO 162
<211> LENGTH: 11
<212> TYPE: DNA
<213> ORGANISM: Unknown
<220> FEATURE:
<223> OTHER INFORMATION: Putative Rhodopsin transcription regulatory factors

<400> SEQUENCE: 162
gaaggaaaga g 11

<210> SEQ ID NO 163
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 163
gctcttaagc ctcag 15

<210> SEQ ID NO 164
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 164
ctcttaagcc tca 13

<210> SEQ ID NO 165
<211> LENGTH: 15

<212> TYPE: DNA
<213> ORGANISM: Unknown
<220> FEATURE:
<223> OTHER INFORMATION: Putative Rhodopsin transcription regulatory factors

<400> SEQUENCE: 165
aggcttaaga gctat 15

<210> SEQ ID NO 166
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 166
acgctaatag ctcttaa 17

<210> SEQ ID NO 167
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 167
agtcacctac gctaatagc 19

<210> SEQ ID NO 168
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 168
attagcgtag gtgactc 17

<210> SEQ ID NO 169
<211> LENGTH: 25
<212> TYPE: DNA
<213> ORGANISM: Unknown
<220> FEATURE:
<223> OTHER INFORMATION: Putative Rhodopsin transcription regulatory factors

<400> SEQUENCE: 169
attagggact gagtcaccta cgcta 25

<210> SEQ ID NO 170
<211> LENGTH: 21
<212> TYPE: DNA
<213> ORGANISM: Unknown
<220> FEATURE:
<223> OTHER INFORMATION: Putative Rhodopsin transcription regulatory factors

<400> SEQUENCE: 170
cgtaggtgac tcagtcccta a 21

<210> SEQ ID NO 171
<211> LENGTH: 11
<212> TYPE: DNA
<213> ORGANISM: Unknown

<220> FEATURE:
<223> OTHER INFORMATION: Putative Rhodopsin transcription regulatory
factors

<400> SEQUENCE: 171
ggtgactcag t 11

<210> SEQ ID NO 172
<211> LENGTH: 11
<212> TYPE: DNA
<213> ORGANISM: Unknown
<220> FEATURE:
<223> OTHER INFORMATION: Putative Rhodopsin transcription regulatory
factors

<400> SEQUENCE: 172
actgagtcac c 11

<210> SEQ ID NO 173
<211> LENGTH: 17
<212> TYPE: DNA
<213> ORGANISM: Unknown
<220> FEATURE:
<223> OTHER INFORMATION: Putative Rhodopsin transcription regulatory
factors

<400> SEQUENCE: 173
tccctaatcc tccattc 17

<210> SEQ ID NO 174
<211> LENGTH: 13
<212> TYPE: DNA
<213> ORGANISM: Unknown
<220> FEATURE:
<223> OTHER INFORMATION: Putative Rhodopsin transcription regulatory
factors

<400> SEQUENCE: 174
ggcattgaat gga 13

<210> SEQ ID NO 175
<211> LENGTH: 19
<212> TYPE: DNA
<213> ORGANISM: Unknown
<220> FEATURE:
<223> OTHER INFORMATION: Putative Rhodopsin transcription regulatory
factors

<400> SEQUENCE: 175
cagaatcaga acctccacc 19

<210> SEQ ID NO 176
<211> LENGTH: 19
<212> TYPE: DNA
<213> ORGANISM: Unknown
<220> FEATURE:
<223> OTHER INFORMATION: Putative Rhodopsin transcription regulatory
factors

<400> SEQUENCE: 176
ttaatgaggt caaggtgga 19

<210> SEQ ID NO 177
<211> LENGTH: 11
<212> TYPE: DNA
<213> ORGANISM: Unknown
<220> FEATURE:
<223> OTHER INFORMATION: Putative Rhodopsin transcription regulatory factors

<400> SEQUENCE: 177
aggtcaaggt g 11

<210> SEQ ID NO 178
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 178
atgaggtcaa ggt 13

<210> SEQ ID NO 179
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 179
gcgttaatga ggtcaag 17

<210> SEQ ID NO 180
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 180
attaacgctg gtc 13

<210> SEQ ID NO 181
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 181
gtcttaatca ccaagcc 17

<210> SEQ ID NO 182
<211> LENGTH: 25
<212> TYPE: DNA
<213> ORGANISM: Unknown
<220> FEATURE:
<223> OTHER INFORMATION: Putative Rhodopsin transcription regulatory factor

<400> SEQUENCE: 182
accaagccaa gctccttaaa ctgct 25

<210> SEQ ID NO 183
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 183
actaggagga agcctag 17

<210> SEQ ID NO 184
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 184
gggccaaggt gac 13

<210> SEQ ID NO 185
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 185
cccctcttag aagccaa 17

<210> SEQ ID NO 186
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 186
ggcctaattg gcttcta 17

<210> SEQ ID NO 187
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 187
gaagccaatt aggcc 15

<210> SEQ ID NO 188
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 188
gggcctaatt ggctt 15

<210> SEQ ID NO 189
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 189
gggcctaatt ggc 13

<210> SEQ ID NO 190
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 190
atattaatcc ccgctgc 17

<210> SEQ ID NO 191
<211> LENGTH: 9
<212> TYPE: DNA
<213> ORGANISM: Unknown
<220> FEATURE:
<223> OTHER INFORMATION: Putative Rhodopsin transcription regulatory factors

<400> SEQUENCE: 191 gcggggatt 9

<210> SEQ ID NO 192
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 192
ggggattaat atg 13

<210> SEQ ID NO 193
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 193
cataatcata ttaatcc 17

<210> SEQ ID NO 194
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 194
attaatatga ttatgaa 17

<210> SEQ ID NO 195
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 195
attaatatga ttatg 15

<210> SEQ ID NO 196
<211> LENGTH: 21
<212> TYPE: DNA
<213> ORGANISM: Unknown
<220> FEATURE:
<223> OTHER INFORMATION: Putative Rhodopsin transcription regulatory factors

<400> SEQUENCE: 196
ttaatatgat tatgaacacc c 21

<210> SEQ ID NO 197
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 197
atgaacaccc ccaat 15

<210> SEQ ID NO 198
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 198
acccccaatc tccca 15

<210> SEQ ID NO 199
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 199
ccccaatctc ccaga 15

<210> SEQ ID NO 200
<211> LENGTH: 21
<212> TYPE: DNA
<213> ORGANISM: Unknown
<220> FEATURE:
<223> OTHER INFORMATION: Putative Rhodopsin transcription regulatory factors

<400> SEQUENCE: 200
atcagcatct gggagattgg g 21

<210> SEQ ID NO 201
<211> LENGTH: 13
<212> TYPE: DNA
<213> ORGANISM: Unknown
<220> FEATURE:
<223> OTHER INFORMATION: Putative Rhodopsin transcription regulatory factor

<400> SEQUENCE: 201
atctgggaga ttg 13

<210> SEQ ID NO 202

<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 202
tctcccagat gctgatt 17

<210> SEQ ID NO 203
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 203
tcagcatctg gga 13

<210> SEQ ID NO 204
<211> LENGTH: 25
<212> TYPE: DNA
<213> ORGANISM: Unknown
<220> FEATURE:
<223> OTHER INFORMATION: Putative Rhodopsin transcription regulatory factors

<400> SEQUENCE: 204
cccagatgct gattcagcca ggagc 25

<210> SEQ ID NO 205
<211> LENGTH: 25
<212> TYPE: DNA
<213> ORGANISM: Unknown
<220> FEATURE:
<223> OTHER INFORMATION: Putative Rhodopsin transcription regulatory factors

<400> SEQUENCE: 205
gctcctggct gaatcagcat ctggg 25

<210> SEQ ID NO 206
<211> LENGTH: 23
<212> TYPE: DNA
<213> ORGANISM: Unknown
<220> FEATURE:
<223> OTHER INFORMATION: Putative Rhodopsin transcription regulatory factors

<400> SEQUENCE: 206
gctcctggct gaatcagcat ctg 23

<210> SEQ ID NO 207
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 207
cctggctgaa tcagcatct 19

<210> SEQ ID NO 208
<211> LENGTH: 11
<212> TYPE: DNA

<213> ORGANISM: Unknown
<220> FEATURE:
<223> OTHER INFORMATION: Putative Rhodopsin transcription regulatory factors

<400> SEQUENCE: 208
gctgattcag c 11

<210> SEQ ID NO 209
<211> LENGTH: 11
<212> TYPE: DNA
<213> ORGANISM: Unknown
<220> FEATURE:
<223> OTHER INFORMATION: Putative Rhodopsin transcription regulatory factors

<400> SEQUENCE: 209
gctgaatcag c 11

<210> SEQ ID NO 210
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 210
ctcctaagct cctggct 17

<210> SEQ ID NO 211
<211> LENGTH: 23
<212> TYPE: DNA
<213> ORGANISM: Unknown
<220> FEATURE:
<223> OTHER INFORMATION: Putative Rhodopsin transcription regulatory factors

<400> SEQUENCE: 211
gtgacctccc cctcctaagc tcc 23

<210> SEQ ID NO 212
<211> LENGTH: 25
<212> TYPE: DNA
<213> ORGANISM: Unknown
<220> FEATURE:
<223> OTHER INFORMATION: Putative Rhodopsin transcription regulatory factors

<400> SEQUENCE: 212
gcttaggagg gggaggtcac tttat 25

<210> SEQ ID NO 213
<211> LENGTH: 23
<212> TYPE: DNA
<213> ORGANISM: Unknown
<220> FEATURE:
<223> OTHER INFORMATION: Putative Rhodopsin transcription regulatory factors

<400> SEQUENCE: 213
aaagtgacct ccccctccta agc 23

<210> SEQ ID NO 214
<211> LENGTH: 17
<212> TYPE: DNA
<213> ORGANISM: Unknown
<220> FEATURE:

<223> OTHER INFORMATION: Putative Rhodopsin transcription regulatory factors

<400> SEQUENCE: 214
taggaggggg aggtcac 17

<210> SEQ ID NO 215
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 215
gtgacctccc cctcc 15

<210> SEQ ID NO 216
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 216
agggggaggt cactttata 19

<210> SEQ ID NO 217
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 217
ccttataaag tgacctc 17

<210> SEQ ID NO 218
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 218
agacccttat aaagtgacc 19

<210> SEQ ID NO 219
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 219
gtcactttat aagggtctg 19

<210> SEQ ID NO 220
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 220
ctttataagg gtctggg 17

<210> SEQ ID NO 221
<211> LENGTH: 21
<212> TYPE: DNA
<213> ORGANISM: Unknown
<220> FEATURE:
<223> OTHER INFORMATION: Putative Rhodopsin transcription regulatory factors

<400> SEQUENCE: 221 gacccccca gacccttata a 21

<210> SEQ ID NO 222
<211> LENGTH: 23
<212> TYPE: DNA
<213> ORGANISM: Unknown
<220> FEATURE:
<223> OTHER INFORMATION: Putative Rhodopsin transcription regulatory factors

<400> SEQUENCE: 222
tctgaccccc ccagaccctt ata 23

<210> SEQ ID NO 223
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 223 ctgaccccc cagac 15

<210> SEQ ID NO 224
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 224 tctgggggg tca 13

<210> SEQ ID NO 225
<211> LENGTH: 25
<212> TYPE: DNA
<213> ORGANISM: Unknown
<220> FEATURE:
<223> OTHER INFORMATION: Putative Rhodopsin transcription regulatory factors

<400> SEQUENCE: 225
tcagggctcc agctggatga ctctg 25

<210> SEQ ID NO 226
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 226
tcatccagct ggagccc 17

<210> SEQ ID NO 227
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 227
cagccactca gggct 15

<210> SEQ ID NO 228
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 228
tcagccactc agggc 15

<210> SEQ ID NO 229
<211> LENGTH: 25
<212> TYPE: DNA
<213> ORGANISM: Unknown
<220> FEATURE:
<223> OTHER INFORMATION: Putative Rhodopsin transcription regulatory factors

<400> SEQUENCE: 229
tgctcccacc caagaatgct gcgaa 25

<210> SEQ ID NO 230
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 230
cagcattctt gggtggg 17

<210> SEQ ID NO 231
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 231
tcccacccaa gaatgct 17

<210> SEQ ID NO 232
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 232
tcttgggtgg gagcagc 17

<210> SEQ ID NO 233
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 233
ttgggtggga gcagcca 17

<210> SEQ ID NO 234
<211> LENGTH: 15
<212> TYPE: DNA
<213> ORGANISM: Unknown
<220> FEATURE:
<223> OTHER INFORMATION: Putative Rhodopsin transcription regulatory factor

<400> SEQUENCE: 234
tgggtgggag cagcc 15

<210> SEQ ID NO 235
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 235
gagcagccac gggtcag 17

<210> SEQ ID NO 236
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 236
ctgacccgtg gctgc 15

<210> SEQ ID NO 237
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 237
cagccacggg tcagc 15

<210> SEQ ID NO 238
<211> LENGTH: 29
<212> TYPE: DNA
<213> ORGANISM: Unknown
<220> FEATURE:
<223> OTHER INFORMATION: Putative Rhodopsin transcription regulatory factors

<400> SEQUENCE: 238
cacaagggcc acagccatga atggcacag 29

<210> SEQ ID NO 239
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 239
ggccacagcc atgaatggc 19

<210> SEQ ID NO 240
<211> LENGTH: 29
<212> TYPE: DNA
<213> ORGANISM: Unknown
<220> FEATURE:
<223> OTHER INFORMATION: Putative Rhodopsin transcription regulatory factors

<400> SEQUENCE: 240
catgaatggc acagaagtcc tgagcccca 29

<210> SEQ ID NO 241
<211> LENGTH: 25
<212> TYPE: DNA
<213> ORGANISM: Unknown
<220> FEATURE:
<223> OTHER INFORMATION: Putative Rhodopsin transcription regulatory factors

<400> SEQUENCE: 241
catggggctc aggacttctg tgcca 25

<210> SEQ ID NO 242
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 242
attctgtttg acatggg 17

<210> SEQ ID NO 243
<211> LENGTH: 11
<212> TYPE: DNA
<213> ORGANISM: Unknown
<220> FEATURE:
<223> OTHER INFORMATION: Putative Rhodopsin transcription regulatory factors

<400> SEQUENCE: 243
ccatgtcaaa c 11

<210> SEQ ID NO 244
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 244
gtgcccctaa tcctcaact 19

<210> SEQ ID NO 245
<211> LENGTH: 17

<212> TYPE: DNA
<213> ORGANISM: Unknown
<220> FEATURE:
<223> OTHER INFORMATION: Putative Rhodopsin transcription regulatory factors

<400> SEQUENCE: 245
cccctaatcc tcaacta 17

<210> SEQ ID NO 246
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 246
agttgaggat taggg 15

<210> SEQ ID NO 247
<211> LENGTH: 21
<212> TYPE: DNA
<213> ORGANISM: Unknown
<220> FEATURE:
<223> OTHER INFORMATION: Putative Rhodopsin transcription regulatory factors

<400> SEQUENCE: 247
ctaggcgcaa attccaatcc t 21

<210> SEQ ID NO 248
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 248
tggaatttgc gcc 13

<210> SEQ ID NO 249
<211> LENGTH: 9
<212> TYPE: DNA
<213> ORGANISM: Unknown
<220> FEATURE:
<223> OTHER INFORMATION: Putative Rhodopsin transcription regulatory factors

<400> SEQUENCE: 249 tggaatttg 9

<210> SEQ ID NO 250
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 250
actagaccaa agaggat 17

<210> SEQ ID NO 251
<211> LENGTH: 21
<212> TYPE: DNA
<213> ORGANISM: Unknown

<220> FEATURE:
<223> OTHER INFORMATION: Putative Rhodopsin transcription regulatory
factors

<400> SEQUENCE: 251
tctagtaccc cgggggcagc c 21

<210> SEQ ID NO 252
<211> LENGTH: 23
<212> TYPE: DNA
<213> ORGANISM: Unknown
<220> FEATURE:
<223> OTHER INFORMATION: Putative Rhodopsin transcription regulatory
factors

<400> SEQUENCE: 252
ccgggggcag ccccctctaa cct 23

<210> SEQ ID NO 253
<211> LENGTH: 13
<212> TYPE: DNA
<213> ORGANISM: Unknown
<220> FEATURE:
<223> OTHER INFORMATION: Putative Rhodopsin transcription regulatory
factors

<400> SEQUENCE: 253
ggggctgccc ccg 13

<210> SEQ ID NO 254
<211> LENGTH: 13
<212> TYPE: DNA
<213> ORGANISM: Unknown
<220> FEATURE:
<223> OTHER INFORMATION: Putative Rhodopsin transcription regulatory
factors

<400> SEQUENCE: 254
agggggctgc ccc 13

<210> SEQ ID NO 255
<211> LENGTH: 23
<212> TYPE: DNA
<213> ORGANISM: Homo sapiens

<400> SEQUENCE: 255
cagccccctc taaccttggg cct 23

<210> SEQ ID NO 256
<211> LENGTH: 13
<212> TYPE: DNA
<213> ORGANISM: Unknown
<220> FEATURE:
<223> OTHER INFORMATION: Putative Rhodopsin transcription regulatory
factors

<400> SEQUENCE: 256
ggcccaaggt tag 13

<210> SEQ ID NO 257
<211> LENGTH: 25
<212> TYPE: DNA
<213> ORGANISM: Unknown
<220> FEATURE:
<223> OTHER INFORMATION: Putative Rhodopsin transcription regulatory
factors

<400> SEQUENCE: 257
ttgggcctca gcagcagggg aggcc 25

<210> SEQ ID NO 258
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 258
ctcagcagca ggggagg 17

<210> SEQ ID NO 259
<211> LENGTH: 21
<212> TYPE: DNA
<213> ORGANISM: Unknown
<220> FEATURE:
<223> OTHER INFORMATION: Putative Rhodopsin transcription regulatory factors

<400> SEQUENCE: 259
ctcagcagca ggggaggcca c 21

<210> SEQ ID NO 260
<211> LENGTH: 23
<212> TYPE: DNA
<213> ORGANISM: Unknown
<220> FEATURE:
<223> OTHER INFORMATION: Putative Rhodopsin transcription regulatory factors

<400> SEQUENCE: 260
ggggtggcct cccctgctgc tga 23

<210> SEQ ID NO 261
<211> LENGTH: 23
<212> TYPE: DNA
<213> ORGANISM: Unknown
<220> FEATURE:
<223> OTHER INFORMATION: Putative Rhodopsin transcription regulatory factors

<400> SEQUENCE: 261
ggggaggcca cccctacacc ttc 23

<210> SEQ ID NO 262
<211> LENGTH: 21
<212> TYPE: DNA
<213> ORGANISM: Unknown
<220> FEATURE:
<223> OTHER INFORMATION: Putative Rhodopsin transcription regulatory factors

<400> SEQUENCE: 262
gggggaaggt gtaggggtgg c 21

<210> SEQ ID NO 263
<211> LENGTH: 23
<212> TYPE: DNA
<213> ORGANISM: Unknown
<220> FEATURE:
<223> OTHER INFORMATION: Putative Rhodopsin transcription regulatory factors

<400> SEQUENCE: 263
ccttccccca gccacagcca tcc 23

<210> SEQ ID NO 264
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 264
tggctggggg aag 13

<210> SEQ ID NO 265
<211> LENGTH: 9
<212> TYPE: DNA
<213> ORGANISM: Unknown
<220> FEATURE:
<223> OTHER INFORMATION: Putative Rhodopsin transcription regulatory factors

<400> SEQUENCE: 265 tgggggaag 9

<210> SEQ ID NO 266
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 266
ggctgtggct ggggg 15

<210> SEQ ID NO 267
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 267
tctgcacagg cgctgct 17

<210> SEQ ID NO 268
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 268
gcagcgcctg tgcagaa 17

<210> SEQ ID NO 269
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 269
tgtgcagaat gaa 13

<210> SEQ ID NO 270
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 270
ggctccttaa ttttttttt 19

<210> SEQ ID NO 271
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 271
ctccttaatt ttttt 15

<210> SEQ ID NO 272
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 272
tttttttttt aagaaataa 19

<210> SEQ ID NO 273
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 273
tatttcttaa aaaaaaa 17

<210> SEQ ID NO 274
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 274
ttttttaaga aataa 15

<210> SEQ ID NO 275
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 275
cattaattat ttcttaa 17

<210> SEQ ID NO 276
<211> LENGTH: 17

<212> TYPE: DNA
<213> ORGANISM: Unknown
<220> FEATURE:
<223> OTHER INFORMATION: Putative Rhodopsin transcription regulatory factors

<400> SEQUENCE: 276
tcattaatta tttctta 17

<210> SEQ ID NO 277
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 277
gcctcattaa ttatttctt 19

<210> SEQ ID NO 278
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 278
aagaaataat taatgaggc 19

<210> SEQ ID NO 279
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 279
aagaaataat taatg 15

<210> SEQ ID NO 280
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 280
agaaataatt aat 13

<210> SEQ ID NO 281
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 281
aaataattaa tgaggct 17

<210> SEQ ID NO 282
<211> LENGTH: 15
<212> TYPE: DNA
<213> ORGANISM: Unknown

<220> FEATURE:
<223> OTHER INFORMATION: Putative Rhodopsin transcription regulatory factors

<400> SEQUENCE: 282
cctcattaat tattt 15

<210> SEQ ID NO 283
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 283
aaataattaa tga 13

<210> SEQ ID NO 284
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 284
ctcattaatt att 13

<210> SEQ ID NO 285
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 285
aataattaat gaggc 15

<210> SEQ ID NO 286
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 286
aataattaat gag 13

<210> SEQ ID NO 287
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 287
taattaatga ggctcct 17

<210> SEQ ID NO 288
<211> LENGTH: 25
<212> TYPE: DNA
<213> ORGANISM: Unknown
<220> FEATURE:
<223> OTHER INFORMATION: Putative Rhodopsin transcription regulatory factors

<400> SEQUENCE: 288
tcccaggtga gtgaggagcc tcatt 25

<210> SEQ ID NO 289
<211> LENGTH: 11
<212> TYPE: DNA
<213> ORGANISM: Unknown
<220> FEATURE:
<223> OTHER INFORMATION: Putative Rhodopsin transcription regulatory factors

<400> SEQUENCE: 289
ggtgagtgag g 11

<210> SEQ ID NO 290
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 290
cactcacctg gga 13

<210> SEQ ID NO 291
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 291
caggctgtcc caggtgagt 19

<210> SEQ ID NO 292
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 292
ctggccttgg ggaac 15

<210> SEQ ID NO 293
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 293
gttccccaag gccagcggg 19

<210> SEQ ID NO 294
<211> LENGTH: 9
<212> TYPE: DNA
<213> ORGANISM: Unknown
<220> FEATURE:
<223> OTHER INFORMATION: Putative Rhodopsin transcription regulatory factors

<400> SEQUENCE: 294 ttggggaac 9

<210> SEQ ID NO 295
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 295
tccccaaggc cag 13

<210> SEQ ID NO 296
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 296
ggcacacatc ccgctgg 17

<210> SEQ ID NO 297
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 297
agcgggatgt gtgcc 15

<210> SEQ ID NO 298
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 298
ggaggagggg cac 13

<210> SEQ ID NO 299
<211> LENGTH: 25
<212> TYPE: DNA
<213> ORGANISM: Unknown
<220> FEATURE:
<223> OTHER INFORMATION: Putative Rhodopsin transcription regulatory factors

<400> SEQUENCE: 299
gatgagttgg gaggaggagg ggcac 25

<210> SEQ ID NO 300
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 300
cctgaaagat gagttgg 17

<210> SEQ ID NO 301
<211> LENGTH: 25
<212> TYPE: DNA
<213> ORGANISM: Unknown
<220> FEATURE:
<223> OTHER INFORMATION: Putative Rhodopsin transcription regulatory factors

<400> SEQUENCE: 301
tcctcgtgtt cctgaaagat gagtt 25

<210> SEQ ID NO 302
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 302
tgaaagatga gtt 13

<210> SEQ ID NO 303
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 303
cgtgttcctg aaagatgag 19

<210> SEQ ID NO 304
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 304
catctttcag gaacacgag 19

<210> SEQ ID NO 305
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 305
aatcctcgtg ttcct 15

<210> SEQ ID NO 306
<211> LENGTH: 25
<212> TYPE: DNA
<213> ORGANISM: Unknown
<220> FEATURE:
<223> OTHER INFORMATION: Putative Rhodopsin transcription regulatory factors

<400> SEQUENCE: 306
ttccagaaag caagaatcct cgtgt 25

<210> SEQ ID NO 307
<211> LENGTH: 25
<212> TYPE: DNA
<213> ORGANISM: Unknown
<220> FEATURE:
<223> OTHER INFORMATION: Putative Rhodopsin transcription regulatory factors

<400> SEQUENCE: 307
ggacactttt ccagaaagca agaat 25

<210> SEQ ID NO 308
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 308
acttttccag aaagcaaga 19

<210> SEQ ID NO 309
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 309
ttgctttctg gaaaagtgt 19

<210> SEQ ID NO 310
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 310
tgctttctgg aaaagtg 17

<210> SEQ ID NO 311
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 311
tctggaaaag tgtcccagc 19

<210> SEQ ID NO 312
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 312
tagggataag tgt 13

<210> SEQ ID NO 313

<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 313
agggataagt gtcta 15

<210> SEQ ID NO 314
<211> LENGTH: 19
<212> TYPE: DNA
<213> ORGANISM: Unknown
<220> FEATURE:
<223> OTHER INFORMATION: Putative Rhodopsin transcription regulatory factor

<400> SEQUENCE: 314
ccattctgtg ctagacact 19

<210> SEQ ID NO 315
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 315
agcacagaat ggg 13

<210> SEQ ID NO 316
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 316
gtgcttaata aatgc 15

<210> SEQ ID NO 317
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 317
tgcttaataa atgctgg 17

<210> SEQ ID NO 318
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 318
tgctggatgg atgcagg 17

<210> SEQ ID NO 319
<211> LENGTH: 27
<212> TYPE: DNA

<213> ORGANISM: Unknown
<220> FEATURE:
<223> OTHER INFORMATION: Putative Rhodopsin transcription regulatory
factors

<400> SEQUENCE: 319
atggatgcag gaaggaatgg aggaatg 27

<210> SEQ ID NO 320
<211> LENGTH: 17
<212> TYPE: DNA
<213> ORGANISM: Unknown
<220> FEATURE:
<223> OTHER INFORMATION: Putative Rhodopsin transcription regulatory
factors

<400> SEQUENCE: 320
ggatgcagga aggaatg 17

<210> SEQ ID NO 321
<211> LENGTH: 13
<212> TYPE: DNA
<213> ORGANISM: Unknown
<220> FEATURE:
<223> OTHER INFORMATION: Putative Rhodopsin transcription regulatory
factors

<400> SEQUENCE: 321
caggaaggaa tgg 13

<210> SEQ ID NO 322
<211> LENGTH: 13
<212> TYPE: DNA
<213> ORGANISM: Unknown
<220> FEATURE:
<223> OTHER INFORMATION: Putative Rhodopsin transcription regulatory
factors

<400> SEQUENCE: 322
aggaaggaat gga 13

<210> SEQ ID NO 323
<211> LENGTH: 17
<212> TYPE: DNA
<213> ORGANISM: Unknown
<220> FEATURE:
<223> OTHER INFORMATION: Putative Rhodopsin transcription regulatory
factors

<400> SEQUENCE: 323
ttcctccatt ccttcct 17

<210> SEQ ID NO 324
<211> LENGTH: 17
<212> TYPE: DNA
<213> ORGANISM: Unknown
<220> FEATURE:
<223> OTHER INFORMATION: Putative Rhodopsin transcription regulatory
factors

<400> SEQUENCE: 324
gaatggagga atgaatg 17

<210> SEQ ID NO 325
<211> LENGTH: 13
<212> TYPE: DNA
<213> ORGANISM: Unknown
<220> FEATURE:

<223> OTHER INFORMATION: Putative Rhodopsin transcription regulatory
      factors

<400> SEQUENCE: 325
atggaggaat gaa 13

<210> SEQ ID NO 326
<211> LENGTH: 17
<212> TYPE: DNA
<213> ORGANISM: Unknown
<220> FEATURE:
<223> OTHER INFORMATION: Putative Rhodopsin transcription regulatory
      factors

<400> SEQUENCE: 326
cccattcatt cctccat 17

<210> SEQ ID NO 327
<211> LENGTH: 13
<212> TYPE: DNA
<213> ORGANISM: Unknown
<220> FEATURE:
<223> OTHER INFORMATION: Putative Rhodopsin transcription regulatory
      factors

<400> SEQUENCE: 327
aggaatgaat ggg 13

<210> SEQ ID NO 328
<211> LENGTH: 19
<212> TYPE: DNA
<213> ORGANISM: Unknown
<220> FEATURE:
<223> OTHER INFORMATION: Putative Rhodopsin transcription regulatory
      factors

<400> SEQUENCE: 328
atgaatggga aggtctaga 19

<210> SEQ ID NO 329
<211> LENGTH: 15
<212> TYPE: DNA
<213> ORGANISM: Unknown
<220> FEATURE:
<223> OTHER INFORMATION: Putative Rhodopsin transcription regulatory
      factor

<400> SEQUENCE: 329
tgaatgggaa ggtct 15

<210> SEQ ID NO 330
<211> LENGTH: 13
<212> TYPE: DNA
<213> ORGANISM: Unknown
<220> FEATURE:
<223> OTHER INFORMATION: Putative Rhodopsin transcription regulatory
      factors

<400> SEQUENCE: 330
gaatgggaag gtc 13

<210> SEQ ID NO 331
<211> LENGTH: 19
<212> TYPE: DNA
<213> ORGANISM: Unknown
<220> FEATURE:
<223> OTHER INFORMATION: Putative Rhodopsin transcription regulatory
      factors

<400> SEQUENCE: 331
atgggaaggt ctagagcat 19

<210> SEQ ID NO 332
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 332
aggctccatg ctc 13

<210> SEQ ID NO 333
<211> LENGTH: 27
<212> TYPE: DNA
<213> ORGANISM: Unknown
<220> FEATURE:
<223> OTHER INFORMATION: Putative Rhodopsin transcription regulatory factors

<400> SEQUENCE: 333
atgtgggcgg gtgagcatgg cttctag 27

<210> SEQ ID NO 334
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 334
gtgggcgggt gagcatg 17

<210> SEQ ID NO 335
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 335
atgtgggcgg gtgag 15

<210> SEQ ID NO 336
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 336
ttaattaaat gtggg 15

<210> SEQ ID NO 337
<211> LENGTH: 21
<212> TYPE: DNA
<213> ORGANISM: Unknown
<220> FEATURE:
<223> OTHER INFORMATION: Putative Rhodopsin transcription regulatory factors

<400> SEQUENCE: 337
ccacatttaa ttaacagctg a 21

<210> SEQ ID NO 338
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 338
cagctgttaa ttaaatgtg 19

<210> SEQ ID NO 339
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 339
cacatttaat taaca 15

<210> SEQ ID NO 340
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 340
cacatttaat taaca 15

<210> SEQ ID NO 341
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 341
acatttaatt aac 13

<210> SEQ ID NO 342
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 342
catttaatta acagctg 17

<210> SEQ ID NO 343
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 343
gctgttaatt aaatg 15

<210> SEQ ID NO 344
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 344
catttaatta acagctg 17

<210> SEQ ID NO 345
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 345
tgttaattaa atg 13

<210> SEQ ID NO 346
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 346
agctgttaat taaat 15

<210> SEQ ID NO 347
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 347
agctgttaat taaat 15

<210> SEQ ID NO 348
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 348
atttaattaa cag 13

<210> SEQ ID NO 349
<211> LENGTH: 25
<212> TYPE: DNA
<213> ORGANISM: Unknown
<220> FEATURE:
<223> OTHER INFORMATION: Putative Rhodopsin transcription regulatory factors

<400> SEQUENCE: 349
tcagggactc agctgttaat taaat 25

<210> SEQ ID NO 350
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 350
ctcagctgtt aattaaa 17

<210> SEQ ID NO 351
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 351
gctgttaatt aaa 13

<210> SEQ ID NO 352
<211> LENGTH: 21
<212> TYPE: DNA
<213> ORGANISM: Unknown
<220> FEATURE:
<223> OTHER INFORMATION: Putative Rhodopsin transcription regulatory factors

<400> SEQUENCE: 352
agggactcag ctgttaatta a 21

<210> SEQ ID NO 353
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 353
ttaattaaca gctga 15

<210> SEQ ID NO 354
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 354
ggactcagct gttaatt 17

<210> SEQ ID NO 355
<211> LENGTH: 25
<212> TYPE: DNA
<213> ORGANISM: Unknown
<220> FEATURE:
<223> OTHER INFORMATION: Putative Rhodopsin transcription regulatory factors

<400> SEQUENCE: 355
attaacagct gagtccctga tgtca 25

<210> SEQ ID NO 356
<211> LENGTH: 23

<212> TYPE: DNA
<213> ORGANISM: Unknown
<220> FEATURE:
<223> OTHER INFORMATION: Putative Rhodopsin transcription regulatory factors

<400> SEQUENCE: 356
tgacatcagg gactcagctg tta 23

<210> SEQ ID NO 357
<211> LENGTH: 21
<212> TYPE: DNA
<213> ORGANISM: Unknown
<220> FEATURE:
<223> OTHER INFORMATION: Putative Rhodopsin transcription regulatory factors

<400> SEQUENCE: 357
taaggatgac atcagggact c 21

<210> SEQ ID NO 358
<211> LENGTH: 21
<212> TYPE: DNA
<213> ORGANISM: Unknown
<220> FEATURE:
<223> OTHER INFORMATION: Putative Rhodopsin transcription regulatory factors

<400> SEQUENCE: 358
agtccctgat gtcatcctta c 21

<210> SEQ ID NO 359
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 359
ctgatgtcat cct 13

<210> SEQ ID NO 360
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 360
tttctaagct cttcgag 17

<210> SEQ ID NO 361
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 361
ttgtttctaa gctcttc 17

<210> SEQ ID NO 362
<211> LENGTH: 19
<212> TYPE: DNA
<213> ORGANISM: Unknown

<220> FEATURE:
<223> OTHER INFORMATION: Putative Rhodopsin transcription regulatory factors

<400> SEQUENCE: 362
gaagagctta gaaacaaag 19

<210> SEQ ID NO 363
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 363
ttagaaacaa agagtgg 17

<210> SEQ ID NO 364
<211> LENGTH: 15
<212> TYPE: DNA
<213> ORGANISM: Unknown
<220> FEATURE:
<223> OTHER INFORMATION: Putative Rhodopsin transcription regulatory factor

<400> SEQUENCE: 364
agagtgggaa atgct 15

<210> SEQ ID NO 365
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 365
agctgggtaa agctagagc 19

<210> SEQ ID NO 366
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 366
taaggcaaat tgggccatt 19

<210> SEQ ID NO 367
<211> LENGTH: 17
<212> TYPE: DNA
<213> ORGANISM: Unknown
<220> FEATURE:
<223> OTHER INFORMATION: Putative Rhodopsin transcription regulatory factor

<400> SEQUENCE: 367
gcaaattggg ccattaa 17

<210> SEQ ID NO 368
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 368
tttaatggcc caatttg 17

<210> SEQ ID NO 369
<211> LENGTH: 21
<212> TYPE: DNA
<213> ORGANISM: Unknown
<220> FEATURE:
<223> OTHER INFORMATION: Putative Rhodopsin transcription regulatory factor

<400> SEQUENCE: 369
ctgagctttt aatggcccaa t 21

<210> SEQ ID NO 370
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 370
gcttttaatg gccca 15

<210> SEQ ID NO 371
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 371
gggccattaa aagctca 17

<210> SEQ ID NO 372
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 372
gccattaaaa gctca 15

<210> SEQ ID NO 373
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 373
attaacggtg gtg 13

<210> SEQ ID NO 374
<211> LENGTH: 25
<212> TYPE: DNA
<213> ORGANISM: Unknown
<220> FEATURE:
<223> OTHER INFORMATION: Putative Rhodopsin transcription regulatory factors

<400> SEQUENCE: 374
cctgtggata gagtgtgaaa gcaac 25

<210> SEQ ID NO 375
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 375
tccacaggat agattga 17

<210> SEQ ID NO 376
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 376
cacaggatag attgaaa 17

<210> SEQ ID NO 377
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 377
ggatagattg aaactgc 17

<210> SEQ ID NO 378
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 378
gatagattga aactgccag 19

<210> SEQ ID NO 379
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 379
tggcagtttc aatct 15

<210> SEQ ID NO 380
<211> LENGTH: 21
<212> TYPE: DNA
<213> ORGANISM: Unknown
<220> FEATURE:
<223> OTHER INFORMATION: Putative Rhodopsin transcription regulatory factors

<400> SEQUENCE: 380
ccagggtcag ggatcaggtg g 21

<210> SEQ ID NO 381
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 381
gggtcaggga tca 13

<210> SEQ ID NO 382
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 382
atcccagggt cagggatca 19

<210> SEQ ID NO 383
<211> LENGTH: 11
<212> TYPE: DNA
<213> ORGANISM: Unknown
<220> FEATURE:
<223> OTHER INFORMATION: Putative Rhodopsin transcription regulatory factors

<400> SEQUENCE: 383
gggtcaggga t 11

<210> SEQ ID NO 384
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 384
ggctggattg agcaatgag 19

<210> SEQ ID NO 385
<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 385
ggctggattg agcaatg 17

<210> SEQ ID NO 386
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 386
tggattgagc aatga 15

<210> SEQ ID NO 387
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 387
agagccaagc agcac 15

<210> SEQ ID NO 388
<211> LENGTH: 23
<212> TYPE: DNA
<213> ORGANISM: Unknown
<220> FEATURE:
<223> OTHER INFORMATION: Putative Rhodopsin transcription regulatory factors

<400> SEQUENCE: 388
tagccccagg ggactctgtg ctg 23

<210> SEQ ID NO 389
<211> LENGTH: 23
<212> TYPE: DNA
<213> ORGANISM: Unknown
<220> FEATURE:
<223> OTHER INFORMATION: Putative Rhodopsin transcription regulatory factors

<400> SEQUENCE: 389
acagagtccc ctggggctag agg 23

<210> SEQ ID NO 390
<211> LENGTH: 15
<212> TYPE: DNA
<213> ORGANISM: Unknown
<220> FEATURE:
<223> OTHER INFORMATION: Putative Rhodopsin transcription regulatory factors

<400> SEQUENCE: 390
ctagccccag gggac 15

<210> SEQ ID NO 391
<211> LENGTH: 23
<212> TYPE: DNA
<213> ORGANISM: Unknown
<220> FEATURE:
<223> OTHER INFORMATION: Putative Rhodopsin transcription regulatory factors

<400> SEQUENCE: 391
gcctcctcca cctctagccc cag 23

<210> SEQ ID NO 392
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 392
tcctgggaat ggg 13

<210> SEQ ID NO 393

<211> LENGTH: 17
<212> TYPE: DNA
<213> ORGANISM: Unknown
<220> FEATURE:
<223> OTHER INFORMATION: Putative Rhodopsin transcription regulatory factors

<400> SEQUENCE: 393
ttttcccatt cccagga 17

<210> SEQ ID NO 394
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 394
gggaatggga aaaacccca 19

<210> SEQ ID NO 395
<211> LENGTH: 23
<212> TYPE: DNA
<213> ORGANISM: Unknown
<220> FEATURE:
<223> OTHER INFORMATION: Putative Rhodopsin transcription regulatory factors

<400> SEQUENCE: 395
gggaatggga aaaaccccaa ctt 23

<210> SEQ ID NO 396
<211> LENGTH: 14
<212> TYPE: DNA
<213> ORGANISM: Unknown
<220> FEATURE:
<223> OTHER INFORMATION: Putative Rhodopsin transcription regulatory factor

<400> SEQUENCE: 396
ggaatgggaa aaac 14

<210> SEQ ID NO 397
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 397
gaatgggaaa aac 13

<210> SEQ ID NO 398
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 398
tggggttttt ccc 13

<210> SEQ ID NO 399
<211> LENGTH: 11
<212> TYPE: DNA

<213> ORGANISM: Unknown
<220> FEATURE:
<223> OTHER INFORMATION: Putative Rhodopsin transcription regulatory factors

<400> SEQUENCE: 399
ggaaaaaccc c 11

<210> SEQ ID NO 400
<211> LENGTH: 19
<212> TYPE: DNA
<213> ORGANISM: Unknown
<220> FEATURE:
<223> OTHER INFORMATION: Putative Rhodopsin transcription regulatory factors

<400> SEQUENCE: 400
gaccccaaag ttggggttt 19

<210> SEQ ID NO 401
<211> LENGTH: 13
<212> TYPE: DNA
<213> ORGANISM: Unknown
<220> FEATURE:
<223> OTHER INFORMATION: Putative Rhodopsin transcription regulatory factors

<400> SEQUENCE: 401
ccaaagttgg ggt 13

<210> SEQ ID NO 402
<211> LENGTH: 427
<212> TYPE: DNA
<213> ORGANISM: Artificial Sequence
<220> FEATURE:
<223> OTHER INFORMATION: Sequence for CMV Enhancer

<400> SEQUENCE: 402
ccgcgttaca taacttacgg taaatggccc gcctggctga ccgcccaacg acccccgccc 60
attgacgtca ataatgacgt atgttcccat agtaacgcca atagggactt tccattgacg 120
tcaatgggtg gagtatttac ggtaaactgc ccacttggca gtacatcaag tgtatcatat 180
gccaagtacg ccccctattg acgtcaatga cggtaaatgg cccgcctggc attatgccca 240
gtacatgacc ttatgggact ttcctacttg gcagtacatc tacgtattag tcatcgctat 300
taccatggtg atgcggtttt ggcagtacat caatgggcgt ggatagcggt ttgactcacg 360
gggatttcca agtctccacc ccattgacgt caatgggagt ttgttttggc accaaaatca 420
acgggac 427

<210> SEQ ID NO 403
<211> LENGTH: 185
<212> TYPE: DNA
<213> ORGANISM: Artificial Sequence
<220> FEATURE:
<223> OTHER INFORMATION: Sequence for rhodopsin promoter conserved Region A

<400> SEQUENCE: 403
gagtgtctaa ttgcttatga tcatgcatgc tctctctccc actaaacatt tattaatgtg 60
ttaggatttc cattagcgcg tgccttgaac tgaaatcatt tgcatatggc tgggaaaaag 120
tggggtgagg gaggaaacag tgccagctcc ccaacaggcg tcaatcacag tgacagatca 180
gatgg 185

<210> SEQ ID NO 404
<211> LENGTH: 72
<212> TYPE: DNA
<213> ORGANISM: Artificial Sequence
<220> FEATURE:
<223> OTHER INFORMATION: Sequence for rhodopsin promoter enhancer element (contains CrxD(-) & CrxE (+) & NRL binding sites)

<400> SEQUENCE: 404
tttctgcagc ggggattaat atgattatga acaccccccaa tctcccagat gctgattcag 60
ccaggaggta cc 72

<210> SEQ ID NO 405
<211> LENGTH: 14
<212> TYPE: DNA
<213> ORGANISM: Artificial Sequence
<220> FEATURE:
<223> OTHER INFORMATION: Sequence for Crx D(-) enhancer

<400> SEQUENCE: 405
gcggggatta atat 14

<210> SEQ ID NO 406
<211> LENGTH: 17
<212> TYPE: DNA
<213> ORGANISM: Artificial Sequence
<220> FEATURE:
<223> OTHER INFORMATION: Sequence for CrxE (+) Enhancer

<400> SEQUENCE: 406
tgaacacccc caatctc 17

<210> SEQ ID NO 407
<211> LENGTH: 12
<212> TYPE: DNA
<213> ORGANISM: Artificial Sequence
<220> FEATURE:
<223> OTHER INFORMATION: Sequence for NRL enhancer

<400> SEQUENCE: 407
tgctgattca gc 12

<210> SEQ ID NO 408
<211> LENGTH: 76
<212> TYPE: DNA
<213> ORGANISM: Artificial Sequence
<220> FEATURE:
<223> OTHER INFORMATION: Sequence for rhodopsin promoter conserved region B

<400> SEQUENCE: 408
tctgctgacc cagcaacact ctttccttct gaggcttaag agctattagc gtaggtgact 60
cagtccctaa tcctcc 76

<210> SEQ ID NO 409
<211> LENGTH: 168
<212> TYPE: DNA
<213> ORGANISM: Homo sapiens

<400> SEQUENCE: 409
gacctgccta ggactctgtg gccgactata ggcgtctccc atcccctaca ccttccccca 60
gccacagcca tcccaccagg agcagcgcct gtgcagaatg aacgaagtca cataggctcc 120
ttaatttttt ttttttttt aagaaataat taatgaggct cctcactc 168

<210> SEQ ID NO 410
<211> LENGTH: 259
<212> TYPE: DNA
<213> ORGANISM: Homo sapiens

<400> SEQUENCE: 410
acctgggaca gcctgagaag ggacatccac caagacctac tgatctggag tcccacgttc 60
cccaaggcca gcgggatgtg tgcccctcct cctcccaact catctttcag gaacacgagg 120
attcttgctt tctggaaaag tgtcccagct tagggataag tgtctagcac agaatggggc 180
acacagtagg tgcttaataa atgctggatg gatgcaggaa ggaatggagg aatgaatggg 240
aagggagaac ataggatcc 259

<210> SEQ ID NO 411
<211> LENGTH: 48
<212> TYPE: DNA
<213> ORGANISM: Simian virus 40

<400> SEQUENCE: 411
aataaaggaa atttattttc atgcaatagt gtgttggttt tttgtgtg 48

<210> SEQ ID NO 412
<211> LENGTH: 593
<212> TYPE: DNA
<213> ORGANISM: Artificial Sequence
<220> FEATURE:
<223> OTHER INFORMATION: Plasmid pSK11

<400> SEQUENCE: 412
ggatccaatc aacctctgga ttacaaaatt tgtgaaagat tgactggtat tcttaactat 60
gttgctcctt ttacgctatg tggatacgct gctttaatgc ctttgtatca tgctattgct 120
tcccgtatgg ctttcatttt ctcctccttg tataaatcct ggttgctgtc tctttatgag 180
gagttgtggc ccgttgtcag gcaacgtggc gtggtgtgca ctgtgtttgc tgacgcaacc 240
cccactggtt ggggcattgc caccacctgt cagctccttt ccgggacttt cgctttcccc 300
ctccctattg ccacggcgga actcatcgcc gcctgccttg cccgctgctg gacaggggct 360
cggctgttgg gcactgacaa ttccgtggtg ttgtcgggga agctgacgtc ctttccatgg 420
ctgctcgcct gtgttgccac ctggattctg cgcgggacgt ccttctgcta cgtcccttcg 480
gccctcaatc cagcggacct tccttcccgc ggcctgctgc cggctctgcg gcctcttccg 540
cgtcttcgcc ttcgccctca gacgagtcgg atctcccttt gggccgcctc ccc 593

<210> SEQ ID NO 413
<211> LENGTH: 581
<212> TYPE: DNA
<213> ORGANISM: Artificial Sequence
<220> FEATURE:
<223> OTHER INFORMATION: Plasmid pSin11

<400> SEQUENCE: 413
gagcatctta ccgccattta ttcccatatt tgttctgttt ttcttgattt gggtatacat 60
ttaaatgtta ataaaacaaa atggtggggc aatcatttac atttttaggg atatgtaatt 120
actagttcag gtgtattgcc acaagacaaa catgttaaga aactttcccg ttatttacgc 180
tctgttcctg ttaatcaacc tctggattac aaaatttgtg aaagattgac tgatattctt 240
aactatgttg ctccttttac gctgtgtgga tatgctgctt tatagcctct gtatctagct 300
attgcttccc gtacggcttt cgttttctcc tccttgtata aatcctggtt gctgtctctt 360
ttagaggagt tgtggcccgt tgtccgtcaa cgtggcgtgg tgtgctctgt gtttgctgac 420
gcaaccccca ctggctgggg cattgccacc acctgtcaac tcctttctgg gactttcgct 480
ttccccctcc cgatcgccac ggcagaactc atcgccgcct gccttgcccg ctgctggaca 540
ggggctaggt tgctgggcac tgataattcc gtggtgttgt c 581

<210> SEQ ID NO 414
<211> LENGTH: 21
<212> TYPE: DNA
<213> ORGANISM: Artificial Sequence
<220> FEATURE:
<223> OTHER INFORMATION: siRNA sequence targeting homologous sequence between human and porcine rhodopsin

<400> SEQUENCE: 414
acctctctgc atggatagtt t 21

<210> SEQ ID NO 415
<211> LENGTH: 21
<212> TYPE: DNA
<213> ORGANISM: Artificial Sequence
<220> FEATURE:
<223> OTHER INFORMATION: siRNA sequence targeting homologous sequence between human and porcine rhodopsin

<400> SEQUENCE: 415
catgttcgtg gtccacttct t 21

<210> SEQ ID NO 416
<211> LENGTH: 64
<212> TYPE: DNA
<213> ORGANISM: Artificial Sequence
<220> FEATURE:
<223> OTHER INFORMATION: Top strand CC miRNA oligonucleotide targeting human rhodopsin

<400> SEQUENCE: 416
tgctgcttct tgtgctggac ggtgacgttt tggccactga ctgacgtcac cgtagcacaa 60
gaag 64

<210> SEQ ID NO 417
<211> LENGTH: 64
<212> TYPE: DNA
<213> ORGANISM: Artificial Sequence
<220> FEATURE:
<223> OTHER INFORMATION: Bottom strand CC miRNA oligonucleotide targeting human rhodopsin

<400> SEQUENCE: 417
cctgcttctt gtgctacggt gacgtcagtc agtggccaaa acgtcaccgt ccagcacaag 60
aagc 64

<210> SEQ ID NO 418
<211> LENGTH: 64
<212> TYPE: DNA
<213> ORGANISM: Artificial Sequence
<220> FEATURE:
<223> OTHER INFORMATION: Top strand Q1 miRNA oligonucleotide targeting human rhodopsin

<400> SEQUENCE: 418
tgctggtagt agtcgattcc acacgagttt tggccactga ctgactcgtg tggtcgacta 60
ctac 64

<210> SEQ ID NO 419
<211> LENGTH: 64
<212> TYPE: DNA
<213> ORGANISM: Artificial Sequence
<220> FEATURE:
<223> OTHER INFORMATION: Bottom strand Q1 miRNA oligonucleotide targeting human rhodopsin

<400> SEQUENCE: 419
cctggtagta gtcgaccaca cgagtcagtc agtggccaaa actcgtgtgg aatcgactac 60
tacc 64

<210> SEQ ID NO 420
<211> LENGTH: 64
<212> TYPE: DNA
<213> ORGANISM: Artificial Sequence
<220> FEATURE:
<223> OTHER INFORMATION: Top strand BB miRNA oligonucleotide targeting human rhodopsin

<400> SEQUENCE: 420
tgctggtaga gcgtgaggaa gttgatgttt tggccactga ctgacatcaa ctttcacgct 60
ctac 64

<210> SEQ ID NO 421
<211> LENGTH: 64
<212> TYPE: DNA
<213> ORGANISM: Artificial Sequence
<220> FEATURE:
<223> OTHER INFORMATION: Bottom strand BB miRNA oligonucleotide targeting human rhodopsin

<400> SEQUENCE: 421
cctggtagag cgtgaaagtt gatgtcagtc agtggccaaa acatcaactt cctcacgctc 60
tacc 64

<210> SEQ ID NO 422
<211> LENGTH: 1551
<212> TYPE: DNA
<213> ORGANISM: Artificial Sequence
<220> FEATURE:
<223> OTHER INFORMATION: DNA sequence of UCOE 1.5

<400> SEQUENCE: 422
cccccggccc tccgcgccta cagctcaagc cacatccgaa gggggaggga gccgggagct 60
gcgcgcgggg ccgccggggg gaggggtggc accgcccacg ccgggcggcc acgaagggcg 120
gggcagcggg cgcgcgcgcg gcggggggag gggccggcgc cgcgcccgct gggaattggg 180
gccctagggg gagggcggag gcgccgacga ccgcggcact taccgttcgc ggcgtggcgc 240
ccggtggtcc ccaaggggag ggaaggggga ggcggggcga ggacagtgac cggagtctcc 300
tcagcggtgg cttttctgct tggcagcctc agcggctggc gccaaaaccg gactccgccc 360
acttcctcgc ccgccggtgc gagggtgtgg aatcctccag acgctggggg agggggagtt 420
gggagcttaa aaactagtac ccctttggga ccactttcag cagcgaactc tcctgtacac 480
caggggtcag ttccacagac gcgggccagg ggtgggtcat tgcggcgtga acaataattt 540
gactagaagt tgattcgggt gtttccggaa ggggccgagt caatccgccg agttggggca 600
cggaaaacaa aaagggaagg ctactaagat ttttctggcg gggggttatca ttggcgtaac 660 tgcagggacc acctcccggg ttgagggggc tggatctcca ggctgcggat taagcccctc 720
ccgtcggcgt taatttcaaa ctgcgcgacg tttctcacct gccttcgcca aggcaggggc 780

-continued

```
cgggacccta ttccaagagg tagtaactag caggactcta gccttccgca attcattgag    840

cgcatttacg gaagtaacgt cgggtactgt ctctggccgc aagggtggga ggagtacgca    900

tttggcgtaa ggtggggcgt agagccttcc cgccattggc ggcggatagg gcgtttacgc    960

gacggcctga cgtagcggaa gacgcgttag tggggggga ggttctagaa aagcggcggc    1020

agcggctcta gcggcagtag cagcagcgcc gggtcccgtg cggaggtgct cctcgcagag   1080

ttgtttctcg agcagcggca gttctcacta cagcgccagg acgagtccgg ttcgtgttcg   1140

tccgcggaga tctctctcat ctcgctcggc tgcgggaaat cgggctgaag cgactgagtc   1200

cgcgatggag gtaacgggtt tgaaatcaat gagttattga aagggcatg gcgaggccgt    1260

tggcgcctca gtggaagtcg gccagccgcc tccgtgggag agaggcagga aatcggacca   1320

attcagtagc agtggggctt aaggtttatg aacggggtct tgagcggagg cctgagcgta   1380

caaacagctt ccccaccctc agcctcccgg cgccatttcc cttcactggg ggtgggggat   1440

ggggagcttt cacatggcgg acgctgcccc gctggggtga aagtggggcg cggaggcggg   1500

aattcttatt ccctttctaa agcacgctgc ttcgggggcc acggcgtctc c            1551
```

<210> SEQ ID NO 423
<211> LENGTH: 2188
<212> TYPE: DNA
<213> ORGANISM: Artificial Sequence
<220> FEATURE:
<223> OTHER INFORMATION: DNA sequence of UCOE 2.2

<400> SEQUENCE: 423

```
aaaacagctt cacatggctt aaaatagggg accaatgtct tttccaatct aagtcccatt     60

tataataaag tccatgttcc atttttaaag gacaatcctt tcggtttaaa accaggcacg    120

attacccaaa caactcacaa cggtaaagca ctgtgaatct tctctgttct gcaatcccaa    180

cttggtttct gctcagaaac cctccctctt tccaatcggt aattaaataa caaaaggaaa    240

aaacttaaga tgcttcaacc ttcaaccccg tttcgtgaca ctttgaaaaa agaatcacct    300

cttgcaaaca cccgctcccg accccgccg ctgaagcccg gcgtccagag gcctaagcgc     360

gggtgcccac ccccacccgg gagcgcgggc ctcgtggtca gcgcatccgc ggggagaaac    420

aaaggccgcg gcacgggggc tcaagggcac tgcgccacac cgcacgcgcc tacccccgcg    480

cggccacgtt aactggcggt cgccgcagcc tcgggacagc cggccgcgcg ccgccaggct    540

cgcggacgcg ggaccacgcg ccgccctccg ggaggcccaa gtctcgaccc agccccgcgt    600

ggcgctgggg gagggggcgc ctccgccgga acgcgggtgg gggaggggag ggggaaatgc    660

gctttgtctc gaaatggggc aaccgtcgcc acagctccct accccctcga gggcagagca    720

gtccccccac taactaccgg gctggccgcg cgccaggcca gccgcgaggc caccgcccga    780

ccctccactc cttcccgcag ctcccggcgc ggggtccggc gagaagggga ggggagggga    840

gcggagaacc gggcccccgg gacgcgtgtg gcatctgaag caccaccagc gagcgagagc    900

tagagagaag gaaagccacc gacttcaccg cctccgagct gctccgggtc gcgggtctgc    960

agcgtctccg gccctccgcg cctacagctc aagccacatc cgaaggggga gggagccggg   1020

agctgcgcgc ggggccgccg gggggagggg tggcaccgcc cacgccgggc ggccacgaag   1080

ggcggggcag cgggcgcgcg cgcggcgggg ggaggggccg gcgccgcgcc cgctgggaat   1140

tggggcccta gggggagggc ggaggcgccg acgaccgcgg cacttaccgt tcgcggcgtg   1200

gcgcccggtg gtccccaagg ggagggaagg gggaggcggg gcgaggacag tgaccggagt   1260

ctcctcagcg gtggcttttc tgcttggcag cctcagcggc tggcgccaaa accggactcc   1320
```

-continued

```
gcccacttcc tcgcccgccg gtgcgagggt gtggaatcct ccagacgctg ggggaggggg   1380
agttgggagc ttaaaaacta gtacccctttt gggaccactt tcagcagcga actctcctgt   1440
acaccagggg tcagttccac agacgcgggc caggggtggg tcattgcggc gtgaacaata   1500
atttgactag aagttgattc gggtgtttcc ggaaggggcc gagtcaatcc gccgagttgg   1560
ggcacggaaa acaaaaaggg aaggctacta agatttttct ggcgggggtt atcattggcg   1620
taactgcagg gaccacctcc cgggttgagg gggctggatc tccaggctgc ggattaagcc   1680
cctcccgtcg gcgttaattt caaactgcgc gacgtttctc acctgccttc gccaaggcag   1740
gggccgggac cctattccaa gaggtagtaa ctagcaggac tctagccttc cgcaattcat   1800
tgagcgcatt tacggaagta acgtcgggta ctgtctctgg ccgcaagggt gggaggagta   1860
cgcatttggc gtaaggtggg gcgtagagcc ttcccgccat tggcggcgga tagggcgttt   1920
acgcgacggc ctgacgtagc ggaagacgcg ttagtggggg ggaaggttct agaaaagcgg   1980
cggcagcggc tctagcggca gtagcagcag cgccgggtcc cgtgcggagg tgctcctcgc   2040
agagttgttt ctcgagcagc ggcagttctc actacagcgc caggacgagt ccggttcgtg   2100
ttcgtccgcg gagatctctc tcatctcgct cggctgcggg aaatcgggct gaagcgactg   2160
atctgcagtc gaggtcgacg gtatcgat                                      2188
```

<210> SEQ ID NO 424
<211> LENGTH: 558
<212> TYPE: DNA
<213> ORGANISM: Homo sapiens

<400> SEQUENCE: 424

```
atgaagttat gggatgtcgt ggctgtctgc ctggtgctgc tccacaccgc gtccgccttc     60
ccgctgcccg ccgcaaatat gccagaggat tatcctgatc agttcgatga tgtcatggat    120
tttattcaag ccaccattaa aagactgaaa aggtcaccag ataaacaaat ggcagtgctt    180
cctagaagag agcggaatcg gcaggctgca gctgccaacc cagagaattc cagaggaaaa    240
ggtcggagag gccagagggg caaaaaccgg ggttgtgtct taactgcaat acatttaaat    300
gtcactgact tgggtctggg ctatgaaacc aaggaggaac tgatttttag gtactgcagc    360
ggctcttgcg atgcagctga gacaacgtac gacaaaatat tgaaaaactt atccagaaat    420
agaaggctgg tgagtgacaa agtagggcag gcatgttgca gacccatcgc ctttgatgat    480
gacctgtcgt ttttagatga taacctggtt taccatattc taagaaagca ttccgctaaa    540
aggtgtggat gtatctga                                                  558
```

<210> SEQ ID NO 425
<211> LENGTH: 185
<212> TYPE: PRT
<213> ORGANISM: Homo sapiens

<400> SEQUENCE: 425

```
Met Lys Leu Trp Asp Val Val Ala Val Cys Leu Val Leu Leu His Thr
1               5                   10                  15

Ala Ser Ala Phe Pro Leu Pro Ala Ala Asn Met Pro Glu Asp Tyr Pro
            20                  25                  30

Asp Gln Phe Asp Asp Val Met Asp Phe Ile Gln Ala Thr Ile Lys Arg
        35                  40                  45

Leu Lys Arg Ser Pro Asp Lys Gln Met Ala Val Leu Pro Arg Arg Glu
    50                  55                  60

Arg Asn Arg Gln Ala Ala Ala Ala Asn Pro Glu Asn Ser Arg Gly Lys
65                  70                  75                  80
```

```
Gly Arg Arg Gly Gln Arg Gly Lys Asn Arg Gly Cys Val Leu Thr Ala
                85                  90                  95

Ile His Leu Asn Val Thr Asp Leu Gly Leu Gly Tyr Glu Thr Lys Glu
            100                 105                 110

Glu Leu Ile Phe Arg Tyr Cys Ser Gly Ser Cys Asp Ala Ala Glu Thr
        115                 120                 125

Thr Tyr Asp Lys Ile Leu Lys Asn Leu Ser Arg Asn Arg Arg Leu Val
    130                 135                 140

Ser Asp Lys Val Gly Gln Ala Cys Cys Arg Pro Ile Ala Phe Asp Asp
145                 150                 155                 160

Asp Leu Ser Phe Leu Asp Asp Asn Leu Val Tyr His Ile Leu Arg Lys
                165                 170                 175

His Ser Ala Lys Arg Cys Gly Cys Ile
            180                 185


<210> SEQ ID NO 426
<211> LENGTH: 603
<212> TYPE: DNA
<213> ORGANISM: Homo sapiens

<400> SEQUENCE: 426

atggctttca cagagcattc accgctgacc cctcaccgtc gggacctctg tagccgctct      60

atctggctag caaggaagat tcgttcagac ctgactgctc ttacggaatc ctatgtgaag     120

catcagggcc tgaacaagaa catcaacctg gactctgcgg atgggatgcc agtggcaagc     180

actgatcagt ggagtgagct gaccgaggca gagcgactcc aagagaacct tcaagcttat     240

cgtaccttcc atgttttgtt ggccaggctc ttagaagacc agcaggtgca ttttacccca     300

accgaaggtg acttccatca agctatacat acccttcttc tccaagtcgc tgcctttgca     360

taccagatag aggagttaat gatactcctg gaatacaaga tcccccgcaa tgaggctgat     420

gggatgccta ttaatgttgg agatggtggt ctctttgaga agaagctgtg gggcctaaag     480

gtgctgcagg agctttcaca gtggacagta aggtccatcc atgaccttcg tttcatttct     540

tctcatcaga ctgggatccc agcacgtggg agccattata ttgctaacaa caagaaaatg     600

tag                                                                   603


<210> SEQ ID NO 427
<211> LENGTH: 200
<212> TYPE: PRT
<213> ORGANISM: Homo sapiens

<400> SEQUENCE: 427

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Ala Asp Gly Met Pro Val Ala Ser Thr Asp Gln Trp
    50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110
```

```
Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200


<210> SEQ ID NO 428
<211> LENGTH: 744
<212> TYPE: DNA
<213> ORGANISM: Homo sapiens

<400> SEQUENCE: 428

atgaccatcc ttttccttac tatggttatt tcatactttg gttgcatgaa ggctgccccc      60

atgaaagaag caaacatccg aggacaaggt ggcttggcct acccaggtgt gcggacccat     120

gggactctgg agagcgtgaa tgggcccaag gcaggttcaa gaggcttgac atcattggct     180

gacactttcg aacacgtgat agaagagctg ttggatgagg accagaaagt tcggcccaat     240

gaagaaaaca ataaggacgc agacttgtac acgtccaggg tgatgctcag tagtcaagtg     300

cctttggagc ctcctcttct ctttctgctg gaggaataca aaaattacct agatgctgca     360

aacatgtcca tgagggtccg gcgccactct gaccctgccc gccgaggggga gctgagcgtg     420

tgtgacagta ttagtgagtg ggtaacggcg gcagacaaaa agactgcagt ggacatgtcg     480

ggcgggacgg tcacagtcct tgaaaaggtc cctgtatcaa aaggccaact gaagcaatac     540

ttctacgaga ccaagtgcaa tcccatgggt tacacaaaag aaggctgcag ggcatagac      600

aaaaggcatt ggaactccca gtgccgaact acccagtcgt acgtgcgggc ccttaccatg     660

gatagcaaaa agagaattgg ctggcgattc ataaggatag acacttcttg tgtatgtaca     720

ttgaccatta aaaggggaag atag                                            744


<210> SEQ ID NO 429
<211> LENGTH: 247
<212> TYPE: PRT
<213> ORGANISM: Homo sapiens

<400> SEQUENCE: 429

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
```

```
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Arg Gly Arg
                245
```

<210> SEQ ID NO 430
<211> LENGTH: 594
<212> TYPE: DNA
<213> ORGANISM: Homo sapiens

<400> SEQUENCE: 430

```
atgcagcgct ggaaggcggc ggccttggcc tcagtgctct gcagctccgt gctgtccatc     60

tggatgtgtc gagagggcct gcttctcagc caccgcctcg gacctgcgct ggtccccctg    120

caccgcctgc ctcgaaccct ggacgcccgg attgcccgcc tggcccagta ccgtgcactc    180

ctgcaggggg ccccggatgc gatggagctg cgcgagctga cgccctgggc tgggcggccc    240

ccaggtccgc gccgtcgggc ggggccccgg cggcggcgcg cgcgtgcgcg gttgggggcg    300

cggccttgcg ggctgcgcga gctggaggtg cgcgtgagcg agctgggcct gggctacgcg    360

tccgacgaga cggtgctgtt ccgctactgc gcaggcgcct gcgaggctgc cgcgcgcgtc    420

tacgacctcg ggctgcgacg actgcgccag cggcggcgcc tgcggcggga gcgggtgcgc    480

gcgcagccct gctgccgccc gacggcctac gaggacgagg tgtccttcct ggacgcgcac    540

agccgctacc acacggtgca cgagctgtcg gcgcgcgagt gcgcctgcgt gtga          594
```

<210> SEQ ID NO 431
<211> LENGTH: 197
<212> TYPE: PRT
<213> ORGANISM: Homo sapiens

<400> SEQUENCE: 431

```
Met Gln Arg Trp Lys Ala Ala Ala Leu Ala Ser Val Leu Cys Ser Ser
1               5                   10                  15

Val Leu Ser Ile Trp Met Cys Arg Glu Gly Leu Leu Leu Ser His Arg
            20                  25                  30

Leu Gly Pro Ala Leu Val Pro Leu His Arg Leu Pro Arg Thr Leu Asp
        35                  40                  45

Ala Arg Ile Ala Arg Leu Ala Gln Tyr Arg Ala Leu Leu Gln Gly Ala
    50                  55                  60

Pro Asp Ala Met Glu Leu Arg Glu Leu Thr Pro Trp Ala Gly Arg Pro
65                  70                  75                  80
```

-continued

```
Pro Gly Pro Arg Arg Arg Ala Gly Pro Arg Arg Arg Arg Ala Arg Ala
                85                  90                  95

Arg Leu Gly Ala Arg Pro Cys Gly Leu Arg Glu Leu Glu Val Arg Val
            100                 105                 110

Ser Glu Leu Gly Leu Gly Tyr Ala Ser Asp Glu Thr Val Leu Phe Arg
        115                 120                 125

Tyr Cys Ala Gly Ala Cys Glu Ala Ala Ala Arg Val Tyr Asp Leu Gly
    130                 135                 140

Leu Arg Arg Leu Arg Gln Arg Arg Arg Leu Arg Arg Glu Arg Val Arg
145                 150                 155                 160

Ala Gln Pro Cys Cys Arg Pro Thr Ala Tyr Glu Asp Glu Val Ser Phe
                165                 170                 175

Leu Asp Ala His Ser Arg Tyr His Thr Val His Glu Leu Ser Ala Arg
            180                 185                 190

Glu Cys Ala Cys Val
        195


<210> SEQ ID NO 432
<211> LENGTH: 19
<212> TYPE: RNA
<213> ORGANISM: Artificial Sequence
<220> FEATURE:
<223> OTHER INFORMATION: non-targeting siRNA siNT

<400> SEQUENCE: 432

uucuccgaac gugucacgu                                                19
```